(12) United States Patent
Aharonov et al.

(10) Patent No.: US 9,096,906 B2
(45) Date of Patent: Aug. 4, 2015

(54) GENE EXPRESSION SIGNATURE FOR CLASSIFICATION OF TISSUE OF ORIGIN OF TUMOR SAMPLES

(71) Applicant: Rosetta Genomics Ltd., Rehovot (IL)

(72) Inventors: Ranit Aharonov, Tel Aviv (IL); Nitzan Rosenfeld, Rehovot (IL); Shai Rosenwald, Nes Ziona (IL); Nir Dromi, Rehovot (IL)

(73) Assignee: Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 13/856,190

(22) Filed: Apr. 3, 2013

(65) Prior Publication Data

US 2013/0259839 A1 Oct. 3, 2013

Related U.S. Application Data

(63) Continuation-in-part of application No. 13/167,489, filed on Jun. 23, 2011, now Pat. No. 8,802,599, which is a continuation-in-part of application No. 12/532,940, filed as application No. PCT/IL2008/000396 on Mar. 20, 2008, now abandoned, said application No. 13/167,489 is a continuation-in-part of application No. PCT/IL2009/001212, filed on Dec. 23, 2009, application No. 13/856,190, filed on Apr. 3, 2013, which is a continuation-in-part of application No. PCT/IL2011/000849, filed on Nov. 1, 2011.

(60) Provisional application No. 60/907,266, filed on Mar. 27, 2007, provisional application No. 60/929,244, filed on Jun. 19, 2007, provisional application No. 61/024,565, filed on Jan. 30, 2008, provisional application No. 61/140,642, filed on Dec. 24, 2008, provisional application No. 61/415,875, filed on Nov. 22, 2010.

(51) Int. Cl.
  *C12Q 1/68* (2006.01)

(52) U.S. Cl.
  CPC ........ *C12Q 1/6886* (2013.01); *C12Q 2600/158* (2013.01); *C12Q 2600/178* (2013.01)

(58) Field of Classification Search
  CPC .. C12Q 1/6886; C12Q 1/6844; C12Q 1/6837; C12Q 2600/178; C12Q 2600/158
  See application file for complete search history.

(56) References Cited

U.S. PATENT DOCUMENTS

| | | |
|---|---|---|
| 2003/0225526 A1 | 12/2003 | Golub et al. |
| 2007/0065844 A1 | 3/2007 | Golub et al. |
| 2008/0269072 A1 | 10/2008 | Hart et al. |
| 2008/0306018 A1 | 12/2008 | Croce et al. |
| 2010/0047784 A1* | 2/2010 | Shlomit et al. ..................... 435/6 |
| 2010/0178653 A1* | 7/2010 | Aharonov et al. ................. 435/6 |
| 2010/0273172 A1* | 10/2010 | Rosenfeld et al. ................. 435/6 |
| 2010/0286044 A1 | 11/2010 | Litman et al. |
| 2011/0312530 A1* | 12/2011 | Aharonov et al. ................ 506/9 |
| 2012/0219958 A1* | 8/2012 | Weidhaas ..................... 435/6.12 |

FOREIGN PATENT DOCUMENTS

| | | | |
|---|---|---|---|
| EP | 1777301 A2 | 4/2007 | |
| IL | WO2012070037 A2 * | 5/2012 | .............. C12Q 1/68 |
| WO | WO 2005/118806 A2 | 12/2005 | |
| WO | WO 2006081284 A2 | 8/2006 | |
| WO | WO 2008029295 A2 | 3/2008 | |
| WO | 2009/033140 A1 | 3/2009 | |
| WO | 2010/073248 A2 | 7/2010 | |

OTHER PUBLICATIONS

Griffiths-Jones et al. (miRBase: microRNA sequences, targets and gene nomenclature, Nucleic Acids Research, 2006, vol. 34, Database issue).*
Goodarzi et al. (Revealing Global Regulatory Perturbations across Human Cancers, Molecular Cell 36, 900-911, Dec. 11, 2009).*
Jiang et al. (miR2Disease: a manually curated database for microRNA deregulation in human disease, Nucleic Acids Research, 2009, vol. 37, Database issue).*
Bentwich et al. (Identification of hundreds of conserved and nonconserved human microRNAs, Nature Genetics, vol. 37, No. 7, Jul. 2005).*
Meiri et al. (A Second-Generation MicroRNA-Based Assay for Diagnosing Tumor Tissue Origin, The Oncologist, May 22, 2012;17:801-812).*
Aharanov et al. (A second-generation microRNA-based assay for diagnosing tumor tissue origin, AACR International Conference on Molecular Diagnostics in Cancer Therapeutic Development—Sep. 27-30, 2010; Denver, CO).*
Chajut et al. (Development and validation of a second generation microRNA-based assay for diagnosing tumor tissue origin, AACR Abstract, Apr. 2, 2011).*
Chajut et al. (hereinafter "Chajut2"; A second generation microRNA-based assay for diagnosing tumor tissue origin, ASCO Abstract, May 20, 2011).*
Rosenfeld et al. (MicroRNAs accurately identify cancer tissue origin, Nature Biotechnology, vol. 26, No. 4, Apr. 2008).*
Rosenwald et al. (Validation of a microRNA-based qRT-PCR test for accurate identification of tumor tissue origin, Modern Pathology (2010) 23, 814-823).*
Mueller et al. (Accurate Classification of Metastatic Brain Tumors Using a Novel MicroRNA-Based Test, The Oncologist, Jan. 27, 2011;16:165-174).*
Varadhachary et al. (Prospective Gene Signature Study Using microRNA to Identify the Tissue of Origin in Patients with Carcinoma of Unknown Primary, Clin Cancer Res, Apr. 29, 2011;17:4063-4070).*

(Continued)

Primary Examiner — Christopher M Babic
Assistant Examiner — Aaron Priest
(74) Attorney, Agent, or Firm — Ron Galant; Polsinelli PC

(57) ABSTRACT

The present invention provides a process for classification of cancers and tissues of origin through the analysis of the expression patterns of specific microRNAs and nucleic acid molecules relating thereto. Classification according to a microRNA tree-based expression framework allows optimization of treatment, and determination of specific therapy.

19 Claims, 30 Drawing Sheets

(56) References Cited

OTHER PUBLICATIONS

Xi et al. (Prognostic Values of microRNAs in Colorectal Cancer, Biomarker Insights 2006:1, 113-121, published online Feb. 7, 2007).*

Kim et al. (miRNA signature associated with outcome of gastric cancer patients following chemotherapy, BMC Medical Genomics, 2011, 4:79).*

Xie et al. (miRCancer: a microRNA-cancer association database constructed by text mining on literature, Bioinformatics, vol. 29 No. 5 2013, pp. 638-644, Jan. 23, 2013).*

Shedden et al. (Accurate Molecular Classification of Human Cancers Based on Gene Expression Using a Simple Classifier with a Pathological Tree-Based Framework, American Journal of Pathology, vol. 163, No. 5, Nov. 2003).*

Ma et al. (Molecular Classification of Human Cancers Using a 92-Gene Real-Time Quantitative Polymerase Chain Reaction Assay, Arch Pathol Lab Med—vol. 130, Apr. 2006).* van Laar et al. (Implementation of a novel microarray-based diagnostic test for cancer of unknown primary, Int. J. Cancer: 125, 1390-1397 (2009)).*

Weidhaas Table 2 with Annotations (attached, Nov. 9, 2010).*

The Office Action received in the related U.S. Appl. No. 13/167,489 on Jul. 12, 2013.

miR200c miRNAMap (hereinafter "Map"; 2005).

Golub, et al., "MicroRNA expression profiles classify human cancers", Nature, vol. 435, No. 9, Jun. 8, 2005.

Shedden, et al., "Accurate Molecular Classification of Human Cancers Based on Gene Expression Using a Simple Classifier with a Pathological Tree-Based Framework", American Journal of Pathology, vol. 163, No. 5, Nov. 2003.

Shi, et al., "Facile means for quantifying microRNA expression by real-time PCR", BioTechniques, vol. 39, pp. 519-525, 2005.

Xi, et al., "Prognostic Values of microRNAs in Colorectal Cancer", Biomarker Insights, vol. 1, pp. 113-121, published online Feb. 7, 2007, pp. 113-121.

Office Action received in the related U.S. Appl. No. 12/782,067, dated Mar. 18, 2013.

Notterman, et al., "Tumor Biiology and Microarray Analysis of Solid Tumors: Colorectal Cancer as a Model System", *Microarrays and Cancer Research*, 2002, Warrington et al., (eds.), Eaton Publishing, Westborough, MA, pp. 81-111.

Strausberg, et al., "Reading the Molecular Signatures of Cancer", Microarrays and Cancer Research, 2002, Warrington, et al. (eds.), Eaton Publishing, Westborough, MA, pp. 81-111.

The PTO form 892 received in the related U.S. Appl. No. 12/532,940 on Oct. 4, 2011.

Jukic, et al., "Microrna profiling analysis of differences between the melanoma of young adults and older adults", *Journal of Translational Medicine*, 2010, vol. 8, No. 27, pp. 1-23.

Leidinger, et al., "High-throughput miRNA profiling of human melanoma blood samples", *BMC Cancer*, 2010, vol. 10: 262, pp. 1-11.

MIR associated with Melanoma, Sep. 2011.

MIR-509 Results, Sep. 2011.

Peng, S. et al., Multi-class cancer classification through gene expression profiles: microRNA versus mRNA, Journal of Genetics and Genomics, 36:409-16 (2009).

Raponi, M. et al., MicroRNA classifiers for predicting prognosis of squamous cell lung cancer, Cancer Res, 69:5776-83 (2009).

Lu, J. et al., MicroRNA expression profiles classify human cancers, Nature, 435:834-8 (2005).

* cited by examiner

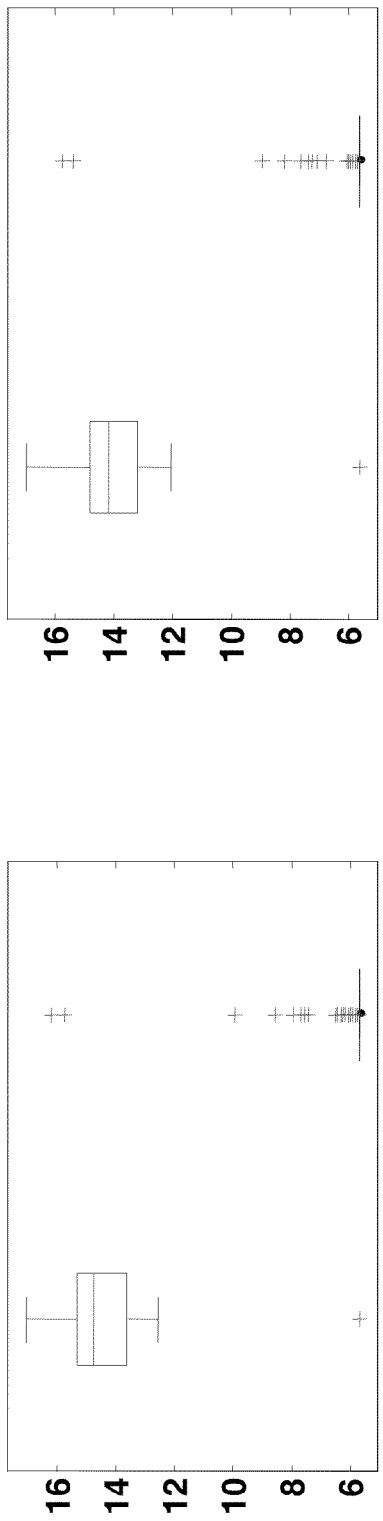
Figure 2A
Figure 2B
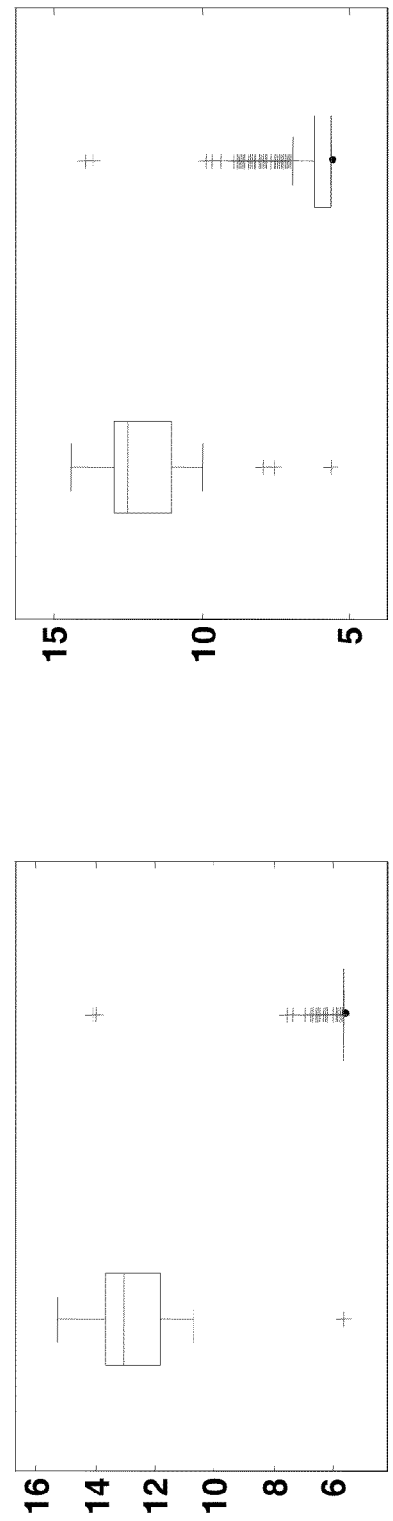
Figure 2C
Figure 2D

GENE EXPRESSION SIGNATURE FOR CLASSIFICATION OF TISSUE OF ORIGIN OF TUMOR SAMPLES

This application is a Continuation in Part of International Patent Application PCT/IL2011/000849, filed Nov. 1, 2011, which claims priority from 61/415,875, filed Nov. 22, 2010 and is a Continuation in Part of Ser. No. 13/167,489, filed Jun. 23, 2011, which is a Continuation in Part of PCT/IL2009/001212, filed Dec. 23, 2009, and claims priority from 61/140,642, filed Dec. 24, 2008, and Continuation in Part of Ser. No. 12/532,940, filed Sep. 24, 2009, which is a U.S. National Stage of International Patent Application PCT/IL2008/000396, filed Mar. 20, 2008, which claims priority from 60/907,266, filed Mar. 27, 2007, 60/929,244, filed Jun. 19, 2007 and 61/024,565 filed Jan. 30, 2008, the contents of which are incorporated herein by reference.

FIELD OF THE INVENTION

The present invention relates to methods and materials for classification of cancers and the identification of their tissue of origin. Specifically the invention relates to microRNA molecules associated with specific cancers, as well as various nucleic acid molecules relating thereto or derived therefrom.

BACKGROUND OF THE INVENTION microRNAs (miRs, miRNAs) are a novel class of non-coding, regulatory RNA genes[1-3] which are involved in oncogenesis[4] and show remarkable tissue-specificity[5-7]. They have emerged as highly tissue-specific biomarkers[2,5,6] postulated to play important roles in encoding developmental decisions of differentiation. Various studies have tied microRNAs to the development of specific malignancies[4]. MicroRNAs are also stable in tissue, stored frozen or as formalin-fixed, paraffin-embedded (FFPE) samples, and in serum.

Hundreds of thousands of patients in the U.S. are diagnosed each year with a cancer that has already metastasized, without a clearly identified primary site. Oncologists and pathologists are constantly faced with a diagnostic dilemma when trying to identify the primary origin of a patient's metastasis. As metastases need to be treated according to their primary origin, accurate identification of the metastases' primary origin can be critical for determining appropriate treatment.

Once a metastatic tumor is found, the patient may undergo a wide range of costly, time consuming, and at times inefficient tests, including physical examination of the patient, histopathology analysis of the biopsy, imaging methods such as chest X-ray, CT and PET scans, in order to identify the primary origin of the metastasis.

Metastatic cancer of unknown primary (CUP) accounts for 3-5% of all new cancer cases, and as a group is usually a very aggressive disease with a poor prognosis[10]. The concept of CUP comes from the limitation of present methods to identify cancer origin, despite an often complicated and costly process which can significantly delay proper treatment of such patients. Recent studies revealed a high degree of variation in clinical management, in the absence of evidence based treatment for CUP[11]. Many protocols were evaluated[12] but have shown relatively small benefit[13]. Determining tumor tissue of origin is thus an important clinical application of molecular diagnostics[9].

Molecular classification studies for tumor tissue origin[14-17] have generally used classification algorithms that did not utilize domain-specific knowledge: tissues were treated as a-priori equivalents, ignoring underlying similarities between tissue types with a common developmental origin in embryogenesis. An exception of note is the study by Shedden and co-workers[18], that was based on a pathology classification tree. These studies used machine-learning methods that average effects of biological features (e.g., mRNA expression levels), an approach which is more amenable to automated processing but does not use or generate mechanistic insights.

Various markers have been proposed to indicate specific types of cancers and tumor tissue of origin. However, the diagnostic accuracy of tumor markers has not yet been defined. There is thus a need for a more efficient and effective method for diagnosing and classifying specific types of cancers.

SUMMARY OF THE INVENTION

The present invention provides specific nucleic acid sequences for use in the identification, classification and diagnosis of specific cancers and tumor tissue of origin. The nucleic acid sequences can also be used as prognostic markers for prognostic evaluation and determination of appropriate treatment of a subject based on the abundance of the nucleic acid sequences in a biological sample. The present invention provides a method for accurate identification of tumor tissue origin.

The invention is based in part on the development of a microRNA-based classifier for tumor classification. microRNA expression levels were measured in 1300 primary and metastatic tumor paraffin-embedded samples. microRNAs were profiled using a custom array platform. Using the custom array platform, a set of over 300 microRNAs was identified for the normalization of the array data and 65 microRNAs were used for the accurate classification of over 40 different tumor types. The accuracy of the assay exceeds 85%.

The findings demonstrate the utility of microRNA as novel biomarkers for the tissue of origin of a metastatic tumor. The classifier has wide biological as well as diagnostic applications.

According to a first aspect, the present invention provides a method of identifying a tissue of origin of a cancer, the method comprising obtaining a biological sample from a subject, measuring the relative abundance in said sample of nucleic acid sequences selected from the group consisting of SEQ ID NOS: 1-390, any combinations thereof, or a sequence having at least about 80% identity thereto; and comparing the measurement to a reference abundance of the nucleic acid by using a classifier algorithm, wherein the relative abundance of said nucleic acid sequences allows for the identification of the tissue of origin of said sample.

According to one aspect, the classifier algorithm is selected from the group consisting of decision tree classifier, K-nearest neighbor classifier (KNN), logistic regression classifier, nearest neighbor classifier, neural network classifier, Gaussian mixture model (GMM), Support Vector Machine (SVM) classifier, nearest centroid classifier, linear regression classifier and random forest classifier. According to one aspect, the sample is obtained from a subject with cancer of unknown primary (CUP), with a primary cancer or with a metastatic cancer.

According to certain embodiments, the cancer is selected from the group consisting of adrenocortical carcinoma; anus or skin squamous cell carcinoma; biliary tract adenocarcinoma; Ewing sarcoma; gastrointestinal stomal tumor (GIST); gastrointestinal tract carcinoid; renal cell carcinoma: chromophobe, clear cell and papillary; pancreatic islet cell tumor;

pheochromocytoma; urothelial cell carcinoma (TCC); lung, head & neck, or esophagus squamous cell carcinoma (SCC); brain: astrocytic tumor, oligodendroglioma; breast adenocarcinoma; uterine cervix squamous cell carcinoma; chondrosarcoma; germ cell cancer; sarcoma; colorectal adenocarcinoma; liposarcoma; hepatocellular carcinoma (HCC); lung large cell or adenocarcinoma; lung carcinoid; pleural mesothelioma; lung small cell carcinoma; B-cell lymphoma; T-cell lymphoma; melanoma; malignant fibrous histiocytoma (MFH) or fibrosarcoma; osteosarcoma; ovarian primitive germ cell tumor; ovarian carcinoma; pancreatic adenocarcinoma; prostate adenocarcinoma; rhabdomyosarcoma; gastric or esophageal adenocarcinoma; synovial sarcoma; non-seminomatous testicular germ cell tumor; seminomatous testicular germ cell tumor; thymoma/thymic carcinoma; follicular thyroid carcinoma; medullary thyroid carcinoma; and papillary thyroid carcinoma.

The invention further provides a method for identifying a cancer of germ cell origin, comprising measuring the relative abundance of SEQ ID NO: 55 or a sequence having at least about 80% identity thereto in said sample; wherein the abundance of said nucleic acid sequence is indicative of a cancer of germ cell origin. According to some embodiments the germ cell is selected from the group consisting of an ovarian primitive cell and a testis cell. According to some embodiments the group of nucleic acid furthers consists of SEQ ID NOS: 29, 62 or a sequence having at least about 80% identity thereto, and the abundance of said nucleic acid sequence is indicative of a testis cell cancer origin selected from the group consisting of seminomatous testicular germ cell and non-seminomatous testicular germ cell.

The invention further provides a method for identifying a cancer origin selected from the group consisting of biliary tract adenocarcinoma and hepatocellular carcinoma, comprising measuring the relative abundance of a nucleic acid sequence selected from the group consisting of SEQ ID NOS: 55, 6, 9, 29 or a sequence having at least about 80% identity thereto in said sample; wherein the abundance of said nucleic acid sequence is indicative of a cancer origin selected from the group consisting of biliary tract adenocarcinoma and hepatocellular carcinoma.

The invention further provides a method for identifying a cancer of brain origin, the method comprising measuring the relative abundance of a nucleic acid sequence selected from the group consisting of SEQ ID NOS: 55, 6, 30, 46, 16, 156, 66, 68 or a sequence having at least about 80% identity thereto in said sample; wherein the abundance of said nucleic acid sequence is indicative of a cancer of brain origin.

According to some embodiments the group of nucleic acid furthers consists of SEQ ID NOS: 40, 60 or a sequence having at least about 80% identity thereto, and wherein the abundance of said nucleic acid sequence is indicative of a brain cancer origin selected from the group consisting of oligodendroglioma and astrocytoma.

The invention further provides a method for identifying a cancer of prostate adenocarcinoma origin, the method comprising measuring the relative abundance of a nucleic acid sequence selected from the group consisting of SEQ ID NOS: 55, 6, 30, 46, 56, 65, 25, 27, 35, 14, 21 or a sequence having at least about 80% identity thereto in said sample; wherein the abundance of said nucleic acid sequence is indicative of a cancer of prostate adenocarcinoma origin.

The invention further provides a method for identifying a cancer of breast adenocarcinoma origin, the method comprising measuring the relative abundance of a nucleic acid sequence selected from the group consisting of SEQ ID NOS: 55, 6, 30, 46, 56, 65, 27, 35, 14, 21, 32, 51, 7, 25, 50, 11, 148, 4, 49, 67 or a sequence having at least about 80% identity thereto in said sample; wherein the abundance of said nucleic acid sequence is indicative of a cancer of breast adenocarcinoma origin.

The invention further provides a method for identifying a cancer of ovarian carcinoma origin, the method comprising measuring the relative abundance of a nucleic acid sequence selected from the group consisting of SEQ ID NOS: 55, 6, 30, 46, 56, 65, 27, 35, 14, 21, 32, 51, 7, 25, 4, 39, 50, 11, 148, 49, 67, 57, 34 or a sequence having at least about 80% identity thereto in said sample; wherein the abundance of said nucleic acid sequence is indicative of a cancer of an ovarian carcinoma origin.

The invention further provides a method for identifying a cancer of thyroid carcinoma origin, the method comprising measuring the relative abundance of a nucleic acid sequence selected from the group consisting of SEQ ID NOS: 55, 6, 30, 46, 56, 65, 25, 27, 35, 14, 21, 32, 51, 7, 11, 148, 4 or a sequence having at least about 80% identity thereto in said sample; wherein the abundance of said nucleic acid sequence is indicative of a cancer of thyroid carcinoma origin.

According to some embodiments the group of nucleic acid furthers consists of SEQ ID NOS: 17, 34 or a sequence having at least about 80% identity thereto, and wherein said thyroid carcinoma origin is selected from the group consisting of follicular and papillary.

The invention further provides a method for identifying a cancer origin selected from the group consisting of lung large cell and lung adenocarcinoma, the method comprising measuring the relative abundance of a nucleic acid sequence selected from the group consisting of SEQ ID NOS: 55, 6, 30, 46, 56, 65, 25, 27, 35, 14, 21, 32, 51, 7, 11, 148, 4, 49, 67, 57, 34 or a sequence having at least about 80% identity thereto in said sample; wherein the abundance of said nucleic acid sequence is indicative of a cancer origin selected from the group consisting of lung large cell and lung adenocarcinoma.

The invention further provides a method for identifying a cancer origin selected from the group consisting of lung large cell and lung adenocarcinoma, the method comprising measuring the relative abundance of a nucleic acid sequence selected from the group consisting of SEQ ID NOS: 55, 6, 30, 46, 56, 65, 25, 27, 35, 14, 21, 32, 51, 7, 11, 148, 4, 49, 67, 57, 34 or a sequence having at least about 80% identity thereto in said sample; wherein the abundance of said nucleic acid sequence is indicative of a cancer origin selected from the group consisting of lung large cell and lung adenocarcinoma.

The invention further provides a method for identifying a cancer of thymic carcinoma origin, the method comprising measuring the relative abundance of a nucleic acid sequence selected from the group consisting of SEQ ID NOS: 55, 6, 30, 46, 56, 65, 25, 27, 35, 14, 21, 32, 51, 7, 50, 4, 39, 3, 34 or a sequence having at least about 80% identity thereto in said sample; wherein the abundance of said nucleic acid sequence is indicative of a cancer of a thymic carcinoma origin.

The invention further provides a method for identifying a cancer origin selected from the group consisting of a urothelial cell carcinoma and squamous cell carcinoma, the method comprising measuring the relative abundance of a nucleic acid sequence selected from the group consisting of SEQ ID NOS: 55, 6, 30, 46, 56, 65, 25, 27, 35, 14, 21, 32, 51, 7, 50, 4, 39, 3, 34, 69, 24, 44 or a sequence having at least about 80% identity thereto in said sample; wherein the abundance of said nucleic acid sequence is indicative of is indicative of a cancer origin selected from the group consisting of urothelial cell carcinoma and squamous cell carcinoma.

According to some embodiments the group of nucleic acid further consists of SEQ ID NOS: 1, 5, 54 or a sequence having at least about 80% identity thereto, and wherein the abundance of said nucleic acid sequence is indicative of squamous-cell-carcinoma origin selected from the group consisting of uterine cervix squamous-cell-carcinoma and non uterine cervix squamous cell carcinoma.

According to some embodiments the group of nucleic acid further consists of SEQ ID NOS: 11, 23 or a sequence having at least about 80% identity thereto in said sample, and wherein the abundance of said nucleic acid sequence is indicative of a non-uterine cervix squamous cell carcinoma origin selected from the group consisting of anus or skin squamous cell carcinoma; and lung, head & neck, and esophagus squamous cell carcinoma.

The invention further provides a method for identifying a cancer origin selected from melanoma and lymphoma, the method comprising measuring the relative abundance of a nucleic acid sequence selected from the group consisting of SEQ ID NOS: 55, 6, 30, 46, 16, 2, 47, 50 or a sequence having at least about 80% identity thereto in said sample; wherein the abundance of said nucleic acid sequence is indicative of a cancer origin selected from the group consisting of melanoma and lymphoma.

According to some embodiments the group of nucleic acid further consists of SEQ ID NOS: 35, 48 or a sequence having at least about 80% identity thereto, and wherein the abundance of said nucleic acid sequence is indicative of a lymphoma cancer origin selected from the group consisting of B-cell lymphoma and T-cell lymphoma.

The invention further provides a method for identifying a cancer of lung small cell carcinoma origin, the method comprising measuring the relative abundance of a nucleic acid sequence selected from the group consisting of SEQ ID NOS: 55, 6, 30, 46, 56, 65, 25, 20, 45 or a sequence having at least about 80% identity thereto in said sample; wherein the abundance of said nucleic acid sequence is indicative of a cancer of lung small cell carcinoma origin.

The invention further provides a method for identifying a cancer of medullary thyroid carcinoma origin, the method comprising measuring the relative abundance of a nucleic acid sequence selected from the group consisting of SEQ ID NOS: 55, 6, 30, 46, 56, 65, 25, 20, 45, 40, 67, 68 or a sequence having at least about 80% identity thereto in said sample; wherein the abundance of said nucleic acid sequence is indicative of a cancer of medullary thyroid carcinoma origin.

The invention further provides a method for identifying a cancer of lung carcinoid origin, the method comprising measuring the relative abundance of a nucleic acid sequence selected from the group consisting of SEQ ID NOS: 55, 6, 30, 46, 56, 65, 25, 20, 45, 40, 67, 68, 64, 53, 37 or a sequence having at least about 80% identity thereto in said sample; wherein the abundance of said nucleic acid sequence is indicative of a cancer of lung carcinoid origin.

The invention further provides a method for identifying a cancer origin selected from the group consisting of gastrointestinal tract carcinoid and pancreatic islet cell tumor, the method comprising measuring the relative abundance of a nucleic acid sequence selected from the group consisting of SEQ ID NOS: 55, 6, 30, 46, 56, 65, 25, 20, 45, 40, 67, 68, 64, 53, 37, 34, 18 or a sequence having at least about 80% identity thereto in said sample; wherein the abundance of said nucleic acid sequence is indicative of a cancer origin selected from the group consisting of gastrointestinal tract carcinoid and pancreatic islet cell tumor.

The invention further provides a method for identifying a cancer origin selected from the group consisting of gastric and esophageal adenocarcinoma, the method comprising measuring the relative abundance of a nucleic acid sequence selected from the group consisting of SEQ ID NOS: 55, 6, 30, 46, 56, 65, 25, 27, 35, 42, 36, 146 or a sequence having at least about 80% identity thereto in said sample; wherein the abundance of said nucleic acid sequence is indicative of a cancer origin elected from the group consisting of gastric and esophageal adenocarcinoma.

The invention further provides a method for identifying a cancer of colorectal adenocarcinoma origin, the method comprising measuring the relative abundance of a nucleic acid sequence selected from the group consisting of SEQ ID NOS: 55, 6, 30, 46, 56, 65, 25, 27, 35, 42, 36, 146, 20, 43 or a sequence having at least about 80% identity thereto in said sample; wherein the abundance of said nucleic acid sequence is indicative of a cancer of colorectal adenocarcinoma origin.

The invention further provides a method for identifying a cancer origin selected from the group consisting of pancreatic adenocarcinoma and biliary tract adenocarcinoma, the method comprising measuring the relative abundance of a nucleic acid sequence selected from the group consisting of SEQ ID NOS: 55, 6, 30, 46, 56, 65, 25, 27, 35, 42, 36, 146, 20, 4351, 49, 16, or a sequence having at least about 80% identity thereto, and wherein the abundance of said nucleic acid sequence is indicative of a cancer origin selected from the group consisting of pancreatic adenocarcinoma or biliary tract adenocarcinoma.

The invention further provides a method for identifying a cancer of renal cell carcinoma origin, the method comprising measuring the relative abundance of a nucleic acid sequence selected from the group consisting of SEQ ID NOS: 55, 6, 30, 46, 16, 2, 66, 68, 19, 29 or a sequence having at least about 80% identity thereto in said sample; wherein the abundance of said nucleic acid sequence is indicative of a cancer of renal cell carcinoma origin.

According to some embodiments the group of nucleic acid further consists of SEQ ID NOS: 36, 147 or a sequence having at least about 80% identity thereto, and wherein the abundance of said nucleic acid sequence is indicative of a chromophobe renal cell carcinoma origin.

According to some embodiments the group of nucleic acid further consists of SEQ ID NOS: 49, 9 or a sequence having at least about 80% identity thereto, and wherein the abundance of said nucleic acid sequence is indicative of a renal cell carcinoma origin selected from the group consisting of clear cell and papillary.

The invention further provides a method for identifying a cancer of pheochromacytoma origin, the method comprising measuring the relative abundance of a nucleic acid sequence selected from the group consisting of SEQ ID NOS: 55, 6, 30, 46, 16, 2, 66, 68, 19, 29, 65, 56 or a sequence having at least about 80% identity thereto in said sample; wherein the abundance of said nucleic acid sequence is indicative of a cancer of pheochromacytoma origin.

The invention further provides a method for identifying a cancer of adrenocortical origin, the method comprising measuring the relative abundance of a nucleic acid sequence selected from the group consisting of SEQ ID NOS: 55, 6, 30, 46, 16, 2, 66, 68, 19, 29, 65, 56, 31, 38, 61 or a sequence having at least about 80% identity thereto in said sample; wherein the abundance of said nucleic acid sequence is indicative of a cancer of adrenocortical origin.

The invention further provides a method for identifying a cancer of gastrointestinal stomal tumor origin, the method comprising measuring the relative abundance of a nucleic acid sequence selected from the group consisting of SEQ ID NOS: 55, 6, 30, 46, 16, 2, 66, 68, 19, 29, 65, 56, 31, 38, 61, 14, 45 or a sequence having at least about 80% identity thereto in said sample; wherein the abundance of said nucleic acid sequence is indicative of a cancer of gastrointestinal stomal tumor origin.

The invention further provides a method for identifying a cancer origin selected from the group consisting of pleural mesothelioma and sarcoma, the method comprising measuring the relative abundance of a nucleic acid sequence selected from the group consisting of SEQ ID NOS: 55, 6, 30, 46, 16, 2, 66, 68, 19, 29, 65, 56, 31, 38, 61, 14, 45, 35, 10, 5 or a sequence having at least about 80% identity thereto in said sample; wherein the abundance of said nucleic acid sequence is indicative of a cancer origin selected from the group consisting of pleural mesothelioma and sarcoma.

According to some embodiments the group of nucleic acid further consists of SEQ ID NOS: 3, 40, 15 or a sequence having at least about 80% identity thereto, and wherein said sarcoma is synovial sarcoma.

According to some embodiments the group of nucleic acid further consists of SEQ ID NOS: 3, 40, 15, 12, 58 or a sequence having at least about 80% identity thereto, and wherein said sarcoma is chondrosarcoma.

According to some embodiments the group of nucleic acid further consists of SEQ ID NOS: 3, 40, 15, 12, 58, 36, 26 or a sequence having at least about 80% identity thereto, and wherein said sarcoma is liposarcoma.

According to some embodiments the group of nucleic acid further consists of SEQ ID NOS: 3, 40, 15, 12, 58, 36, 26, 21, 25, 49 or a sequence having at least about 80% identity thereto and wherein said sarcoma is selected from the group consisting of Ewing sarcoma and osteosarcoma.

According to some embodiments the group of nucleic acid further consists of SEQ ID NOS: 3, 40, 15, 12, 58, 36, 26, 21, 59, 39, 33 or a sequence having at least about 80% identity thereto and wherein said sarcoma is selected from the group consisting of rhabdomyosarcoma; and malignant fibrous histiocytoma and fibrosarcoma.

According to another aspect, the present invention provides a method of distinguishing between cancers of different origins, said method comprising:
  (a) obtaining a biological sample from a subject;
  (b) measuring the relative abundance in said sample of nucleic acid sequences selected from the group consisting of SEQ ID NOS: 1-390 or a sequence having at least about 80% identity thereto; and
  (c) comparing said measurement to a reference abundance of said nucleic acid by using a classifier algorithm;
wherein the relative abundance of said nucleic acid sequence in said sample allows for distinguishing between cancers of different origins.

According to some embodiments the measurement of the relative abundance of SEQ ID NOS: 372, 233, 55, 200, 201 or a sequence having at least about 80% identity thereto in said sample allows for distinguishing between a cancer originating from a germ-cell tumor and a cancer originating from the group consisting of non-germ-cell tumors.

According to some embodiments the measurement of the relative abundance of SEQ ID NOS: 6, 30, 13 or a sequence having at least about 80% identity thereto in said sample allows for distinguishing between a cancer originating from hepatobiliary tumors and a cancer originating from the group consisting of non-germ-cell non-hepatobiliary tumors.

According to some embodiments the measurement of the relative abundance of SEQ ID NOS: 28, 29, 231, 9 or a sequence having at least about 80% identity thereto in said sample allows for distinguishing between a cancer originating from liver tumors and a cancer originating from biliary-tract carcinomas.

According to some embodiments the measurement of the relative abundance of SEQ ID NOS: 46, 5, 12, 30, 29, 28, 32, 13, 152, 49 or a sequence having at least about 80% identity thereto in said sample allows for distinguishing between a cancer originating from the group consisting of tumors from an epithelial origin and a cancer originating from the group consisting of tumors from a non-epithelial origin.

According to some embodiments the measurement of the relative abundance of SEQ ID NOS: 164, 168, 170, 16, 198, 50, 176, 186, 11, 158, 20, 155, 231, 4, 8, 46, 3, 2, 7 or a sequence having at least about 80% identity thereto in said sample allows for distinguishing between a cancer originating from the group consisting of melanoma and lymphoma and a cancer originating from the group consisting of all other non-epithelial tumors.

According to some embodiments the measurement of the relative abundance of SEQ ID NOS: 159, 66, 225, 187, 162, 161, 68, 232, 173, 11, 8, 174, 155, 231, 4, 182, 181, 37 or a sequence having at least about 80% identity thereto in said sample allows for distinguishing between a cancer originating from brain tumors and a cancer originating from the group consisting of all non-brain, non-epithelial tumors.

According to some embodiments the measurement of the relative abundance of SEQ ID NOS: 40, 208, 60, 153, 230, 228, 147, 34, 206, 35, 52, 25, 229, 161, 187, 179 or a sequence having at least about 80% identity thereto in said sample allows for distinguishing between a cancer originating from astrocytoma and a cancer originating from oligodendroglioma.

According to some embodiments, measurement of the relative abundance of SEQ ID NOS: 56, 65, 25, 175, 152, 155, 32, 49, 35, 181, or a sequence having at least about 80% identity thereto in said sample allows for distinguishing between a cancer originating from the group consisting of neuroendocrine tumors and a cancer originating from the group consisting of all non-neuroendocrine, epithelial tumors.

According to some embodiments, measurement of the relative abundance of SEQ ID NOS: 27, 177, 4, 32, 35 or a sequence having at least about 80% identity thereto in said sample allows for distinguishing between a cancer originating from the group consisting of gastrointestinal epithelial tumors and a cancer originating from the group consisting of non-gastrointestinal epithelial tumors.

According to some embodiments, measurement of the relative abundance of SEQ ID NOS: 56, 199, 14, 15, 165, 231, 36, 154, 21, 49 or a sequence having at least about 80% identity thereto in said sample allows for distinguishing between a cancer originating from prostate tumors and a cancer originating from the group consisting of all other non-gastrointestinal epithelial tumors.

According to some embodiments, measurement of the relative abundance of SEQ ID NOS: 222, 62, 29, 28, 211, 214, 227, 215, 218, 152, 216, 212, 224, 13, 194, 192, 221, 217, 205, 219, 32, 193, 223, 220, 210, 209, 213, 163, 30 or a sequence having at least about 80% identity thereto in said sample allows for distinguishing between a cancer originating from seminoma and a cancer originating from the group consisting of non-seminoma testis-tumors.

According to some embodiments, measurement of the relative abundance of SEQ ID NOS: 42, 32, 36, 178, 243, 242, 49, 240, 57, 11, 46, 17, 47, 51, 7, 8, 154, 190, 157, 196, 197, or a sequence having at least about 80% identity thereto in said sample allows for distinguishing between a cancer originating from the group consisting of squamous cell carcinoma, transitional cell carcinoma and thymoma, and a cancer originating from the group consisting of non gastrointestinal adenocarcinoma tumors.

According to some embodiments, measurement of the relative abundance of SEQ ID NOS: 56, 46, 25, 152, 50, 45, 191, 181, 179, 49, 32, 42, 184, 40, 147, 236, 57, 203, 36, or a sequence having at least about 80% identity thereto in said sample allows for distinguishing between a cancer originating from breast adenocarcinoma, and a cancer originating from the group consisting of squamous cell carcinoma, transitional cell carcinoma, thymomas and ovarian carcinoma.

According to some embodiments, measurement of the relative abundance of SEQ ID NOS: 253, 32, 4, 39, 10, 46, 5, 226, 2, 195, 32, 185, 11, 168, 184, 16, 242, 12, 237, 243, 250, 49, 246, 167 or a sequence having at least about 80% identity thereto in said sample allows for distinguishing between a cancer originating from ovarian carcinoma, and a cancer originating from the group consisting of squamous cell carcinoma, transitional cell carcinoma and thymomas.

According to some embodiments, measurement of the relative abundance of SEQ ID NOS: 11, 147, 17, 157, 40, 8, 49, 9, 191, 205, 207, 195, 51, 46, 45, 52, 234, 231, 21, 169, 43, 3, 196, 154, 390, 171, 255, 197, 190, 189, 39, 7, 48, 47, 32, 36, 4, 178, 37, 181, 25, 183, 182, 35, 240, 57, 242, 204, 236, 176, 158, 148, 206, 50, 20, 34, 186, 239, 251, 244, 24, 188, 172, 238 or a sequence having at least about 80% identity thereto in said sample allows for distinguishing between a cancer originating from thyroid carcinoma, and a cancer originating from the group consisting of breast adenocarcinoma, lung large cell carcinoma, lung adenocarcinoma and ovarian carcinoma.

According to some embodiments, measurement of the relative abundance of SEQ ID NOS: 249, 180, 65, 235, 241, 248, 254, 247, 160, 243, 245, 252, 17, 49, 166, 225, 168, 34 or a sequence having at least about 80% identity thereto in said sample allows for distinguishing between a cancer originating from follicular thyroid carcinoma and a cancer originating from papillary thyroid carcinoma.

According to some embodiments, measurement of the relative abundance of SEQ ID NOS: 32, 56, 50, 45, 25, 253, 152, 9, 46, 191, 178, 49, 40, 10, 147, 4, 36, 228, 236, 230, 189, 240, 67, 202, 17 or a sequence having at least about 80% identity thereto in said sample allows for distinguishing between a cancer originating from breast adenocarcinoma and a cancer originating from the group consisting of lung adenocarcinoma and ovarian carcinoma.

According to some embodiments, measurement of the relative abundance of SEQ ID NOS: 56, 11, 168, 16, 237, 21, 52, 12, 154, 279, 9, 39, 47, 23, 50, 167, 383, 34, 35, 388, 5, 359, 245, 254, 10, 240, 236, 202, 4, 25, 203, 231, 20, 158, 186, 258, 244, 172, 2, 235, 256, 28, 277, 296, 374, 153, 181 or a sequence having at least about 80% identity thereto in said sample allows for distinguishing between a cancer originating from lung adenocarcinoma and a cancer originating from ovarian carcinoma.

According to some embodiments, measurement of the relative abundance of SEQ ID NOS: 161, 164, 22, 53, 285, 3, 152, 191, 154, 21, 206, 174, 19, 45, 171, 179, 8, 296, 284, 18, 51, 258, 49, 184, 35, 34, 37, 42, 228, 15, 14, 242, 230, 253, 36, 182, 293, 292, 4, 294, 297, 354, 377, 189, 30, 386, 249, 5, 274 or a sequence having at least about 80% identity thereto in said sample allows for distinguishing between a cancer originating from thymic carcinoma and a cancer originating from the group consisting of transitional cell carcinoma and squamous cell carcinoma.

According to some embodiments, measurement of the relative abundance of SEQ ID NOS: 69, 28, 280, 13, 191, 152, 29, 175, 30, 204, 4, 24, 5, 329, 273, 170, 184, 26, 231, 368, 37, 16, 169, 155, 35, 40, 17 or a sequence having at least about 80% identity thereto in said sample allows for distinguishing between a cancer originating from transitional cell carcinoma and a cancer originating from the group consisting of squamous cell carcinoma.

According to some embodiments, measurement of the relative abundance of SEQ ID NOS: 164, 5, 231, 54, 1, 242, 372, 249, 167, 254, 354, 381, 380, 245, 358, 364, 240, 11, 378 or a sequence having at least about 80% identity thereto in said sample allows for distinguishing between squamous cell carcinoma cancers originating from the uterine cervix, and squamous cell carcinoma cancers originating from the group consisting of anus and skin, lung, head & neck and esophagus.

According to some embodiments, measurement of the relative abundance of SEQ ID NOS: 305, 184, 41, 183, 49, 382, 235, 291, 181, 5, 296, 289, 206, 338, 334, 25, 11, 19, 198, 23 or a sequence having at least about 80% identity thereto in said sample allows for distinguishing between squamous cell carcinoma cancers originating from the group consisting of anus and skin, and between squamous cell carcinoma cancers originating from the group consisting of lung, head & neck and esophagus.

According to some embodiments, measurement of the relative abundance of SEQ ID NOS: 4, 11, 46, 8, 274, 169, 36, 47, 363, 231, 303, 349, 10, 7, 3, 16, 164, 170, 168, 198, 50, 245, 365, 45, 382, 259, 296, 364, 314, 12 or a sequence having at least about 80% identity thereto in said sample allows for distinguishing between a cancer originating from melanoma and a cancer originating from lymphoma.

According to some embodiments, measurement of the relative abundance of SEQ ID NOS: 11, 191, 48, 35, 228 or a sequence having at least about 80% identity thereto in said sample allows for distinguishing between a cancer originating from B-cell lymphoma and a cancer originating from T-cell lymphoma.

According to some embodiments, measurement of the relative abundance of SEQ ID NOS: 158, 20, 176, 186, 148, 36, 51, 172, 260, 265, 67, 188, 277, 284, 302, 68, 168, 242, 204, 162, 177, 27, 65, 263, 155, 191, 190, 45, 59, 43, 56, 266, 14, 15, 8, 7, 39, 189, 249, 231, 293, 2 or a sequence having at least about 80% identity thereto in said sample allows for distinguishing between a cancer originating from lung small cell carcinoma and a cancer originating from the group consisting of lung carcinoid, medullary thyroid carcinoma, gastrointestinal tract carcinoid and pancreatic islet cell tumor.

According to some embodiments, measurement of the relative abundance of SEQ ID NOS: 159, 40, 147, 11, 311, 4, 8, 231, 301, 297, 68, 67, 265, 36 or a sequence having at least about 80% identity thereto in said sample allows for distinguishing between a cancer originating from medullary thyroid carcinoma and a cancer originating from other neuroendocrine tumors selected from the group consisting of lung carcinoid, gastrointestinal tract carcinoid and pancreatic islet cell tumor.

According to some embodiments, measurement of the relative abundance of SEQ ID NOS: 331, 162, 59, 326, 306, 350, 317, 155, 325, 318, 339, 264, 332, 262, 336, 324, 322, 330, 321, 263, 309, 53, 320, 275, 352, 312, 355, 367, 269, 64, 308, 175, 190, 54, 302, 152, 301, 266, 47, 313, 359, 65, 307, 191, 242, 4, 147, 40, 372, 168, 16, 182, 167, 356, 148, 382, 37, 364, 35 or a sequence having at least about 80% identity thereto in said sample allows for distinguishing between a cancer originating from lung carcinoid tumors, and a cancer originating from gastrointestinal neuroendocrine tumors selected from the group consisting of gastrointestinal tract carcinoid and pancreatic islet cell tumor.

According to some embodiments, measurement of the relative abundance of SEQ ID NOS: 263, 288, 18, 286, 162, 225, 287, 206, 205, 296, 258, 313, 377, 373, 256, 153, 259, 265, 303, 268, 267, 165, 15, 272, 14, 202, 236, 203, 4, 168, 310, 298, 27, 29, 34, 228, 3, 349, 35, 26 or a sequence having at least about 80% identity thereto in said sample allows for distinguishing between a cancer originating from pancreatic islet cell tumors and a Gastrointestinal neuroendocrine carcinoid cancer originating from the group consisting of small intestine and duodenum; appendicitis, stomach and pancreas.

According to some embodiments, measurement of the relative abundance of SEQ ID NOS: 36, 267, 268, 165, 15, 14, 356, 167, 372, 272, 370, 42, 41, 146 or a sequence having at least about 80% identity thereto in said sample allows for distinguishing between adenocarcinoma tumors of the gastrointestinal system originating from:
  a) the group consisting of gastric and esophageal adenocarcinoma, and
  b) the group consisting of cholangiocarcinoma or adenocarcinoma of the extrahepatic biliary tract, pancreatic adenocarcinoma and colorectal adenocarcinoma.

According to some embodiments, measurement of the relative abundance of SEQ ID NOS: 42, 184, 67, 158, 20, 186, 284, 389, 203, 240, 236, 146, 204, 43, 176, 202, 49, 46, 38, 363 or a sequence having at least about 80% identity thereto in said sample allows for distinguishing between a cancer originating from colorectal adenocarcinoma and a cancer originating from the group consisting of adenocarcinoma of biliary tract or pancreas.

According to some embodiments, measurement of the relative abundance of SEQ ID NOS: 49, 11, 13, 373, 154, 5, 30, 45, 178, 147, 274, 16, 40, 21, 43, 253, 245, 256, 12, 374, 379, 180, 153, 51, 52, 1, 295, 257, 385, 293, 294 or a sequence having at least about 80% identity thereto in said sample allows for distinguishing between a cancer originating from pancreatic adenocarcinoma, and a cancer originating from the group consisting of cholangiocarcinoma or adenocarcinoma of the extrahepatic biliary tract.

According to some embodiments, measurement of the relative abundance of SEQ ID NOS: 29, 28, 30, 46, 49, 195, 152, 175, 47, 4, 387, 196, 177, 375, 27, 304, 40, 191, 147, 35, 16, 34, 5, 155, 181, 312, 183, 182, 320, 59, 38, 324, 323, 37, 322, 325, 19, 42, 334, 265, 22 or a sequence having at least about 80% identity thereto in said sample allows for distinguishing between a cancer originating from:
  a) renal cell tumors selected from the group consisting of chromophobe renal cell carcinoma, clear cell renal cell carcinoma and papillary renal cell carcinoma, and
  b) the group consisting of sarcomas, adrenal tumors and pleural mesothelioma.

According to some embodiments, measurement of the relative abundance of SEQ ID NOS: 65, 56, 11, 162, 59, 331, 350, 155, 335, 159, 336, 332, 263, 306, 339, 337, 275, 301, 276, 330, 317, 309, 45, 318, 324, 352, 191, 262, 269, 313, 19, 367, 326, 325, 322, 327, 190, 261, 321, 360, 353, 312, 371, 5, 328, 205, 183, 38, 181, 37, 40, 182, 147, 17, 42, 382, 34, 18, 3 or a sequence having at least about 80% identity thereto in said sample allows for distinguishing between a cancer originating from pheochromocytoma, and a cancer originating from the group consisting of all sarcoma, adrenal carcinoma and mesothelioma tumors.

According to some embodiments, measurement of the relative abundance of SEQ ID NOS: 61, 333, 31, 347, 346, 344, 345, 387, 334, 351, 324, 326, 269, 155, 320, 322, 59, 318, 325, 245, 254, 331, 275, 180, 355, 370, 323, 312, 178, 249, 183, 181, 38, 182, 37, 3, 25 or a sequence having at least about 80% identity thereto in said sample allows for distinguishing between a cancer originating from adrenal carcinoma and a cancer originating from the group consisting of mesothelioma and sarcoma tumors.

According to some embodiments, measurement of the relative abundance of SEQ ID NOS: 165, 14, 15, 333, 272, 270, 45, 301, 191, 46, 195, 266, 190, 19, 334, 155, 25, 147, 40, 34 or a sequence having at least about 80% identity thereto in said sample allows for distinguishing between a cancer originating from a gastrointestinal stomal tumor and a cancer originating from the group consisting of mesothelioma and sarcoma tumors.

According to some embodiments, measurement of the relative abundance of SEQ ID NOS: 13, 30, 361, 280, 362, 147, 40, 291, 387, 290, 299, 152, 178, 303, 242, 49, 11, 35, 34, 36, 206, 16, 170, 177, 17 or a sequence having at least about 80% identity thereto in said sample allows for distinguishing between a cancer originating from a chromophobe renal cell carcinoma tumor and a cancer originating from the group consisting of clear cell and papillary renal cell carcinoma tumors.

According to some embodiments, measurement of the relative abundance of SEQ ID NOS: 344, 382, 9, 338, 29, 49, 28, 195, 46, 4, 11, 254 or a sequence having at least about 80% identity thereto in said sample allows for distinguishing between a renal carcinoma cancer originating from a clear cell tumor and a cancer originating from a papillary tumor.

According to some embodiments, measurement of the relative abundance of SEQ ID NOS: 49, 35, 17, 34, 25, 36, 168, 170, 26, 4, 190, 46, 10, 240, 43, 39, 385, 63, 202, 181, 37, 5, 183, 182, 38, 206, 296, 1 or a sequence having at least about 80% identity thereto in said sample allows for distinguishing between a cancer originating from pleural mesothelioma and a cancer originating from the group consisting of sarcoma tumors.

According to some embodiments, measurement of the relative abundance of SEQ ID NOS: 152, 29, 159, 28, 339, 275, 352, 19, 320, 155, 262, 38, 37, 182, 331, 317, 323, 355, 3, 282, 312, 181, 269, 318, 59, 266, 322, 8, 324, 10, 40, 147, 169, 205, 34, 168, 14, 15, 12, 46, 255, 39, 23, 190, 236, 386, 379, 202 or a sequence having at least about 80% identity thereto in said sample allows for distinguishing between a cancer originating from a synovial sarcoma and a cancer originating from the group consisting of other sarcoma tumors.

According to some embodiments, measurement of the relative abundance of SEQ ID NOS: 12, 271, 206, 333, 11, 58, 36, 18, 178, 293, 189, 382, 381, 240, 249, 5, 377, 235, 17, 20, 385, 384, 46, 283 or a sequence having at least about 80% identity thereto in said sample allows for distinguishing between a cancer originating from chondrosarcoma and a cancer originating from the group consisting of other non-synovial sarcoma tumors.

According to some embodiments, measurement of the relative abundance of SEQ ID NOS: 295, 205, 25, 26, 231, 183, 42, 254, 168, 64, 14, 178, 15, 39, 36, 154, 265, 174, 384, 67 or a sequence having at least about 80% identity thereto in said sample allows for distinguishing between a cancer originating from liposarcoma and a cancer originating from the group consisting of other non chondrosarcoma and non synovial sarcoma tumors.

According to some embodiments, measurement of the relative abundance of SEQ ID NOS: 22, 154, 21, 174, 205, 158, 186, 148, 20, 59, 8, 183, 231 or a sequence having at least about 80% identity thereto in said sample allows for distinguishing between a cancer originating from:

a) the group consisting of Ewing sarcoma and osteosarcoma, and b) the group consisting of rhabdomyosarcoma, malignant fibrous histiocytoma and fibrosarcoma.

According to some embodiments, measurement of the relative abundance of SEQ ID NOS: 155, 179, 43, 208, 278, 17, 385, 174, 5, 52, 257, 366, 48, 49, 12, 25, 169, 34, 35, 23, 384, 189, 377, 265, 294, 293, 292 or a sequence having at least about 80% identity thereto in said sample allows for distinguishing between a cancer originating from Ewing sarcoma and a cancer originating from osteosarcoma.

According to some embodiments, measurement of the relative abundance of SEQ ID NOS: 33, 268, 267, 333, 276, 319, 306, 320, 334, 323, 300, 281, 59, 339, 316, 176, 348, 352, 349, 67, 357, 315, 343, 342, 355, 340, 344, 10, 341, 331, 20, 277, 318, 158, 265, 284, 36, 183, 40, 63, 147, 43, 289, 52, 190, 4, 5, 39, 169, 208 or a sequence having at least about 80% identity thereto in said sample allows for distinguishing between a cancer originating from rhabdomyosarcoma and a cancer originating from the group consisting of malignant fibrous histiocytoma and fibrosarcoma.

According to some aspects of the invention the biological sample is selected from the group consisting of bodily fluid, a cell line, a tissue sample, a biopsy sample, a needle biopsy sample, a fine needle biopsy (FNA) sample, a surgically removed sample, and a sample obtained by tissue-sampling procedures such as endoscopy, bronchoscopy, or laparoscopic methods. According to some embodiments, the tissue is a fresh, frozen, fixed, wax-embedded or formalin-fixed paraffin-embedded (FFPE) tissue.

According to additional aspects of the invention the nucleic acid sequence relative abundance is determined by a method selected from the group consisting of nucleic acid hybridization and nucleic acid amplification. According to some embodiments, the nucleic acid hybridization is performed using a solid-phase nucleic acid biochip array or in situ hybridization. According to some embodiments, the nucleic acid amplification method is real-time PCR. According to some embodiments, the real-time PCR comprises forward and reverse primers. According to additional embodiments, the real-time PCR method further comprises a probe. According to additional embodiments, the probe comprises a sequence selected from the group consisting of a sequence that is complementary to a sequence selected from SEQ ID NOS: 1-390; a fragment thereof and a sequence having at least about 80% identity thereto.

According to another aspect, the present invention provides a kit for cancer origin identification, the kit comprising a probe comprising a sequence selected from the group consisting of a sequence that is complementary to a sequence selected from SEQ ID NOS: 1-390; a fragment thereof and a sequence having at least about 80% identity thereto.

These and other embodiments of the present invention will become apparent in conjunction with the figures, description and claims that follow.

Decisions are made at consecutive nodes using microRNA expression levels, until an end-point ("leaf" of the tree) is reached, indicating the predicted class for this sample. In specifying the tree structure, clinico-pathological considerations were combined with properties observed in the training set data.

FIG. 2A-2D demonstrates binary decisions at node #1 of the decision-tree. When training a decision algorithm for a given node, only samples from classes which are possible outcomes of this node are used for training. The "non germ cell" classes (right branch at node #1); are easily distinguished from tumors of the "germ cell" classes (left branch at node #1) using the expression levels of hsa-miR-373 (SEQ ID NO: 233, 2A), hsa-miR-372 (SEQ ID NO: 55, 2B), hsa-miR-371-3p (SEQ ID NO: 200, 2C), and hsa-miR-371-5p (SEQ ID NO: 201, 2D). The boxplot presentations comparing distribution of the expression of the statistically significant miR5 in tumor samples from the "germ cell" classes (left box) and "non germ cell" classes (right box). The line in the box indicates the median value. The box contains 50% of the data and the horizontal lines and crosses (outliers) show the full range of signals in this group.

Figure 3:
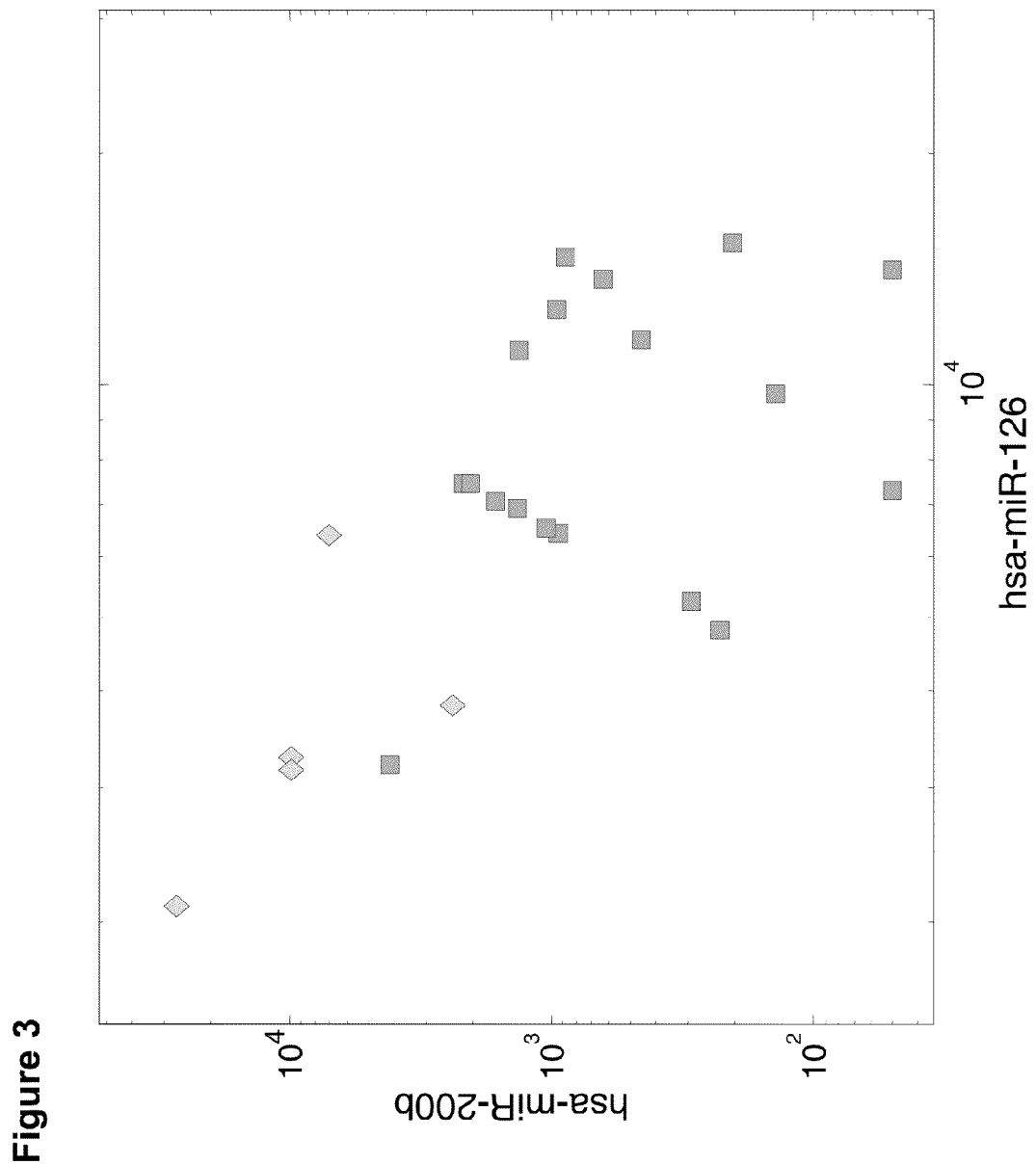

FIG. 3 demonstrates binary decisions at node #3 of the decision-tree. Tumors of hepatocellular carcinoma (HCC) origin (left branch at node #3, marked by squares) are easily distinguished from tumors of biliary tract adenocarcinoma origin (right branch at node #3, marked by diamonds) using the expression levels of hsa-miR-200b (SEQ ID NO: 29, y-axis) and hsa-miR-126 (SEQ ID NO: 9, x-axis).

Figure 4:
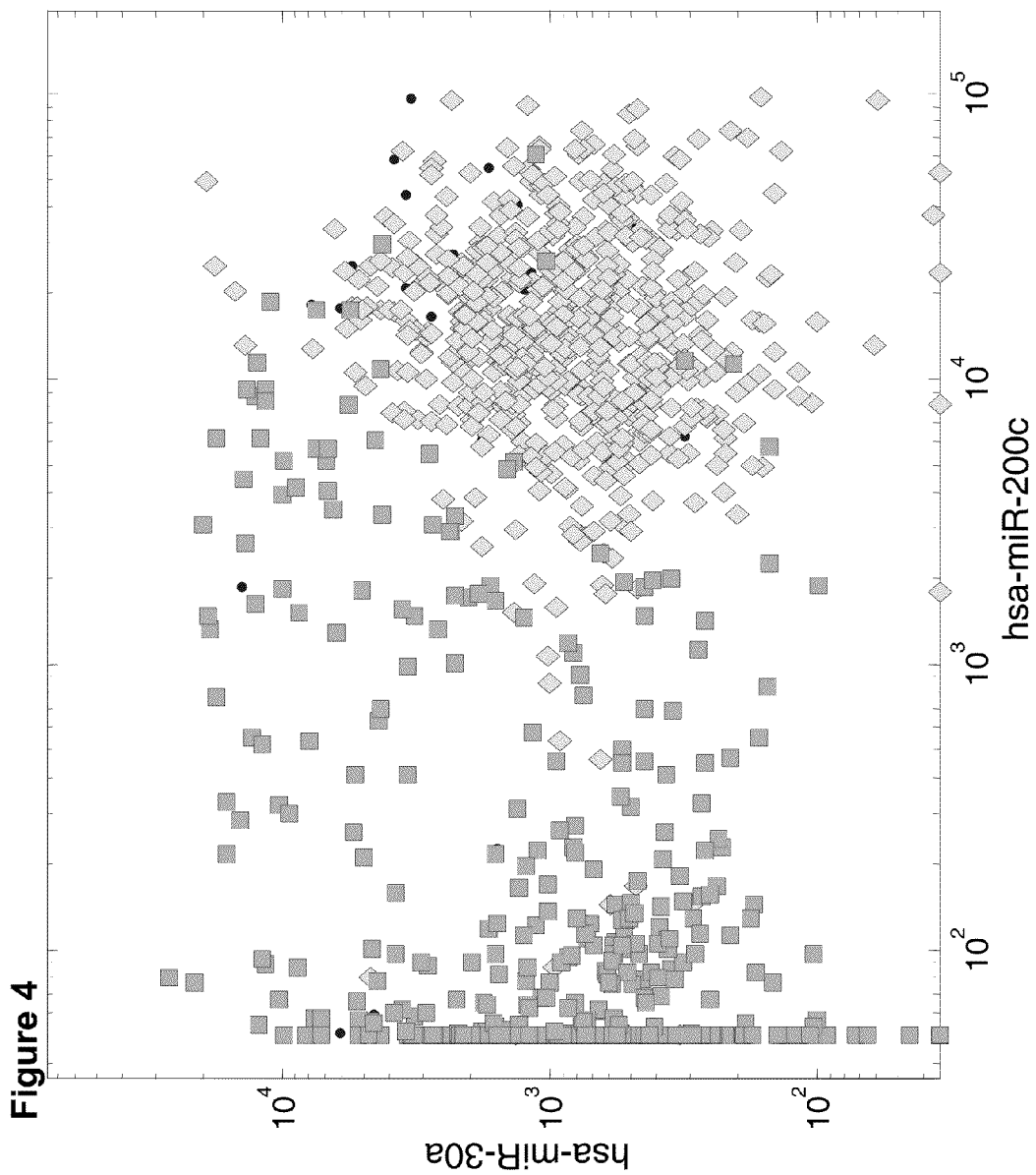

FIG. 4 demonstrates binary decisions at node #4 of the decision-tree. Tumors originating in epithelial (diamonds) are easily distinguished from tumors of non-epithelial origin (squares) using the expression levels of hsa-miR-30a (SEQ ID NO: 46, y-axis) and hsa-miR-200c (SEQ ID NO: 30, x-axis).

Figure 5:
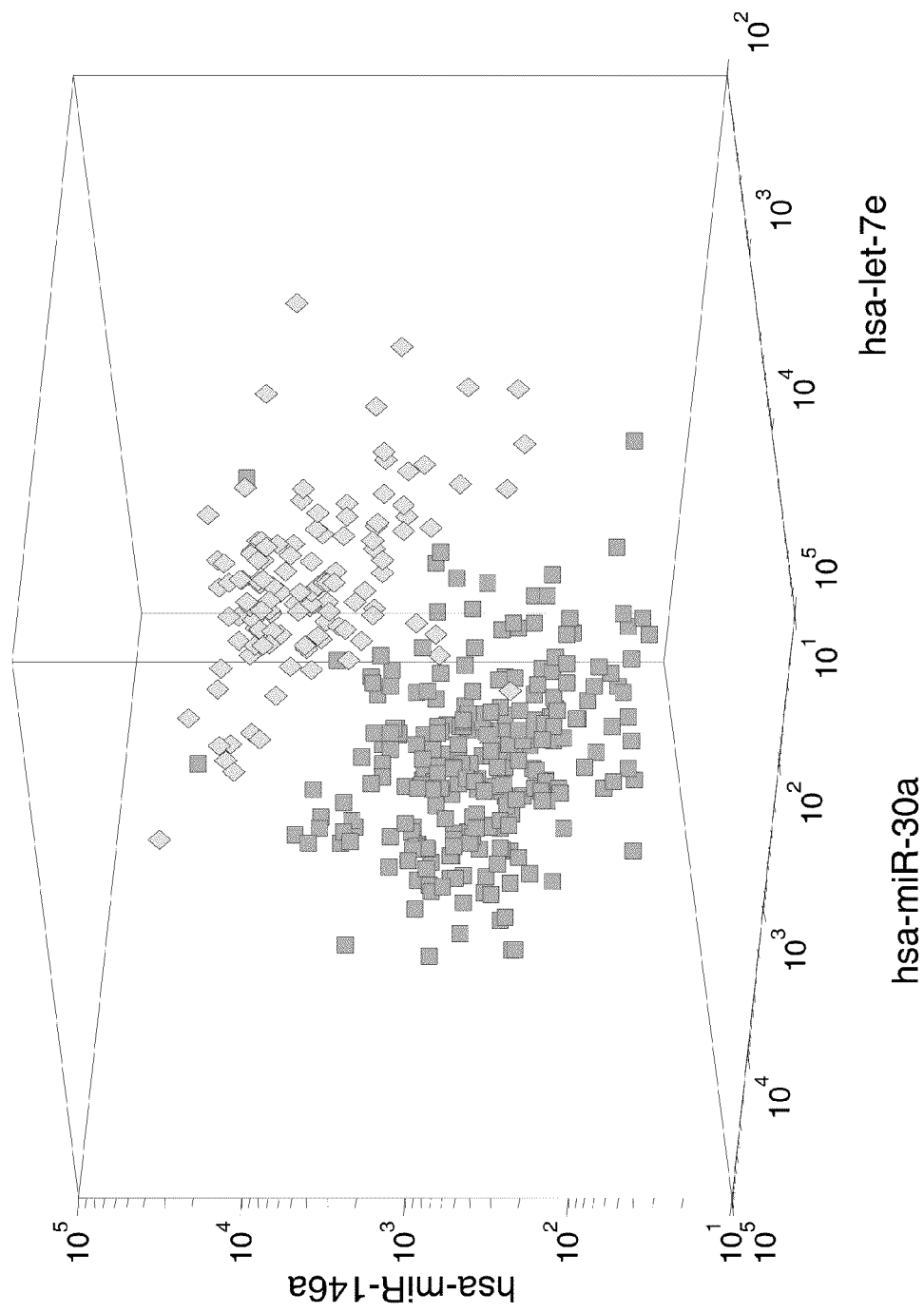

FIG. 5 demonstrates binary decisions at node #5 of the decision-tree. Tumors originating in the lymphoma or melanoma (diamonds) are easily distinguished from tumors of non epithelial, non lymphoma/melanoma origin (squares) using the expression levels of hsa-miR-146a (SEQ ID NO: 16, y-axis), hsa-miR-30a (SEQ ID NO: 46, x-axis) and hsa-let-7e (SEQ ID NO: 2, z-axis).

Figure 6:
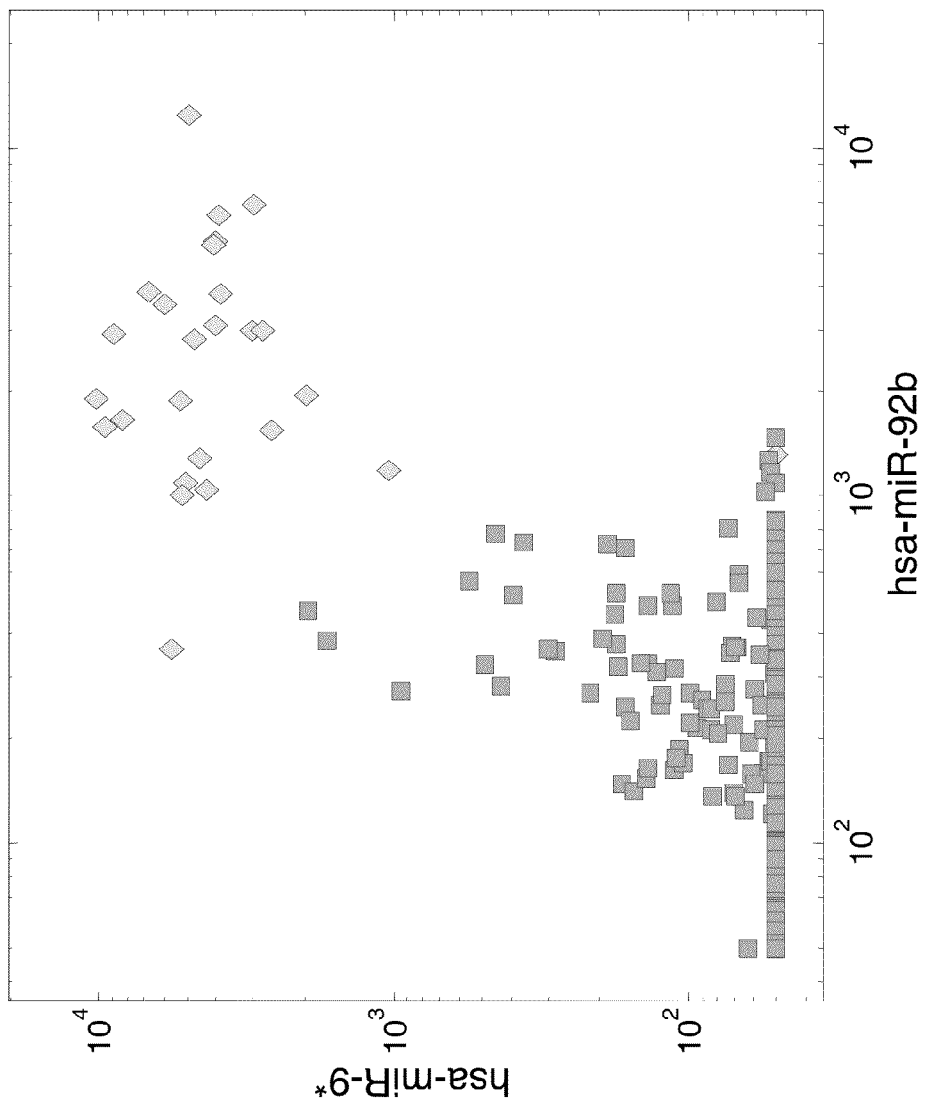

FIG. 6 demonstrates binary decisions at node #6 of the decision-tree. Tumors originating in the brain (left branch at node #6, marked by diamonds) are easily distinguished from tumors of non epithelial, non brain (right branch at node #6, marked by squares) using the expression levels of hsa-miR-9* (SEQ ID NO: 66, y-axis) and hsa-miR-92b (SEQ ID NO: 68, x-axis).

Figure 7:
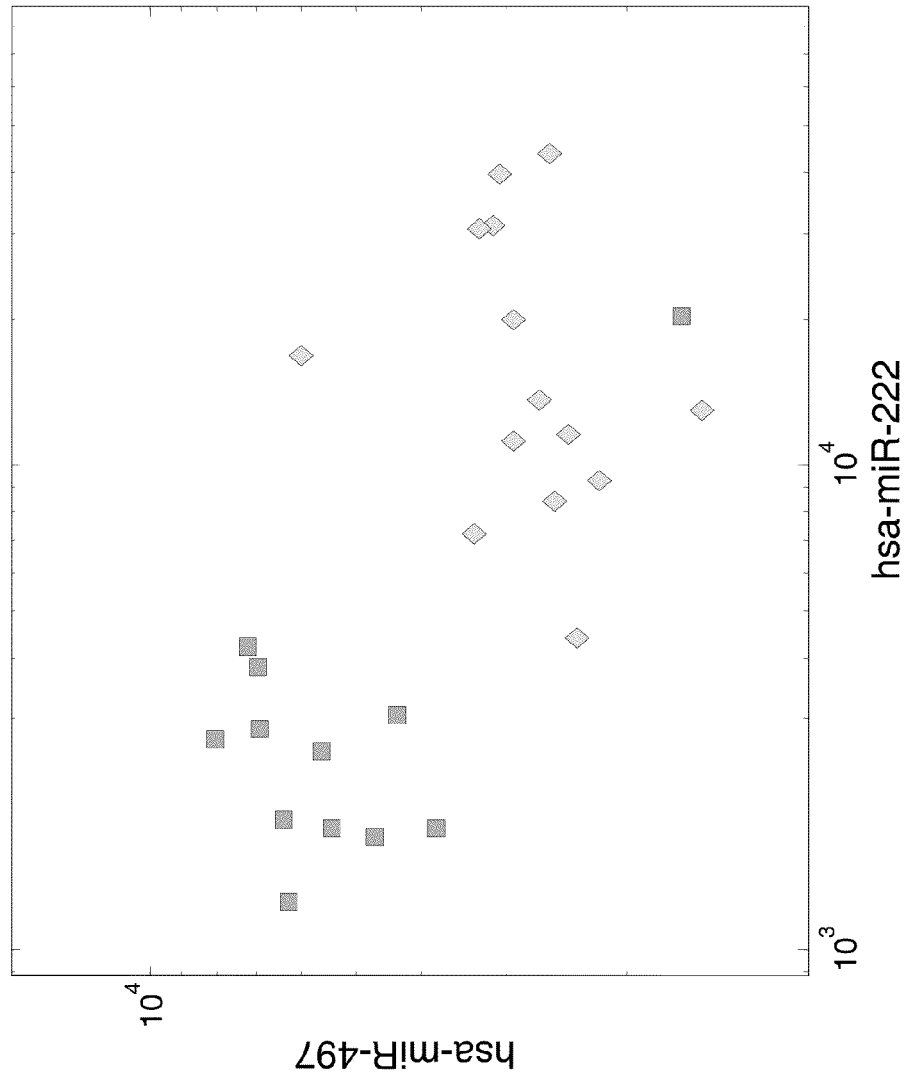

FIG. 7 demonstrates binary decisions at node #7 of the decision-tree. Tumors originating in astrocytoma (right branch at node #7, marked by diamonds) are easily distinguished from tumors of oligodendroglioma origins (left branch at node #7, marked by squares) using the expression levels of hsa-miR-497 (SEQ ID NO: 60, y-axis) and hsa-miR-222 (SEQ ID NO: 40, x-axis).

Figure 8:
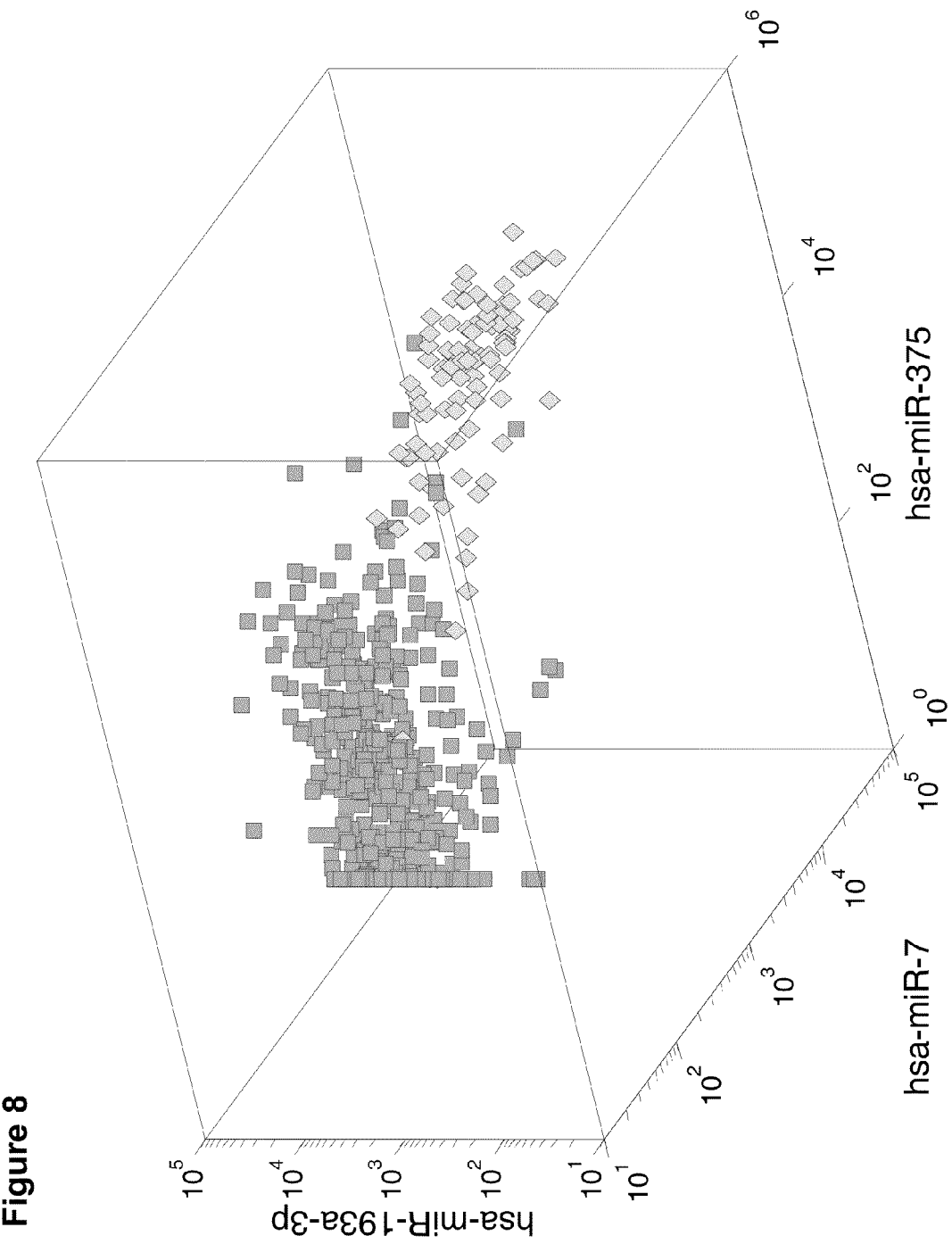

FIG. 8 demonstrates binary decisions at node #8 of the decision-tree. Tumors originating in the neuroendocrine (diamonds) are easily distinguished from tumors of epithelial, origin (squares) using the expression levels of hsa-miR-193a-3p (SEQ ID NO: 181, y-axis), hsa-miR-7 (SEQ ID NO: 65, x-axis) and hsa-miR-375 (SEQ ID NO: 56, z-axis).

Figure 9:
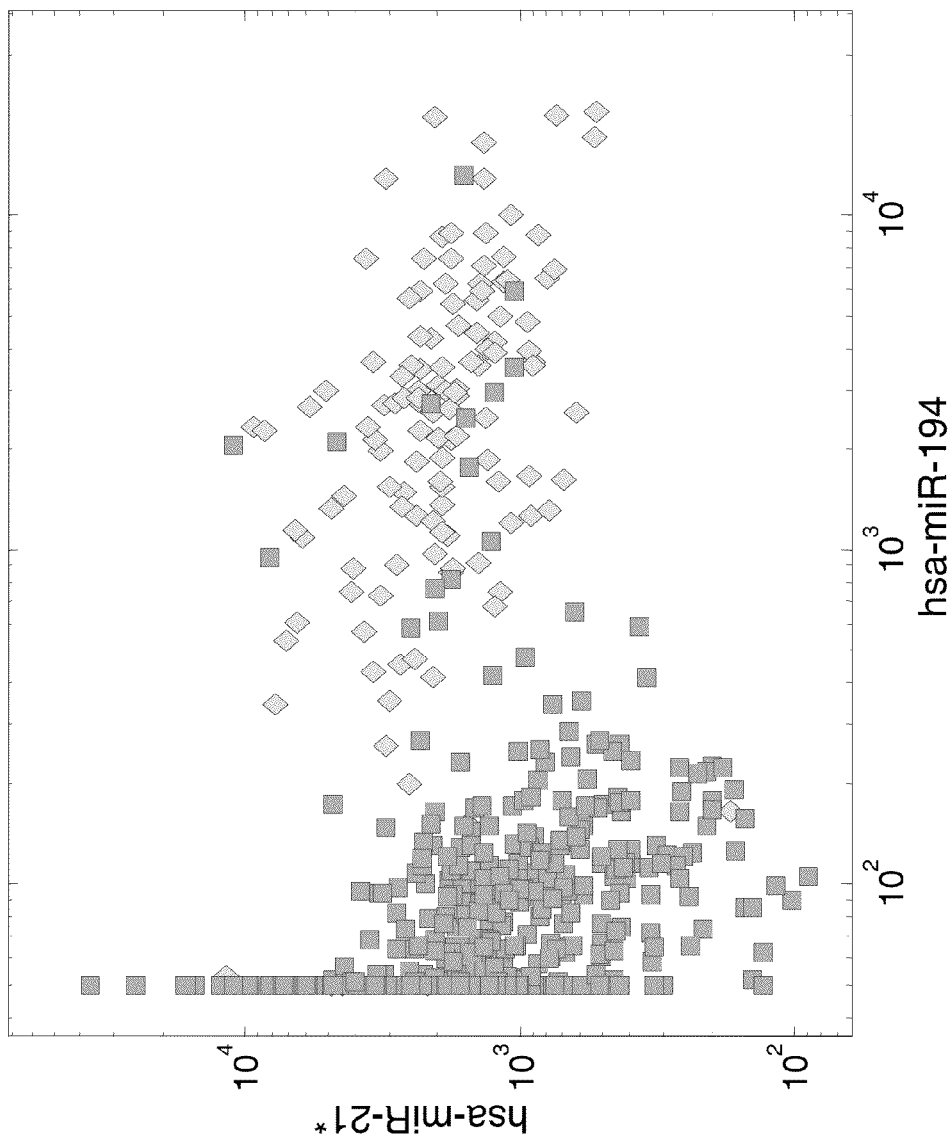

FIG. 9 demonstrates binary decisions at node #9 of the decision-tree. Tumors originating in gastro-intestinal (GI) (left branch at node #9, marked by diamonds) are easily distinguished from tumors of non GI origins (right branch at node #9, marked by squares) using the expression levels of hsa-miR-21* (SEQ ID NO: 35, y-axis) and hsa-miR-194 (SEQ ID NO: 27, x-axis).

Figure 10:
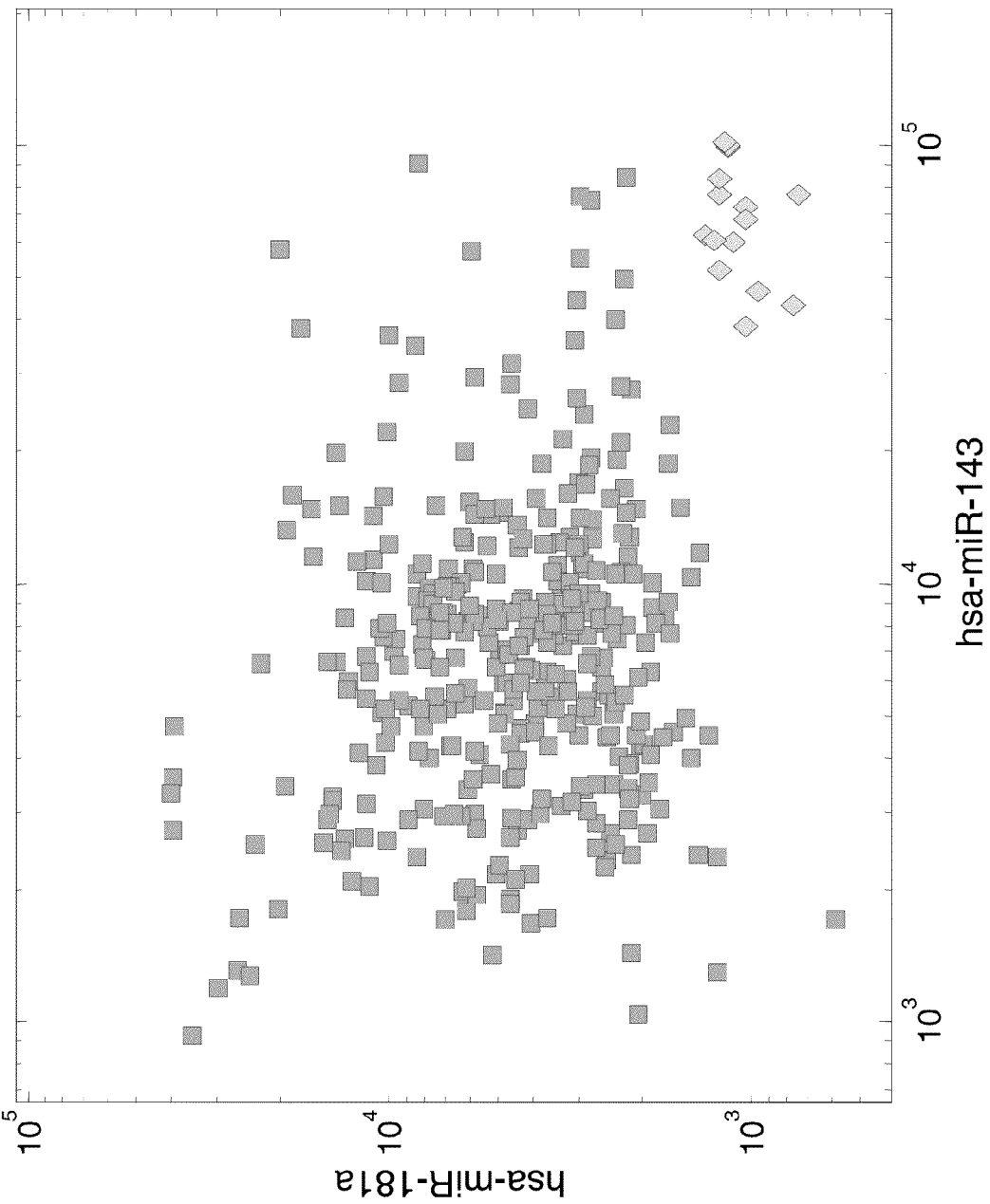

FIG. 10 demonstrates binary decisions at node #10 of the decision-tree. Tumors originating in prostate adenocarcinoma (left branch at node #10, marked by diamonds) are easily distinguished from tumors of non prostate origins (right branch at node #10, marked by squares) using the expression levels of hsa-miR-181a (SEQ ID NO: 21, y-axis) and hsa-miR-143 (SEQ ID NO: 14, x-axis).

Figure 11:
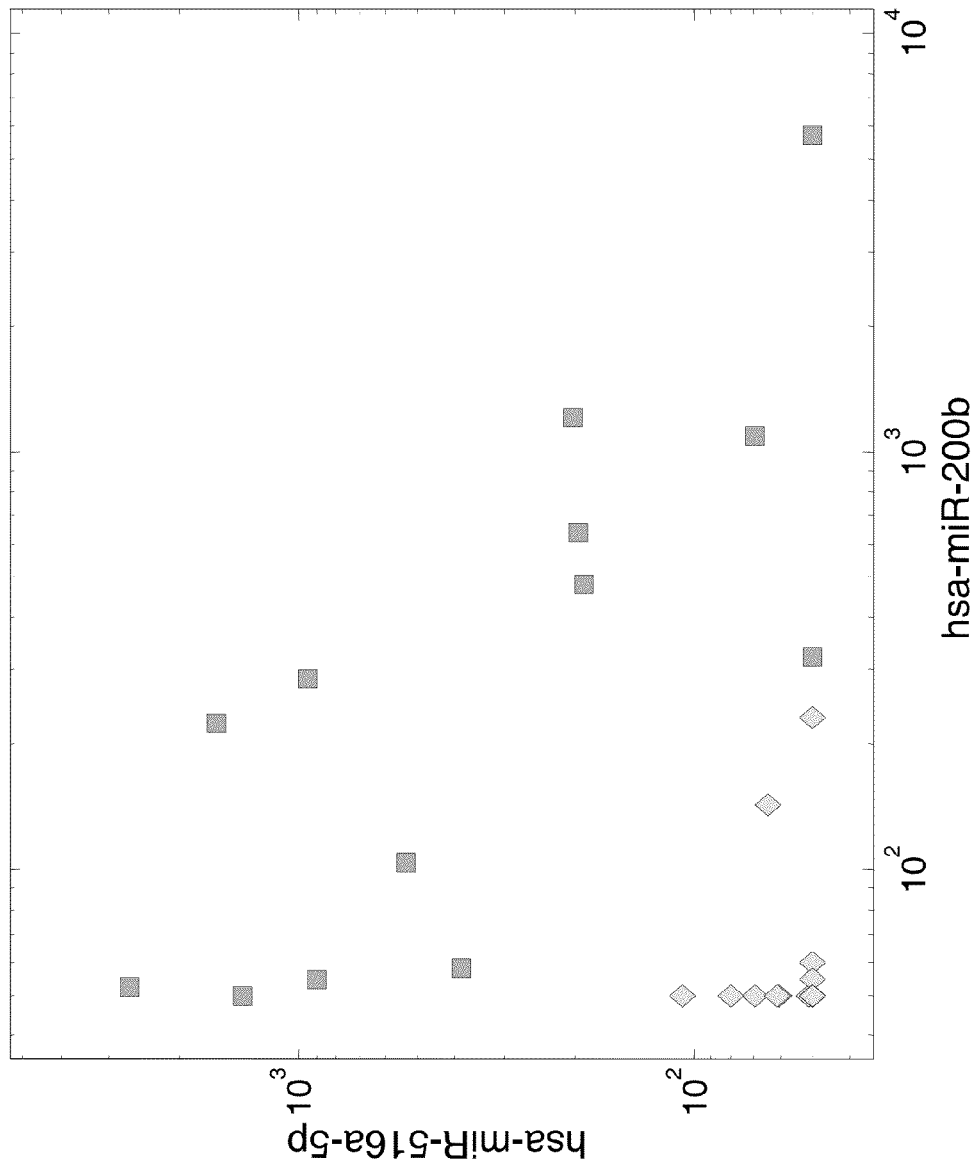

FIG. 11 demonstrates binary decisions at node #12 of the decision-tree. Tumors originating in seminiomatous testicular germ cell (left branch at node #12, marked by diamonds) are easily distinguished from tumors of non seminiomatous origins (right branch at node #12, marked by squares) using the expression levels of hsa-miR-516a-5p (SEQ ID NO: 62, y-axis) and hsa-miR-200b (SEQ ID NO: 29, x-axis).

Figure 12:
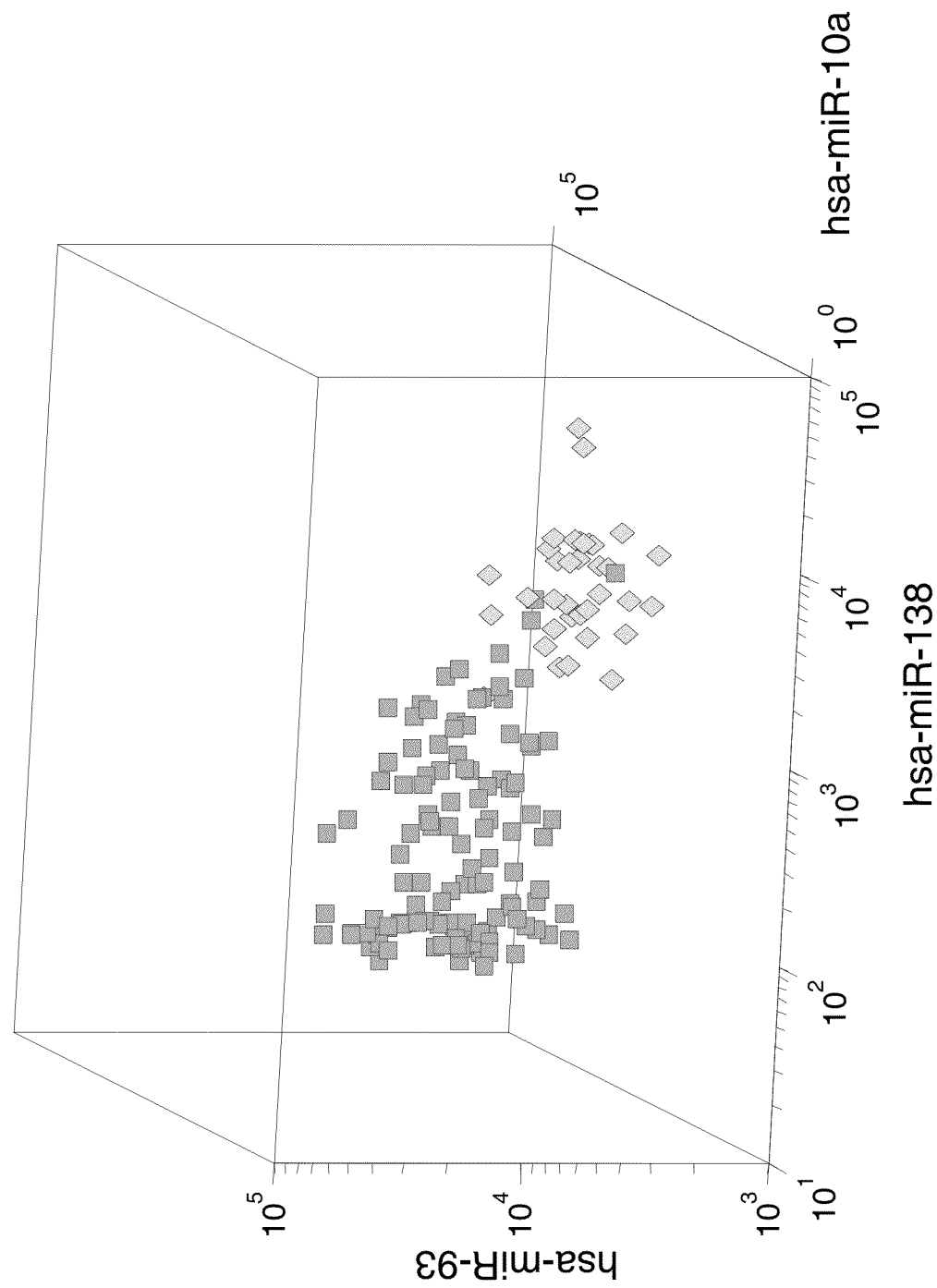

FIG. 12 demonstrates binary decisions at node #16 of the decision-tree. Tumors originating in thyroid carcinoma (diamonds) are easily distinguished from tumors of adenocarcinoma of the lung, breast and ovarian origin (squares) using the expression levels of hsa-miR-93 (SEQ ID NO: 148, y-axis), hsa-miR-138 (SEQ ID NO: 11, x-axis) and hsa-miR-10a (SEQ ID NO: 4, z-axis).

Figure 13:
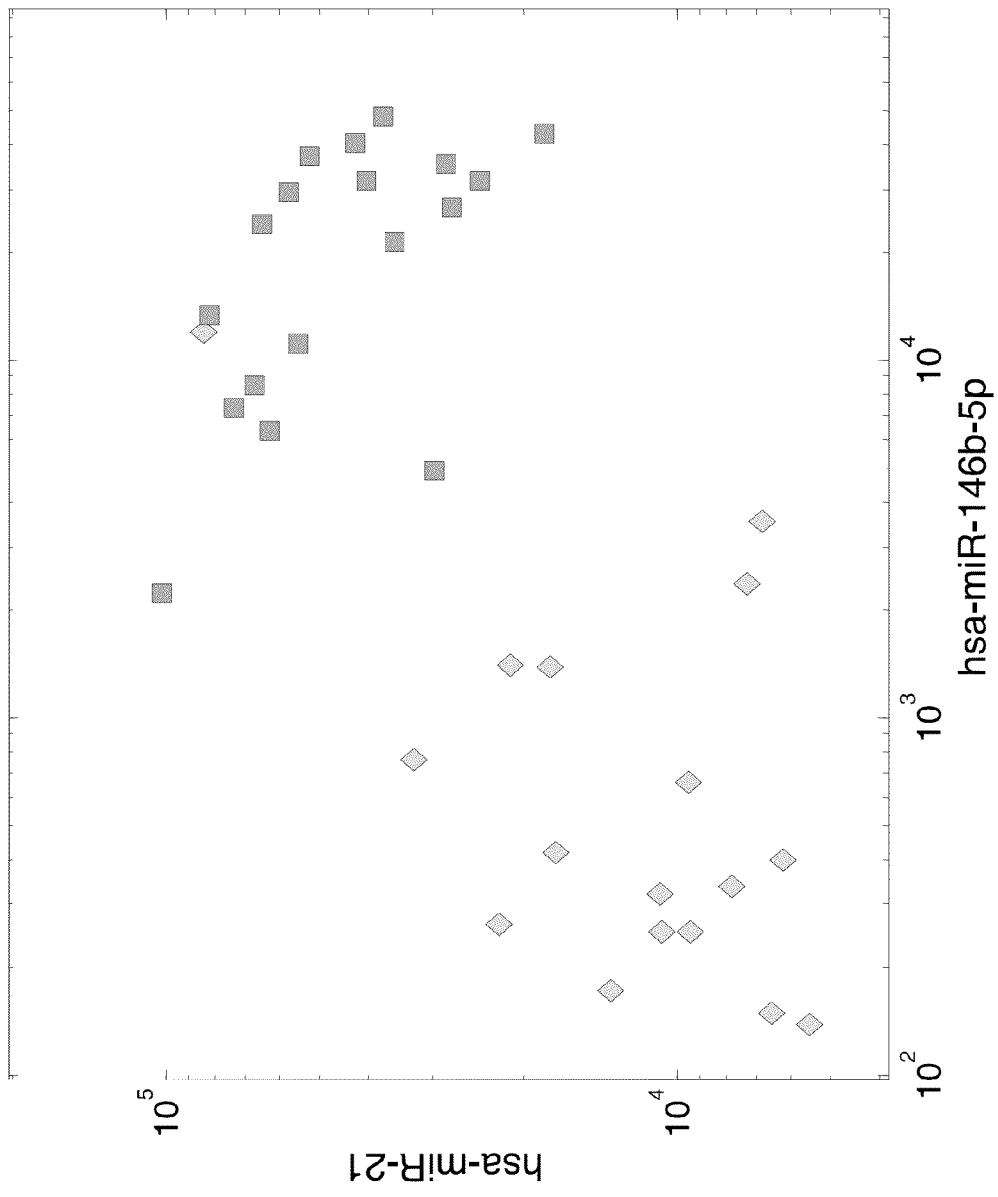

FIG. 13 demonstrates binary decisions at node #17 of the decision-tree. Tumors originating in follicular thyroid carcinoma (left branch at node #17, marked by diamonds) are easily distinguished from tumors of papillary thyroid carcinoma origins (right branch at node #17, marked by squares) using the expression levels of hsa-miR-21 (SEQ ID NO: 34, y-axis) and hsa-miR-146b-5p (SEQ ID NO: 17, x-axis).

Figure 14:
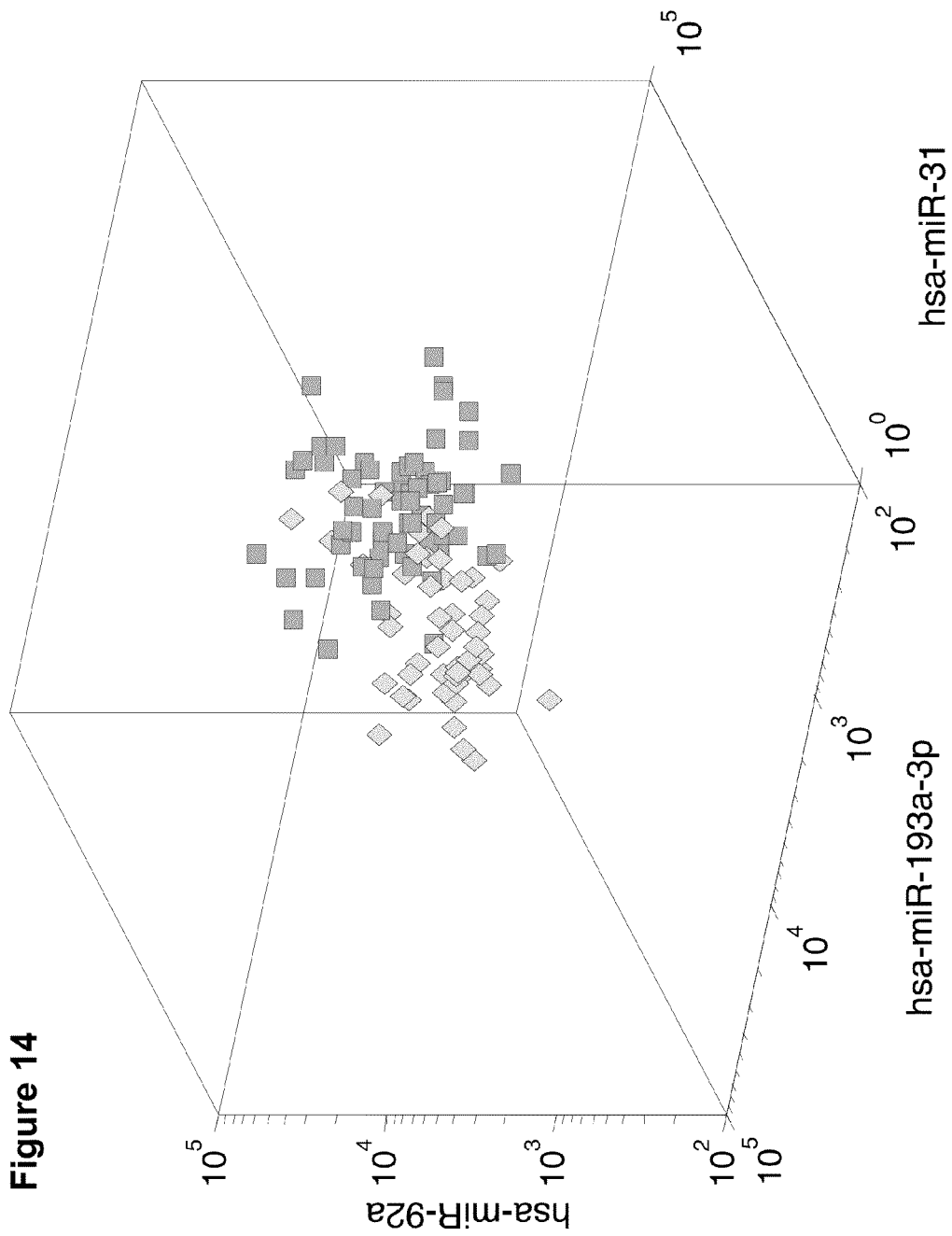

FIG. 14 demonstrates binary decisions at node #18 of the decision-tree. Tumors originating in breast (diamonds) are easily distinguished from tumors of lung and ovarian origin (squares) using the expression levels of hsa-miR-92a (SEQ ID NO: 67, y-axis), hsa-miR-193a-3p (SEQ ID NO: 25, x-axis) and hsa-miR-31 (SEQ ID NO: 49, z-axis).

Figure 15:
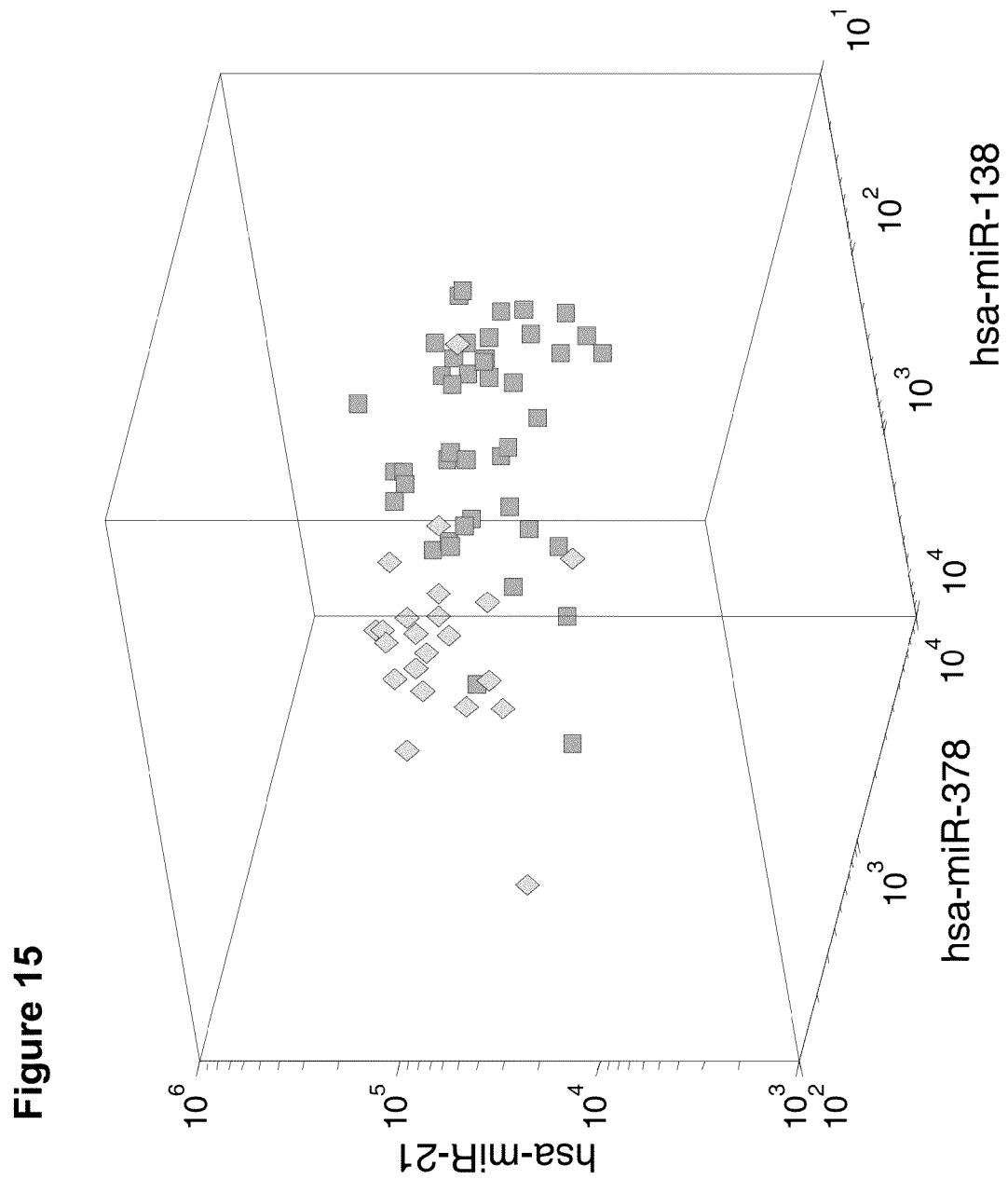

FIG. 15 demonstrates binary decisions at node #19 of the decision-tree. Tumors originating in lung adenocarcinoma (diamonds) are easily distinguished from tumors of ovarian carcinoma origin (squares) using the expression levels of hsa-miR-21 (SEQ ID NO: 34, y-axis), hsa-miR-378 (SEQ ID NO: 57, x-axis) and hsa-miR-138 (SEQ ID NO: 11, z-axis).

Figure 16:
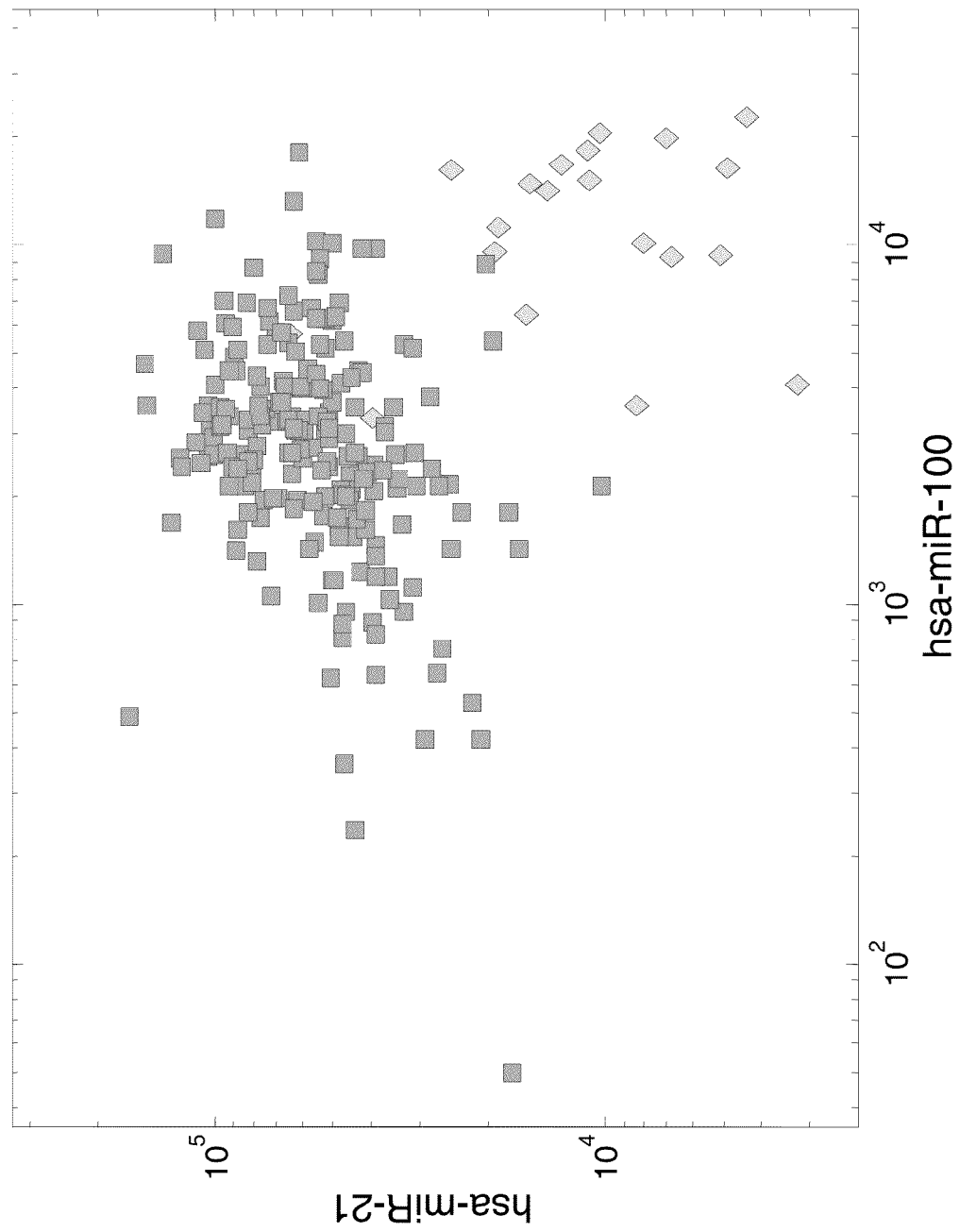

FIG. 16 demonstrates binary decisions at node #20 of the decision-tree. Tumors originating in thymic carcinoma (left branch at node #20, marked by diamonds) are easily distinguished from tumors of urothelial carcinoma, transitional cell carcinoma (TCC) carcinoma and squamous cell carcinoma (SCC) origins (right branch at node #20, marked by squares) using the expression levels of hsa-miR-21 (SEQ ID NO: 34, y-axis) and hsa-miR-100 (SEQ ID NO: 3, x-axis).

Figure 17:
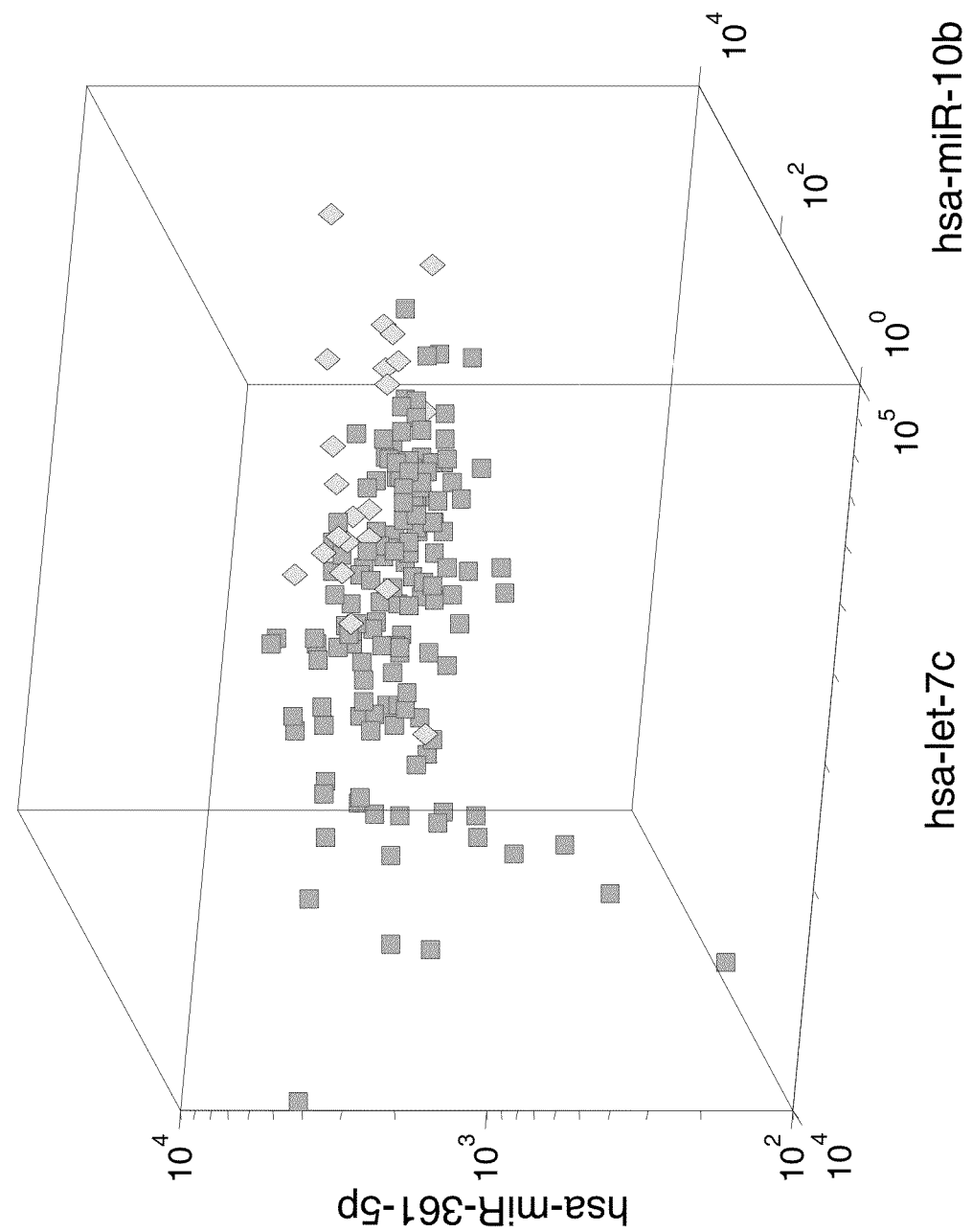

FIG. 17 demonstrates binary decisions at node #22 of the decision-tree. Tumors originating in SCC of the uterine cervix (diamonds) are easily distinguished from tumors of other SCC origin (squares) using the expression levels of hsa-miR-361-5p (SEQ ID NO: 54, y-axis), hsa-let-7c (SEQ ID NO: 1, x-axis) and hsa-miR-10b (SEQ ID NO: 5, z-axis).

Figure 18:
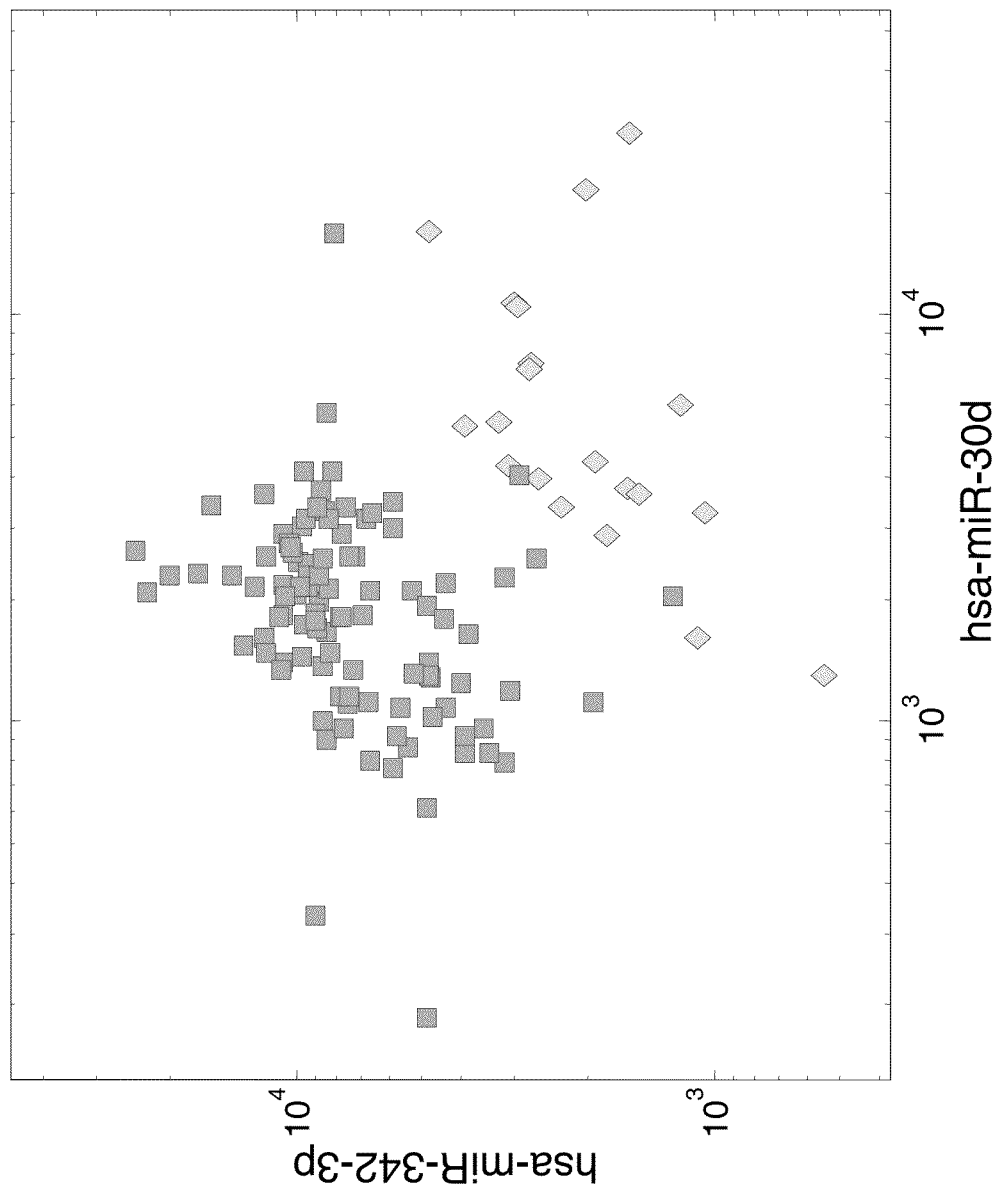

FIG. 18 demonstrates binary decisions at node #24 of the decision-tree. Tumors originating in melanoma (diamonds) are easily distinguished from tumors of lymphoma origin (squares) using the expression levels of hsa-miR-342-3p (SEQ ID NO: 50, y-axis) and hsa-miR-30d (SEQ ID NO: 47, x-axis).

Figure 19:
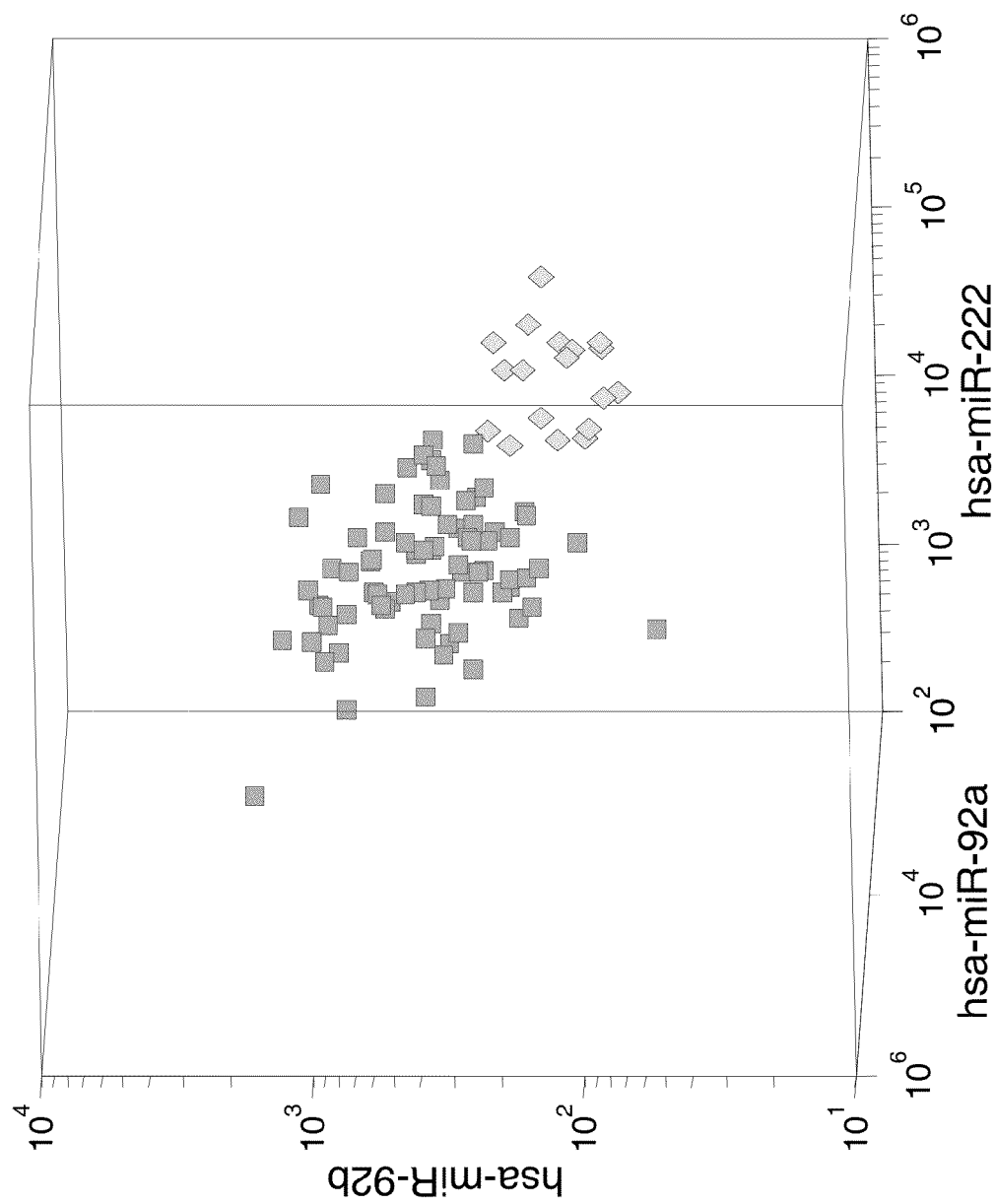

FIG. 19 demonstrates binary decisions at node #27 of the decision-tree. Tumors originating in thyroid carcinoma, medullary (diamonds) are easily distinguished from tumors of other neuroendocrine origin (squares) using the expression levels of hsa-miR-92b (SEQ ID NO: 68, y-axis), hsa-miR-222 (SEQ ID NO: 40, x-axis) and hsa-miR-92a (SEQ ID NO: 67, z-axis).

Figure 20:
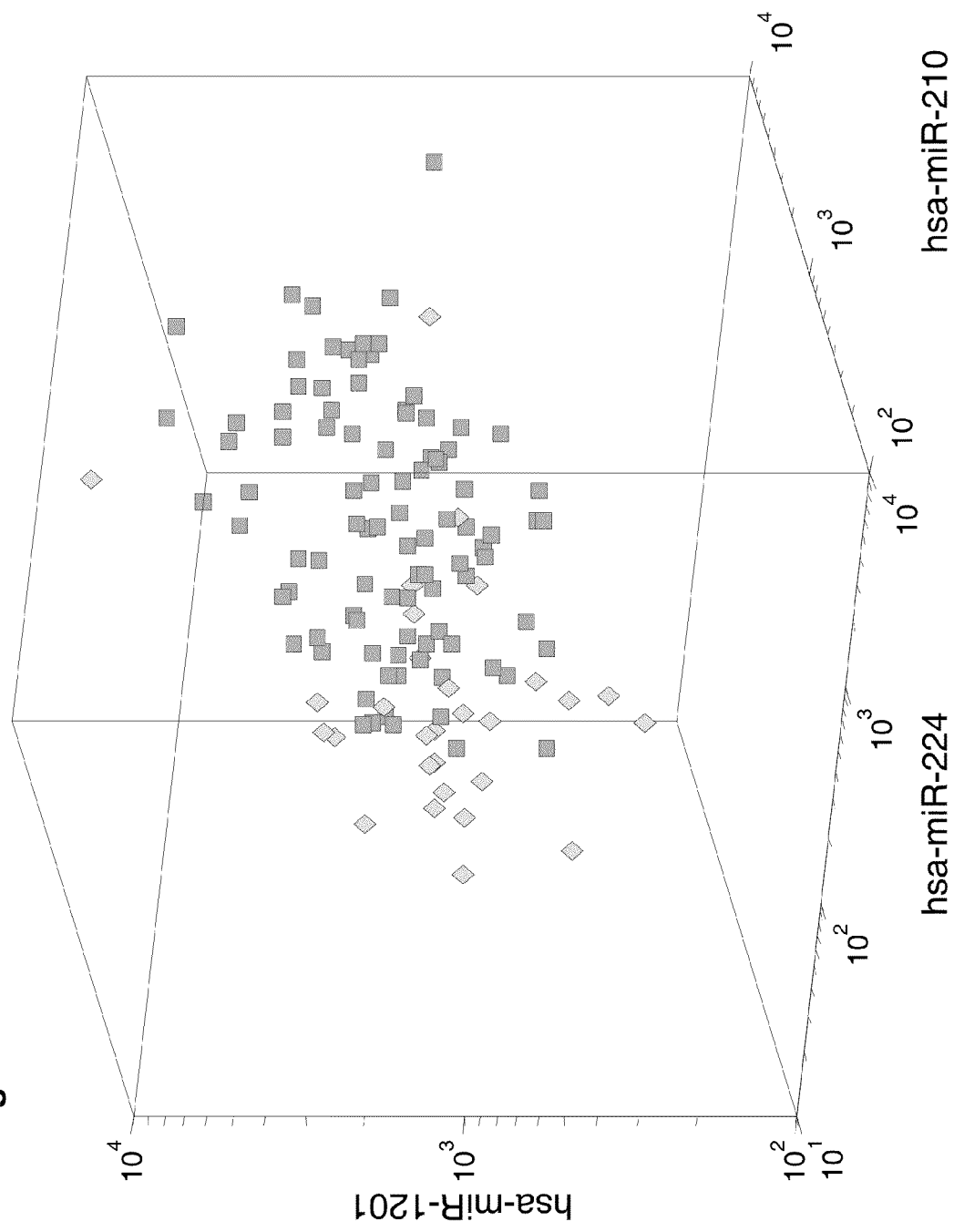

FIG. 20 demonstrates binary decisions at node #30 of the decision-tree. Tumors originating in gastric or esophageal adenocarcinoma (diamonds) are easily distinguished from tumors of other GI adenocarcinoma origin (squares) using the expression levels of hsa-miR-1201 (SEQ ID NO: 146, y-axis), hsa-miR-224 (SEQ ID NO: 42, x-axis) and hsa-miR-210 (SEQ ID NO: 36, z-axis).

Figure 21:
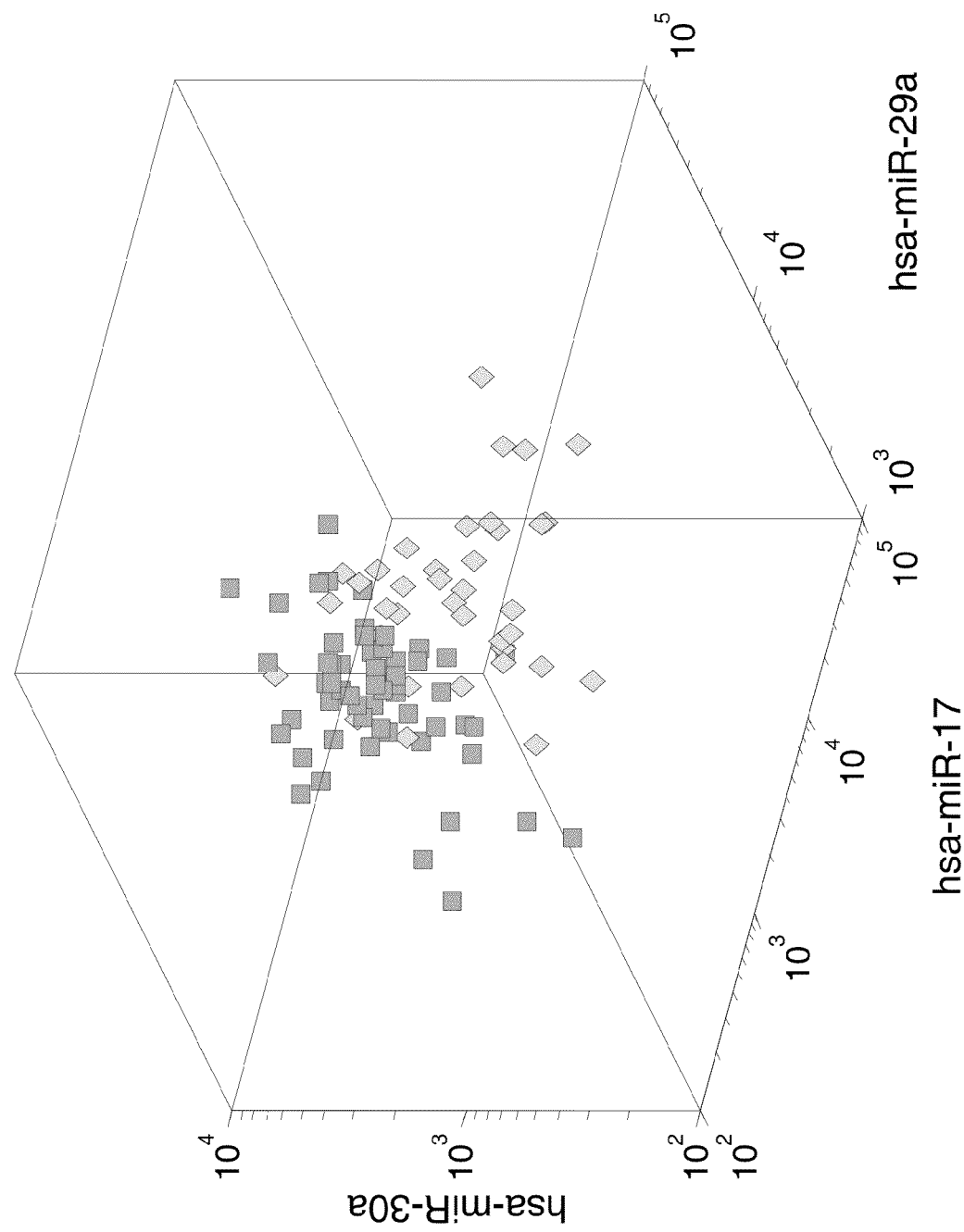

FIG. 21 demonstrates binary decisions at node #31 of the decision-tree. Tumors originating in colorectal adenocarcinoma (diamonds) are easily distinguished from tumors of adenocarcinoma of biliary tract or pancreas origin (squares) using the expression levels of hsa-miR-30a (SEQ ID NO: 46, y-axis), hsa-miR-17 (SEQ ID NO: 20, x-axis) and hsa-miR-29a (SEQ ID NO: 43, z-axis).

Figure 22:
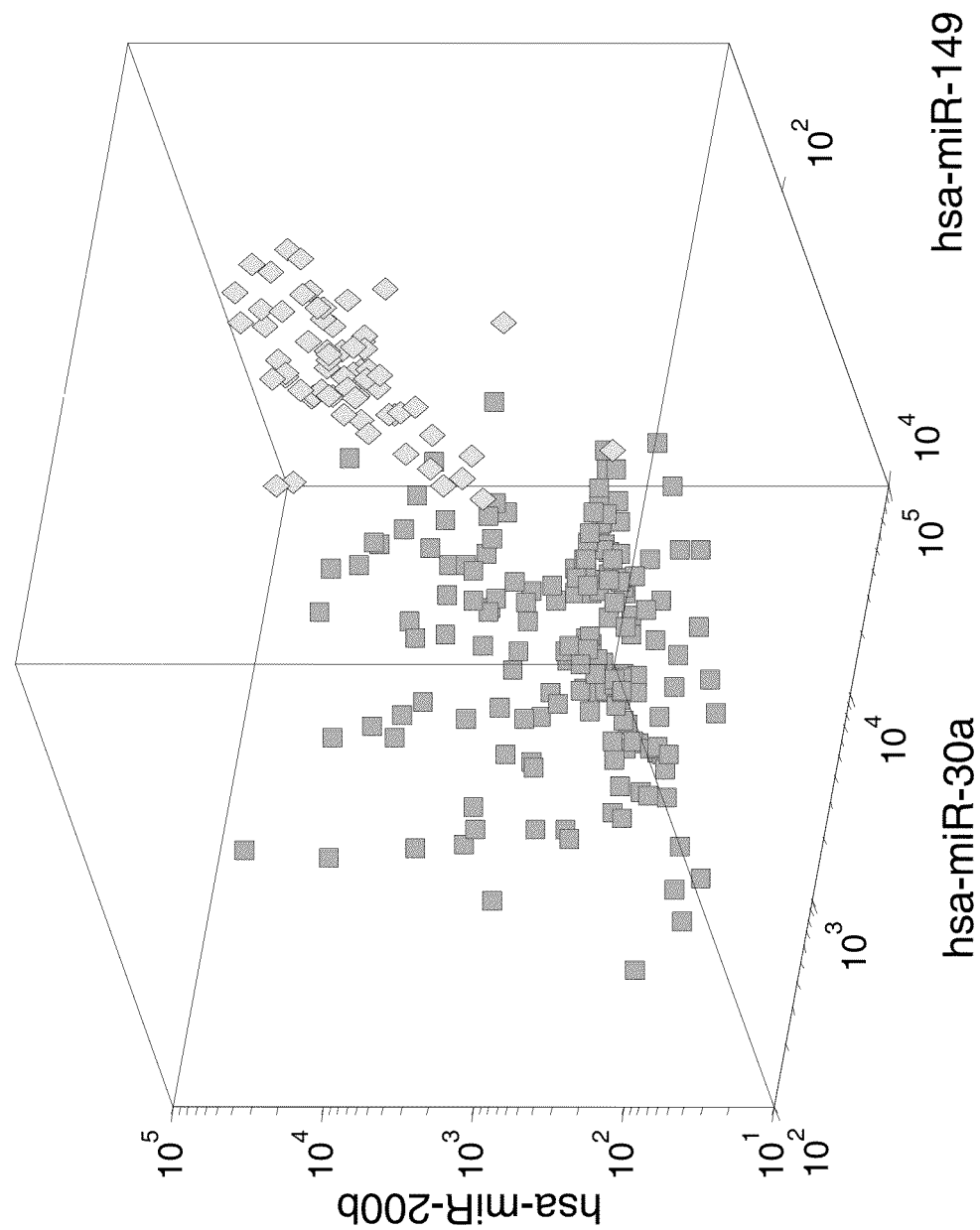

FIG. 22 demonstrates binary decisions at node #33 of the decision-tree. Tumors originating in kidney (diamonds) are easily distinguished from tumors of adrenal, mesothelioma and sarcoma origin (squares) using the expression levels of hsa-miR-200b (SEQ ID NO: 29, y-axis), hsa-miR-30a (SEQ ID NO: 46, x-axis) and hsa-miR-149 (SEQ ID NO: 19, z-axis).

Figure 23:
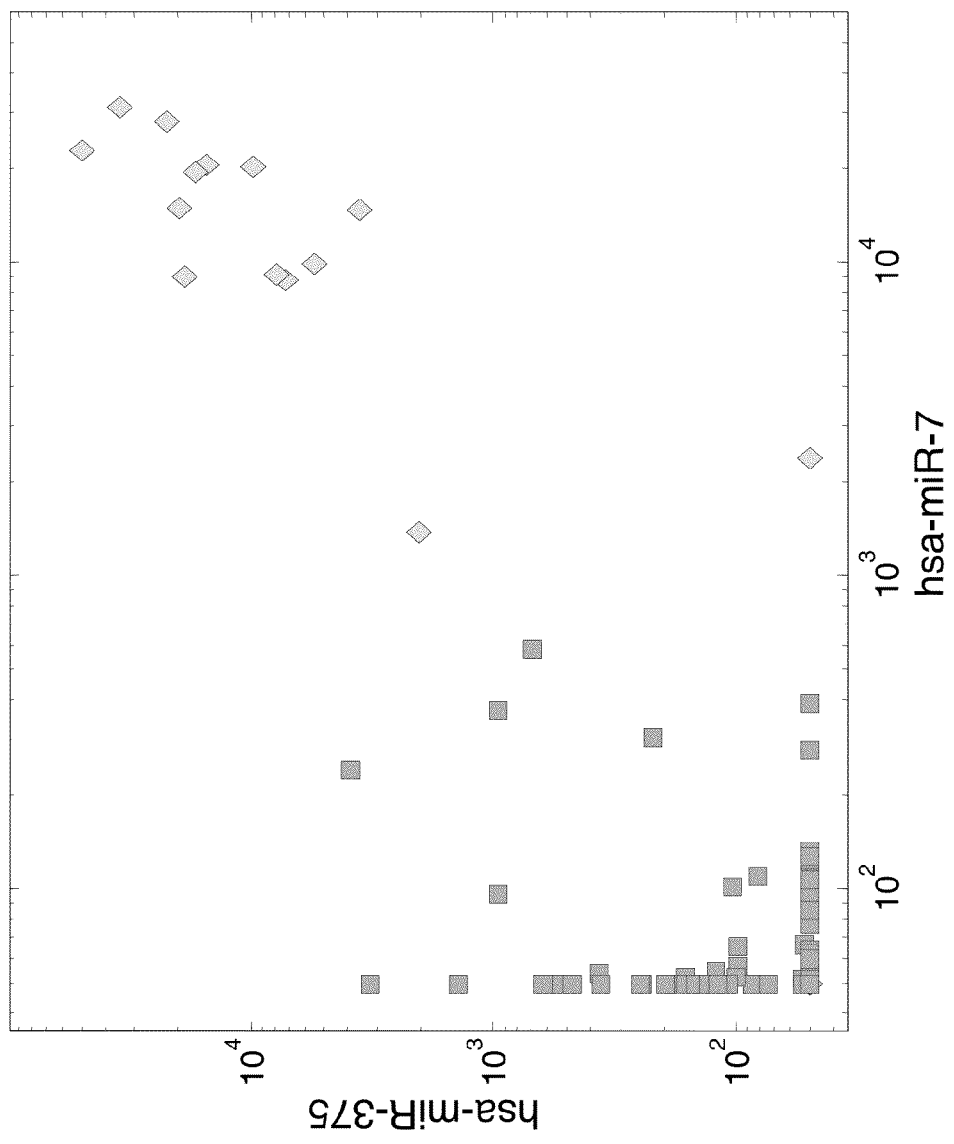

FIG. 23 demonstrates binary decisions at node #34 of the decision-tree. Tumors originating in pheochromocytoma (diamonds) are easily distinguished from tumors of adrenal, mesothelioma and sarcoma origin (squares) using the expression levels of hsa-miR-375 (SEQ ID NO: 56, y-axis) and hsa-miR-7 (SEQ ID NO: 65, x-axis).

Figure 24:
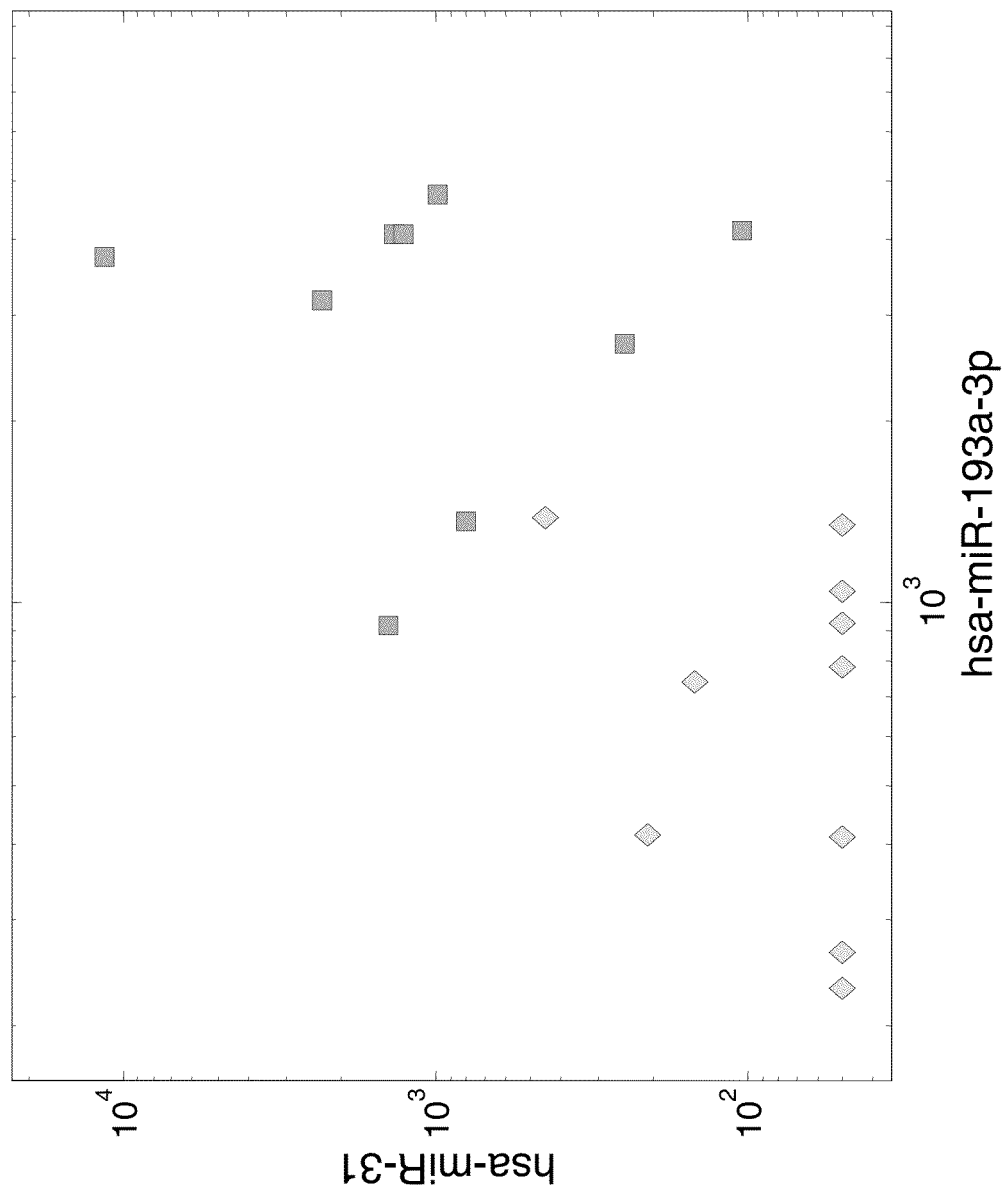

FIG. 24 demonstrates binary decisions at node #44 of the decision-tree. Tumors originating in Ewing sarcoma (diamonds) are easily distinguished from tumors of osteosarcoma origin (squares) using the expression levels of hsa-miR-31 (SEQ ID NO: 49, y-axis) and hsa-miR-193a-3p (SEQ ID NO: 25, x-axis).

Figure 25:
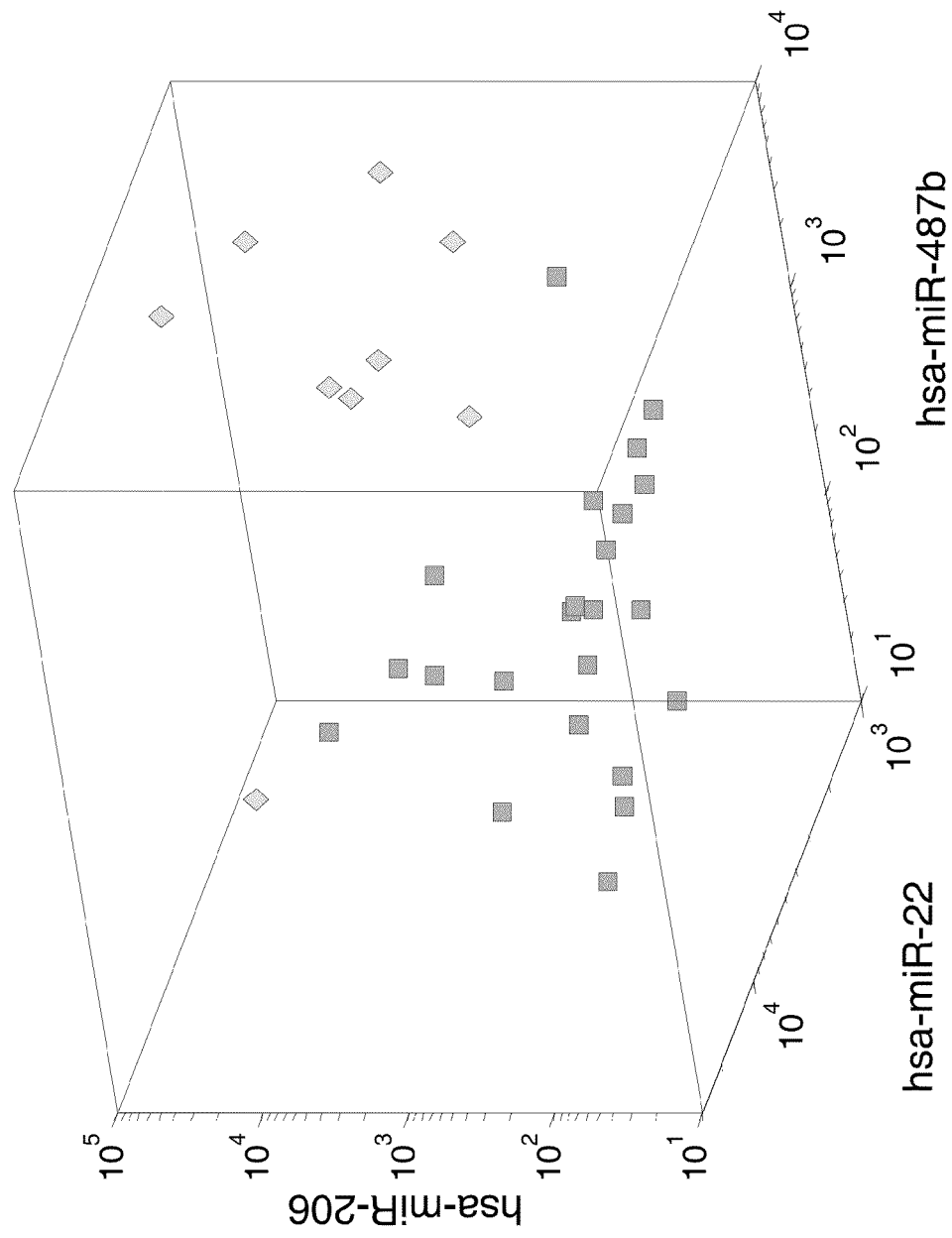

FIG. 25 demonstrates binary decisions at node #45 of the decision-tree. Tumors originating in Rhabdomyosarcoma (diamonds) are easily distinguished from tumors of malignant fibrous histiocytoma (MFH) or fibrosarcoma origin (squares) using the expression levels of hsa-miR-206 (SEQ ID NO: 33, y-axis), hsa-miR-22 (SEQ ID NO: 39, x-axis) and hsa-miR-487b (SEQ ID NO: 59, z-axis).

DETAILED DESCRIPTION OF THE INVENTION

Identification of the tissue-of-origin of a tumor is vital to its management. The present invention is based in part on the discovery that specific nucleic acid sequences can be used for the identification of the tissue-of-origin of a tumor. The present invention provides a sensitive, specific and accurate method which can be used to distinguish between different tumor origins. A new microRNA-based classifier was developed for determining tissue origin of tumors based on 65 microRNAs markers. The classifier uses a specific algorithm and allows a clear interpretation of the specific biomarkers.

According to the present invention each node in the classification tree may be used as an independent differential diagnosis tool, for example in the identification of different types of lung cancers. The possibility to distinguish between different tumor origins facilitates providing the patient with the best and most suitable treatment.

The present invention provides diagnostic assays and methods, both quantitative and qualitative for detecting, diagnosing, monitoring, staging and prognosticating cancers by comparing the levels of the specific microRNA molecules of the invention. Such levels are preferably measured in at least one of biopsies, tumor samples, fine-needle aspiration (FNA), cells, tissues and/or bodily fluids. The methods provided in the present invention are particularly useful for discriminating between different cancers.

All the methods of the present invention may optionally further include measuring levels of additional cancer markers. The cancer markers measured in addition to said microRNA molecules depend on the cancer being tested and are known to those of skill in the art.

Assay techniques can be used to determine levels of gene expression, such as genes encoding the nucleic acids of the present invention in a sample derived from a patient. Such assay methods, which are well known to those of skill in the art, include, but are not limited to, nucleic acid microarrays and biochip analysis, reverse transcriptase PCR (RT-PCR) assays, immunohistochemistry assays, in situ hybridization assays, competitive-binding assays, northern blot analyses and ELISA assays.

According to one embodiment, the assay is based on expression level of 65 microRNAs in RNA extracted from FFPE metastatic tumor tissue.

The expression levels are used to infer the sample origin using analysis techniques such as, but not limited to, decision-tree classifier, K nearest neighbors classifier, logistic regression classifier, linear regression classifier, nearest neighbor classifier, neural network classifier and nearest centroid classifier.

In use of the decision tree classifier the expression levels are used to make binary decisions (at each relevant node) following the pre-defined structure of the binary decision-tree (defined using a training set).

At each node, the expressions of one or several microRNAs are combined together using a function of the form $P=\exp(\beta 0+\beta 1*miR1+\beta 2*miR2+\beta 3*miR3 \ldots)/(1-\exp(\beta 0+\beta 1*miR1+\beta 2*miR2+\beta 3*miR3 \ldots))$, where the values of $\beta 0$, $\beta 1$, $\beta 2$ ... and the identities of the microRNAs have been pre-determined (using a training set). The resulting P is compared to a probability threshold level ($P_{TH}$, which was also determined using the training set), and the classification continues to the left or right branch according to whether P is larger or smaller than the $P_{TH}$ for that node. This continues until an end-point ("leaf") of the tree is reached. According to some embodiments, $P_{TH}=0.5$ for all nodes, and the value of 30 is adjusted accordingly. According to further embodiments, $\beta 0$, $\beta 1$, $\beta 2$, ... are adjusted so that the slope of the log of the odds ratio function is limited.

Training the tree algorithm means determining the tree structure—which nodes there are and what is on each side, and, for each node: which miRs are used, the values of $\beta 0$, $\beta 1$, $\beta 2$ ... and the $P_{TH}$. These are determined by a combination of machine learning, optimization algorithm, and trial and error by experts in machine learning and diagnostic algorithms.

An arbitrary threshold of the expression level of one or more nucleic acid sequences can be set for assigning a sample to one of two groups. Alternatively, in a preferred embodiment, expression levels of one or more nucleic acid sequences of the invention are combined by a method such as logistic regression to define a metric which is then compared to previously measured samples or to a threshold. The threshold is treated as a parameter that can be used to quantify the confidence with which samples are assigned to each class. The threshold can be scaled to favor sensitivity or specificity, depending on the clinical scenario. The correlation value to the reference data generates a continuous score that can be scaled and provides diagnostic information on the likelihood that a sample belongs to a certain class of cancer origin or type. In multivariate analysis the microRNA signature provides a high level of prognostic information.

In another preferred embodiment, expression level of nucleic acids is used to classify a test sample by comparison to a training set of samples. In this embodiment, the test sample is compared in turn to each one of the training set samples. The comparison is performed by comparing the expression levels of one or multiple nucleic acids between the test sample and the specific training sample. Each such pairwise comparison generates a combined metric for the multiple nucleic acids, which can be calculated by various numeric methods such as correlation, cosine, Euclidian distance, mean square distance, or other methods known to those skilled in the art. The training samples are then ranked according to this metric, and the samples with the highest values of the metric (or lowest values, according to the type of metric) are identified, indicating those samples that are most similar to the test sample. By choosing a parameter K, this generates a list that includes the K training samples that are most similar to the test sample. Various methods can then be applied to identify from this list the predicted class of the test sample. In a favored embodiment, the test sample is predicted to belong to the class that has the highest number of representative in the list of K most-similar training samples (this method is known as the K Nearest Neighbors method). Other embodiments may provide a list of predictions including all or part of the classes represented in the list, those classes that are represented more than a given minimum number of times, or other voting schemes whereby classes are grouped together.

1. DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

About

As used herein, the term "about" refers to +/−10%.

Attached

"Attached" or "immobilized", as used herein, to refer to a probe and a solid support means that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Baseline

"Baseline", as used herein, means the initial cycles of PCR, in which there is little change in fluorescence signal.

Biological Sample

"Biological sample", as used herein, means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, blood fraction, plasma, serum, sputum, stool, tears, mucus, hair, skin, urine, effusions, ascitic fluid, amniotic fluid, saliva, cerebrospinal fluid, cervical secretions, vaginal secretions, endometrial secretions, gastrointestinal secretions, bronchial secretions, cell line, tissue sample, or secretions from the breast. A biological sample may be provided by fine-needle aspiration (FNA), pleural effusion or bronchial brushing. A biological sample may be provided by removing a sample of cells from a subject but can also be accomplished by using previously isolated cells (e.g., isolated by another person, at another time, and/or for another purpose), or by performing the methods described herein in vivo. Archival tissues, such as those having treatment or outcome history, may also be used. Biological samples also include explants and primary and/or transformed cell cultures derived from animal or human tissues.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include, but are not limited, to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc.) and based on a statistical model and/or a training set of previously labeled items. A "classification tree" places categorical variables into classes.

Complement

"Complement" or "complementary" is used herein to refer to a nucleic acid may mean Watson-Crick (e.g., A-T/U and C-G) or Hoogsteen base pairing between nucleotides or nucleotide analogs of nucleic acid molecules. A full complement or fully complementary means 100% complementary base pairing between nucleotides or nucleotide analogs of nucleic acid molecules. In some embodiments, the complementary sequence has a reverse orientation (5'-3').

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or low expression levels of the microRNA.

Data Processing Routine

As used herein, a "data processing routine" refers to a process that can be embodied in software that determines the biological significance of acquired data (i.e., the ultimate results of an assay or analysis). For example, the data processing routine can determine a tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis. These numerical values associated with analysis may be values such as peak height and area under the curve.

Data Structure

As used herein, the term "data structure" refers to a combination of two or more data sets, an application of one or more mathematical manipulation to one or more data sets to obtain one or more new data sets, or a manipulation of two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means determining the level of a component, either quantitatively or qualitatively.

Differential Expression

"Differential expression" means qualitative or quantitative differences in the temporal and/or spatial gene expression patterns within and among cells and tissue. Thus, a differentially expressed gene may qualitatively have its expression altered, including an activation or inactivation, in, e.g., normal versus diseased tissue. Genes may be turned on or turned off in a particular state, relative to another state, thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated: up-regulated, resulting in an increased amount of transcript, or down-regulated, resulting in a decreased amount of transcript. The degree to which expression differs needs only to be large enough to quantify via standard characterization techniques such as expression arrays, quantitative reverse transcriptase PCR, northern blot analysis, real-time PCR, in situ hybridization and RNase protection.

Epithelial Tumors

"Epithelial tumors" is meant to include all types of tumors from epithelial origin. Examples of epithelial tumors include, but are not limited to cholangioca or adenoca of extrahepatic biliary tract, urothelial carcinoma, adenocarcinoma of the breast, lung large cell or adenocarcinoma, lung small cell carcinoma, carcinoid, lung, ovarian carcinoma, pancreatic adenocarcinoma, prostatic adenocarcinoma, gastric or esophageal adenocarcinoma, thymoma/thymic carcinoma, follicular thyroid carcinoma, papillary thyroid carcinoma, medullary thyroid carcinoma, anus or skin squamous cell carcinoma, lung, head & neck, or esophagus squamous cell carcinoma, uterine cervix squamous cell carcinoma, gastrointestinal tract carcinoid, pancreatic islet cell tumor and colorectal adenocarcinoma.

Non Epithelial Tumors

"Non epithelial tumors" is meant to include all types of tumors from non epithelial origin. Examples of non epithelial tumors include, but are not limited to adrenocortical carcinoma, chromophobe renal cell carcinoma, clear cell renal cell carcinoma, papillary renal cell carcinoma, pleural mesothelioma, astrocytic tumor, oligodendroglioma, pheochromocytoma, B-cell lymphoma, T-cell lymphoma, melanoma, gastrointestinal stromal tumor (GIST), Ewing Sarcoma, chondrosarcoma, malignant fibrous histiocytoma (MFH) or fibrosarcoma, osteosarcoma, rhabdomyosarcoma, synovial sarcoma and liposarcoma.

Expression Profile

The term "expression profile" is used broadly to include a genomic expression profile, e.g., an expression profile of microRNAs. Profiles may be generated by any convenient means for determining a level of a nucleic acid sequence, e.g., quantitative hybridization of microRNA, labeled microRNA, amplified microRNA, cDNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of the nucleic acid sequences, including all of the listed nucleic acid sequences. According to some embodiments, the term "expression profile" means measuring the relative abundance of the nucleic acid sequences in the measured samples.

Expression Ratio

"Expression ratio", as used herein, refers to relative expression levels of two or more nucleic acids as determined by detecting the relative expression levels of the corresponding nucleic acids in a biological sample.

FDR (False Discovery Rate)

When performing multiple statistical tests, for example in comparing between the signal of two groups in multiple data features, there is an increasingly high probability of obtaining false positive results, by random differences between the groups that can reach levels that would otherwise be considered statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full-length part of a nucleic acid. Thus, a fragment is itself also a nucleic acid.

Gastrointestinal Tumors

"gastrointestinal tumors" is meant to include all types of tumors from gastrointestinal origin. Examples of gastrointestinal tumors include, but are not limited to cholangioca. or adenoca of extrahepatic biliary tract, pancreatic adenocarcinoma, gastric or esophageal adenocarcinoma, and colorectal adenocarcinoma.

Gene

"Gene", as used herein, may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro, comprising all or a part of the coding region and/or 5'- or 3'-untranslated sequences linked thereto.

Germ Cell Tumors

"Germ cell tumors" as used herein, include, but are not limited, to non-seminomatous testicular germ cell tumors, seminomatous testicular germ cell tumors and ovarian primitive germ cell tumors.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2nd ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

High Expression miR-205 Tumors

"High expression miR-205 tumors" as used herein include, but are not limited, to urothelial carcinoma (TCC), thymoma/thymic carcinoma, anus or skin squamous cell carcinoma, lung, head&neck, or esophagus squamous cell carcinoma and uterine cervix squamous cell carcinoma.

Low Expression 205 Tumors

"Low expression miR-205 tumors" as used herein include, but are not limited, to lung, large cell or adenocarcinoma, follicular thyroid carcinoma and papillary thyroid carcinoma.

Host Cell

"Host cell", as used herein, may be a naturally occurring cell or a transformed cell that may contain a vector and may support replication of the vector. Host cells may be cultured cells, explants, cells in vivo, and the like. Host cells may be prokaryotic cells, such as E. coli, or eukaryotic cells, such as yeast, insect, amphibian, or mammalian cells, such as CHO and HeLa cells.

Identity

"Identical" or "identity", as used herein, in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST or BLAST 2.0.

In Situ Detection

"In situ detection", as used herein, means the detection of expression or expression levels in the original site, hereby meaning in a tissue sample such as biopsy.

K-Nearest Neighbor

The phrase "K-nearest neighbor" refers to a classification method that classifies a point by calculating the distances between it and points in the training data set. It then assigns the point to the class that is most common among its K-nearest neighbors (where K is an integer).

Leaf

A leaf, as used herein, is the terminal group in a classification or decision tree.

Label

"Label", as used herein, means a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression can allow one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e., the ratio of the probability of belonging to the first group (P) over the probability of belonging to the second group (1−P), as a linear combination of the different expression levels (in log-space). The logistic regression output can be used as a classifier by prescribing that a case or sample will be classified into the first type if P is greater than 0.5 or 50%. Alternatively, the calculated probability P can be used as a variable in other contexts, such as a 1D or 2D threshold classifier.

Metastasis

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

Neuroendocrine Tumors

"Neuroendocrine tumors" is meant to include all types of tumors from neuroendocrine origin. Examples of neuroendocrine tumors include, but are not limited to lung small cell carcinoma, lung carcinoid, gastrointestinal tract carcinoid, pancreatic islet cell tumor and medullary thyroid carcinoma.

Node

A "node" is a decision point in a classification (i.e., decision) tree. Also, a point in a neural net that combines input from other nodes and produces an output through application of an activation function.

Nucleic Acid

"Nucleic acid" or "oligonucleotide" or "polynucleotide", as used herein, mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones, non-ionic backbones and non-ribose backbones, including those described in U.S. Pat. Nos. 5,235,033 and 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridine or cytidine modified at the 5-position, e.g., 5-(2-amino) propyl uridine, 5-bromo uridine; adenosine and guanosine modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 2005; 438:685-689, Soutschek et al., Nature 2004; 432:173-178, and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe", as used herein, means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single-stranded nucleic acids described herein. However, if the number of mutations is so great that no hybridization can occur under even the least stringent of hybridization conditions, the sequence is not a complementary target sequence. A probe may be single-stranded or partially single- and partially double-stranded. The strandedness of the probe is dictated by the structure, composition, and properties of the target sequence. Probes may be directly labeled or indirectly labeled such as with biotin to which a streptavidin complex may later bind.

Reference Value

As used herein, the term "reference value" or "reference expression profile" refers to a criterion expression value to which measured values are compared in order to identify a specific cancer. The reference value may be based on the abundance of the nucleic acids, or may be based on a combined metric score thereof.

In preferred embodiments the reference value is determined from statistical analysis of studies that compare microRNA expression with known clinical outcomes.

Sarcoma

Sarcoma is meant to include all types of tumors from sarcoma origin. Examples of sarcoma tumors include, but are not limited to gastrointestinal stromal tumor (GIST), Ewing sarcoma, chondrosarcoma, malignant fibrous histiocytoma (MFH) or fibrosarcoma, osteosarcoma, rhabdomyosarcoma, synovial sarcoma and liposarcoma.

Sensitivity

"Sensitivity", as used herein, may mean a statistical measure of how well a binary classification test correctly identifies a condition, for example, how frequently it correctly classifies a cancer into the correct class out of two possible classes. The sensitivity for class A is the proportion of cases that are determined to belong to class "A" by the test out of the cases that are in class "A", as determined by some absolute or gold standard.

Specificity

"Specificity", as used herein, may mean a statistical measure of how well a binary classification test correctly identifies a condition, for example, how frequently it correctly classifies a cancer into the correct class out of two possible classes. The specificity for class A is the proportion of cases that are determined to belong to class "not A" by the test out of the cases that are in class "not A", as determined by some absolute or gold standard.

Stringent Hybridization Conditions

"Stringent hybridization conditions", as used herein, mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$, may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary", as used herein, means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical", as used herein, means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target Nucleic Acid

"Target nucleic acid", as used herein, means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

1D/2D Threshold Classifier

"1D/2D threshold classifier", as used herein, may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Tissue Sample

As used herein, a tissue sample is tissue obtained from a tissue biopsy using methods well known to those of ordinary skill in the related medical arts. The phrase "suspected of being cancerous", as used herein, means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Tumor

"Tumor", as used herein, refers to all neoplastic cell growth and proliferation, whether malignant or benign, and all pre-cancerous and cancerous cells and tissues.

Variant

"Variant", as used herein, referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild-type" sequence refers to a coding, a non-coding or an interface sequence which is an allelic form of sequence that performs the natural or normal function for that sequence. Wild-type sequences include multiple allelic forms of a cognate sequence, for example, multiple alleles of a wild type sequence may encode silent or conservative changes to the protein sequence that a coding sequence encodes.

The present invention employs miRNAs for the identification, classification and diagnosis of specific cancers and the identification of their tissues of origin.

1. microRNA Processing

A gene coding for microRNA (miRNA) may be transcribed leading to production of a miRNA primary transcript known as the pri-miRNA. The pri-miRNA may comprise a hairpin with a stem and loop structure. The stem of the hairpin may comprise mismatched bases. The pri-miRNA may comprise several hairpins in a polycistronic structure.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also cut off the terminal loop two helical turns away from the base of the stem loop, leaving an additional 5' phosphate and a ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs, but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al. Science 2004; 304:594-596). Otherwise, such interactions are known only in plants (Bartel & Bartel 2003; 132:709-717).

A number of studies have looked at the base-pairing requirement between miRNA and its mRNA target for achieving efficient inhibition of translation (reviewed by Bartel 2004; 116:281-297). In mammalian cells, the first 8 nucleotides of the miRNA may be important (Doench & Sharp GenesDev 2004; 18:504-511). However, other parts of the microRNA may also participate in mRNA binding. Moreover, sufficient base pairing at the 3' can compensate for insufficient pairing at the 5' (Brennecke et al., PloS Biol 2005; 3:e85). Computation studies, analyzing miRNA binding on whole genomes have suggested a specific role for bases 2-7 at the 5' of the miRNA in target binding but the role of the first nucleotide, found usually to be "A" was also recognized (Lewis et al. Cell 2005; 120:15-20). Similarly, nucleotides 1-7 or 2-8 were used to identify and validate targets by Krek et al. (Nat Genet. 2005; 37:495-500).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

2. Nucleic Acids

Nucleic acids are provided herein. The nucleic acids comprise the sequences of SEQ ID NOS: 1-390 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single-strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559, which is incorporated herein by reference.

TABLE 1

SEQ ID NOS of sequences used in the invention
SEQ ID NOs 1-34 are in accordance with Sanger database version 10;
SEQ ID NOs 35-390 are in accordance with Sanger database version 11;

| hairpin SEQ ID NO | miR SEQ ID NO | miR name |
|---|---|---|
| 70 | 1 | hsa-let-7c |
| 71 | 2, 156 | hsa-let-7e |
| 72 | 3 | hsa-miR-100 |
| 73 | 4 | hsa-miR-10a |
| 74 | 5 | hsa-miR-10b |
| 75 | 6 | hsa-miR-122 |
| 76 | 7 | hsa-miR-125a-5p |
| 77, 78 | 8 | hsa-miR-125b |
| 79 | 9 | hsa-miR-126 |
| 80 | 10 | hsa-miR-130a |
| 81, 82 | 11 | hsa-miR-138 |
| 83 | 12 | hsa-miR-140-3p |
| 84 | 13 | hsa-miR-141 |
| 85 | 14 | hsa-miR-143 |
| 86 | 15 | hsa-miR-145 |
| 87 | 16 | hsa-miR-146a |
| 88 | 17 | hsa-miR-146b-5p |
| 89 | 18 | hsa-miR-148a |
| 90 | 19 | hsa-miR-149 |
| 91 | 20 | hsa-miR-17 |
| 92, 93 | 21 | hsa-miR-181a |
| 92, 93 | 22 | hsa-miR-181a* |
| 94 | 23 | hsa-miR-185 |
| 95 | 24 | hsa-miR-191 |
| 96 | 25 | hsa-miR-193a-3p |
| 96 | 26 | hsa-miR-193a-5p |
| 97, 98 | 27 | hsa-miR-194 |
| 99 | 28 | hsa-miR-200a |
| 100 | 29 | hsa-miR-200b |
| 101 | 30 | hsa-miR-200c |
| 102 | 31 | hsa-miR-202 |
| 103 | 32 | hsa-miR-205 |
| 104 | 33 | hsa-miR-206 |
| 105 | 34 | hsa-miR-21 |
| 105 | 35 | hsa-miR-21* |
| 106 | 36 | hsa-miR-210 |
| 107 | 37 | hsa-miR-214 |
| 107 | 38 | hsa-miR-214* |
| 108 | 39 | hsa-miR-22 |
| 109 | 40 | hsa-miR-222 |
| 110 | 41 | hsa-miR-223 |
| 111 | 42 | hsa-miR-224 |
| 112 | 43 | hsa-miR-29a |
| 113 | 44, 191 | hsa-miR-29c |
| 113 | 45 | hsa-miR-29c* |
| 114 | 46 | hsa-miR-30a |
| 115 | 47 | hsa-miR-30d |
| 116 | 48 | hsa-miR-30e |
| 117 | 49 | hsa-miR-31 |
| 118 | 50 | hsa-miR-342-3p |
| 119 | 51 | hsa-miR-345 |
| 120 | 52 | hsa-miR-34a |
| 121 | 53 | hsa-miR-34c-5p |
| 122 | 54 | hsa-miR-361-5p |
| 123 | 55 | hsa-miR-372 |

TABLE 1-continued

SEQ ID NOS of sequences used in the invention
SEQ ID NOs 1-34 are in accordance with Sanger database version 10;
SEQ ID NOs 35-390 are in accordance with Sanger database version 11;

| hairpin SEQ ID NO | miR SEQ ID NO | miR name |
|---|---|---|
| 124 | 56 | hsa-miR-375 |
| 125 | 57, 202 | hsa-miR-378 |
| 126 | 58 | hsa-miR-455-5p |
| 127 | 59 | hsa-miR-487b |
| 128 | 60, 208 | hsa-miR-497 |
| 129, 130, 131 | 61 | hsa-miR-509-3p |
| 132, 133 | 62, 211 | hsa-miR-516a-5p |
| 134 | 63 | hsa-miR-574-5p |
| 135 | 64 | hsa-miR-652 |
| 136, 137, 138 | 65 | hsa-miR-7 |
| 139, 140, 141 | 66 | hsa-miR-9* |
| 142, 143 | 67 | hsa-miR-92a |
| 144 | 68 | hsa-miR-92b |
| 145 | 69 | hsa-miR-934 |
| 149 | 146 | hsa-miR-1201 |
| 150 | 147 | hsa-miR-221 |
| 151 | 148 | hsa-miR-93 |
|  | 152 | hsa-miR-182 |
|  | 153 | hsa-let-7d |
|  | 154 | hsa-miR-181b |
|  | 155 | hsa-miR-127-3p |
|  | 157 | hsa-let-7i |
|  | 158 | hsa-miR-106a |
|  | 159 | hsa-miR-124 |
|  | 160 | hsa-miR-1248 |
|  | 161 | hsa-miR-128 |
|  | 162 | hsa-miR-129-3p |
|  | 163 | hsa-miR-1323 |
|  | 164 | hsa-miR-142-5p |
|  | 165 | hsa-miR-143* |
|  | 166 | hsa-miR-146b-3p |
|  | 167 | hsa-miR-149* |
|  | 168 | hsa-miR-150 |
|  | 169 | hsa-miR-152 |
|  | 170 | hsa-miR-155 |
|  | 171 | hsa-miR-15a |
|  | 172 | hsa-miR-15b |
|  | 173 | hsa-miR-181c |
|  | 174 | hsa-miR-181d |
|  | 175 | hsa-miR-183 |
|  | 176 | hsa-miR-18a |
|  | 177 | hsa-miR-192 |
|  | 178 | hsa-miR-193b |
|  | 179 | hsa-miR-195 |
|  | 180 | hsa-miR-1973 |
|  | 181 | hsa-miR-199a-3p |
|  | 182 | hsa-miR-199a-5p |
|  | 183 | hsa-miR-199b-5p |
|  | 184 | hsa-miR-203 |
|  | 185 | hsa-miR-205* |
|  | 186 | hsa-miR-20a |
|  | 187 | hsa-miR-219-2-3p |
|  | 188 | hsa-miR-25 |
|  | 189 | hsa-miR-27b |
|  | 190 | hsa-miR-29b |
|  | 192 | hsa-miR-302a |
|  | 193 | hsa-miR-302a* |
|  | 194 | hsa-miR-302d |
|  | 195 | hsa-miR-30a* |
|  | 196 | hsa-miR-30c |
|  | 197 | hsa-miR-331-3p |
|  | 198 | hsa-miR-342-5p |
|  | 199 | hsa-miR-363 |
|  | 200 | hsa-miR-371-3p |
|  | 201 | hsa-miR-371-5p |
|  | 203 | hsa-miR-422a |
|  | 204 | hsa-miR-425 |
|  | 205 | hsa-miR-451 |
|  | 206 | hsa-miR-455-3p |
|  | 207 | hsa-miR-486-5p |
|  | 209 | hsa-miR-498 |
|  | 210 | hsa-miR-512-5p |
|  | 212 | hsa-miR-516b |
|  | 213 | hsa-miR-517a |
|  | 214 | hsa-miR-517c |
|  | 215 | hsa-miR-518a-3p |
|  | 216 | hsa-miR-518e |
|  | 217 | hsa-miR-518f* |
|  | 218 | hsa-miR-519a |
|  | 219 | hsa-miR-519d |
|  | 220 | hsa-miR-520a-5p |
|  | 221 | hsa-miR-520c-3p |
|  | 222 | hsa-miR-520d-5p |
|  | 223 | hsa-miR-524-5p |
|  | 224 | hsa-miR-527 |
|  | 225 | hsa-miR-551b |
|  | 226 | hsa-miR-625 |
|  | 227 | hsa-miR-767-5p |
|  | 228 | hsa-miR-886-3p |
|  | 229 | hsa-miR-9 |
|  | 230 | hsa-miR-886-5p |
|  | 231 | hsa-miR-99a |
|  | 232 | hsa-miR-99a* |
|  | 233 | hsa-miR-373 |
|  | 234 | hsa-miR-1977 |
|  | 235 | hsa-miR-1978 |
|  | 236 | MID-00689 |
|  | 237, 369 | MID-15684 |
|  | 238 | MID-15867 |
|  | 239 | MID-15907 |
|  | 240 | MID-15965 |
|  | 241 | MID-16318 |
|  | 242 | MID-16489 |
|  | 243 | MID-16869 |
|  | 244 | MID-17144 |
|  | 245 | MID-18336 |
|  | 246 | MID-18422 |
|  | 247 | MID-19340 |
|  | 248 | MID-19533 |
|  | 249 | MID-20524 |
|  | 250 | MID-20703 |
|  | 251 | MID-21271 |
|  | 252 | MID-22664 |
|  | 253 | MID-23256 |
|  | 254 | MID-23291 |
|  | 255 | MID-23794 |
|  | 390 | MID-00405 |
|  | 256 | hsa-let-7a |
|  | 257 | hsa-let-7b |
|  | 258 | hsa-let-7f |
|  | 259 | hsa-let-7g |
|  | 260 | hsa-miR-106b |
|  | 261 | hsa-miR-1180 |
|  | 262 | hsa-miR-127-5p |
|  | 263 | hsa-miR-129* |
|  | 264 | hsa-miR-129-5p |
|  | 265 | hsa-miR-130b |
|  | 266 | hsa-miR-132 |
|  | 267 | hsa-miR-133a |
|  | 268 | hsa-miR-133b |
|  | 269 | hsa-miR-134 |
|  | 270 | hsa-miR-139-5p |
|  | 271 | hsa-miR-140-5p |
|  | 272 | hsa-miR-145* |
|  | 273 | hsa-miR-148b |
|  | 274 | hsa-miR-151-3p |
|  | 275 | hsa-miR-154 |
|  | 276 | hsa-miR-154* |
|  | 277 | hsa-miR-17* |
|  | 278 | hsa-miR-181a-2* |
|  | 279 | hsa-miR-1826 |
|  | 280 | hsa-miR-187 |
|  | 281 | hsa-miR-188-5p |
|  | 282 | hsa-miR-196a |
|  | 283 | hsa-miR-1979 |
|  | 284 | hsa-miR-19b |
|  | 285 | hsa-miR-20b |
|  | 286 | hsa-miR-216a |

TABLE 1-continued

SEQ ID NOS of sequences used in the invention
SEQ ID NOs 1-34 are in accordance with Sanger database version 10;
SEQ ID NOs 35-390 are in accordance with Sanger database version 11;

| hairpin SEQ ID NO | miR SEQ ID NO | miR name |
|---|---|---|
| | 287 | hsa-miR-216b |
| | 288 | hsa-miR-217 |
| | 289 | hsa-miR-22* |
| | 290 | hsa-miR-221* |
| | 291 | hsa-miR-222* |
| | 292 | hsa-miR-23a |
| | 293 | hsa-miR-23b |
| | 294 | hsa-miR-24 |
| | 295 | hsa-miR-26a |
| | 296 | hsa-miR-26b |
| | 297 | hsa-miR-27a |
| | 298 | hsa-miR-28-3p |
| | 299 | hsa-miR-296-5p |
| | 300 | hsa-miR-299-3p |
| | 301 | hsa-miR-29b-2* |
| | 302 | hsa-miR-301a |
| | 303 | hsa-miR-30b |
| | 304 | hsa-miR-30e* |
| | 305 | hsa-miR-31* |
| | 306 | hsa-miR-323-3p |
| | 307 | hsa-miR-324-5p |
| | 308 | hsa-miR-328 |
| | 309 | hsa-miR-329 |
| | 310 | hsa-miR-330-3p |
| | 311 | hsa-miR-335 |
| | 312 | hsa-miR-337-5p |
| | 313 | hsa-miR-338-3p |
| | 314 | hsa-miR-361-3p |
| | 315 | hsa-miR-362-3p |
| | 316 | hsa-miR-362-5p |
| | 317 | hsa-miR-369-5p |
| | 318 | hsa-miR-370 |
| | 319 | hsa-miR-376a |
| | 320 | hsa-miR-376c |
| | 321 | hsa-miR-377* |
| | 322 | hsa-miR-379 |
| | 323 | hsa-miR-381 |
| | 324 | hsa-miR-382 |
| | 325 | hsa-miR-409-3p |
| | 326 | hsa-miR-409-5p |
| | 327 | hsa-miR-410 |
| | 328 | hsa-miR-411 |
| | 329 | hsa-miR-425* |
| | 330 | hsa-miR-431* |
| | 331 | hsa-miR-432 |
| | 332 | hsa-miR-433 |
| | 333 | hsa-miR-483-3p |
| | 334 | hsa-miR-483-5p |
| | 335 | hsa-miR-485-3p |
| | 336 | hsa-miR-485-5p |
| | 337 | hsa-miR-487a |
| | 338 | hsa-miR-494 |
| | 339 | hsa-miR-495 |
| | 340 | hsa-miR-500 |
| | 341 | hsa-miR-500* |
| | 342 | hsa-miR-501-3p |
| | 343 | hsa-miR-502-3p |
| | 344 | hsa-miR-503 |
| | 345 | hsa-miR-506 |
| | 346 | hsa-miR-509-3-5p |
| | 347 | hsa-miR-513a-5p |
| | 348 | hsa-miR-532-3p |
| | 349 | hsa-miR-532-5p |
| | 350 | hsa-miR-539 |
| | 351 | hsa-miR-542-5p |
| | 352 | hsa-miR-543 |
| | 353 | hsa-miR-598 |
| | 354 | hsa-miR-612 |
| | 355 | hsa-miR-654-3p |
| | 356 | hsa-miR-658 |
| | 357 | hsa-miR-660 |
| | 358 | hsa-miR-665 |
| | 359 | hsa-miR-708 |
| | 360 | hsa-miR-873 |
| | 361 | hsa-miR-874 |
| | 362 | hsa-miR-891a |
| | 363 | hsa-miR-99b |
| | 364 | MID-00064 |
| | 365 | MID-00078 |
| | 366 | MID-00144 |
| | 367 | MID-00465 |
| | 368 | MID-00672 |
| | 370 | MID-15986 |
| | 371 | MID-16270 |
| | 372 | MID-16469 |
| | 373 | MID-16582 |
| | 374 | MID-16748 |
| | 389 | MID-17356 (3651) |
| | 375 | MID-17375 |
| | 376 | MID-17576 |
| | 377 | MID-17866 |
| | 378 | MID-18307 |
| | 379 | MID-18395 |
| | 380 | MID-19898 |
| | 381 | MID-19962 |
| | 382 | MID-22331 |
| | 383 | MID-22912 |
| | 384 | MID-23017 |
| | 385 | MID-23168 |
| | 386 | MID-23178 |
| | 387 | MID-23751 |
| | 388 | hsa-miR-423-5p |

3. Nucleic Acid Complexes

The nucleic acid may further comprise one or more of the following: a peptide, a protein, a RNA-DNA hybrid, an antibody, an antibody fragment, a Fab fragment, and an aptamer.

4. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise any of the sequences of SEQ ID NOS: 1-390 or variants thereof.

The pri-miRNA may comprise a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole, as calculated by the Vienna algorithm with default parameters, as described in Hofacker et al. (Monatshefte f Chemie 1994; 125:167-188), the contents of which are incorporated herein by reference. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

5. Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-390 or variants thereof 6. miRNA The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-69, 146-148, 152-390 or variants thereof 7. Probes A probe comprising a nucleic acid described herein is also provided. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides. The probe may comprise a nucleic acid that is complementary to a sequence selected from the group consisting of SEQ ID NOS: 1-390 or variants thereof 8. Biochip A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. Diagnostics

As used herein, the term "diagnosing" refers to classifying pathology, or a symptom, determining a severity of the pathology (e.g., grade or stage), monitoring pathology progression, forecasting an outcome of pathology and/or prospects of recovery.

As used herein, the phrase "subject in need thereof" refers to an animal or human subject who is known to have cancer, at risk of having cancer (e.g., a genetically predisposed subject, a subject with medical and/or family history of cancer, a subject who has been exposed to carcinogens, occupational hazard, environmental hazard) and/or a subject who exhibits suspicious clinical signs of cancer (e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Additionally or alternatively, the subject in need thereof can be a healthy human subject undergoing a routine well-being check up.

Analyzing presence of malignant or pre-malignant cells can be effected in vivo or ex vivo, whereby a biological sample (e.g., biopsy, blood) is retrieved. Such biopsy samples comprise cells and may be an incisional or excisional biopsy. Alternatively, the cells may be retrieved from a complete resection.

While employing the present teachings, additional information may be gleaned pertaining to the determination of treatment regimen, treatment course and/or to the measurement of the severity of the disease.

As used herein the phrase "treatment regimen" refers to a treatment plan that specifies the type of treatment, dosage, follow-up plans, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skill in the art are capable of adjusting the type of treatment with the dosage, schedule and duration of treatment.

A method of diagnosis is also provided. The method comprises detecting an expression level of a specific cancer-associated nucleic acid in a biological sample. The sample may be derived from a patient. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue arrays may be performed. When comparing the fingerprints between individual samples the skilled artisan can make a diagnosis, a prognosis, or a prediction based on the findings. It is further understood that the nucleic acid sequences which indicate the diagnosis may differ from those which indicate the prognosis and molecular profiling of the condition of the cells or exosomes may lead to distinctions between responsive or refractory conditions or may be predictive of outcomes.

10. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly (T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus may include, for example, a solid support.

The following examples are presented in order to more fully illustrate some embodiments of the invention. They should, in no way be construed, however, as limiting the broad scope of the invention.

EXAMPLES

Methods

1. Tumor Samples 1300 primary and metastatic tumor FFPE were used in the study. Tumor samples were obtained from several sources. Institutional review approvals were obtained for all samples in accordance with each institute's institutional review board or IRB equivalent guidelines. Samples included primary tumors and metastases of defined origins, according to clinical records. Tumor content was at least 50% for >95% of samples, as determined by a pathologist based on hematoxylin-eosin (H&E) stained slides.

2. RNA Extraction

For FFPE samples, total RNA was isolated from seven to ten 10-µm-thick tissue sections using the miR extraction protocol developed at Rosetta Genomics. Briefly, the sample was incubated a few times in xylene at 57° C. to remove paraffin excess, followed by ethanol washes. Proteins were degraded by proteinase K solution at 45° C. for a few hours. The RNA was extracted with acid phenol:chloroform followed by ethanol precipitation and DNAse digestion. Total RNA quantity and quality was checked by spectrophotometer (Nanodrop ND-1000).

3. miR Array Platform

Custom microarrays (Agilent Technologies, Santa Clara, Calif.) were produced by printing DNA oligonucleotide probes to: 982 miRs sequences, 17 negative controls, 23 spikes, and 10 positive controls (total of 1032 probes). Each probe, printed in triplicate, carried up to 28-nucleotide (nt) linker at the 3' end of the microRNA's complement sequence. 17 negative control probes were designed using as sequences which do not match the genome. Two groups of positive control probes were designed to hybridize to miR array: (i) synthetic small RNAs were spiked to the RNA before labeling to verify the labeling efficiency; and (ii) probes for abundant small RNA (e.g., small nuclear RNAs (U43, U24, Z30, U6, U48, U44), 5.8 s and 5 s ribosomal RNA are spotted on the array to verify RNA quality.

4. Cy-Dye Labeling of miRNA for miR Array

One µg of total RNA were labeled by ligation (Thomson et al. Nature Methods 2004; 1:47-53) of an RNA-linker, p-rCrU-Cy/dye (Eurogentec or equivalent), to the 3' end with Cy3 or Cy5. The labeling reaction contained total RNA, spikes (0.1-100 fmoles), 400 ng RNA-linker-dye, 15% DMSO, 1× ligase buffer and 20 units of T4 RNA ligase (NEB), and proceeded at 4° C. for 1 h, followed by 1 h at 37° C., followed by 4° C. up to 40 min.

The labeled RNA was mixed with 30 µl hybridization mixture (mixture of 45 µL of the 10×GE Agilent Blocking Agent and 246 µL of 2× Hi-RPM Hybridization). The labeling mixture was incubated at 100° C. for 5 minutes followed by ice incubation in water bath for 5 minutes. Slides were Hybridize at 54° C. for 16-20 hours, followed by two washes. The first wash was conducted at room temperature with Agilent GE Wash Buffer 1 for 5 min followed by a second wash with Agilent GE Wash Buffer 2 at 37° C. for 5 min.

Arrays were scanned using an Agilent Microarray Scanner Bundle G2565BA (resolution of 5 µm at XDR Hi 100%, XDR Lo 5%). Array images were analyzed using Feature Extraction 10.7 software (Agilent).

5. Array Signal Calculation and Normalization

Triplicate spots were combined to produce one signal for each probe by taking the logarithmic mean of reliable spots. All data were log 2-transformed and the analysis was performed in log 2-space. A reference data vector for normalization R was calculated by taking the median expression level for each probe across all samples. For each sample data vector S, a 2nd degree polynomial F was found so as to provide the best fit between the sample data and the reference data, such that R≈F(S). Remote data points ("outliers") were not used for fitting the polynomial F. For each probe in the sample (element Si in the vector S), the normalized value (in log-space) Mi was calculated from the initial value Si by transforming it with the polynomial function F, so that Mi=F(Si).

6. Logistic Regression

The aim of a logistic regression model is to use several features, such as expression levels of several microRNAs, to assign a probability of belonging to one of two possible groups, such as two branches of a node in a binary decision-tree. Logistic regression models the natural log of the odds ratio, i.e., the ratio of the probability of belonging to the first group, for example, the left branch in a node of a binary decision-tree (P) over the probability of belonging to the second group, for example, the right branch in such a node (1−P), as a linear combination of the different expression levels (in log-space). The logistic regression assumes that:

$$\ln\left(\frac{P}{1-P}\right) = \beta_0 + \sum_{i=1}^{N} \beta_i \cdot M_i = \beta_0 + \beta_1 \cdot M_1 + \beta_2 \cdot M_2 + \ldots,$$

where $\beta_0$ is the bias, $M_i$ is the expression level (normalized, in log 2-space) of the i-th microRNA used in the decision node, and $\beta_i$ is its corresponding coefficient. $\beta_i>0$ indicates that the probability to take the left branch (P) increases when the expression level of this microRNA (Mi) increases, and the opposite for $\beta i<0$. If a node uses only a single microRNA (M), then solving for P results in:

$$P = \frac{e^{\beta_0 + \beta_1 \cdot M}}{1 + e^{\beta_0 + \beta_1 \cdot M}}.$$

The regression error on each sample is the difference between the assigned probability P and the true "probability" of this sample, i.e., 1 if this sample is in the left branch group and 0 otherwise. The training and optimization of the logistic regression model calculates the parameters β and the p-values [for each microRNA by the Wald statistic and for the overall model by the $\chi^2$ (chi-square) difference], maximizing the likelihood of the data given the model and minimizing the total regression error $$\sum_{\substack{\text{Samples} \\ \text{in} \\ \text{first} \\ \text{group}}} (1-P_j) + \sum_{\substack{\text{Samples} \\ \text{in} \\ \text{second} \\ \text{group}}} P_j.$$

The probability output of the logistic model is here converted to a binary decision by comparing P to a threshold, denoted by $P^{TH}$ i.e., if $P>P_{TH}$ then the sample belongs to the left branch ("first group") and vice versa. Choosing at each node the branch which has a probability >0.5, i.e., using a probability threshold of 0.5, leads to a minimization of the sum of the regression errors. However, as the goal was the minimization of the overall number of misclassifications (and not of their probability), a modification which adjusts the probability threshold ($P_{TH}$) was used in order to minimize the overall number of mistakes at each node (Table 2). For each node the threshold to a new probability threshold $P_{TH}$ was optimized such that the number of classification errors is minimized. This change of probability threshold is equivalent (in terms of classifications) to a modification of the bias $\beta_0$, which may reflect a change in the prior frequencies of the classes. Once the threshold was chosen $\beta_0$ was modified such that the threshold will be shifted back to 0.5. In addition, β0, β1, β2, . . . were adjusted so that the slope of the log of the odds ratio function is limited.

7. Stepwise Logistic Regression and Feature Selection

The original data contain the expression levels of multiple microRNAs for each sample, i.e., multiple of data features. In training the classifier for each node, only a small subset of these features was selected and used for optimizing a logistic regression model. In the initial training this was done using a forward stepwise scheme. The features were sorted in order of decreasing log-likelihoods, and the logistic model was started off and optimized with the first feature. The second feature was then added, and the model re-optimized. The regression error of the two models was compared: if the addition of the feature did not provide a significant advantage (a $\chi^2$ difference less than 7.88, p-value of 0.005), the new feature was discarded. Otherwise, the added feature was kept. Adding a new feature may make a previous feature redundant (e.g., if they are very highly correlated). To check for this, the process iteratively checks if the feature with lowest likelihood can be discarded (without losing $\chi^2$ difference as above). After ensuring that the current set of features is compact in this sense, the process continues to test the next feature in the sorted list, until features are exhausted. No limitation on the number of features was inserted into the algorithm.

The stepwise logistic regression method was used on subsets of the training set samples by re-sampling the training set with repetition ("bootstrap"), so that each of the 20 runs contained somewhat different training set. All the features that took part in one of the 20 models were collected. A robust set of 1-3 features per each node was selected by comparing features that were repeatedly chosen in the bootstrap sets to previous evidence, and considering their signal strengths and reliability. When using these selected features to construct the classifier, the stepwise process was not used and the training optimized the logistic regression model parameters only.

8. K-Nearest-Neighbors (KNN) Classification Algorithm

The KNN algorithm (see e.g., Ma et al., Arch Pathol Lab Med 2006; 130:465-73) calculates the distance (Pearson correlation) of any sample to all samples in the training set, and classifies the sample by the majority vote of the k samples which are most similar (k being a parameter of the classifier). The correlation is calculated on the pre-defined set of microRNAs (the microRNAs that were used by the decision-tree). KNN algorithms with k=1; 10 were compared, and the optimal performer was selected, using k=5. The KNN was based on comparing the expression of all 65 microRNAs in each sample to all other samples in the training database.

9. Reporting a Final Answer (Prediction):

The decision-tree and KNN each return a predicted tissue of origin and histological type where applicable. The tissue of origin and histological type may be one of the exact origins and types in the training or a variant thereof. For example, whereas the training includes brain oligondendrioglioma and brain astrocytoma, the answer may simply be brain carcinoma. In addition to the tissue of origin and histological type, the KNN and decision-tree each return a confidence measure. The KNN returns the number of samples within the K nearest neighbors that agreed with the answer reported by the KNN (denoted by V), and the decision-tree returns the probability of the result (P), which is the multiplication of the probabilities at each branch point made on the way to that answer. The classifier returns the two different predictions or a single prediction in case the predictions concur, can be unified into a single answer (for example into the prediction brain if the KNN returned brain oligondendrioglioma and the decision-tree brain astrocytoma), or if based on V and P, one answer is chosen to override the other.

Example 1

Decision-Tree Classification Algorithm

Figure 1A:
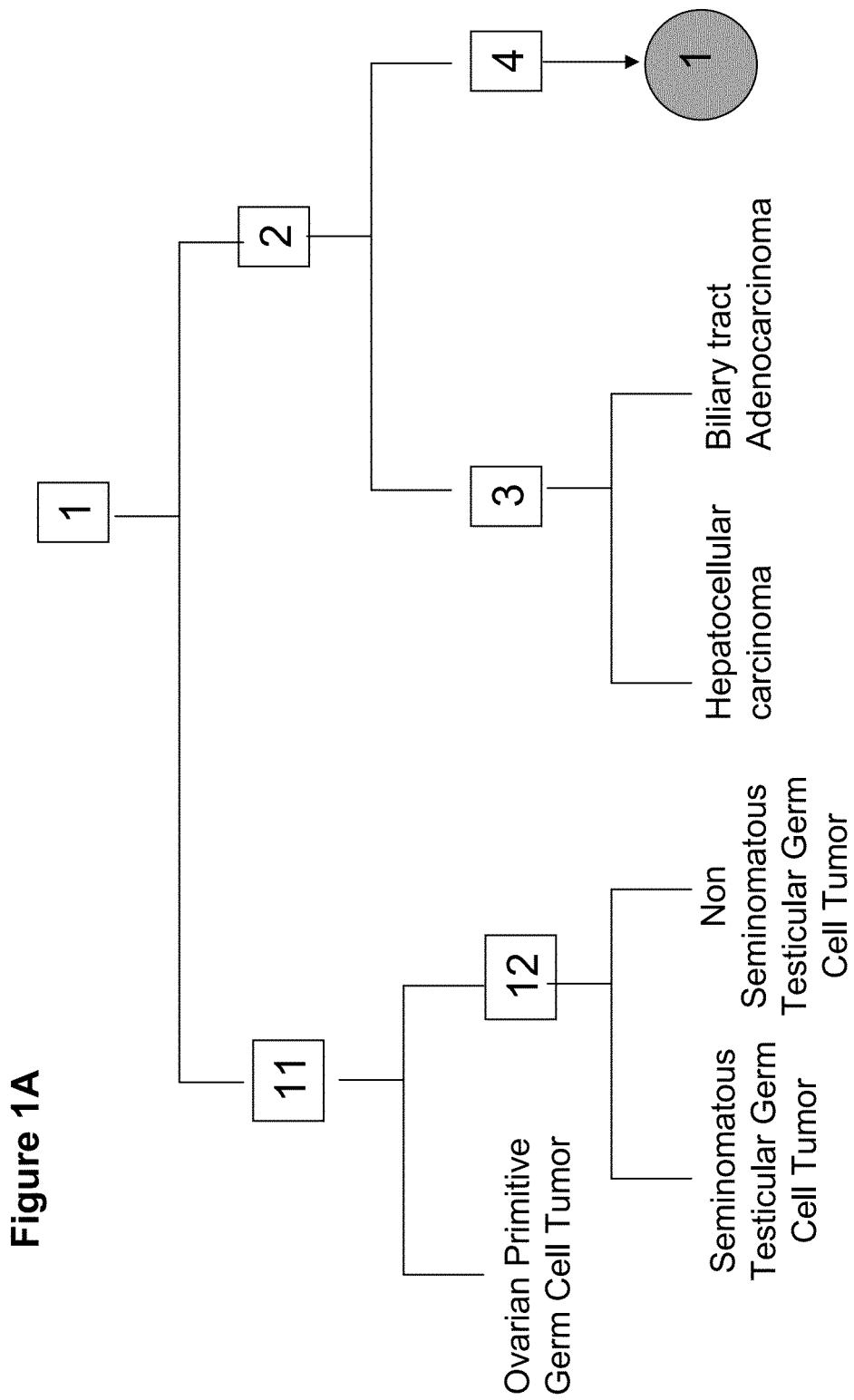
FIGS. 1A-1F demonstrate the structure of the binary decision-tree classifier, with 45 nodes and 46 leaves. Each node is a binary decision between two sets of samples, those to the left and right of the node. A series of binary decisions, starting at node #1 and moving downwards, lead to one of the possible tumor types, which are the "leaves" of the tree. A sample which is classified to the right branch at node #1 continues to node #2, otherwise it continues to node #11. A sample which is classified to the right branch at node #2 continues to node #4, otherwise it continues to node #3. A sample that reaches node #3, is further classified to either the left branch at node #3, and is assigned to the "hepatocellular carcinoma" class, or to the right branch at node #3, and is assigned to the "biliary tract adenocarcinoma" class.
Figure 1B:
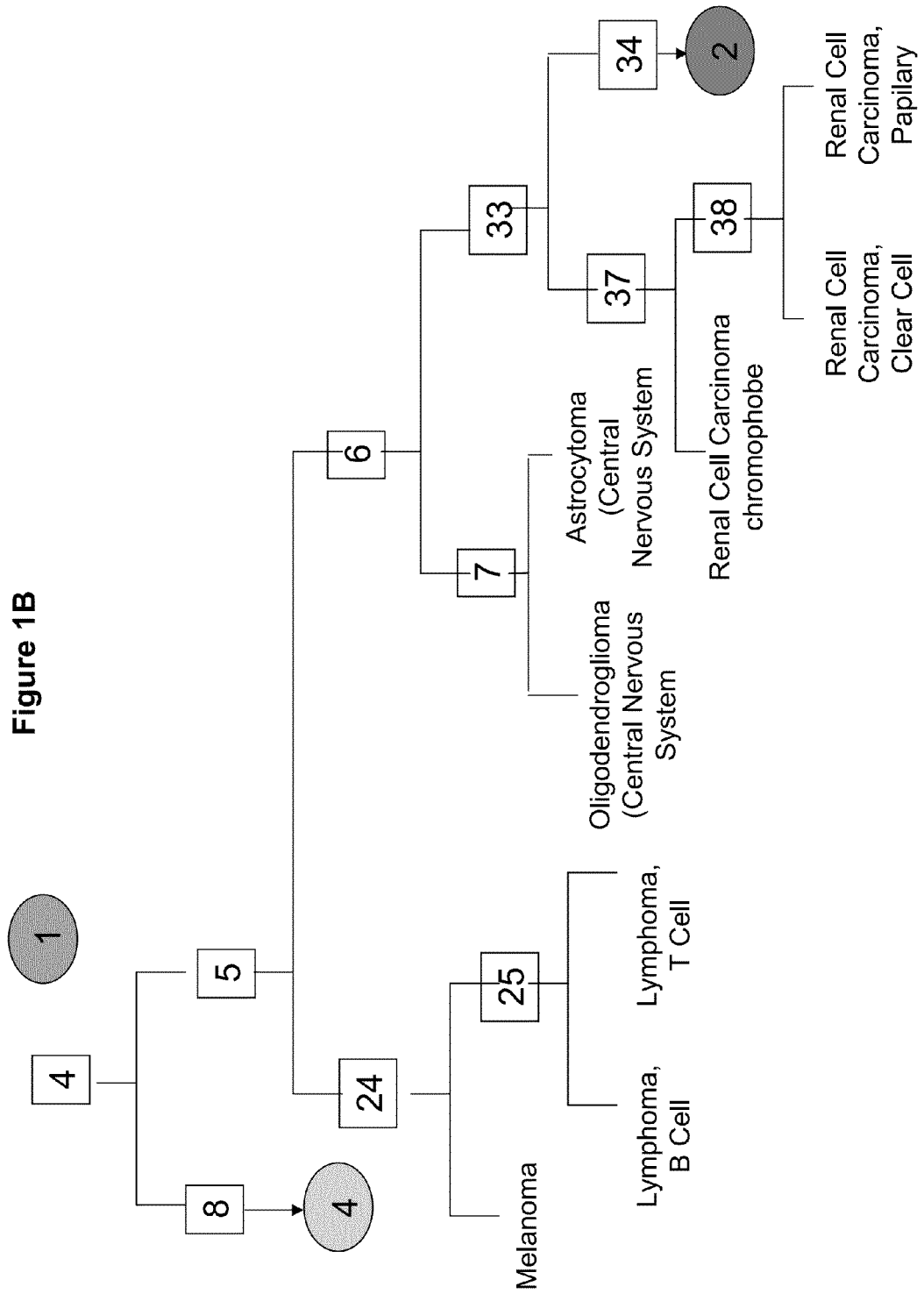
Figure 1C:
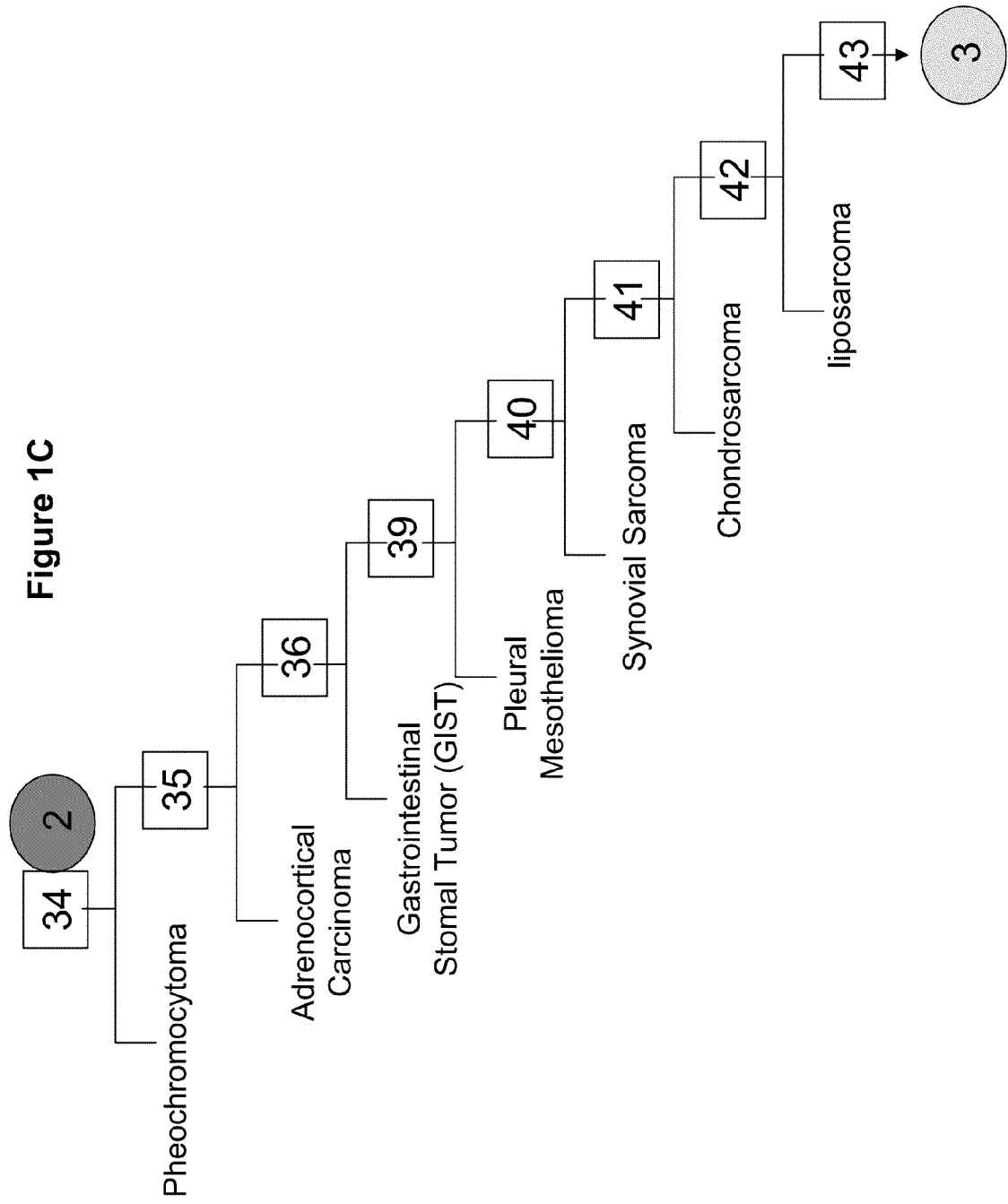
Figure 1D:
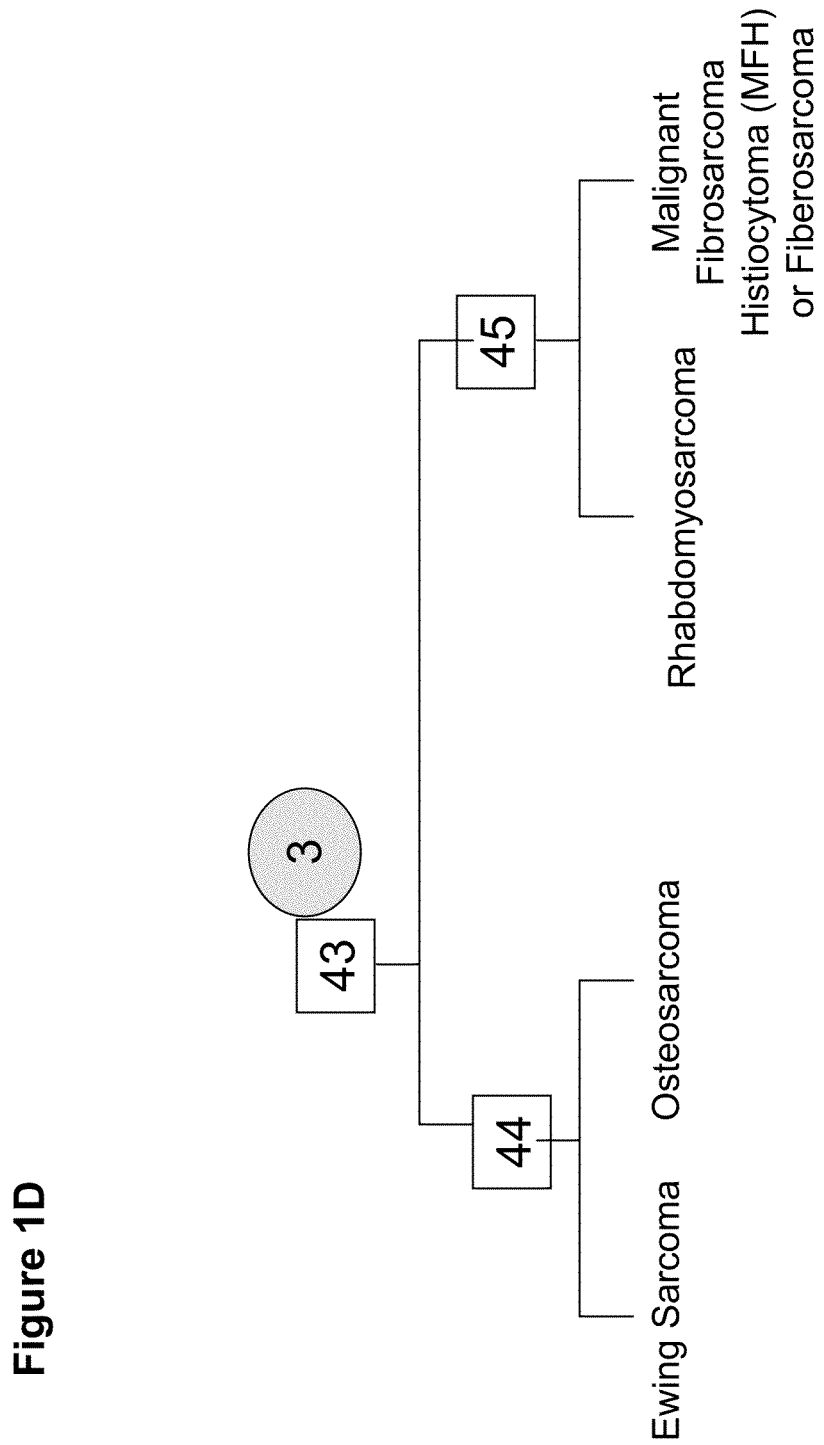
Figure 1E:
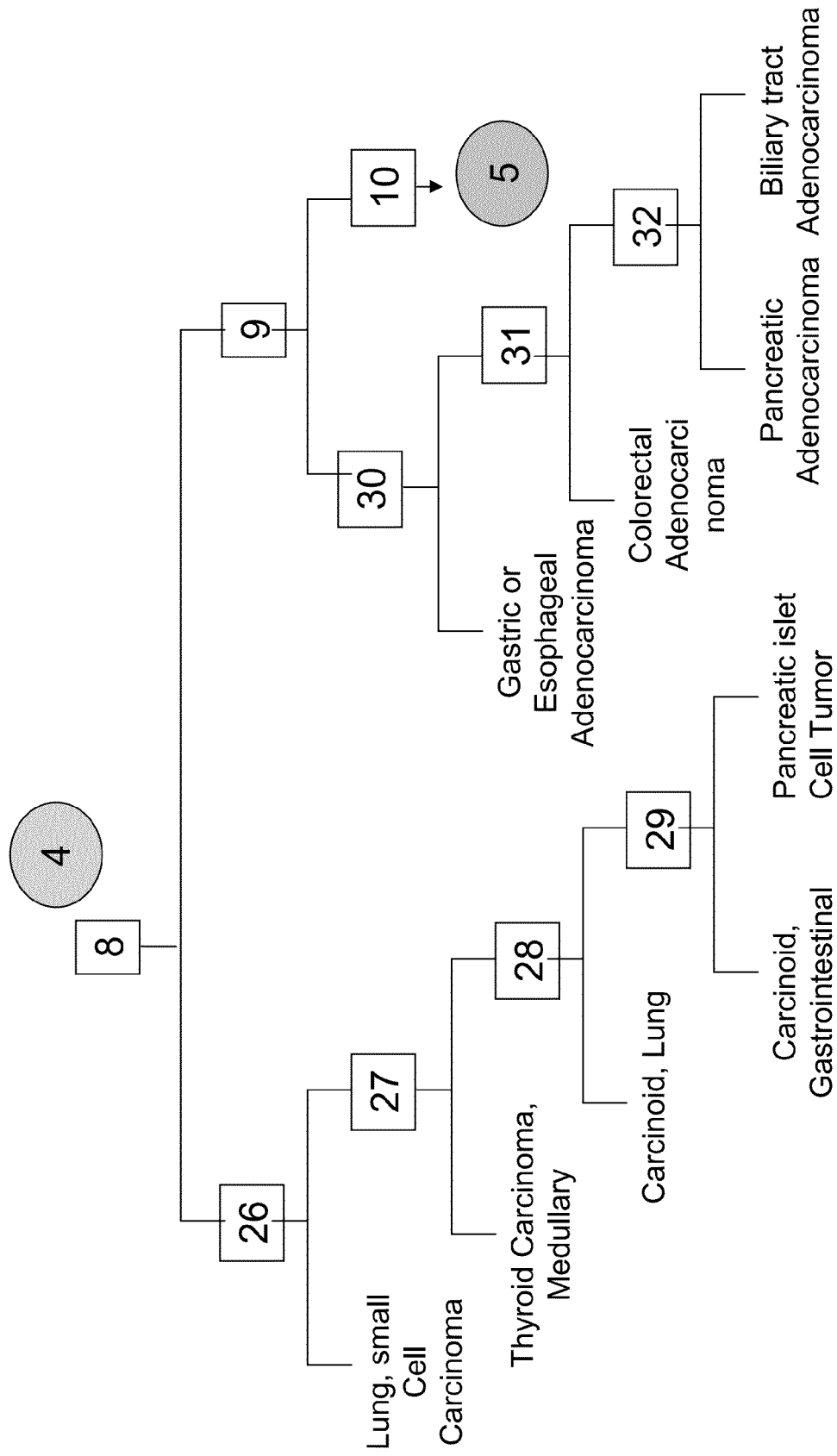
Figure 1F:
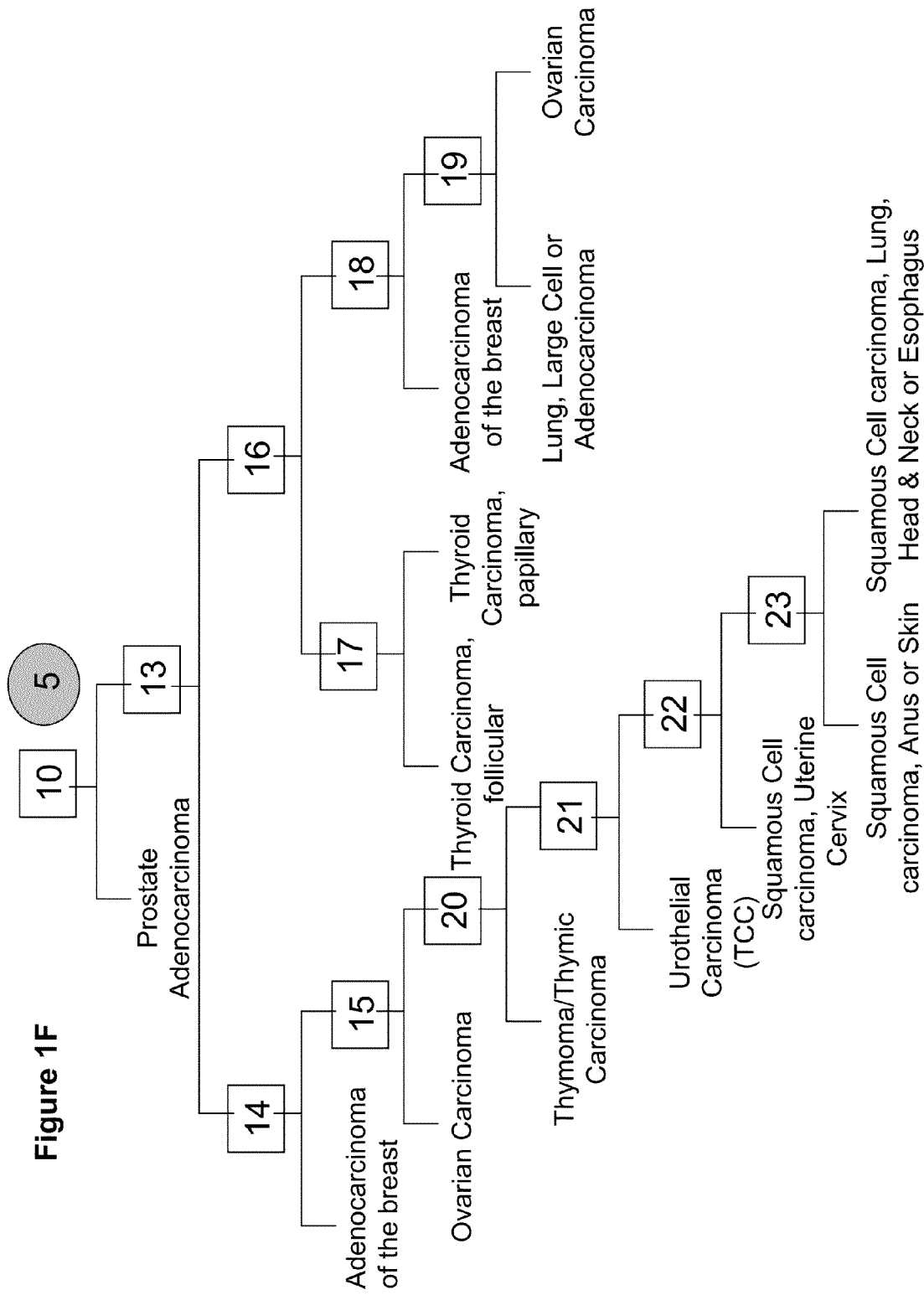

A tumor classifier was built using the microRNA expression levels by applying a binary tree classification scheme (FIGS. 1A-F). This framework is set up to utilize the specificity of microRNAs in tissue differentiation and embryogenesis: different microRNAs are involved in various stages of tissue specification, and are used by the algorithm at different decision points or "nodes". The tree breaks up the complex multi-tissue classification problem into a set of simpler binary decisions. At each node, classes which branch out earlier in the tree are not considered, reducing interference from irrelevant samples and further simplifying the decision. The decision at each node can then be accomplished using only a small number of microRNA biomarkers, which have well-defined roles in the classification (Table 2). The structure of the binary tree was based on a hierarchy of tissue development and morphological similarity[18], which was modified by prominent features of the microRNA expression patterns. For example, the expression patterns of microRNAs indicated a significant difference between germ cell tumors and tumors of non-germ cell origin, and these are therefore distinguished at node #1 (FIG. 2) into separate branches (FIG. 1A).

For each of the individual nodes logistic regression models were used, a robust family of classifiers which are frequently used in epidemiological and clinical studies to combine continuous data features into a binary decision (FIGS. 2-25 and Methods). Since gene expression classifiers have an inherent redundancy in selecting the gene features, bootstrapping was used on the training sample set as a method to select a stable microRNA set for each node (Methods). This resulted in a small number (usually 2-3) of microRNA features per node, totaling 65 microRNAs for the full classifier (Table 2). This approach provides a systematic process for identifying new biomarkers for differential expression.

TABLE 2 bmicroRNAs used per class in the tree classifier

| miR List: | Class |
|---|---|
| hsa-miR-372 (SEQ ID NO: 55) | Germ cell cancer |
| hsa-miR-372, hsa-miR-122 (SEQ ID NO: 6), hsa-miR-126 (SEQ ID NO: 9), hsa-miR-200b (SEQ ID NO: 29) | Biliary tract adenocarcinoma |
| hsa-miR-372, hsa-miR-122, hsa-miR-126, hsa-miR-200b | Hepatocellular carcinoma (HCC) |
| hsa-miR-372, hsa-miR-122, hsa-miR-200c (SEQ ID NO: 30), hsa-miR-30a (SEQ ID NO: 46), hsa-miR-146a (SEQ ID NO: 16), hsa-let-7e (SEQ ID NO: 156), hsa-miR-9* (SEQ ID NO: 66), hsa-miR-92b (SEQ ID NO: 68) | Brain tumor |
| hsa-miR-372, hsa-miR-122, hsa-miR-200c, hsa-miR-30a, hsa-miR-146a, hsa-let-7e, hsa-miR-9*, hsa-miR-92b, hsa-miR-222 (SEQ ID NO: 40), hsa-miR-497 (SEQ ID NO: 60) | Brain-oligodendroglioma |
| hsa-miR-372, hsa-miR-122, hsa-miR-200c, hsa-miR-30a, hsa-miR-146a, hsa-let-7e, hsa-miR-9*, hsa-miR-92b, hsa-miR-222, hsa-miR-497 | Brain-astrocytoma |
| hsa-miR-372, hsa-miR-122, hsa-miR-200c, hsa-miR-30a, hsa-miR-375 (SEQ ID NO: 56), hsa-miR-7 (SEQ ID NO: 65), hsa-miR-193a-3p (SEQ ID NO: 25), hsa-miR-194 (SEQ ID NO: 27), hsa-miR-21* (SEQ ID NO: 35), hsa-miR-143 (SEQ ID NO: 14), hsa-miR-181a (SEQ ID NO: 21) | Prostate Adenocarcinoma |
| hsa-miR-372 | Ovarian primitive germ cell tumor |
| hsa-miR-372 | Testis |
| hsa-miR-372, hsa-miR-200b, hsa-miR-516a-5p (SEQ ID NO: 62) | Seminomatous testicular germ cell tumor |
| hsa-miR-372, hsa-miR-200b, hsa-miR-516a-5p | Non seminomatous testicular germ cell tumor |

TABLE 2-continued bmicroRNAs used per class in the tree classifier

| miR List: | Class |
|---|---|
| hsa-miR-372, hsa-miR-122, hsa-miR-200c, hsa-miR-30a, hsa-miR-7, hsa-miR-194, hsa-miR-21*, hsa-miR-143, hsa-miR-181a, hsa-miR-205 (SEQ ID NO: 32), hsa-miR-345 (SEQ ID NO: 51), hsa-miR-125a-5p (SEQ ID NO: 7), hsa-miR-193a-3p (SEQ ID NO: 25), hsa-miR-375, hsa-miR-342-3p (SEQ ID NO: 50) | Breast adenocarcinoma |
| hsa-miR-372, hsa-miR-122, hsa-miR-200c, hsa-miR-30a, hsa-miR-7, hsa-miR-193a-3p, hsa-miR-194, hsa-miR-21*, hsa-miR-143, hsa-miR-181a, hsa-miR-345, hsa-miR-125a-5p, hsa-miR-193a-3p, hsa-miR-375, hsa-miR-342-3p, hsa-miR-205 (SEQ ID NO: 32), hsa-miR-10a (SEQ ID NO: 4), hsa-miR-22 (SEQ ID NO: 39) | Ovarian carcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-138 (SEQ ID NO: 11), hsa-miR-93 (SEQ ID NO: 148), hsa-miR-10a (SEQ ID NO: 4) | Thyroid carcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-138, hsa-miR-93, hsa-miR-10a, hsa-miR-146b-5p (SEQ ID NO: 17), hsa-miR-21 (SEQ ID NO: 34) | Thyroid carcinoma follicular |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-138, hsa-miR-93, hsa-miR-10a, hsa-miR-146b-5p, hsa-miR-21 | Thyroid carcinoma papillary |
| hsa-miR-372, hsa-miR-122, hsa-miR-200c, hsa-miR-30a, hsa-miR-375, hsa-miR-7, hsa-miR-194, hsa-miR-21*, hsa-miR-143, hsa-miR-181a, hsa-miR-205, hsa-miR-345, hsa-miR-125a-5p, hsa-miR-138, hsa-miR-93, hsa-miR-10a, hsa-miR-193a-3p (SEQ ID NO: 25), hsa-miR-31 (SEQ ID NO: 49), hsa-miR-92a (SEQ ID NO: 67) | Breast adenocarcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-93, hsa-miR-10a, hsa-miR-193a-3p, hsa-miR-31, hsa-miR-92a, hsa-miR-138 (SEQ ID NO: 11), hsa-miR-378 (SEQ ID NO: 57), hsa-miR-21 (SEQ ID NO: 34) | Lung large cell or adenocarcinoma |
| hsa-miR-372, hsa-miR-122, hsa-miR-200c, hsa-miR-30a, hsa-miR-375, hsa-miR-7, hsa-miR-194, hsa-miR-21*, hsa-miR-143, hsa-miR-181a, hsa-miR-205, hsa-miR-345, hsa-miR-125a-5p, hsa-miR-93, hsa-miR-10a, hsa-miR-193a-3p, hsa-miR-31, hsa-miR-92a, hsa-miR-138, hsa-miR-378, hsa-miR-21 | Ovarian carcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-342-3p, hsa-miR-10a, hsa-miR-22, hsa-miR-100, hsa-miR-21 | Thymoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-342-3p, hsa-miR-205, hsa-miR-10a, hsa-miR-22, hsa-miR-100, hsa-miR-21, hsa-miR-934 (SEQ ID NO: 69), hsa-miR-191 (SEQ ID NO: 24), hsa-miR-29c (SEQ ID NO: 44) | Urothelial carcinoma (TCC) |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-342-3p, hsa-miR-10a, hsa-miR-22, hsa-miR-100, hsa-miR-21, hsa-miR-934, hsa-miR-191, hsa-miR-29c | Squamous cell carcinoma (SCC) |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-342-3p, hsa-miR-10a, hsa-miR-22, hsa-miR-100, hsa-miR-21, hsa-miR-934, hsa-miR-191, hsa-miR-29c, hsa-miR-10b (SEQ ID NO: 5), hsa-let-7c (SEQ ID NO: 1), hsa-miR-361-5p (SEQ ID NO: 54) | Uterine cervix SCC |

TABLE 2-continued bmicroRNAs used per class in the tree classifier

| miR List: | Class |
|---|---|
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-193a-3p, hsa-miR-375, hsa-miR-342-3p, hsa-miR-205, hsa-miR-10a, hsa-miR-22, hsa-miR-100, hsa-miR-21, hsa-miR-934, hsa-miR-191, hsa-miR-29c, hsa-miR-10b, hsa-let-7c, hsa-miR-361-5p, hsa-miR-138, hsa-miR-185 (SEQ ID NO: 23) | Anus or Skin SCC |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-143, hsa-miR-181a, hsa-miR-205, hsa-miR-345, hsa-miR-125a-5p, hsa-miR-342-3p, hsa-miR-10a, hsa-miR-22, hsa-miR-100, hsa-miR-21, hsa-miR-934, hsa-miR-191, hsa-miR-29c, hsa-let-7c, hsa-miR-361-5p, hsa-miR-10b, hsa-miR-138, hsa-miR-185 | Lung, Head & Neck or Esophagus SCC |
| hsa-miR-372, hsa-miR-122, hsa-miR-200c, hsa-miR-30a, hsa-miR-146a (SEQ ID NO: 16), hsa-let-7e (SEQ ID NO: 2), hsa-miR-30d (SEQ ID NO: 47), hsa-miR-342-3p | Melanoma |
| hsa-miR-372, hsa-miR-122, hsa-miR-200c, hsa-miR-30a, hsa-miR-146a, hsa-let-7e, hsa-miR-30d, hsa-miR-342-3p | Lymphoma |
| hsa-miR-372, hsa-miR-122, hsa-miR-200c, hsa-miR-30a, hsa-miR-146a, hsa-let-7e, hsa-miR-30d, hsa-miR-342-3p, hsa-miR-21*, hsa-miR-30e (SEQ ID NO: 48) | B cell lymphoma |
| hsa-miR-372, hsa-miR-122, hsa-miR-200c, hsa-miR-30a, hsa-miR-146a, hsa-let-7e, hsa-miR-30a, hsa-miR-30d, hsa-miR-342-3p, hsa-miR-21*, hsa-miR-30e | T cell lymphoma |
| hsa-miR-372, hsa-miR-122, hsa-miR-200c, hsa-miR-30a, hsa-miR-375, hsa-miR-7, hsa-miR-193a-3p, hsa-miR-17 (SEQ ID NO: 20), hsa-miR-29c* (SEQ ID NO: 45) | Lung small cell carcinoma |
| hsa-miR-372, hsa-miR-122, hsa-miR-200c, hsa-miR-30a, hsa-miR-375, hsa-miR-7, hsa-miR-193a-3p, hsa-miR-17, hsa-miR-29c*, hsa-miR-222 (SEQ ID NO: 40), hsa-miR-92a (SEQ ID NO: 67), hsa-miR-92b (SEQ ID NO: 68) | Medullary thyroid carcinoma |
| hsa-miR-372, hsa-miR-122, hsa-miR-200c, hsa-miR-30a, hsa-miR-375, hsa-miR-7, hsa-miR-193a-3p, hsa-miR-17, hsa-miR-29c*, hsa-miR-222, hsa-miR-92a, hsa-miR-92b, hsa-miR-652 (SEQ ID NO: 64), hsa-miR-34c-5p (SEQ ID NO: 53), hsa-miR-214 (SEQ ID NO: 37) | Lung carcinoid |
| hsa-miR-372, hsa-miR-122, hsa-miR-200c, hsa-miR-30a, hsa-miR-375, hsa-miR-7, hsa-miR-193a-3p, hsa-miR-17, hsa-miR-29c*, hsa-miR-222, hsa-miR-92a, hsa-miR-92b, hsa-miR-652, hsa-miR-34c-5p, hsa-miR-214, hsa-miR-21 (SEQ ID NO: 34), hsa-miR-148a (SEQ ID NO: 18) | Gastrointestinal (GI) tract carcinoid |
| hsa-miR-372, hsa-miR-122, hsa-miR-200c, hsa-miR-30a, hsa-miR-375, hsa-miR-7, hsa-miR-193a-3p, hsa-miR-17, hsa-miR-29c*, hsa-miR-222, hsa-miR-92a, hsa-miR-92b, hsa-miR-652, hsa-miR-34c-5p, hsa-miR-214, hsa-miR-21, hsa-miR-148a | Pancreas islet cell tumor |
| hsa-miR-372, hsa-miR-122, hsa-miR-200c, hsa-miR-30a, hsa-miR-375, hsa-miR-7, hsa-miR-193a-3p, hsa-miR-194 (SEQ ID NO: 27), hsa-miR-21*(SEQ ID NO: 35), hsa-miR-224 (SEQ ID NO: 42), hsa-miR-210 (SEQ ID NO: 36), hsa-miR-1201 (SEQ ID NO: 146) | Gastric or Esophageal Adenocarcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-224, hsa-miR-210, hsa-miR-1201, hsa-miR-17 (SEQ ID NO: 20), hsa-miR-29a (SEQ ID NO: 43) | Colorectal Adenocarcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-224, hsa-miR-210, hsa-miR-1201, hsa-miR-17, hsa-miR-29a | Pancreas or bile |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-224, hsa-miR-210, hsa-miR-1201, hsa-miR-17, hsa-miR-29a, hsa-miR-345 (SEQ ID NO: 51), hsa-miR-31 (SEQ ID NO: 49), hsa-miR-146a (SEQ ID NO: 16) | Pancreatic adenocarcinoma |
| hsa-miR-372, hsa-miR-122, hsa-miR-200c, hsa-miR-30a, hsa-miR-375, hsa-miR-7, hsa-miR-193a-3p, hsa-miR-194, hsa-miR-21*, hsa-miR-224, hsa-miR-210, hsa-miR-1201, hsa-miR-17, hsa-miR-29a, hsa-miR-345, hsa-miR-31, hsa-miR-146a | Biliary tract adenocarcinoma |
| hsa-miR-372, hsa-miR-122, hsa-miR-200c, hsa-miR-30a, hsa-miR-146a (SEQ ID NO: 16), hsa-let-7e, hsa-miR-9* (SEQ ID NO: 66), hsa-miR-92b (SEQ ID NO: 68), hsa-miR-149 (SEQ ID NO: 19), hsa-miR-200b (SEQ ID NO: 29) | Renal cell carcinoma chromophobe |
| hsa-miR-372, hsa-miR-122, hsa-miR-200c, hsa-miR-30a, hsa-miR-146a, hsa-let-7e, hsa-miR-9*, hsa-miR-92b, hsa-miR-30a, hsa-miR-149, hsa-miR-200b, hsa-miR-7 (SEQ ID NO: 65), hsa-miR-375 | Pheochromocytoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202 (SEQ ID NO: 31), hsa-miR-214* (SEQ ID NO: 38), hsa-miR-509-3p (SEQ ID NO: 61) | Adrenocortical |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143 (SEQ ID NO: 14), hsa-miR-29c* | Gastrointestinal stomal tumor (GIST) |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-210 (SEQ ID NO: 36), hsa-miR-221 (SEQ ID NO: 147) | Renal cell carcinoma chromophobe |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-210, hsa-miR-221, hsa-miR-31 (SEQ ID NO: 49), hsa-miR-126 (SEQ ID NO: 9) | Renal cell carcinoma clear cell |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-210, hsa-miR-221, hsa-miR-31, hsa-miR-126 | Renal cell carcinoma papilary |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7 (SEQ ID NO: 65), hsa-miR-375, hsa-miR-202 (SEQ ID NO: 31), hsa-miR-214* (SEQ ID NO: 38), hsa-miR-509-3p (SEQ ID NO: 61), hsa-miR-143 (SEQ ID NO: 14), hsa-miR-29c*, hsa-miR-21* (SEQ ID NO: 35), hsa-miR-130a (SEQ ID NO: 10), hsa-miR-10b (SEQ ID NO: 5) | Pleural mesothelioma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b | Sarcoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100 (SEQ ID NO: 3), hsa-miR-222 (SEQ ID NO: 40), hsa-miR-145 (SEQ ID NO: 15) | Synovial sarcoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p (SEQ ID NO: 12), hsa-miR-455-5p (SEQ ID NO: 58) | Chondrosarcoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p, hsa-miR-455-5p, hsa-miR-210 (SEQ ID NO: 36), hsa-miR-193a-5p (SEQ ID NO: 26) | Liposarcoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p, hsa-miR-455-5p, hsa-miR-210, hsa-miR-193a-5p, hsa-miR-181a, hsa-miR-193a-3p (SEQ ID NO: 25), hsa-miR-31 (SEQ ID NO: 49) | Ewing sarcoma |
| hsa-miR-372, hsa-miR-122, hsa-miR-200c, hsa-miR-30a, hsa-miR-146a, hsa-let-7e, hsa-miR-9*, hsa-miR-92b, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p, hsa-miR-455-5p, hsa-miR-210, hsa-miR-193a-5p, hsa-miR-181a, hsa-miR-193a-3p, hsa-miR-31 | Osteosarcoma |

TABLE 2-continued bmicroRNAs used per class in the tree classifier

| miR List: | Class |
|---|---|
| hsa-miR-372, hsa-miR-122, hsa-miR-200c, hsa-miR-30a, hsa-miR-146a, hsa-let-7e, hsa-miR-30a, hsa-miR-9*, hsa-miR-92b, hsa-miR-30a, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p, hsa-miR-455-5p, hsa-miR-210, hsa-miR-193a-5p, hsa-miR-181a, hsa-miR-487b (SEQ ID NO: 59), hsa-miR-22 (SEQ ID NO: 39), hsa-miR-206 (SEQ ID NO: 33) | Rhabdomyo sarcoma |
| hsa-miR-372, hsa-miR-122, hsa-miR-200c, hsa-miR-30a, hsa-miR-146a, hsa-let-7e, hsa-miR-30a, hsa-miR-9*, hsa-miR-92b, hsa-miR-30a, hsa-miR-149, hsa-miR-200b, hsa-miR-7, hsa-miR-375, hsa-miR-202, hsa-miR-214*, hsa-miR-509-3p, hsa-miR-143, hsa-miR-29c*, hsa-miR-21*, hsa-miR-130a, hsa-miR-10b, hsa-miR-100, hsa-miR-222, hsa-miR-145, hsa-miR-140-3p, hsa-miR-455-5p, hsa-miR-210, hsa-miR-193a-5p, hsa-miR-181a, hsa-miR-487b, hsa-miR-22, hsa-miR-206 | Malignant fibrous histiocytoma (MFH) or fibrosarcoma |

Example 2

Expression of miRs Provides for Distinguishing Between Tumors

TABLE 3 miR expression (in florescence units) distinguishing between the group consisting of germ-cell tumors and the group consisting of all other tumors

| median values | fold-change | p-value | SEQ ID NO. | miR name |
|---|---|---|---|---|
| 2.7e+004-5.0e+001 | 545.73 (+) | <e-240 | 233 | hsa-miR-373 |
| 1.8e+004-5.0e+001 | 365.93 (+) | <e-240 | 55 | hsa-miR-372 |
| 8.6e+003-5.0e+001 | 171.72 (+) | <e-240 | 200 | hsa-miR-371-3p |
| 5.9e+003-5.1e+001 | 115.94 (+) | 7.3e-249 | 201 | hsa-miR-371-5p |

+ for all the listed miRs, the higher expression is in tumors from a germ-cell origin.

hsa-miR-372 (SEQ ID NO: 55) is used at node 1 of the binary-tree-classifier detailed in the invention to distinguish between germ-cell tumors and all other tumors.

FIGS. 2A-D are boxplot presentations comparing distribution of the expression of the statistically significant miRs in tumor samples from the "germ cell" class (left box) and "non germ cell" class (right box).

TABLE 4 miR expression (in florescence units) distinguishing between the group consisting of hepatobiliary tumors and the group consisting of non germ-cell non-hepatobiliary tumors

| median values | fold-change | p-value | SEQ ID NO. | miR name |
|---|---|---|---|---|
| 1.0e+005-5.0e+001 | 2024.31 (+) | 1.1e-123 | 6 | hsa-miR-122 |
| 7.4e+001-8.1e+003 | 109.63 (−) | 3.6e-010 | 30 | hsa-miR-200c |
| 5.0e+001-1.4e+003 | 27.92 (−) | 4.8e-010 | 13 | hsa-miR-141 |

+ the higher expression of this miR is in tumors from a hepatobiliary origin
− the higher expression of this miR is in tumors from a non germ-cell, non-hepatobiliary origin hsa-miR-122 (SEQ ID NO: 6) is used at node 2 of the binary-tree-classifier detailed in the invention to distinguish between hepatobiliary tumors and non germ-cell non-hepatobiliary tumors.

TABLE 5 miR expression (in florescence units) distinguishing between the group consisting of liver tumors and the group consisting of biliary-tract carcinomas (cholangiocarcinoma or gallbladder adenocarcinoma)

| median values | fold-change | p-value | SEQ ID NO. | miR name |
|---|---|---|---|---|
| 6.1e+003-4.1e+002 | 14.74 (+) | 5.5e-005 | 28 | hsa-miR-200a |
| 9.7e+003-9.0e+002 | 10.74 (+) | 2.4e-004 | 29 | hsa-miR-200b |
| 1.9e+003-7.0e+003 | 3.67 (−) | 8.5e-004 | 231 | hsa-miR-99a |
| 3.3e+003-7.5e+003 | 2.28 (−) | 6.2e-004 | 9 | hsa-miR-126 |

+ the higher expression of this miR is in biliary tract carcinomas
− the higher expression of this miR is in liver tumors hsa-miR-126 (SEQ ID NO: 9) and hsa-miR-200b (SEQ ID NO: 29) are used at node 3 of the binary-tree-classifier detailed in the invention to distinguish between liver tumors and biliary-tract carcinoma.

FIG. 3 demonstrates that tumors of hepatocellular carcinoma (HCC) origin (marked by squares) are easily distinguished from tumors of biliary tract adenocarcinoma origin (marked by diamonds) using the expression levels of hsa-miR-200b (SEQ ID NO: 29, y-axis) and hsa-miR-126 (SEQ ID NO: 9, x-axis).

TABLE 6 miR expression (in florescence units) distinguishing between the group consisting of tumors from an epithelial origin and the group consisting of tumors from a non-epithelial origin

| median values | fold-change | p-value | SEQ ID NO. | miR name |
|---|---|---|---|---|
| 1.5e+004-7.7e+001 | 196.43 (+) | 1.5e-300 | 30 | hsa-miR-200c |
| 9.0e+003-5.0e+001 | 180.07 (+) | 1.3e-208 | 29 | hsa-miR-200b |
| 3.9e+003-5.0e+001 | 78.09 (+) | 2.2e-187 | 28 | hsa-miR-200a |
| 2.7e+003-5.0e+001 | 54.64 (+) | 7.0e-078 | 32 | hsa-miR-205 |
| 2.6e+003-5.0e+001 | 51.98 (+) | 1.2e-265 | 13 | hsa-miR-141 |
| 5.4e+002-9.2e+001 | 5.90 (+) | 6.3e-048 | 152 | hsa-miR-182 |
| 1.1e+003-2.5e+002 | 4.35 (+) | 4.8e-022 | 49 | hsa-miR-31 |

+ for all the listed miRs, the higher expression is in tumors from epithelial origins A combination of the expression level of any of the miRs detailed in table 6 with the expression level of any of hsa-miR-30a (SEQ ID NO: 46), hsa-miR-10b (SEQ ID NO: 5) and hsa-miR-140-3p (SEQ ID NO: 12) also provides for distinguishing between tumors from epithelial origins and tumors from non-epithelial origins. This is demonstrated at node 4 of the binary-tree-classifier detailed in the invention with hsa-miR-200c (SEQ ID NO: 30) and hsa-miR-30a (SEQ ID NO: 46) (FIG. 4). Tumors originating in epithelial (diamonds) are easily distinguished from tumors of non-epithelial origin (squares) using the expression levels of hsa-miR-30a (SEQ ID NO: 46, y-axis) and hsa-miR-200c (SEQ ID NO: 30, x-axis).

TABLE 7 miR expression (in florescence units) distinguishing between the group consisting of melanoma and lymphoma (B-cell, T-cell), and the group consisting of all other non-epithelial tumors

| median values | fold-change | p-value | SEQ ID NO. | miR name |
|---|---|---|---|---|
| 2.0e+003-7.0e+001 | 28.25 (−) | 1.9e-074 | 164 | hsa-miR-142-5p |
| 1.2e+004-6.3e+002 | 18.86 (−) | 6.0e-061 | 168 | hsa-miR-150 |
| 5.4e+003-3.1e+002 | 17.29 (−) | 5.6e-060 | 170 | hsa-miR-155 |

TABLE 7-continued miR expression (in florescence units) distinguishing between
the group consisting of melanoma and lymphoma
(B-cell, T-cell), and the group consisting of all other
non-epithelial tumors

| median values | fold-change | p-value | SEQ ID NO. | miR name |
|---|---|---|---|---|
| 4.2e+003-3.5e+002 | 12.03 (−) | 8.4e−068 | 16 | hsa-miR-146a |
| 5.9e+002-1.4e+002 | 4.25 (−) | 8.2e−048 | 198 | hsa-miR-342-5p |
| 7.5e+003-1.9e+003 | 4.02 (−) | 4.8e−056 | 50 | hsa-miR-342-3p |
| 8.9e+002-2.5e+002 | 3.53 (−) | 6.0e−035 | 176 | hsa-miR-18a |
| 4.4e+003-1.4e+003 | 3.28 (−) | 8.0e−038 | 186 | hsa-miR-20a |
| 7.9e+002-2.6e+002 | 3.03 (−) | 7.3e−005 | 11 | hsa-miR-138 |
| 6.6e+003-2.3e+003 | 2.82 (−) | 4.0e−039 | 158 | hsa-miR-106a |
| 4.1e+003-1.4e+003 | 2.82 (−) | 2.4e−037 | 20 | hsa-miR-17 |
| 6.2e+001-5.9e+002 | 9.53 (+) | 3.7e−027 | 155 | hsa-miR-127-3p |
| 1.2e+003-7.0e+003 | 5.71 (+) | 1.5e−047 | 231 | hsa-miR-99a |
| 3.9e+002-1.7e+003 | 4.25 (+) | 6.6e−022 | 4 | hsa-miR-10a |
| 1.0e+004-4.1e+004 | 3.91 (+) | 3.2e−037 | 8 | hsa-miR-125b |
| 6.5e+002-2.2e+003 | 3.37 (+) | 2.4e−023 | 46 | hsa-miR-30a |
| 1.9e+003-5.6e+003 | 2.98 (+) | 1.0e−025 | 3 | hsa-miR-100 |
| 2.5e+003-7.1e+003 | 2.89 (+) | 1.8e−051 | 2 | hsa-let-7e |
| 2.9e+003-8.4e+003 | 2.86 (+) | 8.1e−047 | 7 | hsa-miR-125a-5p |

+ the higher expression of this miR is in the group of non-epithelial tumors excluding melanoma and lymphoma
− the higher expression of this miR is in the group consisting of melanoma and lymphoma hsa-miR-146a (SEQ ID NO: 16), hsa-let-7e (SEQ ID NO: 2) and hsa-miR-30a (SEQ ID NO: 46) are used at node 5 of the binary-tree-classifier detailed in the invention to distinguish between the group consisting of melanoma and lymphoma, and the group consisting of all other non-epithelial tumors. FIG. 5 demonstrates that tumors originating in the lymphoma or melanoma (diamonds) are easily distinguished from tumors of non epithelial, non lymphoma/melanoma origin (squares) using the expression levels of hsa-miR-146a (SEQ ID NO: 16, y-axis), hsa-miR-30a (SEQ ID NO: 46, x-axis) and hsa-let-7e (SEQ ID NO: 2, z-axis).

TABLE 8 miR expression (in florescence units) distinguishing
between the group consisting of brain tumors
(astrocytic tumor and oligodendroglioma) and the group
consisting of all non-brain, non-epithelial tumors

| median values | fold-change | p-value | SEQ ID NO. | miR name |
|---|---|---|---|---|
| 9.1e+003-5.0e+001 | 182.94 (+) | 3.8e−059 | 159 | hsa-miR-124 |
| 4.4e+003-5.0e+001 | 88.33 (+) | 1.1e−125 | 66 | hsa-miR-9* |
| 2.1e+003-6.0e+001 | 34.97 (+) | 6.0e−035 | 225 | hsa-miR-551b |
| 9.9e+002-5.0e+001 | 19.73 (+) | 3.0e−116 | 187 | hsa-miR-219-2-3p |
| 6.5e+002-5.0e+001 | 12.95 (+) | 1.8e−021 | 162 | hsa-miR-129-3p |
| 1.1e+003-1.0e+002 | 10.52 (+) | 2.0e−034 | 161 | hsa-miR-128 |
| 2.3e+003-2.5e+002 | 9.45 (+) | 2.2e−052 | 68 | hsa-miR-92b |
| 5.2e+002-6.8e+001 | 7.61 (+) | 6.7e−019 | 232 | hsa-miR-99a* |
| 6.9e+002-9.2e+001 | 7.45 (+) | 5.5e−023 | 173 | hsa-miR-181c |
| 2.2e+003-3.5e+002 | 6.34 (+) | 7.4e−007 | 11 | hsa-miR-138 |
| 1.2e+005-2.4e+004 | 4.78 (+) | 1.7e−014 | 8 | hsa-miR-125b |
| 1.8e+003-3.9e+002 | 4.70 (+) | 7.2e−014 | 174 | hsa-miR-181d |
| 8.5e+002-1.8e+002 | 4.64 (+) | 2.2e−002 | 155 | hsa-miR-127-3p |
| 1.6e+004-3.5e+003 | 4.60 (+) | 2.4e−010 | 231 | hsa-miR-99a |
| 8.5e+001-1.1e+003 | 13.55 (−) | 2.4e−014 | 4 | hsa-miR-10a |
| 7.7e+002-6.6e+003 | 8.58 (−) | 8.4e−017 | 182 | hsa-miR-199a-5p |
| 5.7e+002-4.7e+003 | 8.12 (−) | 1.8e−013 | 181 | hsa-miR-199a-3p |
| 2.8e+002-1.9e+003 | 6.81 (−) | 1.4e−012 | 37 | hsa-miR-214 |

+ the higher expression of this miR is in the group consisting of brain tumors
− the higher expression of this miR is in the group consisting of all non-brain, non-epithelial tumors hsa-miR-9* (SEQ ID NO: 66) and hsa-miR-92b (SEQ ID NO: 68) are used at node 6 of the binary-tree-classifier detailed in the invention to distinguish between brain tumors and the group consisting of all non-brain, non-epithelial tumors. FIG. 6 demonstrates that tumors originating in the brain (marked by diamonds) are easily distinguished from tumors of non epithelial, non brain origin (marked by squares) using the expression levels of hsa-miR-9* (SEQ ID NO: 66, y-axis) and hsa-miR-92b (SEQ ID NO: 68, x-axis).

TABLE 9 miR expression (in florescence units) distinguishing between
astrocytic tumors and oligodendrogliomas

| median values | fold-change | p-value | SEQ ID NO. | miR name |
|---|---|---|---|---|
| 2.5e+003-2.3e+002 | 11.10 (+) | 5.1e−011 | 230 | hsa-miR-886-5p |
| 4.4e+003-4.9e+002 | 9.06 (+) | 1.1e−009 | 228 | hsa-miR-886-3p |
| 1.0e+004-1.7e+003 | 5.99 (+) | 7.7e−008 | 147 | hsa-miR-221 |
| 1.3e+004-2.6e+003 | 5.03 (+) | 2.6e−006 | 40 | hsa-miR-222 |
| 3.3e+004-7.3e+003 | 4.54 (+) | 3.9e−004 | 34 | hsa-miR-21 |
| 8.4e+002-2.2e+002 | 3.78 (+) | 3.7e−006 | 206 | hsa-miR-455-3p |
| 6.0e+002-1.8e+002 | 3.30 (+) | 1.3e−002 | 35 | hsa-miR-21* |
| 5.8e+003-1.8e+003 | 3.15 (+) | 2.4e−005 | 52 | hsa-miR-34a |
| 1.1e+003-3.5e+002 | 3.04 (+) | 1.0e−003 | 25 | hsa-miR-193a-3p |
| 1.6e+002-8.2e+002 | 5.17 (−) | 1.2e−004 | 229 | hsa-miR-9 |
| 4.6e+002-2.3e+003 | 5.09 (−) | 7.1e−003 | 161 | hsa-miR-128 |
| 4.1e+002-1.8e+003 | 4.43 (−) | 1.3e−002 | 187 | hsa-miR-219-2-3p |
| 3.8e+003-1.3e+004 | 3.31 (−) | 1.9e−002 | 179 | hsa-miR-195 |

+ the higher expression of this miR is in astrocytic tumors
− the higher expression of this miR is in oligodendrogliomas A combination of the expression level of any of the miRs detailed in table 9 with the expression level of hsa-miR-497 (SEQ ID NO: 208) or hsa-let-7d (SEQ ID NO: 153) also provides for classification of brain tumors as astrocytic tumors or oligodendrogliomas. This is demonstrated at node 7 of the binary-tree-classifier detailed in the invention with hsa-miR-222 (SEQ ID NO: 40) and hsa-miR-497 (SEQ ID NO: 208). In another embodiment of the invention, the expression levels of hsa-miR-222 (SEQ ID NO: 40) and hsa-let-7d (SEQ ID NO: 153) are combined to distinguish between astrocytic tumors and oligodendrogliomas.

FIG. 7 demonstrates that tumors originating in astrocytoma (marked by diamonds) are easily distinguished from tumors of oligodendroglioma origins (marked by squares) using the expression levels of hsa-miR-497 (SEQ ID NO: 208, y-axis) and hsa-miR-222 (SEQ ID NO: 40, x-axis).

TABLE 10 miR expression (in florescence units) distinguishing
between the group consisting of neuroendocrine tumors
and the group consisting of all non-neuroendocrine,
epithelial tumors

| median values | fold-change | p-value | SEQ ID NO. | miR name |
|---|---|---|---|---|
| 3.8e+004-1.5e+002 | 259.47 (+) | 5.3e−086 | 56 | hsa-miR-375 |
| 3.6e+003-5.2e+001 | 70.47 (+) | 4.4e−145 | 65 | hsa-miR-7 |
| 1.3e+003-1.8e+002 | 6.89 (+) | 4.7e−044 | 175 | hsa-miR-183 |
| 1.9e+003-4.4e+002 | 4.42 (+) | 3.5e−025 | 152 | hsa-miR-182 |
| 1.2e+003-3.0e+002 | 4.16 (+) | 5.5e−028 | 155 | hsa-miR-127-3p |
| 5.6e+001-7.0e+003 | 124.66 (−) | 1.4e−023 | 32 | hsa-miR-205 |
| 1.5e+002-1.4e+003 | 9.25 (−) | 1.8e−019 | 49 | hsa-miR-31 |
| 3.4e+002-1.4e+003 | 4.12 (−) | 9.5e−032 | 35 | hsa-miR-21* |

+ the higher expression of this miR is in the group consisting of neuroendocrine tumors
− the higher expression of this miR is in the group consisting of all non-neuroendocrine, epithelial tumors hsa-miR-375 (SEQ ID NO: 56), hsa-miR-7 (SEQ ID NO: 65) and hsa-miR-193a-3p (SEQ ID NO: 25) are used at node 8 of the binary-tree-classifier detailed in the invention to distinguish between the group consisting of neuroendocrine tumors and the group consisting of all non-neuroendocrine, epithelial tumors. FIG. 8 demonstrates that tumors originating in the neuroendocrine (diamonds) are easily distinguished from tumors of epithelial, origin (squares) using the expression levels of hsa-miR-193a-3p (SEQ ID NO: 25, y-axis), hsa-miR-7 (SEQ ID NO: 65, x-axis) and hsa-miR-375 (SEQ ID NO: 56, z-axis).

TABLE 11 miR expression (in florescence units) distinguishing between the group consisting of gastrointestinal (GI) epithelial tumors and the group consisting of non-GI epithelial tumors

| median values | fold-change | p-value | SEQ ID NO. | miR name |
|---|---|---|---|---|
| 2.6e+003-7.1e+001 | 36.09 (+) | 2.5e−127 | 27 | hsa-miR-194 |
| 3.9e+003-1.2e+002 | 33.26 (+) | 1.6e−117 | 177 | hsa-miR-192 |
| 2.6e+003-6.7e+002 | 3.88 (+) | 3.3e−021 | 4 | hsa-miR-10a |
| 5.0e+001-2.1e+004 | 411.76 (−) | 6.5e−045 | 32 | hsa-miR-205 |

+ the higher expression of this miR is in the group consisting of GI epithelial tumors
− the higher expression of this miR is in the group consisting of non-GI epithelial tumors hsa-miR-194 (SEQ ID NO: 27) and hsa-miR-21* (SEQ ID NO: 35) are used at node 9 of the binary-tree-classifier detailed in the invention to distinguish between GI epithelial tumors and non-GI epithelial tumors.

FIG. 9 demonstrates that tumors originating in gastro-intestinal (GI) (marked by diamonds) are easily distinguished from tumors of non GI origins (marked by squares) using the expression levels of hsa-miR-21* (SEQ ID NO: 35, y-axis) and hsa-miR-194 (SEQ ID NO: 27, x-axis).

TABLE 12 miR expression (in florescence units) distinguishing between prostate tumors and all other non-GI epithelial tumors

| median values | fold-change | p-value | SEQ ID NO. | miR name |
|---|---|---|---|---|
| 5.1e+003-5.2e+001 | 96.76 (+) | 3.7e−016 | 56 | hsa-miR-375 |
| 1.0e+003-5.5e+001 | 18.27 (+) | 4.0e−025 | 199 | hsa-miR-363 |
| 6.8e+004-7.2e+003 | 9.41 (+) | 1.0e−025 | 14 | hsa-miR-143 |
| 1.2e+005-1.4e+004 | 8.14 (+) | 7.8e−022 | 15 | hsa-miR-145 |
| 2.8e+003-3.5e+002 | 7.89 (+) | 1.5e−012 | 165 | hsa-miR-143* |
| 2.1e+004-4.4e+003 | 4.76 (+) | 2.2e−011 | 231 | hsa-miR-99a |
| 4.6e+002-2.1e+003 | 4.58 (−) | 8.0e−007 | 36 | hsa-miR-210 |
| 2.7e+002-1.1e+003 | 3.84 (−) | 7.8e−017 | 154 | hsa-miR-181b |
| 1.2e+003-4.3e+003 | 3.76 (−) | 1.2e−014 | 21 | hsa-miR-181a |
| 5.5e+002-2.0e+003 | 3.63 (−) | 2.3e−002 | 49 | hsa-miR-31 |

+ the higher expression of this miR is in prostate tumors
− the higher expression of this miR is in the group consisting of all other non-GI epithelial tumors hsa-miR-143 (SEQ ID NO: 14) and hsa-miR-181a (SEQ ID NO: 21) are used at node 10 of the binary-tree-classifier detailed in the invention to distinguish between prostate tumors and all other non-GI epithelial tumors.

FIG. 10 demonstrates that tumors originating in prostate adenocarcinoma (marked by diamonds) are easily distinguished from tumors of non prostate origins (marked by squares) using the expression levels of hsa-miR-181a (SEQ ID NO: 21, y-axis) and hsa-miR-143 (SEQ ID NO: 14, x-axis).

TABLE 13 miR expression (in florescence units) distinguishing between seminiomatous and non-seminiomatous testicular tumors

| median values | fold-change | p-value | SEQ ID NO. | miR name |
|---|---|---|---|---|
| 4.3e+003-7.6e+002 | 5.63 (+) | 6.6e−004 | 152 | hsa-miR-182 |
| 1.0e+002-2.1e+003 | 20.46 (−) | 6.2e−005 | 216 | hsa-miR-518e |

TABLE 13-continued miR expression (in florescence units) distinguishing between seminiomatous and non-seminiomatous testicular tumors

| median values | fold-change | p-value | SEQ ID NO. | miR name |
|---|---|---|---|---|
| 7.8e+001-1.2e+003 | 15.29 (−) | 4.5e−005 | 212 | hsa-miR-516b |
| 6.8e+001-8.2e+002 | 11.94 (−) | 2.2e−005 | 224 | hsa-miR-527 |
| 2.1e+002-2.2e+003 | 10.40 (−) | 1.9e−006 | 13 | hsa-miR-141 |
| 5.3e+002-5.0e+003 | 9.48 (−) | 5.0e−004 | 194 | hsa-miR-302d |
| 1.4e+002-1.3e+003 | 8.97 (−) | 4.1e−006 | 192 | hsa-miR-302a |
| 2.7e+002-2.3e+003 | 8.78 (−) | 2.9e−003 | 221 | hsa-miR-520c-3p |
| 1.3e+002-1.2e+003 | 8.65 (−) | 8.3e−004 | 217 | hsa-miR-518f* |
| 3.4e+003-2.9e+004 | 5.98 (−) | 2.6e−007 | 205 | hsa-miR-451 |
| 2.8e+002-1.7e+003 | 5.98 (−) | 1.1e−002 | 219 | hsa-miR-519d |
| 2.0e+002-1.2e+003 | 5.90 (−) | 6.8e−005 | 32 | hsa-miR-205 |
| 2.0e+002-1.1e+003 | 5.59 (−) | 5.8e−006 | 193 | hsa-miR-302a* |
| 1.9e+002-1.0e+003 | 5.27 (−) | 6.7e−003 | 223 | hsa-miR-524-5p |
| 1.5e+002-8.0e+002 | 5.22 (−) | 5.4e−003 | 220 | hsa-miR-520a-5p |
| 2.2e+002-1.1e+003 | 5.21 (−) | 4.1e−003 | 210 | hsa-miR-512-5p |
| 3.2e+002-1.4e+003 | 4.57 (−) | 9.2e−003 | 209 | hsa-miR-498 |
| 7.2e+002-3.2e+003 | 4.51 (−) | 3.1e−002 | 213 | hsa-miR-517a |
| 6.4e+002-2.9e+003 | 4.47 (−) | 2.9e−002 | 163 | hsa-miR-1323 |
| 9.5e+002-4.1e+003 | 4.29 (−) | 1.3e−004 | 30 | hsa-miR-200c |

+ the higher expression of this miR is in seminioma tumors
− the higher expression of this miR is in non-seminioma tumors A combination of the expression level of any of the miRs detailed in table 13 with the expression level of hsa-miR-200b (SEQ ID NO: 29), hsa-miR-200a (SEQ ID NO: 28), hsa-miR-516a-5p (SEQ ID NO: 211), hsa-miR-767-5p (SEQ ID NO: 227), hsa-miR-518a-3p (SEQ ID NO: 215), hsa-miR-520d-5p (SEQ ID NO: 222), hsa-miR-519a (SEQ ID NO: 218) and hsa-miR-517c (SEQ ID NO: 214) also provides for classification of seminoma and non-seminoma testis-tumors.

hsa-miR-516a-5p (SEQ ID NO: 211) and hsa-miR-200b (SEQ ID NO: 29) are used at node 12 of the binary-tree-classifier detailed in the invention to distinguish between seminoma and non-seminoma testis-tumors.

FIG. 11 demonstrates that tumors originating in seminiomatous testicular germ cell (marked by diamonds) are easily distinguished from tumors of non seminiomatous origins (marked by squares) using the expression levels of hsa-miR-516a-5p (SEQ ID NO: 211, y-axis) and hsa-miR-200b (SEQ ID NO: 29, x-axis).

TABLE 14 miR expression (in florescence units) distinguishing between the group consisting of squamous cell carcinoma (SCC), transitional cell carcinoma (TCC), thymoma and the group consisting of non gastrointestinal (GI) adenocarcinoma tumors

| median values | fold-change | p-value | SEQ ID NO. | miR name |
|---|---|---|---|---|
| 4.6e+004-1.4e+002 | 321.76 (+) | 1.6e−059 | 32 | hsa-miR-205 |
| 2.9e+003-4.9e+002 | 5.96 (+) | 8.6e−015 | 36 | hsa-miR-210 |
| 2.5e+003-6.6e+002 | 3.82 (+) | 2.6e−016 | 178 | hsa-miR-193b |
| 2.5e+003-6.8e+002 | 3.67 (+) | 1.8e−008 | 243 | MID-16869 |
| 3.4e+003-9.7e+002 | 3.53 (+) | 2.2e−011 | 242 | MID-16489 |
| 3.7e+003-1.3e+003 | 2.82 (+) | 8.2e−004 | 49 | hsa-miR-31 |
| 6.4e+003-2.3e+003 | 2.78 (+) | 1.7e−010 | 240 | MID-15965 |
| 1.4e+003-5.2e+002 | 2.71 (+) | 2.7e−017 | 57 | hsa-miR-378 |
| 2.8e+002-2.2e+003 | 8.05 (−) | 2.9e−023 | 11 | hsa-miR-138 |
| 7.3e+002-2.7e+003 | 3.70 (−) | 1.5e−018 | 46 | hsa-miR-30a |
| 8.6e+002-2.2e+003 | 2.60 (−) | 4.0e−013 | 17 | hsa-miR-146b-5p |
| 1.8e+003-4.3e+003 | 2.44 (−) | 1.5e−021 | 47 | hsa-miR-30d |
| 4.5e+002-1.1e+003 | 2.38 (−) | 2.6e−019 | 51 | hsa-miR-345 |
| 4.2e+003-9.6e+003 | 2.30 (−) | 3.8e−014 | 7 | hsa-miR-125a-5p |
| 1.9e+004-4.3e+004 | 2.26 (−) | 3.0e−009 | 8 | hsa-miR-125b |
| 9.4e+002-2.1e+003 | 2.24 (−) | 3.2e−008 | 154 | hsa-miR-181b |
| 7.4e+002-1.6e+003 | 2.13 (−) | 3.3e−010 | 190 | hsa-miR-29b |

TABLE 14-continued miR expression (in florescence units) distinguishing between the group consisting of squamous cell carcinoma (SCC), transitional cell carcinoma (TCC), thymoma and the group consisting of non gastrointestinal (GI) adenocarcinoma tumors

| median values | fold-change | p-value | SEQ ID NO. | miR name |
| --- | --- | --- | --- | --- |
| 6.6e+003-1.3e+004 | 2.04 (−) | 4.6e−014 | 157 | hsa-let-7i |
| 2.4e+003-4.8e+003 | 2.04 (−) | 7.9e−010 | 196 | hsa-miR-30c |

+ the higher expression of this miR is in SCC, TCC and thymoma
− the higher expression of this miR is in non GI adenocarcinoma Node 13 of the binary-tree-classifier separates tissues with high expression of miR-205 (SCC marker) such as SCC, TCC and thymomas from adenocarcinomas.

Breast adenocarcinoma and ovarian carcinoma are excluded from this separation due to a wide range of expression of miR-205.

A combination of the expression level of any of the miRs detailed in table 14 with the expression level of hsa-miR-331-3p (SEQ ID NO: 197) also provides for this classification.

hsa-miR-205 (SEQ ID NO: 32), hsa-miR-345 (SEQ ID NO: 51) and hsa-miR-125a-5p (SEQ ID NO: 7) are used at node 13 of the binary-tree-classifier detailed in the invention.

TABLE 15 miR expression (in florescence units) distinguishing between the group consisting of breast adenocarcinoma and the group consisting of SCC, TCC, thymomas and ovarian carcinoma

| median values | fold-change | p-value | SEQ ID NO. | miR name |
| --- | --- | --- | --- | --- |
| 1.3e+003-5.0e+001 | 25.95 (+) | 4.1e−029 | 56 | hsa-miR-375 |
| 2.7e+003-8.3e+002 | 3.25 (+) | 1.6e−014 | 46 | hsa-miR-30a |
| 4.4e+003-1.4e+003 | 3.09 (+) | 9.5e−022 | 25 | hsa-miR-193a-3p |
| 1.2e+003-4.1e+002 | 2.94 (+) | 2.1e−009 | 152 | hsa-miR-182 |
| 5.5e+003-2.2e+003 | 2.48 (+) | 7.3e−014 | 50 | hsa-miR-342-3p |
| 6.6e+002-2.7e+002 | 2.48 (+) | 6.3e−008 | 45 | hsa-miR-29c* |
| 5.0e+002-2.2e+002 | 2.26 (+) | 5.8e−007 | 191 | hsa-miR-29c |
| 7.3e+003-3.3e+003 | 2.19 (+) | 1.3e−004 | 181 | hsa-miR-199a-3p |
| 2.2e+003-1.1e+003 | 2.05 (+) | 2.0e−006 | 179 | hsa-miR-195 |
| 2.2e+003-3.1e+003 | 13.81 (−) | 9.6e−014 | 49 | hsa-miR-31 |
| 6.3e+003-4.0e+004 | 6.32 (−) | 9.3e−008 | 32 | hsa-miR-205 |
| 8.9e+001-5.1e+002 | 5.72 (−) | 5.3e−010 | 42 | hsa-miR-224 |
| 1.5e+002-6.3e+002 | 4.05 (−) | 6.7e−007 | 184 | hsa-miR-203 |
| 5.7e+003-1.5e+004 | 2.64 (−) | 5.8e−018 | 40 | hsa-miR-222 |
| 3.8e+003-9.2e+003 | 2.41 (−) | 1.0e−018 | 147 | hsa-miR-221 |
| 4.8e+002-1.1e+003 | 2.39 (−) | 4.9e−010 | 236 | MID-00689 |
| 6.0e+002-1.4e+003 | 2.37 (−) | 1.2e−010 | 57 | hsa-miR-378 |
| 2.3e+002-5.2e+002 | 2.24 (−) | 2.2e−008 | 203 | hsa-miR-422a |
| 1.2e+003-2.6e+003 | 2.22 (−) | 1.5e−007 | 36 | hsa-miR-210 |

+ the higher expression of this miR is in breast adenocarcinoma
− the higher expression of this miR is in SCC, TCC, thymomas and ovarian carcinoma hsa-miR-193a-3p (SEQ ID NO: 25), hsa-miR-375 (SEQ ID NO: 56) and hsa-miR-342-3p (SEQ ID NO: 50) are used at node 14 of the binary-tree-classifier detailed in the invention. According to another embodiment, hsa-miR-193a-3p (SEQ ID NO: 25), hsa-miR-375 (SEQ ID NO: 56) and hsa-miR-224 (SEQ ID NO: 42) may be used at node 14 of the binary-tree-classifier detailed in the invention.

TABLE 16 miR expression (in florescence units) distinguishing between the group consisting of ovarian carcinoma and the group consisting of SCC, TCC and thymomas

| median values | fold-change | p-value | SEQ ID NO. | miR name |
| --- | --- | --- | --- | --- |
| 3.1e+003-5.5e+002 | 5.57 (+) | 1.2e−012 | 4 | hsa-miR-10a |
| 5.1e+003-1.5e+003 | 3.41 (+) | 1.7e−014 | 10 | hsa-miR-130a |
| 2.5e+002-7.5e+001 | 3.39 (+) | 1.3e−014 | 195 | hsa-miR-30a* |
| 2.4e+003-8.8e+002 | 2.68 (+) | 5.5e−009 | 5 | hsa-miR-10b |
| 2.9e+002-1.2e+002 | 2.48 (+) | 2.5e−012 | 226 | hsa-miR-625 |
| 8.8e+003-3.9e+003 | 2.28 (+) | 7.7e−012 | 2 | hsa-let-7e |
| 1.6e+003-7.3e+002 | 2.20 (+) | 3.6e−007 | 46 | hsa-miR-30a |
| 1.2e+003-4.6e+004 | 37.52 (−) | 1.0e−033 | 32 | hsa-miR-205 |
| 5.0e+001-2.7e+002 | 5.42 (−) | 4.2e−018 | 185 | hsa-miR-205* |
| 6.0e+001 2.8e+002 | 4.63 (−) | 1.1e−009 | 11 | hsa-miR-138 |
| 5.7e+002-2.4e+003 | 4.18 (−) | 5.2e−010 | 168 | hsa-miR-150 |
| 2.9e+002-8.0e+002 | 2.74 (−) | 2.5e−003 | 184 | hsa-miR-203 |
| 2.9e+002-7.6e+002 | 2.62 (−) | 2.1e−006 | 16 | hsa-miR-146a |
| 1.4e+003-3.4e+003 | 2.49 (−) | 1.9e−007 | 242 | MID-16489 |
| 9.5e+002-2.3e+003 | 2.42 (−) | 2.3e−015 | 12 | hsa-miR-140-3p |
| 7.6e+002-1.8e+003 | 2.37 (−) | 5.2e−006 | 237 | MID-15684 |
| 1.1e+003-2.5e+003 | 2.23 (−) | 9.8e−005 | 243 | MID-16869 |
| 2.1e+003-4.6e+003 | 2.18 (−) | 5.9e−004 | 250 | MID-20703 |
| 2.7e+003-5.8e+003 | 2.13 (−) | 6.5e−012 | 39 | hsa-miR-22 |
| 4.3e+002-9.2e+002 | 2.13 (−) | 1.0e−003 | 253 | MID-23256 |
| 1.7e+003-3.7e+003 | 2.12 (−) | 1.4e−002 | 49 | hsa-miR-31 |
| 1.7e+003-3.6e+003 | 2.06 (−) | 1.3e−003 | 246 | MID-18422 |
| 2.1e+003-4.4e+003 | 2.04 (−) | 1.4e−007 | 167 | hsa-miR-149* |

+ the higher expression of this miR is in ovarian carcinoma
− the higher expression of this miR is in SCC, TCC and thymomas hsa-miR-205 (SEQ ID NO: 32), hsa-miR-10a (SEQ ID NO: 4) and hsa-miR-22 (SEQ ID NO: 39) are used at node 15 of the binary-tree-classifier detailed in the invention.

TABLE 17 miR expression (in florescence units) distinguishing between the group consisting of thyroid carcinoma (follicular and papillary) and the group consisting of breast adenocarcinoma, lung large cellcarcinoma, lung adenocarcinoma and ovarian carcinoma

| median values | fold-change | p-value | SEQ ID NO. | miR name |
| --- | --- | --- | --- | --- |
| 4.1e+003-1.2e+002 | 33.86 (+) | 7.4e−033 | 11 | hsa-miR-138 |
| 3.4e+004-6.7e+003 | 5.03 (+) | 1.4e−009 | 147 | hsa-miR-221 |
| 4.9e+003-1.0e+003 | 4.74 (+) | 1.0e−006 | 17 | hsa-miR-146b-5p |
| 2.2e+004-5.8e+003 | 3.71 (+) | 2.8e−027 | 157 | hsa-let-7i |
| 3.9e+004-1.1e+004 | 3.63 (+) | 7.9e−009 | 40 | hsa-miR-222 |
| 5.4e+004-1.9e+004 | 2.78 (+) | 1.5e−014 | 8 | hsa-miR-125b |
| 1.3e+003-4.9e+002 | 2.78 (+) | 5.0e−003 | 49 | hsa-miR-31 |
| 6.9e+003-2.8e+003 | 2.48 (+) | 1.3e−008 | 9 | hsa-miR-126 |
| 8.1e+002-3.4e+002 | 2.36 (+) | 4.8e−007 | 191 | hsa-miR-29c |
| 1.3e+003-5.7e+003 | 2.33 (+) | 3.8e−003 | 205 | hsa-miR-451 |
| 4.8e+002-2.2e+002 | 2.16 (+) | 1.3e−003 | 207 | hsa-miR-486-5p |
| 4.9e+002-2.3e+002 | 2.12 (+) | 8.0e−006 | 195 | hsa-miR-30a* |
| 1.4e+003-6.6e+002 | 2.11 (+) | 2.7e−011 | 51 | hsa-miR-345 |
| .5e+003-1.7e+003 | 2.10 (+) | 1.5e−006 | 46 | hsa-miR-30a |
| 6.4e+002-3.2e+002 | 1.97 (+) | 1.5e−006 | 45 | hsa-miR-29c* |
| 7.4e+003-4.0e+003 | 1.88 (+) | 3.4e−007 | 52 | hsa-miR-34a |
| 6.1e+003-3.3e+003 | 1.88 (+) | 5.9e−008 | 234 | hsa-miR-1977 |
| 7.5e+003-4.1e+003 | 1.85 (+) | 1.5e−005 | 231 | hsa-miR-99a |
| 7.6e+003-4.1e+003 | 1.85 (+) | 2.7e−004 | 21 | hsa-miR-181a |
| 1.0e+003-5.5e+002 | 1.82 (+) | 5.1e−008 | 169 | hsa-miR-152 |
| 1.1e+004-6.0e+003 | 1.79 (+) | 3.7e−008 | 43 | hsa-miR-29a |
| 5.4e+003-3.0e+003 | 1.77 (+) | 2.9e−005 | 3 | hsa-miR-100 |
| 5.9e+003-3.4e+003 | 1.73 (+) | 7.3e−007 | 196 | hsa-miR-30c |
| 2.1e+003-1.2e+003 | 1.69 (+) | 4.6e−004 | 154 | hsa-miR-181b |
| 4.4e+002-2.6e+002 | 1.66 (+) | 6.4e−003 | 390 | MID-00405 |
| 5.5e+002-3.3e+002 | 1.65 (+) | 5.3e−006 | 171 | hsa-miR-15a |
| 1.3e+003-8.1e+002 | 1.60 (+) | 6.0e−003 | 255 | MID-23794 |
| 2.3e+003-1.4e+003 | 1.57 (+) | 8.3e−007 | 197 | hsa-miR-331-3p |
| 1.8e+003-1.1e+003 | 1.57 (+) | 1.4e−005 | 190 | hsa-miR-29b |
| 3.6e+003-2.3e+003 | 1.56 (+) | 1.4e−003 | 189 | hsa-miR-27b |
| 6.6e+003-4.3e+003 | 1.52 (+) | 3.6e−005 | 39 | hsa-miR-22 |

TABLE 17-continued miR expression (in florescence units) distinguishing between the group consisting of thyroid carcinoma (follicular and papillary) and the group consisting of breast adenocarcinoma, lung large cellcarcinoma, lung adenocarcinoma and ovarian carcinoma

| median values | fold-change | p-value | SEQ ID NO. | miR name |
|---|---|---|---|---|
| 9.9e+003-6.5e+003 | 1.52 (+) | 2.2e−006 | 7 | hsa-miR-125a-5p |
| 7.8e+002-5.2e+002 | 1.51 (+) | 6.2e−006 | 48 | hsa-miR-30e |
| 4.3e+003-2.8e+003 | 1.51 (+) | 1.2e−002 | 47 | hsa-miR-30d |
| 1.0e+002-2.2e+003 | 22.05 (−) | 2.2e−005 | 32 | hsa-miR-205 |
| 2.1e+002-1.8e+003 | 8.83 (−) | 4.8e−020 | 36 | hsa-miR-210 |
| 3.2e+002-1.4e+003 | 4.34 (−) | 8.7e−011 | 4 | hsa-miR-10a |
| 4.9e+002-1.8e+003 | 3.59 (−) | 4.6e−014 | 178 | hsa-miR-193b |
| 1.0e+003-2.8e+003 | 2.74 (−) | 8.3e−006 | 37 | hsa-miR-214 |
| 2.0e+003-5.5e+003 | 2.67 (−) | 4.4e−005 | 181 | hsa-miR-199a-3p |
| 1.1e+003-2.8e+003 | 2.65 (−) | 3.1e−011 | 25 | hsa-miR-193a-3p |
| 2.7e+002-7.2e+002 | 2.63 (−) | 1.3e−004 | 183 | hsa-miR-199b-5p |
| 3.1e+002-8.1e+003 | 2.57 (−) | 1.6e−005 | 182 | hsa-miR-199a-5p |
| 5.1e+002-1.2e+003 | 2.41 (−) | 4.7e−006 | 35 | hsa-miR-21* |
| 2.0e+003-4.8e+003 | 2.39 (−) | 9.3e−003 | 240 | MID-15965 |
| 3.4e+002-8.0e+002 | 2.35 (−) | 3.0e−006 | 57 | hsa-miR-378 |
| 8.2e+002-1.9e+003 | 2.25 (−) | 1.2e−003 | 242 | MID-16489 |
| 6.0e+002-1.3e+003 | 2.18 (−) | 1.4e−011 | 204 | hsa-miR-425 |
| 3.0e+002-6.1e+002 | 2.06 (−) | 5.3e−006 | 236 | MID-00689 |
| 2.3e+002-4.5e+002 | 1.96 (−) | 2.0e−006 | 176 | hsa-miR-18a |
| 2.3e+003-4.3e+003 | 1.85 (−) | 3.5e−006 | 158 | hsa-miR-106a |
| 2.4e+003-4.4e+003 | 1.79 (−) | 1.9e−010 | 148 | hsa-miR-93 |
| 2.9e+002-5.2e+002 | 1.79 (−) | 1.9e−007 | 206 | hsa-miR-455-3p |
| 1.3e+003-2.3e+003 | 1.78 (−) | 7.8e−005 | 50 | hsa-miR-342-3p |
| 1.4e+003-2.5e+003 | 1.75 (−) | 6.0e−006 | 20 | hsa-miR-17 |
| 2.8e+004-4.8e+004 | 1.75 (−) | 5.1e−006 | 34 | hsa-miR-21 |
| 1.4e+003-2.4e+003 | 1.74 (−) | 1.1e−004 | 186 | hsa-miR-20a |
| 2.4e+002-4.1e+002 | 1.72 (−) | 8.4e−004 | 239 | MID-15907 |
| 3.0e+002-4.8e+002 | 1.62 (−) | 9.9e−003 | 251 | MID-21271 |
| 2.2e+003-3.6e+003 | 1.60 (−) | 4.3e−002 | 244 | MID-17144 |
| 3.8e+003-6.1e+003 | 1.59 (−) | 4.7e−006 | 24 | hsa-miR-191 |
| 1.0e+003-1.6e+003 | 1.59 (−) | 2.0e−005 | 188 | hsa-miR-25 |
| 2.1e+003-3.2e+003 | 1.57 (−) | 1.9e−002 | 172 | hsa-miR-15b |
| 2.6e+003-4.0e+003 | 1.56 (−) | 9.5e−003 | 238 | MID-15867 |

+ the higher expression of this miR is in thyroid carcinoma
− the higher expression of this miR is in breast adenocarcinoma, lung large cell carcinoma, lung adenocarcinoma and ovarian carcinoma FIG. 12 demonstrates binary decisions at node #16 of the decision-tree. Tumors originating in thyroid carcinoma (diamonds) are easily distinguished from tumors of adenocarcinoma of the lung, breast and ovarian origin (squares) using the expression levels of hsa-miR-93 (SEQ ID NO: 148, y-axis), hsa-miR-138 (SEQ ID NO: 11, x-axis) and hsa-miR-10a (SEQ ID NO: 4, z-axis).

TABLE 18 miR expression (in florescence units) distinguishing between follicular thyroid carcinoma and papillary thyroid carcinoma

| median values | fold-change | p-value | SEQ ID NO. | miR name |
|---|---|---|---|---|
| 6.6e+003-7.1e+002 | 9.34 (+) | 4.5e−011 | 249 | MID-20524 |
| 1.7e+003-2.2e+002 | 7.80 (+) | 1.9e−008 | 180 | hsa-miR-1973 |
| 4.5e+002-5.9e+001 | 7.58 (+) | 8.3e−005 | 65 | hsa-miR-7 |
| 2.5e+003-3.8e+002 | 6.52 (+) | 4.8e−007 | 235 | hsa-miR-1978 |
| 2.2e+003-3.6e+002 | 6.14 (+) | 1.5e−008 | 241 | MID-16318 |
| 4.2e+002-7.1e+001 | 6.00 (+) | 3.0e−004 | 248 | MID-19533 |
| 9.6e+002-1.7e+002 | 5.76 (+) | 1.6e−008 | 254 | MID-23291 |
| 9.9e+002-1.9e+002 | 5.33 (+) | 3.2e−005 | 247 | MID-19340 |
| 6.4e+002-1.2e+002 | 5.17 (+) | 6.8e−009 | 160 | hsa-miR-1248 |
| 1.5e+003-3.0e+002 | 4.97 (+) | 1.1e−006 | 243 | MID-16869 |
| 2.7e+002-6.1e+002 | 4.48 (+) | 1.4e−010 | 245 | MID-18336 |
| 5.0e+002-1.2e+002 | 4.00 (+) | 7.0e−004 | 252 | MID-22664 |
| 4.0e+002-2.5e+004 | 62.88 (−) | 6.7e−011 | 17 | hsa-miR-146b-5p |
| 4.4e+002-8.2e+003 | 18.72 (−) | 2.5e−008 | 49 | hsa-miR-31 |
| 5.0e+001-9.3e+002 | 18.69 (−) | 5.0e−012 | 166 | hsa-miR-146b-3p |
| 7.6e+001-8.3e+002 | 10.86 (−) | 4.8e−006 | 225 | hsa-miR-551b |

TABLE 18-continued miR expression (in florescence units) distinguishing between follicular thyroid carcinoma and papillary thyroid carcinoma

| median values | fold-change | p-value | SEQ ID NO. | miR name |
|---|---|---|---|---|
| 3.1e+002-3.3e+003 | 10.71 (−) | 3.2e−007 | 168 | hsa-miR-150 |
| 1.1e+004-4.7e+004 | 4.40 (−) | 3.4e−007 | 34 | hsa-miR-21 |

+ the higher expression of this miR is in follicular thyroid carcinoma
− the higher expression of this miR is in papillary thyroid carcinoma FIG. 13 demonstrates binary decisions at node #17 of the decision-tree. Tumors originating in follicular thyroid carcinoma (marked by diamonds) are easily distinguished from tumors of papillary thyroid carcinoma origins (marked by squares) using the expression levels of hsa-miR-21 (SEQ ID NO: 34, y-axis) and hsa-miR-146b-5p (SEQ ID NO: 17, x-axis).

TABLE 19 miR expression (in florescence units) distinguishing between the group consisting of breast adenocarcinoma and the group consisting of lung adenocarcinoma and ovarian carcinoma

| median values | fold-change | p-value | SEQ ID NO. | miR name |
|---|---|---|---|---|
| 6.3e+003 − 6.0e+002 | 10.55 (+) | 8.8e−005 | 32 | hsa-miR-205 |
| 1.3e+003 − 1.5e+002 | 8.43 (+) | 7.9e−006 | 56 | hsa-miR-375 |
| 5.5e+003 − 1.7e+003 | 3.17 (+) | 7.7e−012 | 50 | hsa-miR-342-3p |
| 6.6e+002 − 2.6e+002 | 2.52 (+) | 2.2e−008 | 45 | hsa-miR-29c* |
| 4.4e+002 − 2.0e+003 | 2.23 (+) | 2.2e−012 | 25 | hsa-miR-193a-3p |
| 9.5e+002 − 4.3e+002 | 2.20 (+) | 7.9e−005 | 253 | MID-23256 |
| 1.2e+003 − 5.6e+002 | 2.15 (+) | 4.9e−005 | 152 | hsa-miR-182 |
| 3.7e+003 − 1.9e+003 | 1.94 (+) | 5.3e−005 | 9 | hsa-miR-126 |
| 2.7e+003 − 1.4e+003 | 1.90 (+) | 2.9e−004 | 46 | hsa-miR-30a |
| 5.0e+002 − 2.8e+002 | 1.78 (+) | 1.1e−004 | 191 | hsa-miR-29c |
| 2.4e+003 − 1.4e+003 | 1.72 (+) | 1.5e−006 | 178 | hsa-miR-193b |
| 2.2e+002 − 1.3e+003 | 5.79 (−) | 7.7e−006 | 49 | hsa-miR-31 |
| 5.7e+003 − 1.5e+004 | 2.69 (−) | 3.0e−010 | 40 | hsa-miR-222 |
| 1.4e+003 − 3.4e+003 | 2.50 (−) | 1.6e−006 | 10 | hsa-miR-130a |
| 3.8e+003 − 9.3e+003 | 2.41 (−) | 1.2e−009 | 147 | hsa-miR-221 |
| 9.3e+002 − 2.2e+003 | 2.33 (−) | 2.2e−002 | 4 | hsa-miR-10a |
| 1.2e+003 − 2.5e+003 | 2.09 (−) | 1.5e−005 | 36 | hsa-miR-210 |
| 1.3e+003 − 2.6e+003 | 2.01 (−) | 9.9e−005 | 228 | hsa-miR-886-3p |
| 4.8e+002 − 9.4e+002 | 1.95 (−) | 4.6e−004 | 236 | MID-00689 |
| 5.3e+002 − 1.0e+003 | 1.92 (−) | 6.3e−004 | 230 | hsa-miR-886-5p |
| 1.8e+003 − 3.3e+003 | 1.86 (−) | 7.1e−005 | 189 | hsa-miR-27b |
| 3.6e+003 − 6.4e+003 | 1.79 (−) | 6.1e−003 | 240 | MID-15965 |
| 2.7e+003 − 4.7e+003 | 1.75 (−) | 3.5e−005 | 67 | hsa-miR-92a |
| 6.0e+002 − 1.0e+003 | 1.73 (−) | 3.0e−004 | 202 | hsa-miR-378 |
| 8.0e+002 − 1.4e+003 | 1.71 (−) | 2.9e−004 | 17 | hsa-miR-146b-5p |

+ the higher expression of this miR is in breast adenocarcinoma
− the higher expression of this miR is in lung adenocarcinoma and ovarian carcinoma FIG. 14 demonstrates binary decisions at node #18 of the decision-tree. Tumors originating in breast (diamonds) are easily distinguished from tumors of lung and ovarian origin (squares) using the expression levels of hsa-miR-92a (SEQ ID NO: 67, y-axis), hsa-miR-193a-3p (SEQ ID NO: 25, x-axis) and hsa-miR-31 (SEQ ID NO: 49, z-axis).

TABLE 20 miR expression (inflorescence units) distinguishing between lung adenocarcinoma and ovarian carcinoma

| median values | fold-change | p-value | SEQ ID NO. | miR name |
|---|---|---|---|---|
| 1.4e+003 − 5.2e+001 | 27.96 (+) | 3.5e−008 | 56 | hsa-miR-375 |
| 5.5e+002 − 6.0e+001 | 9.19 (+) | 8.1e−009 | 11 | hsa-miR-138 |
| 3.2e+003 − 5.7e+002 | 5.65 (+) | 5.6e−004 | 168 | hsa-miR-150 |

TABLE 20-continued miR expression (inflorescence units) distinguishing between lung adenocarcinoma and ovarian carcinoma

| median values | fold-change | p-value | SEQ ID NO. | miR name |
|---|---|---|---|---|
| 9.7e+002 – 2.9e+002 | 3.35 (+) | 2.2e–004 | 16 | hsa-miR-146a |
| 2.3e+003 – 7.6e+002 | 2.96 (+) | 3.2e–003 | 237 | MID-15684 |
| 8.4e+003 – 2.9e+003 | 2.88 (+) | 1.7e–010 | 21 | hsa-miR-181a |
| 7.0e+003 – 2.6e+003 | 2.69 (+) | 9.2e–008 | 52 | hsa-miR-34a |
| 2.4e+003 – 9.5e+002 | 2.58 (+) | 3.2e–007 | 12 | hsa-miR-140-3p |
| 2.1e+003 – 8.8e+002 | 2.39 (+) | 2.1e–007 | 154 | hsa-miR-18 lb |
| 1.4e+005 – 6.3e+004 | 2.28 (+) | 1.9e–003 | 279 | hsa-miR-1826 |
| 3.2e+003 – 1.4e+003 | 2.25 (+) | 6.1e–003 | 9 | hsa-miR-126 |
| 6.1e+003 – 2.7e+003 | 2.24 (+) | 2.3e–006 | 39 | hsa-miR-22 |
| 4.2e+003 – 2.2e+003 | 1.93 (+) | 8.9e–005 | 47 | hsa-miR-30d |
| 1.9e+003 – 1.0e+003 | 1.90 (+) | 3.5e–006 | 23 | hsa-miR-185 |
| 2.8e+003 – 1.5e+003 | 1.88 (+) | 1.4e–003 | 50 | hsa-miR-342-3p |
| 3.6e+003 – 2.1e+003 | 1.69 (+) | 1.8e–002 | 167 | hsa-miR-149* |
| 9.7e+002 – 5.9e+002 | 1.66 (+) | 8.7e–005 | 383 | MID-22912 |
| 6.8e+004 – 4.2e+004 | 1.64 (+) | 5.4e–004 | 34 | hsa-miR-21 |
| 1.8e+003 – 1.2e+003 | 1.55 (+) | 5.1e–004 | 35 | hsa-miR-21* |
| 1.4e+003 – 8.9e+002 | 1.54 (+) | 1.7e–004 | 388 | hsa-miR-423-5p |
| 4.4e+002 – 2.4e+003 | 5.38 (–) | 1.0e–007 | 5 | hsa-miR-10b |
| 1.9e+002 – 7.2e+002 | 3.77 (–) | 3.3e–006 | 359 | hsa-miR-708 |
| 6.4e+002 – 2.1e+003 | 3.27 (–) | 5.8e–003 | 245 | MID-18336 |
| 1.8e+002 – 5.4e+002 | 2.96 (–) | 6.6e–003 | 254 | MID-23291 |
| 1.7e+003 – 5.1e+003 | 2.95 (–) | 3.4e–005 | 10 | hsa-miR-130a |
| 2.8e+003 – 8.1e+003 | 2.86 (–) | 3.7e–003 | 240 | MID-15965 |
| 5.1e+002 – 1.3e+003 | 2.65 (–) | 3.7e–004 | 236 | MID-00689 |
| 6.1e+002 – 1.6e+003 | 2.63 (–) | 1.8e–004 | 202 | hsa-miR-378 |
| 1.3e+003 – 3.1e+003 | 2.39 (–) | 1.2e–002 | 4 | hsa-miR-10a |
| 1.0e+003 – 2.3e+003 | 2.30 (–) | 1.8e–006 | 25 | hsa-miR-193a-3p |
| 2.6e+002 – 5.6e+002 | 2.15 (–) | 4.1e–004 | 203 | hsa-miR-422a |
| 3.0e+003 – 6.1e+003 | 2.04 (–) | 1.8e–002 | 231 | hsa-miR-99a |
| 2.0e+003 – 3.9e+003 | 2.01 (–) | 3.5e–005 | 20 | hsa-miR-17 |
| 3.3e+003 – 6.4e+003 | 1.96 (–) | 3.5e–005 | 158 | hsa-miR-106a |
| 1.8e+003 – 3.5e+003 | 1.88 (–) | 3.1e–005 | 186 | hsa-miR-20a |
| 3.2e+003 – 5.9e+003 | 1.85 (–) | 1.2e–004 | 258 | hsa-let-7f |
| 2.4e+003 – 4.4e+003 | 1.85 (–) | 2.0e–003 | 244 | MID-17144 |
| 2.0e+003 – 3.5e+003 | 1.72 (–) | 8.7e–004 | 172 | hsa-miR-15b |
| 5.2e+003 – 8.8e+003 | 1.69 (–) | 5.3e–004 | 2 | hsa-let-7e |
| 4.1e+002 – 6.8e+002 | 1.66 (–) | 1.2e–002 | 235 | hsa-miR-1978 |
| 3.3e+004 – 5.4e+004 | 1.66 (–) | 3.3e–005 | 256 | hsa-let-7a |
| 2.8e+003 – 4.7e+003 | 1.65 (–) | 3.5e–003 | 28 | hsa-miR-200a |
| 5.2e+002 – 8.5e+002 | 1.62 (–) | 1.6e–004 | 277 | hsa-miR-17* |
| 3.7e+002 – 5.8e+002 | 1.57 (–) | 1.9e–003 | 296 | hsa-miR-26b |
| 1.0e+005 – 1.6e+005 | 1.56 (–) | 3.7e–002 | 374 | MID-16748 |
| 6.0e+003 – 9.1e+003 | 1.53 (–) | 2.1e–005 | 153 | hsa-let-7d |
| 3.8e+003 – 5.7e+003 | 1.50 (–) | 4.1e–003 | 181 | hsa-miR-199a-3p |

+ the higher expression of this miR is in lung adenocarcinoma
– the higher expression of this miR is in ovarian carcinoma FIG. 15 demonstrates binary decisions at node #19 of the decision-tree. Tumors originating in lung adenocarcinoma (diamonds) are easily distinguished from tumors of ovarian carcinoma origin (squares) using the expression levels of hsa-miR-21 (SEQ ID NO: 34, y-axis), hsa-miR-378 (SEQ ID NO: 202, x-axis) and hsa-miR-138 (SEQ ID NO: 11, z-axis).

TABLE 21 miR expression (in florescence units) distinguishing between the group consisting of thymic carcinoma and the group consisting of TCC and SCC

| median values | fold-change | p-value | SEQ ID NO | miR name |
|---|---|---|---|---|
| 5.3e+002 – 5.9e+001 | 9.00 (+) | 5.7e–026 | 161 | hsa-miR-128 |
| 7.4e+002 – 9.2e+001 | 8.04 (+) | 2.2e–007 | 164 | hsa-miR-142-5p |
| 6.8e+002 – 8.8e+001 | 7.82 (+) | 2.6e–021 | 22 | hsa-miR-181a* |
| 7.1e+002 – 1.2e+002 | 6.09 (+) | 1.2e–006 | 53 | hsa-miR-34c-5p |
| 9.1e+002 – 1.8e+002 | 5.06 (+) | 2.2e–008 | 285 | hsa-miR-20b |
| 1.3e+004 – 2.8e+003 | 4.59 (+) | 7.5e–014 | 3 | hsa-miR-100 |
| 1.6e+003 – 3.6e+002 | 4.39 (+) | 7.1e–007 | 152 | hsa-miR-182 |
| 8.7e+002 – 2.0e+002 | 4.37 (+) | 6.4e–010 | 191 | hsa-miR-29c |

TABLE 21-continued miR expression (in florescence units) distinguishing between the group consisting of thymic carcinoma and the group consisting of TCC and SCC

| median values | fold-change | p-value | SEQ ID NO | miR name |
|---|---|---|---|---|
| 3.7e+003 – 9.1e+002 | 4.09 (+) | 2.6e–014 | 154 | hsa-miR-181b |
| 1.5e+004 – 3.8e+003 | 3.82 (+) | 4.8e–009 | 21 | hsa-miR-181a |
| 2.1e+003 – 6.4e+002 | 3.25 (+) | 6.4e–006 | 206 | hsa-miR-455-3p |
| 8.7e+002 – 2.7e+002 | 3.23 (+) | 1.5e–010 | 174 | hsa-miR-181d |
| 9.4e+002 – 2.9e+002 | 3.23 (+) | 1.9e–004 | 19 | hsa-miR-149 |
| 7.3e+002 – 2.6e+002 | 2.80 (+) | 2.5e–008 | 45 | hsa-miR-29c* |
| 8.7e+002 – 3.2e+002 | 2.69 (+) | 2.2e–007 | 171 | hsa-miR-15a |
| 2.7e+003 – 1.0e+003 | 2.66 (+) | 5.1e–005 | 179 | hsa-miR-195 |
| 4.4e+004 – 1.8e+004 | 2.46 (+) | 8.2e–008 | 8 | hsa-miR-125b |
| 7.3e+002 – 3.2e+002 | 2.26 (+) | 2.8e–004 | 296 | hsa-miR-26b |
| 2.7e+002 – 1.2e+002 | 2.22 (+) | 2.4e–003 | 284 | hsa-miR-19b |
| 5.7e+002 – 2.6e+002 | 2.17 (+) | 7.8e–005 | 18 | hsa-miR-148a |
| 9.1e+002 – 4.4e+002 | 2.06 (+) | 1.4e–006 | 51 | hsa-miR-345 |
| 7.5e+003 – 3.8e+003 | 2.00 (+) | 1.6e–002 | 258 | hsa-let-7f |
| 1.8e+002 – 4.4e+003 | 24.66 (–) | 3.9e–008 | 49 | hsa-miR-31 |
| 5.8e+001 – 1.0e+003 | 17.65 (–) | 1.0e–007 | 184 | hsa-miR-203 |
| 2.2e+002 – 1.6e+003 | 7.43 (–) | 4.5e–018 | 35 | hsa-miR-21* |
| 1.1e+004 – 5.5e+004 | 4.97 (–) | 1.5e–032 | 34 | hsa-miR-21 |
| 6.2e+002 – 2.5e+003 | 4.06 (–) | 2.0e–008 | 37 | hsa-miR-214 |
| 1.6e+002 – 5.8e+002 | 3.69 (–) | 6.3e–005 | 42 | hsa-miR-224 |
| 6.9e+002 – 2.5e+003 | 3.58 (–) | 2.3e–009 | 228 | hsa-miR-886-3p |
| 4.8e+003 – 1.7e+004 | 3.47 (–) | 3.9e–009 | 15 | hsa-miR-145 |
| 2.7e+003 – 8.2e+003 | 3.08 (–) | 2.7e–008 | 14 | hsa-miR-143 |
| 1.3e+003 – 3.7e+003 | 2.93 (–) | 6.7e–005 | 242 | MID-16489 |
| 2.5e+002 – 7.4e+002 | 2.91 (–) | 4.3e–006 | 230 | hsa-miR-886-5p |
| 3.5e+002 – 1.0e+003 | 2.90 (–) | 5.6e–004 | 253 | MID-23256 |
| 1.1e+003 – 3.0e+003 | 2.82 (–) | 7.9e–006 | 36 | hsa-miR-210 |
| 2.2e+003 – 5.8e+003 | 2.63 (–) | 1.2e–007 | 182 | hsa-miR-199a-5p |
| 5.0e+003 – 1.2e+004 | 2.48 (–) | 3.8e–006 | 293 | hsa-miR-23b |
| 7.5e+003 – 1.8e+004 | 2.44 (–) | 1.1e–008 | 292 | hsa-miR-23a |
| 2.7e+002 – 6.6e+002 | 2.43 (–) | 5.4e–003 | 4 | hsa-miR-10a |
| 9.0e+002 – 2.2e+003 | 2.43 (–) | 5.5e–015 | 294 | hsa-miR-24 |
| 3.8e+003 – 8.8e+003 | 2.35 (–) | 3.0e–004 | 297 | hsa-miR-27a |
| 2.3e+002 – 5.2e+002 | 2.28 (–) | 1.6e–002 | 354 | hsa-miR-612 |
| 1.8e+003 – 3.9e+003 | 2.22 (–) | 1.1e–006 | 377 | MID-17866 |
| 1.6e+003 – 3.3e+003 | 2.11 (–) | 2.4e–004 | 189 | hsa-miR-27b |
| 6.9e+003 – 1.4e+004 | 2.08 (–) | 1.5e–004 | 30 | hsa-miR-200c |
| 3.8e+004 – 7.9e+004 | 2.05 (–) | 1.8e–008 | 386 | MID-23178 |
| 1.5e+003 – 3.1e+003 | 2.04 (–) | 2.0e–002 | 249 | MID-20524 |
| 4.6e+002 – 9.3e+002 | 2.03 (–) | 5.6e–002 | 5 | hsa-miR-10b |
| 2.5e+002 – 5.0e+002 | 2.03 (–) | 3.2e–005 | 274 | hsa-miR-151-3p |

+ the higher expression of this miR is in thymic carcinoma
– the higher expression of this miR is in TCC and SCC FIG. 16 demonstrates binary decisions at node #20 of the decision-tree. Tumors originating in thymic carcinoma (marked by diamonds) are easily distinguished from tumors of urothelial carcinoma, transitional cell carcinoma (TCC) carcinoma and squamous cell carcinoma (SCC) origins (marked by squares) using the expression levels of hsa-miR-21 (SEQ ID NO: 34, y-axis) and hsa-miR-100 (SEQ ID NO: 3, x-axis).

TABLE 22 miR expression (in florescence units) distinguishing between TCC and SCC (of anus, skin, lung, head & neck, esophagus or uterine cervix)

| median values | fold-change | p-value | SEQ ID NO | miR name |
|---|---|---|---|---|
| 2.5e+002 – 5.0e+001 | 5.05 (+) | 7.4e–036 | 69 | hsa-miR-934 |
| 9.1e+003 – 2.2e+003 | 4.14 (+) | 1.2e–012 | 28 | hsa-miR-200a |
| 2.1e+002 – 5.3e+001 | 3.87 (+) | 8.4e–007 | 280 | hsa-miR-187 |
| 6.0e+003 – 1.9e+003 | 3.19 (+) | 9.8e–008 | 13 | hsa-miR-141 |
| 5.6e+002 – 1.8e+002 | 3.15 (+) | 4.7e–013 | 191 | hsa-miR-29c |
| 9.4e+002 – 3.0e+002 | 3.13 (+) | 8.1e–008 | 152 | hsa-miR-182 |
| 1.8e+004 – 6.2e+003 | 2.99 (+) | 3.9e–010 | 29 | hsa-miR-200b |
| 3.2e+002 – 1.1e+002 | 2.81 (+) | 8.8e–009 | 175 | hsa-miR-183 |

TABLE 22-continued miR expression (in florescence units) distinguishing between TCC and SCC (of anus, skin, lung, head & neck, esophagus or uterine cervix)

| median values | fold-change | p-value | SEQ ID NO | miR name |
|---|---|---|---|---|
| 3.1e+004 – 1.2e+004 | 2.65 (+) | 8.1e-005 | 30 | hsa-miR-200c |
| 2.1e+003 – 8.1e+002 | 2.63 (+) | 6.2e-020 | 204 | hsa-miR-425 |
| 1.2e+003 – 4.8e+002 | 2.41 (+) | 6.3e-007 | 4 | hsa-miR-10a |
| 8.5e+003 – 3.7e+003 | 2.30 (+) | 2.4e-024 | 24 | hsa-miR-191 |
| 1.8e+003 – 8.4e+002 | 2.14 (+) | 2.7e-006 | 5 | hsa-miR-10b |
| 3.5e+002 – 1.7e+002 | 2.09 (+) | 2.0e-006 | 329 | hsa-miR-425* |
| 3.4e+002 – 1.6e+002 | 2.08 (+) | 8.0e-005 | 273 | hsa-miR-148b |
| 3.1e+002 – 8.1e+002 | 2.60 (–) | 1.6e-005 | 170 | hsa-miR-155 |
| 5.0e+002 – 1.2e+003 | 2.49 (–) | 1.0e-002 | 184 | hsa-miR-203 |
| 1.5e+002 – 3.5e+002 | 2.39 (–) | 3.0e-011 | 26 | hsa-miR-193a-5p |
| 1.9e+003 – 4.5e+003 | 2.35 (–) | 1.3e-008 | 231 | hsa-miR-99a |
| 1.2e+002 – 2.7e+002 | 2.28 (–) | 1.6e-003 | 368 | MID-00672 |
| 1.4e+003 – 3.2e+003 | 2.25 (–) | 1.3e-005 | 37 | hsa-miR-214 |
| 3.9e+002 – 8.7e+002 | 2.23 (–) | 1.5e-004 | 16 | hsa-miR-146a |
| 3.5e+002 – 7.6e+002 | 2.15 (–) | 4.2e-005 | 169 | hsa-miR-152 |
| 1.5e+002 – 3.3e+002 | 2.15 (–) | 4.4e-004 | 155 | hsa-miR-127-3p |
| 8.4e+002 – 1.7e+003 | 2.08 (–) | 1.6e-005 | 35 | hsa-miR-21* |
| 7.7e+003 – 1.6e+004 | 2.07 (–) | 5.3e-012 | 40 | hsa-miR-222 |
| 4.4e+002 – 9.0e+002 | 2.06 (–) | 1.5e-005 | 17 | hsa-miR-146b-5p |

+ the higher expression of this miR is in TCC
– the higher expression of this miR is in SCC hsa-miR-934 (SEQ ID NO: 69), hsa-miR-191 (SEQ ID NO: 24) and hsa-miR-29c (SEQ ID NO: 191) are used at node #21 of the binary-tree-classifier detailed in the invention to distinguish between TCC and SCC.

TABLE 23 miR expression (in florescence units) distinguishing between SCC of the uterine cervix and other SCC tumors (anus, skin, lung, head & neck or esophagus)

| median values | auROC | fold-change | p-value | SEQ ID NO | miR name |
|---|---|---|---|---|---|
| 2.4e+002 – 9.2e+001 | 0.65 | 2.57 (+) | 2.0e-002 | 164 | hsa-miR-142-5p |
| 1.6e+003 – 7.6e+002 | 0.85 | 2.13 (+) | 1.7e-005 | 5 | hsa-miR-10b |
| 8.9e+003 – 4.4e+003 | 0.74 | 2.01 (+) | 2.1e-004 | 231 | hsa-miR-99a |
| 1.2e+003 – 9.8e+002 | 0.71 | 1.24 (+) | 1.2e-002 | 54 | hsa-miR-361-5p |
| 3.4e+004 – 2.7e+004 | 0.71 | 1.24 (+) | 3.9e-004 | 1 | hsa-let-7c |
| 1.3e+003 – 4.3e+003 | 0.81 | 3.39 (–) | 9.9e-006 | 242 | MID-16489 |
| 3.9e+002 – 1.2e+003 | 0.74 | 3.10 (–) | 2.1e-003 | 372 | MID-16469 |
| 1.1e+003 – 3.3e+003 | 0.84 | 3.09 (–) | 1.3e-008 | 249 | MID-20524 |
| 1.7e+003 – 5.2e+003 | 0.78 | 3.01 (–) | 2.4e-005 | 167 | hsa-miR-149* |
| 2.7e+002 – 8.0e+002 | 0.79 | 2.97 (–) | 1.4e-004 | 254 | MID-23291 |
| 2.2e+002 – 6.2e+002 | 0.76 | 2.77 (–) | 1.7e-004 | 354 | hsa-miR-612 |
| 5.7e+002 – 1.5e+003 | 0.76 | 2.65 (–) | 7.8e-006 | 381 | MID-19962 |
| 2.3e+002 – 6.0e+002 | 0.79 | 2.63 (–) | 2.1e-005 | 380 | MID-19898 |
| 9.8e+002 – 2.4e+003 | 0.78 | 2.44 (–) | 2.8e-005 | 245 | MID-18336 |
| 1.2e+002 – 2.8e+002 | 0.73 | 2.34 (–) | 5.3e-003 | 358 | hsa-miR-665 |
| 6.1e+002 – 1.4e+003 | 0.70 | 2.31 (–) | 6.1e-003 | 364 | MID-00064 |
| 2.9e+003 – 6.7e+003 | 0.81 | 2.30 (–) | 8.8e-008 | 240 | MID-15965 |
| 1.2e+002 – 2.8e+002 | 0.66 | 2.26 (–) | 1.5e-002 | 11 | hsa-miR-138 |
| 1.0e+002 – 2.3e+002 | 0.77 | 2.24 (–) | 8.9e-005 | 378 | MID-18307 |

+ the higher expression of this miR is in SCC of the uterine cervix
– the higher expression of this miR is in other SCC tumors FIG. 17 demonstrates binary decisions at node #22 of the decision-tree. Tumors originating in SCC of the uterine cervix (diamonds) are easily distinguished from tumors of other SCC origin (squares) using the expression levels of hsa-miR-361-5p (SEQ ID NO: 54, y-axis), hsa-let-7c (SEQ ID NO: 1, x-axis) and hsa-miR-10b (SEQ ID NO: 5, z-axis).

TABLE 24 miR expression (in florescence units) distinguishing between anus or skin SCC and upper SCC tumors (lung, head & neck or esophagus)

| median values | auROC | fold-change | p-value | SEQ ID NO | miR name |
|---|---|---|---|---|---|
| 3.2e+002 – 5.0e+001 | 0.78 | 6.38 (+) | 3.0e-006 | 305 | hsa-miR-31* |
| 4.3e+003 – 8.0e+002 | 0.80 | 5.39 (+) | 1.8e-006 | 184 | hsa-miR-203 |
| 8.6e+002 – 2.5e+002 | 0.78 | 3.49 (+) | 1.8e-006 | 41 | hsa-miR-223 |
| 1.7e+003 – 5.4e+002 | 0.80 | 3.12 (+) | 3.5e-006 | 183 | hsa-miR-199b-5p |
| 9.4e+003 – 3.5e+003 | 0.70 | 2.73 (+) | 2.4e-003 | 49 | hsa-miR-31 |
| 8.7e+003 – 3.2e+003 | 0.86 | 2.71 (+) | 3.6e-007 | 382 | MID-22331 |
| 1.9e+003 – 7.1e+002 | 0.87 | 2.68 (+) | 1.7e-008 | 235 | hsa-miR-1978 |
| 2.4e+002 – 9.2e+001 | 0.83 | 2.55 (+) | 9.6e-009 | 291 | hsa-miR-222* |
| 6.8e+003 – 2.9e+003 | 0.74 | 2.31 (+) | 7.4e-004 | 181 | hsa-miR-199a-3p |
| 1.5e+003 – 6.7e+002 | 0.88 | 2.28 (+) | 7.1e-007 | 5 | hsa-miR-10b |
| 5.3e+002 – 2.4e+002 | 0.75 | 2.21 (+) | 1.4e-004 | 296 | hsa-miR-26b |
| 3.4e+002 – 1.6e+002 | 0.74 | 2.19 (+) | 7.7e-005 | 289 | hsa-miR-22* |
| 1.3e+003 – 6.0e+002 | 0.71 | 2.13 (+) | 1.2e-003 | 206 | hsa-miR-455-3p |
| 7.9e+003 – 3.8e+003 | 0.84 | 2.11 (+) | 4.2e-006 | 338 | hsa-miR-494 |
| 2.9e+002 – 1.4e+002 | 0.73 | 2.08 (+) | 1.1e-004 | 334 | hsa-miR-483-5p |
| 2.8e+003 – 1.3e+003 | 0.82 | 2.07 (+) | 4.5e-006 | 25 | hsa-miR-193a-3p |
| 1.1e+002 – 3.3e+002 | 0.77 | 3.03 (–) | 2.3e-005 | 11 | hsa-miR-138 |
| 1.3e+002 – 3.1e+002 | 0.65 | 2.29 (–) | 1.5e-002 | 19 | hsa-miR-149 |
| 9.7e+001 – 2.1e+002 | 0.75 | 2.16 (–) | 4.0e-005 | 198 | hsa-miR-342-5p |
| 1.1e+003 – 1.8e+003 | 0.83 | 1.63 (–) | 1.1e-006 | 23 | hsa-miR-185 |

+ the higher expression of this miR is in anus or skin SCC
– the higher expression of this miR is in upper SCC tumors hsa-miR-10b (SEQ ID NO: 5), hsa-miR-138 (SEQ ID NO: 11) and hsa-miR-185 (SEQ ID NO: 23) are used at node 23 of the binary-tree-classifier detailed in the invention to distinguish between anus or skin SCC and upper SCC tumors.

TABLE 25 miR expression (in florescence units) distinguishing between melanoma and lymphoma (B-cell or T-cell) tumors

| median values | auROC | fold-change | p-value | SEQ ID NO | miR name |
|---|---|---|---|---|---|
| 1.7e+003 – 3.0e+002 | 0.89 | 5.81 (+) | 2.8e-010 | 4 | hsa-miR-10a |
| 1.9e+003 – 6.0e+002 | 0.80 | 3.13 (+) | 7.9e-005 | 11 | hsa-miR-138 |
| 1.7e+003 – 5.7e+002 | 0.94 | 2.98 (+) | 2.3e-011 | 46 | hsa-miR-30a |
| 2.5e+004 – 8.8e+003 | 0.87 | 2.83 (+) | 1.1e-009 | 8 | hsa-miR-125b |
| 6.2e+002 – 2.3e+002 | 0.94 | 2.74 (+) | 9.2e-011 | 274 | hsa-miR-151-3p |
| 9.2e+002 – 3.4e+002 | 0.87 | 2.70 (+) | 1.9e-007 | 169 | hsa-miR-152 |
| 1.6e+002 – 6.0e+001 | 0.77 | 2.60 (+) | 2.0e-004 | 36 | hsa-miR-210 |
| 4.8e+003 – 1.9e+003 | 0.90 | 2.56 (+) | 2.1e-011 | 47 | hsa-miR-30d |
| 1.2e+003 – 5.5e+002 | 0.88 | 2.26 (+) | 2.5e-008 | 363 | hsa-miR-99b |
| 2.4e+003 – 1.1e+003 | 0.85 | 2.24 (+) | 1.4e-006 | 231 | hsa-miR-99a |
| 6.5e+002 – 3.0e+002 | 0.80 | 2.17 (+) | 2.2e-005 | 303 | hsa-miR-30b |
| 6.4e+002 – 3.0e+002 | 0.86 | 2.14 (+) | 2.9e-008 | 349 | hsa-miR-532-5p |
| 2.1e+002 – 1.0e+002 | 0.86 | 2.08 (+) | 1.6e-006 | 10 | hsa-miR-130a |
| 5.4e+003 – 2.6e+003 | 0.81 | 2.06 (+) | 8.3e-006 | 7 | hsa-miR-125a-5p |
| 3.6e+003 – 1.8e+003 | 0.82 | 2.05 (+) | 2.5e-006 | 3 | hsa-miR-100 |
| 7.9e+003 – 3.9e+003 | 0.69 | 2.04 (+) | 1.5e-002 | 16 | hsa-miR-146a |
| 1.6e+002 – 2.2e+003 | 0.93 | 13.84 (–) | 1.1e-014 | 164 | hsa-miR-142-5p |
| 7.2e+002 – 7.5e+003 | 0.93 | 10.40 (–) | 1.1e-013 | 170 | hsa-miR-155 |
| 2.0e+003 – 1.4e+004 | 0.90 | 7.18 (–) | 2.2e-010 | 168 | hsa-miR-150 |
| 1.7e+002 – 7.0e+002 | 0.91 | 4.14 (–) | 5.2e-011 | 198 | hsa-miR-342-5p |
| 2.2e+003 – 8.3e+003 | 0.97 | 3.83 (–) | 6.2e-019 | 50 | hsa-miR-342-3p |

TABLE 25-continued miR expression (in florescence units) distinguishing between melanoma and lymphoma (B-cell or T-cell) tumors

| median values | au-ROC | fold-change | p-value | SEQ ID NO. | miR name |
|---|---|---|---|---|---|
| 9.1e+002 – 2.6e+003 | 0.86 | 2.87 (−) | 1.3e−008 | 245 | MID-18336 |
| 2.3e+002 – 6.4e+002 | 0.77 | 2.74 (−) | 2.4e−004 | 365 | MID-00078 |
| 1.9e+002 – 5.2e+002 | 0.78 | 2.68 (−) | 4.7e−004 | 45 | hsa-miR-29c* |
| 2.8e+003 – 6.6e+003 | 0.74 | 2.34 (−) | 1.6e−003 | 382 | MID-22331 |
| 3.4e+003 – 7.9e+003 | 0.85 | 2.30 (−) | 1.2e−004 | 259 | hsa-let-7g |
| 3.8e+002 – 8.5e+002 | 0.75 | 2.25 (−) | 4.3e−003 | 296 | hsa-miR-26b |
| 7.5e+002 – 1.6e+003 | 0.78 | 2.16 (−) | 2.3e−004 | 364 | MID-00064 |
| 6.3e+002 – 1.3e+003 | 0.79 | 2.08 (−) | 7.9e−005 | 314 | hsa-miR-361-3p |
| 2.7e+003 – 5.4e+003 | 0.80 | 2.05 (−) | 7.5e−007 | 12 | hsa-miR-140-3p |

+ the higher expression of this miR is in melanoma
− the higher expression of this miR is in lymphoma FIG. 18 demonstrates binary decisions at node #24 of the decision-tree. Tumors originating in melanoma (diamonds) are easily distinguished from tumors of lymphoma origin (squares) using the expression levels of hsa-miR-342-3p (SEQ ID NO: 50, y-axis) and hsa-miR-30d (SEQ ID NO: 47, x-axis).

TABLE 26 miR expression (in florescence units) distinguishing between B-cell lymphoma and T-cell lymphoma

| median values | auROC | fold-change | p-value | SEQ ID NO. | miR name |
|---|---|---|---|---|---|
| 8.3e+002 – 2.8e+002 | 0.74 | 2.96 (+) | 3.7e−005 | 11 | hsa-miR-138 |
| 6.7e+002 – 2.8e+002 | 0.72 | 2.37 (+) | 2.2e−003 | 191 | hsa-miR-29c |
| 1.2e+003 – 5.9e+002 | 0.76 | 2.02 (+) | 1.4e−003 | 48 | hsa-miR-30e |
| 6.7e+002 – 1.8e+003 | 0.79 | 2.77 (−) | 1.1e−006 | 35 | hsa-miR-21* |
| 1.5e+003 – 3.9e+003 | 0.68 | 2.68 (−) | 2.6e−003 | 228 | hsa-miR-886-3p |

+ the higher expression of this miR is in B-cell lymphoma
− the higher expression of this miR is in T-cell lymphoma hsa-miR-30e (SEQ ID NO: 48) and hsa-miR-21* (SEQ ID NO: 35) are used at node 25 of the binary-tree-classifier detailed in the invention to distinguish between B-cell lymphoma and T-cell lymphoma.

TABLE 27 miR expression (in florescence units) distinguishing between lung small cell carcinoma and other neuroendocrine tumors selected from the group consisting of lung carcinoid, medullary thyroid carcinoma, gastrointestinal tract carcinoid and pancreatic islet cell tumor

| median values | au-ROC | fold-change | p-value | SEQ ID NO. | miR name |
|---|---|---|---|---|---|
| 1.2e+004 – 1.2e+003 | 0.99 | 9.68 (+) | 3.3e−021 | 158 | hsa-miR-106a |
| 7.3e+003 – 7.9e+002 | 1.00 | 9.17 (+) | 3.4e−022 | 20 | hsa-miR-17 |
| 1.4e+003 – 1.6e+002 | 0.99 | 8.53 (+) | 8.2e−022 | 176 | hsa-miR-18a |
| 5.8e+003 – 7.0e+002 | 1.00 | 8.38 (+) | 7.4e−021 | 186 | hsa-miR-20a |
| 1.1e+004 – 1.5e+003 | 0.98 | 7.71 (+) | 1.7e−022 | 148 | hsa-miR-93 |
| 4.7e+003 – 6.7e+002 | 0.89 | 6.99 (+) | 1.0e−008 | 36 | hsa-miR-210 |
| 2.2e+003 – 3.7e+002 | 0.95 | 5.87 (+) | 2.8e−016 | 51 | hsa-miR-345 |
| 8.9e+003 – 1.8e+003 | 0.95 | 4.96 (+) | 1.6e−010 | 172 | hsa-miR-15b |
| 8.2e+003 – 1.8e+003 | 0.98 | 4.68 (+) | 6.3e−020 | 260 | hsa-miR-106b |
| 1.e+003 – 2.4e+002 | 0.91 | 4.62 (+) | 7.7e−010 | 265 | hsa-miR-130b |
| 8.0e+003 – 1.8e+003 | 0.94 | 4.33 (+) | 2.7e−013 | 67 | hsa-miR-92a |
| 4.1e+003 – 9.8e+002 | 0.98 | 4.15 (+) | 2.6e−019 | 188 | hsa-miR-25 |
| 1.1e+003 – 3.4e+002 | 0.98 | 3.40 (+) | 7.9e−016 | 277 | hsa-miR-17* |

TABLE 27-continued miR expression (in florescence units) distinguishing between lung small cell carcinoma and other neuroendocrine tumors selected from the group consisting of lung carcinoid, medullary thyroid carcinoma, gastrointestinal tract carcinoid and pancreatic islet cell tumor

| median values | au-ROC | fold-change | p-value | SEQ ID NO. | miR name |
|---|---|---|---|---|---|
| 2.5e+003 – 8.3e+002 | 0.99 | 2.96 (+) | 1.8e−011 | 284 | hsa-miR-19b |
| 5.1e+002 – 1.8e+002 | 0.74 | 2.84 (+) | 6.1e−004 | 302 | hsa-miR-301a |
| 7.9e+002 – 2.9e+002 | 0.91 | 2.78 (+) | 8.7e−010 | 68 | hsa-miR-92b |
| 9.9e+002 – 4.3e+002 | 0.69 | 2.28 (+) | 5.1e−002 | 168 | hsa-miR-150 |
| 2.5e+003 – 1.1e+003 | 0.70 | 2.24 (+) | 4.5e−003 | 242 | MID-16489 |
| 1.4e+003 – 6.6e+002 | 0.91 | 2.12 (+) | 1.1e−009 | 204 | hsa-miR-425 |
| 5.0e+001 – 1.6e+003 | 0.91 | 31.23 (−) | 4.5e−009 | 162 | hsa-miR-129-3p |
| 1.1e+002 – 1.6e+003 | 0.91 | 14.13 (−) | 8.6e−009 | 177 | hsa-miR-192 |
| 7.6e+001 – 7.9e+002 | 0.91 | 10.42 (−) | 1.5e−008 | 27 | hsa-miR-194 |
| 5.5e+002 – 5.0e+003 | 0.92 | 9.14 (−) | 1.7e−009 | 65 | hsa-miR-7 |
| 7.1e+001 – 5.7e+002 | 0.78 | 8.02 (−) | 5.8e−005 | 263 | hsa-miR-129* |
| 2.5e+002 – 1.6e+003 | 0.80 | 6.30 (−) | 3.5e−005 | 155 | hsa-miR-127-3p |
| 1.5e+002 – 9.1e+002 | 0.96 | 6.05 (−) | 3.5e−015 | 191 | hsa-miR-29c |
| 3.3e+002 – 2.0e+003 | 0.93 | 5.99 (−) | 3.3e−013 | 190 | hsa-miR-29b |
| 1.7e+002 – 9.9e+002 | 0.99 | 5.76 (−) | 1.3e−020 | 45 | hsa-miR-29c* |
| 1.2e+002 – 6.6e+002 | 0.75 | 5.60 (−) | 8.0e−004 | 59 | hsa-miR-487b |
| 1.8e+003 – 8.0e+003 | 0.90 | 4.44 (−) | 1.6e−012 | 43 | hsa-miR-29a |
| 1.3e+004 – 4.9e+004 | 0.88 | 3.87 (−) | 3.3e−006 | 56 | hsa-miR-375 |
| 1.6e+002 – 5.5e+002 | 0.95 | 3.37 (−) | 9.6e−011 | 266 | hsa-miR-132 |
| 4.0e+003 – 1.2e+004 | 0.82 | 2.98 (−) | 9.4e−006 | 14 | hsa-miR-143 |
| 7.8e+003 – 2.3e+004 | 0.85 | 2.89 (−) | 6.1e−006 | 15 | hsa-miR-145 |
| 1.2e+004 – 3.4e+004 | 0.79 | 2.83 (−) | 4.3e−005 | 8 | hsa-miR-125b |
| 4.5e+003 – 1.2e+004 | 0.97 | 2.70 (−) | 1.7e−014 | 7 | hsa-miR-125a-5p |
| 1.9e+003 – 5.0e+003 | 0.89 | 2.67 (−) | 3.6e−010 | 39 | hsa-miR-22 |
| 2.5e+003 – 5.7e+003 | 0.79 | 2.25 (−) | 8.7e−004 | 189 | hsa-miR-27b |
| 1.1e+003 – 2.4e+003 | 0.64 | 2.18 (−) | 4.1e−002 | 249 | MID-20524 |
| 2.2e+003 – 4.8e+003 | 0.72 | 2.14 (−) | 8.5e−003 | 231 | hsa-miR-99a |
| 9.6e+003 – 2.0e+004 | 0.82 | 2.12 (−) | 1.3e−003 | 293 | hsa-miR-23b |
| 5.1e+003 – 1.0e+004 | 0.80 | 2.01 (−) | 6.3e−005 | 2 | hsa-let-7e |

+ the higher expression of this miR is in lung small cell carcinoma
− the higher expression of this miR is in other neuroendocrine tumors hsa-miR-17 (SEQ ID NO: 20) and hsa-miR-29c* (SEQ ID NO: 45) are used at node #26 of the binary-tree-classifier detailed in the invention to distinguish between lung small cell carcinoma and other neuroendocrine tumors.

TABLE 28 miR expression (in florescence units) distinguishing between medullary thyroid carcinoma and other neuroendocrine tumors selected from the group consisting of lung carcinoid, gastrointestinal tract carcinoid and pancreatic islet cell tumor

| median values | au-ROC | fold-change | p-value | SEQ ID NO. | miR name |
|---|---|---|---|---|---|
| 4.4e+003 – 5.5e+001 | 0.84 | 79.70 (+) | 1.5e−007 | 159 | hsa-miR-124 |
| 4.0e+004 – 4.9e+003 | 0.98 | 8.07 (+) | 1.6e−015 | 40 | hsa-miR-222 |
| 1.9e+004 – 2.8e+003 | 0.98 | 6.85 (+) | 4.8e−016 | 147 | hsa-miR-221 |
| 1.1e+003 – 2.0e+002 | 0.70 | 5.55 (+) | 1.8e−003 | 11 | hsa-miR-138 |
| 3.2e+002 – 7.8e+001 | 0.83 | 4.12 (+) | 7.6e−007 | 311 | hsa-miR-335 |
| 5.8e+003 – 1.5e+003 | 0.86 | 3.91 (+) | 1.3e−006 | 4 | hsa-miR-10a |
| 6.3e+004 – 1.7e+004 | 0.83 | 3.61 (+) | 3.9e−006 | 8 | hsa-miR-125b |
| 1.1e+004 – 3.2e+003 | 0.79 | 3.43 (+) | 5.5e−005 | 231 | hsa-miR-99a |
| 4.3e+002 – 2.0e+002 | 0.78 | 2.10 (+) | 2.8e−004 | 301 | hsa-miR-29b-2* |
| 7.9e+003 – 3.8e+003 | 0.82 | 2.06 (+) | 4.4e−005 | 297 | hsa-miR-27a |
| 1.4e+002 – 4.0e+002 | 0.95 | 2.95 (−) | 7.5e−011 | 68 | hsa-miR-92b |
| 1.1e+003 – 2.8e+003 | 0.87 | 2.50 (−) | 3.2e−006 | 67 | hsa-miR-92a |

TABLE 28-continued miR expression (in florescence units) distinguishing between medullary thyroid carcinoma and other neuroendocrine tumors selected from the group consisting of lung carcinoid, gastrointestinal tract carcinoid and pancreatic islet cell tumor

| median values | au-ROC | fold-change | p-value | SEQ ID NO. | miR name |
|---|---|---|---|---|---|
| 1.8e+002 – 3.7e+002 | 0.76 | 2.07 (−) | 2.0e-003 | 265 | hsa-miR-130b |
| 4.4e+002 – 9.0e+002 | 0.75 | 2.04 (−) | 2.1e-003 | 36 | hsa-miR-210 |

+ the higher expression of this miR is in medullary thyroid carcinoma
− the higher expression of this miR is in other neuroendocrine tumors FIG. 19 demonstrates binary decisions at node #27 of the decision-tree. Tumors originating in medullary thyroid carcinoma (diamonds) are easily distinguished from tumors of other neuroendocrine origin (squares) using the expression levels of hsa-miR-92b (SEQ ID NO: 68, y-axis), hsa-miR-222 (SEQ ID NO: 40, x-axis) and hsa-miR-92a (SEQ ID NO: 67, z-axis).

TABLE 29 miR expression (in florescence units) distinguishing between lung carcinoid tumors and GI neuroendocrine tumors selected from the group consisting of gastrointestinal tract carcinoid and pancreatic islet cell tumor

| median values | au-ROC | fold-change | p-value | SEQ ID NO. | miR name |
|---|---|---|---|---|---|
| 4.0e+003 – 9.9e+001 | 0.90 | 40.08 (+) | 1.9e-010 | 331 | hsa-miR-432 |
| 6.0e+003 – 1.5e+002 | 0.86 | 39.24 (+) | 4.6e-008 | 162 | hsa-miR-129-3p |
| 6.3e+002 – 1.9e+002 | 0.87 | 34.16 (+) | 7.8e-009 | 59 | hsa-miR-487b |
| 1.3e+003 – 5.5e+001 | 0.88 | 23.36 (+) | 2.9e-010 | 326 | hsa-miR-409-5p |
| 1.1e+003 – 5.0e+001 | 0.88 | 21.14 (+) | 5.2e-010 | 306 | hsa-miR-323-3p |
| 1.0e+003 – 5.5e+001 | 0.87 | 18.59 (+) | 1.5e-009 | 350 | hsa-miR-539 |
| 7.9e+002 – 5.6e+001 | 0.84 | 14.25 (+) | 1.4e-008 | 317 | hsa-miR-369-5p |
| 1.0e+004 – 7.2e+002 | 0.86 | 13.95 (+) | 3.2e-007 | 155 | hsa-miR-127-3p |
| 1.7e+003 – 1.2e+002 | 0.86 | 13.60 (+) | 2.1e-008 | 325 | hsa-miR-409-3p |
| 1.6e+003 – 1.2e+002 | 0.88 | 13.10 (+) | 4.2e-009 | 318 | hsa-miR-370 |
| 9.5e+002 – 7.3e+001 | 0.81 | 13.03 (+) | 3.1e-006 | 339 | hsa-miR-495 |
| 9.5e+002 – 7.4e+001 | 0.84 | 12.92 (+) | 5.7e-007 | 264 | hsa-miR-129-5p |
| 6.4e+002 – 5.0e+001 | 0.91 | 12.84 (+) | 1.6e-013 | 332 | hsa-miR-433 |
| 6.5e+002 – 5.7e+001 | 0.88 | 11.52 (+) | 5.1e-011 | 262 | hsa-miR-127-5p |
| 5.6e+002 – 5.2e+001 | 0.90 | 10.76 (+) | 2.7e-012 | 336 | hsa-miR-485-5p |
| 2.0e+003 – 1.9e+002 | 0.86 | 10.44 (+) | 4.2e-008 | 324 | hsa-miR-382 |
| 7.9e+002 – 7.8e+001 | 0.83 | 10.20 (+) | 1.3e-007 | 322 | hsa-miR-379 |
| 6.0e+002 – 5.9e+001 | 0.89 | 10.15 (+) | 9.6e-012 | 330 | hsa-miR-431* |
| 4.7e+002 – 5.0e+001 | 0.90 | 9.41 (+) | 6.1e-012 | 321 | hsa-miR-377* |
| 1.3e+003 – 1.4e+002 | 0.80 | 9.40 (+) | 1.5e-005 | 263 | hsa-miR-129* |
| 4.7e+002 – 5.0e+001 | 0.86 | 9.35 (+) | 1.8e-008 | 309 | hsa-miR-329 |
| 4.9e+002 – 5.3e+001 | 0.79 | 9.24 (+) | 3.1e-005 | 53 | hsa-miR-34c-5p |
| 1.1e+003 – 1.2e+002 | 0.83 | 9.05 (+) | 6.4e-007 | 320 | hsa-miR-376c |
| 1.1e+003 – 1.2e+002 | 0.86 | 8.81 (+) | 2.3e-008 | 275 | hsa-miR-154 |
| 6.5e+002 – 8.4e+001 | 0.83 | 7.73 (+) | 8.1e-007 | 352 | hsa-miR-543 |
| 9.9e+002 – 1.3e+002 | 0.82 | 7.49 (+) | 3.2e-007 | 312 | hsa-miR-337-5p |
| 6.2e+002 – 8.8e+001 | 0.86 | 7.10 (+) | 3.0e-008 | 355 | hsa-miR-654-3p |
| 3.5e+002 – 5.0e+001 | 0.91 | 7.05 (+) | 3.2e-013 | 367 | MID-00465 |
| 6.0e+002 – 1.0e+002 | 0.84 | 5.76 (+) | 5.9e-007 | 269 | hsa-miR-134 |
| 3.2e+003 – 8.5e+002 | 0.91 | 3.84 (+) | 1.2e-011 | 64 | hsa-miR-652 |
| 3.2e+002 – 1.1e+002 | 0.83 | 2.84 (+) | 2.3e-005 | 308 | hsa-miR-328 |
| 2.6e+003 – 9.4e+002 | 0.74 | 2.78 (+) | 1.1e-003 | 175 | hsa-miR-183 |

TABLE 29-continued miR expression (in florescence units) distinguishing between lung carcinoid tumors and GI neuroendocrine tumors selected from the group consisting of gastrointestinal tract carcinoid and pancreatic islet cell tumor

| median values | au-ROC | fold-change | p-value | SEQ ID NO. | miR name |
|---|---|---|---|---|---|
| 2.8e+003 – 1.0e+003 | 0.87 | 2.73 (+) | 3.0e-006 | 190 | hsa-miR-29b |
| 3.9e+003 – 1.6e+003 | 0.88 | 2.49 (+) | 6.9e-010 | 54 | hsa-miR-361-5p |
| 4.1e+002 – 1.7e+002 | 0.67 | 2.44 (+) | 2.1e-002 | 302 | hsa-miR-301a |
| 4.0e+003 – 1.7e+003 | 0.79 | 2.41 (+) | 5.9e-004 | 152 | hsa-miR-182 |
| 4.0e+002 – 1.7e+002 | 0.88 | 2.39 (+) | 4.7e-007 | 301 | hsa-miR-29b-2* |
| 8.7e+002 – 3.7e+002 | 0.77 | 2.36 (+) | 6.8e-005 | 266 | hsa-miR-132 |
| 7.7e+003 – 3.3e+003 | 0.82 | 2.34 (+) | 5.4e-006 | 47 | hsa-miR-30d |
| 3.7e+002 – 1.6e+002 | 0.70 | 2.32 (+) | 5.8e-003 | 313 | hsa-miR-338-3p |
| 3.3e+002 – 1.5e+002 | 0.66 | 2.16 (+) | 1.3e-002 | 359 | hsa-miR-708 |
| 5.5e+003 – 2.5e+003 | 0.68 | 2.16 (+) | 4.2e-002 | 65 | hsa-miR-7 |
| 2.1e+003 – 9.9e+002 | 0.78 | 2.13 (+) | 7.0e-005 | 307 | hsa-miR-324-5p |
| 1.2e+003 – 5.9e+002 | 0.81 | 2.02 (+) | 1.6e-004 | 191 | hsa-miR-29c |
| 3.5e+002 – 1.9e+003 | 0.88 | 5.36 (−) | 1.0e-007 | 242 | MID-16489 |
| 6.5e+002 – 1.9e+003 | 0.76 | 2.96 (−) | 4.9e-004 | 4 | hsa-miR-10a |
| 1.3e+003 – 3.6e+003 | 0.84 | 2.79 (−) | 1.9e-006 | 147 | hsa-miR-221 |
| 2.2e+003 – 5.9e+003 | 0.81 | 2.75 (−) | 8.5e-006 | 40 | hsa-miR-222 |
| 2.6e+002 – 6.8e+002 | 0.76 | 2.56 (−) | 7.4e-004 | 372 | MID-16469 |
| 3.5e+002 – 8.9e+002 | 0.71 | 2.56 (−) | 4.7e-003 | 168 | hsa-miR-150 |
| 1.5e+002 – 3.7e+002 | 0.83 | 2.55 (−) | 4.8e-005 | 16 | hsa-miR-146a |
| 1.9e+003 – 4.7e+003 | 0.82 | 2.40 (−) | 1.7e-005 | 182 | hsa-miR-199a-5p |
| 1.3e+003 – 3.0e+003 | 0.79 | 2.35 (−) | 1.2e-004 | 167 | hsa-miR-149* |
| 2.1e+002 – 4.8e+002 | 0.84 | 2.26 (−) | 3.1e-005 | 356 | hsa-miR-658 |
| 1.2e+003 – 2.8e+003 | 0.74 | 2.25 (−) | 1.4e-003 | 148 | hsa-miR-93 |
| 1.4e+003 – 3.1e+003 | 0.70 | 2.23 (−) | 1.9e-002 | 382 | MID-22331 |
| 8.0e+002 – 1.8e+003 | 0.83 | 2.21 (−) | 2.9e-005 | 37 | hsa-miR-214 |
| 4.4e+002 – 8.9e+002 | 0.79 | 2.01 (−) | 2.1e-004 | 364 | MID-00064 |
| 2.1e+002 – 4.2e+002 | 0.78 | 2.01 (−) | 1.1e-003 | 35 | hsa-miR-21* |

+ the higher expression of this miR is in lung carcinoid tumors
− the higher expression of this miR is in GI neuroendocrine tumors hsa-miR-652 (SEQ ID NO: 64), hsa-miR-34c-5p (SEQ ID NO: 53) and hsa-miR-214 (SEQ ID NO: 37) are used at node 28 of the binary-tree-classifier detailed in the invention to distinguish between lung carcinoid tumors and GI neuroendocrine tumors.

TABLE 30 miR expression (in florescence units) distinguishing between pancreatic islet cell tumors and GI neuroendocrine carcinoid tumors selected from the group consisting of small intestine and duodenum; appendicitis, stomach and pancreas

| median values | au-ROC | fold-change | p-value | SEQ ID NO. | miR name |
|---|---|---|---|---|---|
| 1.1e+002 2.3e+003 | 0.80 | 20.91 (+) | 2.8e-004 | 263 | hsa-miR-129* |
| 5.0e+001 4.8e+002 | 0.72 | 9.61 (+) | 6.6e-003 | 288 | hsa-miR-217 |
| 1.9e+002 1.6e+003 | 0.90 | 8.54 (+) | 6.8e-006 | 18 | hsa-miR-148a |
| 5.2e+001 4.3e+002 | 0.68 | 8.34 (+) | 2.7e-002 | 286 | hsa-miR-216a |
| 2.5e+002 1.8e+003 | 0.74 | 7.22 (+) | 4.4e-003 | 162 | hsa-miR-129-3p |
| 9.9e+001 6.6e+002 | 0.74 | 6.65 (+) | 2.3e-003 | 225 | hsa-miR-551b |
| 5.0e+001 3.0e+002 | 0.75 | 6.04 (+) | 5.4e-003 | 287 | hsa-miR-216b |
| 1.9e+002 7.1e+002 | 0.92 | 3.75 (+) | 7.3e-007 | 206 | hsa-miR-455-3p |
| 3.4e+003 1.3e+004 | 0.79 | 3.65 (+) | 2.5e-003 | 205 | hsa-miR-451 |
| 2.6e+002 8.9e+002 | 0.83 | 3.43 (+) | 2.8e-004 | 296 | hsa-miR-26b |
| 2.6e+003 8.7e+003 | 0.91 | 3.29 (+) | 3.6e-004 | 258 | hsa-let-7f |
| 1.6e+002 5.2e+002 | 0.78 | 3.25 (+) | 3.2e-003 | 313 | hsa-miR-338-3p |
| 2.4e+003 6.6e+003 | 0.85 | 2.71 (+) | 5.0e-005 | 377 | MID-17866 |

TABLE 30-continued miR expression (in florescence units) distinguishing between pancreatic islet cell tumors and GI neuroendocrine carcinoid tumors selected from the group consisting of small intestine and duodenum; appendicitis, stomach and pancreas

| median values | auROC | fold-change | p-value | SEQ ID NO. | miR name |
|---|---|---|---|---|---|
| 7.6e+003 1.9e+004 | 0.88 | 2.45 (+) | 1.2e−005 | 373 | MID-16582 |
| 2.7e+004 6.4e+004 | 0.80 | 2.42 (+) | 1.0e−003 | 256 | hsa-let-7a |
| 4.7e+003 1.1e+004 | 0.89 | 2.36 (+) | 1.8e−004 | 153 | hsa-let-7d |
| 2.8e+003 6.4e+003 | 0.86 | 2.28 (+) | 2.2e−003 | 259 | hsa-let-7g |
| 2.3e+002 4.8e+002 | 0.69 | 2.11 (+) | 1.0e−002 | 265 | hsa-miR-130b |
| 3.1e+003 6.4e+003 | 0.75 | 2.09 (+) | 7.5e−003 | 303 | hsa-miR-30b |
| 9.7e+002 1.0e+002 | 0.81 | 9.40 (−) | 5.4e−004 | 268 | hsa-miR-133b |
| 1.0e+003 1.1e+002 | 0.80 | 9.22 (−) | 5.4e−004 | 267 | hsa-miR-133a |
| 1.9e+003 2.3e+002 | 0.93 | 8.37 (−) | 2.1e−006 | 165 | hsa-miR-143* |
| 9.2e+004 1.1e+004 | 0.94 | 8.18 (−) | 3.7e−008 | 15 | hsa-miR-145 |
| 5.3e+002 6.6e+001 | 0.91 | 8.05 (−) | 7.0e−006 | 272 | hsa-miR-145* |
| 3.8e+004 5.2e+003 | 0.96 | 7.30 (−) | 3.7e−009 | 14 | hsa-miR-143 |
| 2.0e+003 3.1e+002 | 0.88 | 6.35 (−) | 6.2e−006 | 202 | hsa-miR-378 |
| 1.4e+003 2.9e+002 | 0.88 | 4.99 (−) | 8.1e−006 | 236 | MID-00689 |
| 6.4e+003 1.4e+002 | 0.88 | 4.74 (−) | 7.9e−006 | 203 | hsa-miR-422a |
| 3.6e+003 9.2e+002 | 0.82 | 3.91 (−) | 2.4e−004 | 4 | hsa-miR-10a |
| 1.1e+003 3.0e+002 | 0.78 | 3.78 (−) | 4.4e−003 | 168 | hsa-miR-150 |
| 3.6e+002 1.1e+002 | 0.81 | 3.23 (−) | 3.4e−004 | 310 | hsa-miR-330-3p |
| 6.7e+002 2.1e+002 | 0.95 | 3.16 (−) | 4.6e−007 | 298 | hsa-miR-28-3p |
| 2.2e+003 7.2e+002 | 0.74 | 3.09 (−) | 1.4e−002 | 27 | hsa-miR-194 |
| 2.1e+004 7.5e+003 | 0.91 | 2.72 (−) | 7.6e−005 | 29 | hsa-miR-200b |
| 2.2e+004 8.5e+003 | 0.87 | 2.57 (−) | 2.8e−006 | 34 | hsa-miR-21 |
| 1.7e+003 6.7e+002 | 0.74 | 2.56 (−) | 8.0e−003 | 228 | hsa-miR-886-3p |
| 3.8e+003 1.5e+003 | 0.77 | 2.50 (−) | 3.6e−003 | 3 | hsa-miR-100 |
| 5.3e+002 2.5e+002 | 0.94 | 2.14 (−) | 4.3e−007 | 349 | hsa-miR-532-5p |
| 5.0e+002 2.4e+002 | 0.82 | 2.06 (−) | 8.5e−004 | 35 | hsa-miR-21* |
| 3.3e+002 1.6e+002 | 0.77 | 2.01 (−) | 5.7e−003 | 26 | hsa-miR-193a-5p |

+ the higher expression of this miR is in pancreatic islet cell tumors
− the higher expression of this miR is in GI neuroendocrine carcinoid tumors hsa-miR-21 (SEQ ID NO: 34), and hsa-miR-148a (SEQ ID NO: 18) are used at node 29 of the binary-tree-classifier detailed in the invention to distinguish between pancreatic islet cell tumors and GI neuroendocrine carcinoid tumors.

TABLE 31 miR expression (in florescence units) distinguishing between gastric or esophageal adenocarcinoma and other adenocarcinoma tumors of the gastrointestinal system selected from the group consisting of cholangiocarcinoma or adenocarcinoma of extrahepatic biliary tract, pancreatic adenocarcinoma and colorectal adenocarcinoma

| median values | auROC | fold-change | p-value | SEQ ID NO. | miR name |
|---|---|---|---|---|---|
| 6.7e+001 6.2e+002 | 0.74 | 9.14 (+) | 4.6e−008 | 267 | hsa-miR-133a |
| 6.3e+001 5.5e+002 | 0.74 | 8.73 (+) | 3.9e−008 | 268 | hsa-miR-133b |
| 5.9e+002 2.5e+003 | 0.75 | 4.26 (+) | 3.9e−007 | 165 | hsa-miR-143* |
| 2.8e+004 7.9e+004 | 0.71 | 2.82 (+) | 4.5e−004 | 15 | hsa-miR-145 |
| 1.3e+004 3.2e+004 | 0.68 | 2.55 (+) | 1.3e−003 | 14 | hsa-miR-143 |
| 5.1e+002 1.3e+003 | 0.71 | 2.53 (+) | 8.2e−004 | 356 | hsa-miR-658 |
| 3.1e+003 7.2e+003 | 0.72 | 2.33 (+) | 2.2e−004 | 167 | hsa-miR-149* |
| 1.4e+003 3.1e+003 | 0.69 | 2.22 (+) | 7.2e−004 | 376 | MID-17576 |
| 6.5e+002 1.4e+003 | 0.71 | 2.20 (+) | 3.0e−004 | 372 | MID-16469 |
| 1.5e+002 3.2e+002 | 0.69 | 2.14 (+) | 3.0e−004 | 272 | hsa-miR-145* |
| 1.4e+003 2.9e+003 | 0.74 | 2.11 (+) | 3.8e−004 | 370 | MID-15986 |
| 3.6e+002 5.5e+001 | 0.83 | 6.57 (−) | 5.4e−008 | 42 | hsa-miR-224 |

TABLE 31-continued miR expression (in florescence units) distinguishing between gastric or esophageal adenocarcinoma and other adenocarcinoma tumors of the gastrointestinal system selected from the group consisting of cholangiocarcinoma or adenocarcinoma of extrahepatic biliary tract, pancreatic adenocarcinoma and colorectal adenocarcinoma

| median values | auROC | fold-change | p-value | SEQ ID NO. | miR name |
|---|---|---|---|---|---|
| 4.0e+002 1.5e+002 | 0.73 | 2.61 (−) | 1.1e−004 | 41 | hsa-miR-223 |
| 1.2e+003 9.0e+002 | 0.67 | 1.28 (−) | 1.2e−002 | 146 | hsa-miR-1201 |

+ the higher expression of this miR is in gastric or esophageal adenocarcinoma
− the higher expression of this miR is in other adenocarcinoma tumors of the gastrointestinal system FIG. 20 demonstrates binary decisions at node #30 of the decision-tree. Tumors originating in gastric or esophageal adenocarcinoma (diamonds) are easily distinguished from tumors of other GI adenocarcinoma origin (squares) using the expression levels of hsa-miR-1201 (SEQ ID NO: 146, y-axis), hsa-miR-224 (SEQ ID NO: 42, x-axis) and hsa-miR-210 (SEQ ID NO: 36, z-axis).

TABLE 32 miR expression (in florescence units) distinguishing between colorectal adenocarcinoma and cholangiocarcinoma or adenocarcinoma of biliary tract or pancreas

| median values | auROC | fold-change | p-value | SEQ ID NO. | miR name |
|---|---|---|---|---|---|
| 2.1e+002 5.4e+002 | 0.69 | 2.55 (+) | 4.0e−003 | 42 | hsa-miR-224 |
| 1.8e+002 4.2e+002 | 0.70 | 2.28 (+) | 1.2e−003 | 184 | hsa-miR-203 |
| 3.2e+003 6.2e+003 | 0.77 | 1.91 (+) | 5.1e−007 | 67 | hsa-miR-92a |
| 3.1e+003 5.6e+003 | 0.81 | 1.81 (+) | 4.6e−007 | 158 | hsa-miR-106a |
| 1.8e+003 3.2e+003 | 0.81 | 1.81 (+) | 1.3e−007 | 20 | hsa-miR-17 |
| 1.8e+003 3.2e+003 | 0.76 | 1.80 (+) | 7.9e−005 | 186 | hsa-miR-20a |
| 1.1e+003 1.9e+003 | 0.76 | 1.75 (+) | 1.4e−005 | 284 | hsa-miR-19b |
| 1.6e+003 2.6e+003 | 0.70 | 1.67 (+) | 3.0e−003 | 389 | MID-17356 |
| 3.1e+002 5.1e+002 | 0.75 | 1.63 (+) | 2.1e−005 | 203 | hsa-miR-422a |
| 4.5e+003 7.2e+003 | 0.67 | 1.60 (+) | 5.6e−003 | 240 | MID-15965 |
| 6.9e+002 1.1e+003 | 0.76 | 1.59 (+) | 1.7e−005 | 236 | MID-00689 |
| 1.1e+003 1.6e+003 | 0.68 | 1.53 (+) | 2.5e−003 | 146 | hsa-miR-1201 |
| 9.1e+002 1.4e+003 | 0.69 | 1.49 (+) | 5.2e−004 | 204 | hsa-miR-425 |
| 6.5e+003 9.3e+003 | 0.77 | 1.44 (+) | 1.2e−005 | 43 | hsa-miR-29a |
| 4.5e+002 6.4e+002 | 0.75 | 1.44 (+) | 7.3e−006 | 176 | hsa-miR-18a |
| 9.1e+002 1.3e+003 | 0.72 | 1.41 (+) | 1.4e−004 | 202 | hsa-miR-378 |
| 1.8e+003 5.3e+002 | 0.69 | 3.39 (−) | 2.0e−003 | 49 | hsa-miR-31 |
| 2.0e+003 8.2e+002 | 0.82 | 2.39 (−) | 2.2e−008 | 46 | hsa-miR-30a |
| 3.7e+002 2.5e+002 | 0.66 | 1.47 (−) | 1.3e−002 | 38 | hsa-miR-214* |
| 1.3e+003 9.0e+002 | 0.73 | 1.41 (−) | 2.2e−003 | 363 | hsa-miR-99b |

+ the higher expression of this miR is in colorectal adenocarcinoma
− the higher expression of this miR is in other cholangiocarcinoma or adenocarcinoma tumors of biliary tract or pancreas FIG. 21 demonstrates binary decisions at node #31 of the decision-tree. Tumors originating in colorectal adenocarcinoma (diamonds) are easily distinguished from tumors of cholangiocarcinoma or adenocarcinoma of biliary tract or pancreas origin (squares) using the expression levels of hsa-miR-30a (SEQ ID NO: 46, y-axis), hsa-miR-17 (SEQ ID NO: 20, x-axis) and hsa-miR-29a (SEQ ID NO: 43, z-axis).

TABLE 33 miR expression (in florescence units) distinguishing between cholangiocarcinoma or adenocarcinoma of extrahepatic biliary tract and pancreatic adenocarcinoma

| median values | | auROC | fold-change | p-value | SEQ ID NO. | miR name |
|---|---|---|---|---|---|---|
| 1.1e+003 | 3.4e+003 | 0.81 | 3.06 (+) | 1.5e−003 | 49 | hsa-miR-31 |
| 1.4e+002 | 3.3e+002 | 0.71 | 2.36 (+) | 1.1e−002 | 11 | hsa-miR-138 |
| 1.7e+003 | 3.0e+003 | 0.70 | 1.77 (+) | 1.7e−002 | 13 | hsa-miR-141 |
| 1.1e+004 | 1.8e+004 | 0.70 | 1.65 (+) | 1.5e−002 | 373 | MID-16582 |
| 8.4e+002 | 1.4e+003 | 0.69 | 1.63 (+) | 9.6e−002 | 154 | hsa-miR-181b |
| 4.3e+002 | 7.0e+002 | 0.69 | 1.62 (+) | 5.1e−001 | 5 | hsa-miR-10b |
| 9.3e+003 | 1.5e+004 | 0.68 | 1.61 (+) | 7.4e−002 | 30 | hsa-miR-200c |
| 2.7e+002 | 4.2e+002 | 0.72 | 1.58 (+) | 1.3e−002 | 45 | hsa-miR-29c* |
| 1.0e+003 | 1.5e+003 | 0.66 | 1.47 (+) | 1.1e−001 | 178 | hsa-miR-193b |
| 6.6e+003 | 9.0e+003 | 0.75 | 1.36 (+) | 1.2e−002 | 147 | hsa-miR-221 |
| 4.7e+002 | 6.4e+002 | 0.70 | 1.36 (+) | 4.0e−002 | 274 | hsa-miR-151-3p |
| 5.4e+002 | 7.3e+002 | 0.66 | 1.34 (+) | 2.4e−002 | 16 | hsa-miR-146a |
| 1.1e+004 | 1.5e+004 | 0.71 | 1.32 (+) | 3.7e−002 | 40 | hsa-miR-222 |
| 3.8e+003 | 4.9e+003 | 0.71 | 1.30 (+) | 8.4e−002 | 21 | hsa-miR-181a |
| 6.0e+003 | 6.8e+003 | 0.66 | 1.14 (+) | 6.3e−002 | 43 | hsa-miR-29a |
| 5.9e+002 | 3.3e+002 | 0.74 | 1.81 (−) | 2.1e−002 | 253 | MID-23256 |
| 1.9e+003 | 1.1e+003 | 0.66 | 1.70 (−) | 8.0e−002 | 245 | MID-18336 |
| 4.5e+004 | 2.7e+004 | 0.73 | 1.68 (−) | 7.4e−003 | 256 | hsa-let-7a |
| 2.7e+003 | 1.8e+003 | 0.65 | 1.51 (−) | 9.2e−002 | 12 | hsa-miR-140-3p |
| 1.4e+005 | 9.3e+004 | 0.75 | 1.47 (−) | 5.4e−003 | 374 | MID-16748 |
| 8.9e+004 | 6.1e+004 | 0.66 | 1.45 (−) | 2.9e−002 | 379 | MID-18395 |
| 4.7e+002 | 3.3e+002 | 0.69 | 1.41 (−) | 6.6e−002 | 180 | hsa-miR-1973 |
| 6.0e+003 | 4.3e+003 | 0.68 | 1.40 (−) | 2.6e−002 | 153 | hsa-let-7d |
| 4.4e+002 | 3.2e+002 | 0.75 | 1.39 (−) | 7.1e−002 | 51 | hsa-miR-345 |
| 6.1e+003 | 4.4e+003 | 0.70 | 1.38 (−) | 3.9e−002 | 52 | hsa-miR-34a |
| 3.3e+004 | 2.4e+004 | 0.73 | 1.37 (−) | 1.4e−002 | 1 | hsa-let-7c |
| 2.0e+004 | 1.5e+004 | 0.68 | 1.36 (−) | 2.8e−002 | 295 | hsa-miR-26a |
| 3.9e+004 | 2.9e+004 | 0.77 | 1.35 (−) | 3.3e−003 | 257 | hsa-let-7b |
| 6.1e+003 | 4.8e+003 | 0.66 | 1.26 (−) | 6.5e−002 | 385 | MID-23168 |
| 1.3e+004 | 1.0e+004 | 0.67 | 1.21 (−) | 9.0e−002 | 293 | hsa-miR-23b |
| 2.4e+004 | 2.1e+004 | 0.68 | 1.18 (−) | 2.6e−002 | 294 | hsa-miR-24 |

+ the higher expression of this miR is in pancreatic adenocarcinoma
− the higher expression of this miR is in cholangiocarcinoma or adenocarcinoma of extrahepatic biliary tract hsa-miR-345 (SEQ ID NO: 51), hsa-miR-31 (SEQ ID NO: 49) and hsa-miR-146a (SEQ ID NO: 16) are used at node #32 of the binary-tree-classifier detailed in the invention to distinguish between cholangio cancer or adenocarcinoma of extrahepatic biliary tract and pancreatic adenocarcinoma.

TABLE 34 miR expression (in florescence units) distinguishing between kidney tumors selected from the group consisting of chromophobe renal cell carcinoma, clear cell renal cell carcinoma and papillary renal cell carcinoma and other tumors selected from the group consisting of sarcoma, adrenal (pheochromocytoma, adrenocortical carcinoma) and mesothelioma (pleural mesothelioma)

| median values | | auROC | fold-change | p-value | SEQ ID NO. | miR name |
|---|---|---|---|---|---|---|
| 5.0e+001 | 4.8e+003 | 0.94 | 96.12 (+) | 7.6e−042 | 29 | hsa-miR-200b |
| 5.0e+001 | 2.3e+003 | 0.94 | 45.03 (+) | 3.3e−044 | 28 | hsa-miR-200a |
| 5.0e+001 | 7.7e+002 | 0.82 | 15.36 (+) | 1.1e−015 | 30 | hsa-miR-200c |
| 1.2e+003 | 1.1e+004 | 0.96 | 9.73 (+) | 8.6e−041 | 46 | hsa-miR-30a |
| 1.2e+002 | 1.1e+003 | 0.74 | 9.21 (+) | 1.1e−008 | 49 | hsa-miR-31 |
| 1.9e+002 | 1.7e+003 | 0.94 | 8.87 (+) | 8.6e−039 | 195 | hsa-miR-30a* |
| 7.5e+001 | 5.0e+002 | 0.74 | 6.58 (+) | 1.1e−009 | 152 | hsa-miR-182 |
| 5.0e+001 | 2.5e+002 | 0.76 | 5.07 (+) | 9.8e−011 | 175 | hsa-miR-183 |
| 2.2e+003 | 8.3e+003 | 0.92 | 3.81 (+) | 5.0e−033 | 47 | hsa-miR-30d |
| 1.5e+003 | 5.1e+003 | 0.83 | 3.52 (+) | 2.5e−016 | 4 | hsa-miR-10a |
| 7.3e+001 | 2.3e+002 | 0.75 | 3.15 (+) | 6.4e−011 | 387 | MID-23751 |
| 3.2e+003 | 9.5e+003 | 0.89 | 2.95 (+) | 1.1e−025 | 196 | hsa-miR-30c |
| 1.4e+002 | 4.0e+002 | 0.76 | 2.80 (+) | 2.1e−012 | 177 | hsa-miR-192 |
| 9.8e+001 | 2.5e+002 | 0.79 | 2.52 (+) | 1.7e−015 | 375 | MID-17375 |
| 9.0e+001 | 2.2e+002 | 0.75 | 2.43 (+) | 2.1e−012 | 27 | hsa-miR-194 |
| 1.2e+002 | 2.8e+002 | 0.76 | 2.40 (+) | 6.5e−013 | 304 | hsa-miR-30e* |
| 6.7e+003 | 1.6e+004 | 0.75 | 2.37 (+) | 1.6e−012 | 40 | hsa-miR-222 |
| 2.5e+002 | 5.9e+002 | 0.69 | 2.33 (+) | 9.5e−006 | 191 | hsa-miR-29c |
| 4.5e+003 | 9.8e+003 | 0.74 | 2.20 (+) | 1.4e−011 | 147 | hsa-miR-221 |
| 4.5e+002 | 9.8e+002 | 0.61 | 2.19 (+) | 7.6e−003 | 35 | hsa-miR-21* |
| 2.8e+002 | 6.1e+002 | 0.71 | 2.15 (+) | 3.7e−007 | 16 | hsa-miR-146a |
| 2.4e+004 | 4.9e+004 | 0.64 | 2.07 (+) | 1.2e−003 | 34 | hsa-miR-21 |
| 2.3e+003 | 4.7e+003 | 0.66 | 2.06 (+) | 5.4e−004 | 5 | hsa-miR-10b |
| 1.2e+003 | 1.2e+002 | 0.85 | 9.53 (−) | 2.1e−018 | 155 | hsa-miR-127-3p |
| 1.2e+003 | 1.6e+002 | 0.89 | 7.57 (−) | 4.9e−023 | 181 | hsa-miR-199a-3p |
| 3.7e+002 | 5.0e+001 | 0.86 | 7.45 (−) | 1.2e−019 | 312 | hsa-miR-337-5p |
| 1.0e+003 | 1.4e+002 | 0.82 | 7.21 (−) | 1.7e−015 | 183 | hsa-miR-199b-5p |
| 1.7e+004 | 2.6e+003 | 0.86 | 6.48 (−) | 1.4e−017 | 182 | hsa-miR-199a-5p |
| 2.9e+002 | 5.0e+001 | 0.86 | 5.73 (−) | 3.5e−019 | 320 | hsa-miR-376c |
| 3.4e+002 | 6.5e+001 | 0.86 | 5.23 (−) | 2.6e−016 | 59 | hsa-miR-487b |
| 4.9e+002 | 9.4e+001 | 0.82 | 5.18 (−) | 9.7e−016 | 38 | hsa-miR-214* |
| 2.4e+002 | 5.0e+001 | 0.86 | 4.83 (−) | 2.2e−017 | 324 | hsa-miR-382 |
| 2.1e+002 | 5.0e+001 | 0.83 | 4.27 (−) | 6.6e−017 | 323 | hsa-miR-381 |
| 5.0e+003 | 1.2e+003 | 0.81 | 4.22 (−) | 2.7e−013 | 37 | hsa-miR-214 |
| 2.1e+002 | 5.0e+001 | 0.86 | 4.21 (−) | 8.5e−018 | 322 | hsa-miR-379 |
| 2.1e+002 | 5.0e+001 | 0.83 | 4.14 (−) | 1.2e−015 | 325 | hsa-miR-409-3p |

TABLE 34-continued miR expression (in florescence units) distinguishing between kidney tumors selected from the group consisting of chromophobe renal cell carcinoma, clear cell renal cell carcinoma and papillary renal cell carcinoma and other tumors selected from the group consisting of sarcoma, adrenal (pheochromocytoma, adrenocortical carcinoma) and mesothelioma (pleural mesothelioma)

| median values | | auROC | fold-change | p-value | SEQ ID NO. | miR name |
|---|---|---|---|---|---|---|
| 2.5e+002 | 6.7e+001 | 0.86 | 3.76 (−) | 2.8e−016 | 19 | hsa-miR-149 |
| 2.6e+002 | 7.5e+001 | 0.71 | 3.51 (−) | 2.8e−007 | 42 | hsa-miR-224 |
| 3.2e+002 | 9.9e+001 | 0.79 | 3.25 (−) | 1.3e−011 | 334 | hsa-miR-483-5p |
| 3.0e+002 | 1.5e+002 | 0.79 | 2.08 (−) | 9.5e−012 | 265 | hsa-miR-130b |
| 2.0e+002 | 1.0e+002 | 0.76 | 2.00 (−) | 4.8e−009 | 22 | hsa-miR-181a* |

+ the higher expression of this miR is in kidney tumors
− the higher expression of this miR is in sarcoma, adrenal and mesothelioma tumors FIG. 22 demonstrates binary decisions at node #33 of the decision-tree. Tumors originating in kidney (diamonds) are easily distinguished from tumors of adrenal, mesothelioma and sarcoma origin (squares) using the expression levels of hsa-miR-200b (SEQ ID NO: 29, y-axis), hsa-miR-30a (SEQ ID NO: 46, x-axis) and hsa-miR-149 (SEQ ID NO: 19, z-axis).

TABLE 35 miR expression (in florescence units) distinguishing between pheochromocytoma (neuroendocrine tumor of the adrenal) and all sarcoma, adrenal carcinoma and mesothelioma tumors

| median values | | auROC | fold-change | p-value | SEQ ID NO. | miR name |
|---|---|---|---|---|---|---|
| 5.0e+001 | 1.5e+004 | 0.96 | 295.36 (+) | 6.7e−067 | 65 | hsa-miR-7 |
| 5.0e+001 | 9.8e+003 | 0.91 | 196.58 (+) | 5.0e−036 | 56 | hsa-miR-375 |
| 1.3e+002 | 4.0e+003 | 0.85 | 29.73 (+) | 3.2e−009 | 11 | hsa-miR-138 |
| 5.0e+001 | 1.0e+003 | 0.94 | 20.53 (+) | 1.5e−021 | 162 | hsa-miR-129-3p |
| 2.7e+002 | 4.0e+003 | 0.84 | 15.11 (+) | 3.0e−008 | 59 | hsa-miR-487b |
| 1.5e+002 | 2.2e+003 | 0.81 | 14.54 (+) | 7.4e−008 | 331 | hsa-miR-432 |
| 7.0e+001 | 8.7e+002 | 0.84 | 12.45 (+) | 9.4e−011 | 350 | hsa-miR-539 |
| 9.6e+002 | 1.2e+004 | 0.80 | 12.36 (+) | 8.3e−005 | 155 | hsa-miR-127-3p |
| 5.8e+001 | 6.8e+002 | 0.80 | 11.61 (+) | 1.2e−0083 | 35 | hsa-miR-485-3p |
| 5.0e+001 | 5.7e+002 | 0.87 | 11.48 (+) | 2.7e−008 | 159 | hsa-miR-124 |
| 5.3e+001 | 5.6e+002 | 0.86 | 10.67 (+) | 2.3e−014 | 336 | hsa-miR-485-5p |
| 5.0e+001 | 5.2e+002 | 0.83 | 10.38 (+) | 1.2e−012 | 332 | hsa-miR-433 |
| 5.0e+001 | 5.1e+002 | 0.94 | 10.28 (+) | 1.1e−029 | 263 | hsa-miR-129* |
| 5.0e+001 | 4.8e+002 | 0.82 | 9.55 (+) | 9.6e−008 | 306 | hsa-miR-323-3p |
| 1.2e+002 | 1.2e+003 | 0.79 | 9.22 (+) | 1.0e−005 | 339 | hsa-miR-495 |
| 5.8e+001 | 5.2e+002 | 0.80 | 9.01 (+) | 4.4e−006 | 337 | hsa-miR-487a |
| 1.6e+002 | 1.4e+003 | 0.80 | 8.75 (+) | 4.8e−006 | 275 | hsa-miR-154 |
| 7.1e+001 | 6.1e+002 | 0.90 | 8.56 (+) | 6.0e−013 | 301 | hsa-miR-29b-2* |
| 5.3e+001 | 4.5e+002 | 0.78 | 8.54 (+) | 3.7e−005 | 276 | hsa-miR-154* |
| 5.3e+001 | 4.1e+002 | 0.83 | 7.77 (+) | 4.7e−009 | 330 | hsa-miR-431* |
| 9.8e+001 | 7.4e+002 | 0.81 | 7.56 (+) | 1.3e−006 | 317 | hsa-miR-369-5p |
| 6.4e+001 | 4.8e+002 | 0.80 | 7.56 (+) | 1.4e−007 | 309 | hsa-miR-329 |
| 2.4e+002 | 1.8e+003 | 0.90 | 7.28 (+) | 1.4e−009 | 45 | hsa-miR-29c* |
| 1.5e+002 | 1.1e+003 | 0.79 | 7.24 (+) | 1.5e−005 | 318 | hsa-miR-370 |
| 2.2e+002 | 1.5e+003 | 0.80 | 6.74 (+) | 1.5e−005 | 324 | hsa-miR-382 |
| 1.3e+002 | 8.6e+002 | 0.76 | 6.53 (+) | 3.1e−004 | 352 | hsa-miR-543 |
| 2.3e+002 | 1.5e+003 | 0.89 | 6.44 (+) | 2.6e−008 | 191 | hsa-miR-29c |
| 9.6e+001 | 6.2e+002 | 0.79 | 6.40 (+) | 1.1e−005 | 262 | hsa-miR-127-5p |
| 1.5e+002 | 9.6e+002 | 0.77 | 6.39 (+) | 2.3e−004 | 269 | hsa-miR-134 |
| 5.4e+001 | 3.3e+002 | 0.90 | 6.03 (+) | 2.1e−012 | 313 | hsa-miR-338-3p |
| 2.2e+002 | 1.3e+003 | 0.84 | 5.80 (+) | 4.8e−008 | 19 | hsa-miR-149 |
| 5.0e+001 | 2.7e+002 | 0.82 | 5.32 (+) | 7.5e−012 | 367 | MID-00465 |
| 1.1e+002 | 5.6e+002 | 0.78 | 5.27 (+) | 5.3e−005 | 326 | hsa-miR-409-5p |
| 1.8e+002 | 9.6e+002 | 0.76 | 5.26 (+) | 3.1e−004 | 325 | hsa-miR-409-3p |
| 1.8e+002 | 9.2e+002 | 0.76 | 5.25 (+) | 8.2e−004 | 322 | hsa-miR-379 |
| 5.0e+001 | 2.5e+002 | 0.79 | 5.05 (+) | 4.6e−008 | 327 | hsa-miR-410 |
| 8.1e+002 | 4.0e+003 | 0.97 | 4.95 (+) | 3.4e−011 | 190 | hsa-miR-29b |
| 7.6e+001 | 3.7e+002 | 0.93 | 4.85 (+) | 7.6e−019 | 261 | hsa-miR-1180 |
| 6.4e+001 | 2.8e+002 | 0.79 | 4.43 (+) | 1.0e−005 | 321 | hsa-miR-377* |
| 5.0e+001 | 2.0e+002 | 0.81 | 4.09 (+) | 2.9e−009 | 360 | hsa-miR-873 |

TABLE 35-continued miR expression (in florescence units) distinguishing between pheochromocytoma (neuroendocrine tumor of the adrenal) and all sarcoma, adrenal carcinoma and mesothelioma tumors

| median values | | auROC | fold-change | p-value | SEQ ID NO. | miR name |
|---|---|---|---|---|---|---|
| 5.3e+001 | 2.1e+002 | 0.88 | 4.08 (+) | 1.2e−012 | 353 | hsa-miR-598 |
| 3.3e+002 | 1.3e+003 | 0.73 | 4.01 (+) | 3.0e−003 | 312 | hsa-miR-337-5p |
| 6.6e+001 | 2.6e+002 | 0.77 | 3.96 (+) | 8.8e−005 | 371 | MID-16270 |
| 2.1e+003 | 7.2e+003 | 0.85 | 3.51 (+) | 6.2e−005 | 5 | hsa-miR-10b |
| 6.7e+001 | 2.3e+002 | 0.68 | 3.40 (+) | 2.6e−002 | 328 | hsa-miR-411 |
| 6.9e+003 | 2.2e+004 | 0.77 | 3.17 (+) | 4.3e−004 | 205 | hsa-miR-451 |
| 1.3e+003 | 1.1e+002 | 0.90 | 12.33 (−) | 2.9e−008 | 183 | hsa-miR-199b-5p |
| 5.5e+002 | 1.1e+002 | 0.86 | 4.75 (−) | 2.4e−006 | 38 | hsa-miR-214* |
| 1.5e+004 | 3.2e+003 | 0.84 | 4.48 (−) | 2.9e−005 | 181 | hsa-miR-199a-3p |
| 5.9e+003 | 1.3e+003 | 0.85 | 4.47 (−) | 6.8e−005 | 37 | hsa-miR-214 |
| 7.8e+003 | 1.8e+003 | 0.80 | 4.23 (−) | 5.9e−004 | 40 | hsa-miR-222 |
| 1.8e+004 | 4.5e+003 | 0.87 | 4.13 (−) | 9.0e−006 | 182 | hsa-miR-199a-5p |
| 5.2e+003 | 1.3e+003 | 0.80 | 4.11 (−) | 6.4e−004 | 147 | hsa-miR-221 |
| 7.0e+002 | 1.9e+002 | 0.85 | 3.72 (−) | 4.7e−007 | 17 | hsa-miR-146b-5p |
| 3.1e+002 | 8.9e+001 | 0.72 | 3.48 (−) | 2.3e−003 | 42 | hsa-miR-224 |
| 2.7e+003 | 8.0e+002 | 0.81 | 3.42 (−) | 3.8e−005 | 382 | MID-22331 |
| 2.6e+004 | 7.9e+003 | 0.79 | 3.35 (−) | 1.1e−004 | 34 | hsa-miR-21 |
| 4.2e+002 | 1.4e+002 | 0.74 | 3.08 (−) | 1.3e−003 | 18 | hsa-miR-148a |
| 6.3e+003 | 2.1e+003 | 0.83 | 3.03 (−) | 2.6e−005 | 3 | hsa-miR-100 |

+ the higher expression of this miR is in pheochromocytoma
− the higher expression of this miR is in sarcoma, adrenal carcinoma and mesothelioma tumors FIG. 23 demonstrates binary decisions at node #34 of the decision-tree. Tumors originating in pheochromocytoma (diamonds) are easily distinguished from tumors of adrenal, mesothelioma and sarcoma origin (squares) using the expression levels of hsa-miR-375 (SEQ ID NO: 56, y-axis) and hsa-miR-7 (SEQ ID NO: 65, x-axis).

TABLE 36 miR expression (in florescence units) distinguishing between adrenal carcinoma and mesothelioma or sarcoma tumors

| median values | | auROC | fold-change | p-value | SEQ ID NO. | miR name |
|---|---|---|---|---|---|---|
| 5.0e+001 | 2.6e+003 | 0.98 | 51.10 (+) | 1.3e−040 | 61 | hsa-miR-509-3p |
| 5.4e+001 | 1.3e+003 | 0.76 | 24.55 (+) | 4.9e−007 | 333 | hsa-miR-483-3p |
| 5.0e+001 | 1.2e+003 | 0.99 | 24.01 (+) | 8.1e−066 | 31 | hsa-miR-202 |
| 6.4e+001 | 1.4e+003 | 0.95 | 21.83 (+) | 2.6e−024 | 347 | hsa-miR-513a-5p |
| 5.0e+001 | 6.0e+002 | 0.96 | 12.08 (+) | 9.3e−030 | 346 | hsa-miR-509-3-5p |
| 1.9e+002 | 2.2e+003 | 0.92 | 11.82 (+) | 2.2e−016 | 344 | hsa-miR-503 |
| 5.0e+001 | 5.1e+002 | 0.98 | 10.25 (+) | 3.8e−033 | 345 | hsa-miR-506 |
| 6.1e+001 | 5.9e+002 | 0.96 | 9.70 (+) | 1.2e−026 | 387 | MID-23751 |
| 3.1e+002 | 2.7e+003 | 0.71 | 8.66 (+) | 6.0e−005 | 334 | hsa-miR-483-5p |
| 1.4e+002 | 1.1e+003 | 0.91 | 7.79 (+) | 1.1e−015 | 351 | hsa-miR-542-5p |
| 2.0e+002 | 1.2e+003 | 0.72 | 5.77 (+) | 8.5e−005 | 324 | hsa-miR-382 |
| 1.0e+002 | 5.5e+002 | 0.75 | 5.44 (+) | 3.1e−007 | 326 | hsa-miR-409-5p |
| 1.4e+002 | 7.2e+002 | 0.73 | 5.31 (+) | 2.7e−004 | 269 | hsa-miR-134 |
| 7.9e+002 | 3.9e+003 | 0.69 | 4.98 (+) | 8.9e−003 | 155 | hsa-miR-127-3p |
| 2.1e+002 | 1.0e+003 | 0.68 | 4.93 (+) | 6.4e−003 | 320 | hsa-miR-376c |
| 1.6e+002 | 7.8e+002 | 0.69 | 4.84 (+) | 2.6e−003 | 322 | hsa-miR-379 |
| 2.2e+002 | 1.0e+003 | 0.72 | 4.53 (+) | 4.9e−005 | 59 | hsa-miR-487b |
| 1.5e+002 | 6.6e+002 | 0.69 | 4.49 (+) | 1.3e−003 | 318 | hsa-miR-370 |
| 1.7e+002 | 7.8e+002 | 0.71 | 4.45 (+) | 2.9e−004 | 325 | hsa-miR-409-3p |
| 1.1e+003 | 4.7e+003 | 0.92 | 4.19 (+) | 3.9e−011 | 245 | MID-18336 |
| 2.9e+002 | 1.1e+003 | 0.84 | 3.79 (+) | 1.8e−007 | 254 | MID-23291 |
| 1.4e+002 | 5.0e+002 | 0.70 | 3.71 (+) | 1.5e−004 | 331 | hsa-miR-432 |
| 1.5e+002 | 5.3e+002 | 0.69 | 3.60 (+) | 1.6e−003 | 275 | hsa-miR-154 |
| 3.1e+002 | 1.1e+003 | 0.90 | 3.48 (+) | 7.2e−011 | 180 | hsa-miR-1973 |
| 1.7e+002 | 5.4e+002 | 0.63 | 3.22 (+) | 6.9e−002 | 355 | hsa-miR-654-3p |
| 1.1e+003 | 3.5e+003 | 0.86 | 3.14 (+) | 8.6e−009 | 370 | MID-15986 |
| 1.8e+002 | 5.4e+002 | 0.64 | 3.07 (+) | 4.5e−002 | 323 | hsa-miR-381 |
| 2.9e+002 | 8.9e+002 | 0.63 | 3.07 (+) | 5.8e−002 | 312 | hsa-miR-337-5p |
| 1.8e+003 | 5.6e+003 | 0.88 | 3.03 (+) | 1.0e−008 | 178 | hsa-miR-193b |
| 1.4e+003 | 4.2e+003 | 0.81 | 3.02 (+) | 1.6e−006 | 249 | MID-20524 |
| 1.7e+003 | 9.5e+001 | 0.96 | 18.32 (−) | 1.3e−015 | 183 | hsa-miR-199b-5p |
| 1.9e+004 | 1.7e+003 | 0.95 | 10.80 (−) | 9.7e−014 | 181 | hsa-miR-199a-3p |
| 6.5e+002 | 6.1e+001 | 0.97 | 10.75 (−) | 2.6e−016 | 38 | hsa-miR-214* |
| 2.4e+004 | 2.5e+003 | 0.97 | 9.43 (−) | 1.9e−015 | 182 | hsa-miR-199a-5p |
| 7.1e+003 | 9.0e+002 | 0.96 | 7.89 (−) | 1.2e−011 | 37 | hsa-miR-214 |
| 7.5e+003 | 1.5e+003 | 0.90 | 4.87 (−) | 1.8e−012 | 3 | hsa-miR-100 |

TABLE 36-continued miR expression (in florescence units) distinguishing between adrenal carcinoma and mesothelioma or sarcoma tumors

| median values | | auROC | fold-change | p-value | SEQ ID NO. | miR name |
|---|---|---|---|---|---|---|
| 2.5e+003 | 7.6e+002 | 0.83 | 3.37 (−) | 3.6e−006 | 25 | hsa-miR-193a-3p |
| 1.3e+003 | 4.3e+002 | 0.80 | 3.05 (−) | 2.5e−006 | 169 | hsa-miR-152 |

+ the higher expression of this miR is in adrenal carcinoma
− the higher expression of this miR is in sarcoma and mesothelioma tumors hsa-miR-202 (SEQ ID NO: 31), hsa-miR-509-3p (SEQ ID NO: 61) and hsa-miR-214* (SEQ ID NO: 38) are used at node 35 of the binary-tree-classifier detailed in the invention to distinguish between adrenal carcinoma and sarcoma or mesothelioma tumors.

TABLE 37 miR expression (in florescence units) distinguishing between GIST and mesothelioma or sarcoma tumors

| median values | | auROC | fold-change | p-value | SEQ ID NO. | miR name |
|---|---|---|---|---|---|---|
| 2.4e+002 | 5.6e+003 | 0.97 | 23.39 (+) | 4.2e−033 | 165 | hsa-miR-143* |
| 4.9e+003 | 1.0e+005 | 0.97 | 21.41 (+) | 1.7e−025 | 14 | hsa-miR-143 |
| 8.1e+003 | 1.5e+005 | 0.99 | 18.42 (+) | 4.2e−026 | 15 | hsa-miR-145 |
| 5.0e+001 | 7.9e+002 | 0.87 | 15.77 (+) | 1.5e−010 | 333 | hsa-miR-483-3p |
| 6.2e+001 | 8.4e+002 | 0.98 | 13.54 (+) | 1.5e−037 | 272 | hsa-miR-145* |
| 1.6e+002 | 1.6e+003 | 0.99 | 9.58 (+) | 2.7e−024 | 270 | hsa-miR-139-5p |
| 1.8e+002 | 1.8e+003 | 0.96 | 9.49 (+) | 2.7e−019 | 45 | hsa-miR-29c* |
| 6.1e+001 | 5.8e+002 | 0.95 | 9.48 (+) | 7.9e−028 | 301 | hsa-miR-29b-2* |
| 1.9e+002 | 1.5e+003 | 0.94 | 7.89 (+) | 1.9e−015 | 191 | hsa-miR-29c |
| 1.2e+003 | 6.3e+003 | 0.96 | 5.12 (+) | 8.8e−014 | 46 | hsa-miR-30a |
| 1.9e+002 | 7.3e+002 | 0.93 | 3.84 (+) | 6.6e−013 | 195 | hsa-miR-30a* |
| 2.4e+002 | 8.7e+002 | 0.92 | 3.66 (+) | 1.8e−008 | 266 | hsa-miR-132 |
| 6.1e+002 | 2.2e+003 | 0.91 | 3.52 (+) | 4.2e−008 | 190 | hsa-miR-29b |
| 1.9e+002 | 6.5e+002 | 0.82 | 3.50 (+) | 1.5e−006 | 19 | hsa-miR-149 |
| 2.6e+002 | 9.0e+002 | 0.82 | 3.47 (+) | 4.8e−005 | 334 | hsa-miR-483-5p |
| 9.3e+002 | 1.9e+002 | 0.70 | 5.00 (−) | 2.1e−003 | 155 | hsa-miR-127-3p |
| 3.4e+003 | 7.1e+002 | 0.88 | 4.74 (−) | 2.3e−007 | 25 | hsa-miR-193a-3p |
| 7.0e+003 | 1.9e+003 | 0.79 | 3.64 (−) | 5.5e−004 | 147 | hsa-miR-221 |
| 9.8e+003 | 2.8e+003 | 0.78 | 3.54 (−) | 1.1e−003 | 40 | hsa-miR-222 |
| 3.2e+004 | 9.8e+003 | 0.75 | 3.26 (−) | 1.1e−003 | 34 | hsa-miR-21 |

+ the higher expression of this miR is in GIST
− the higher expression of this miR is in sarcoma and mesothelioma tumors hsa-miR-29C* (SEQ ID NO: 45) and hsa-miR-143 (SEQ ID NO: 14) are used at node 36 of the binary-tree-classifier detailed in the invention to distinguish between GIST and sarcoma or mesothelioma tumors.

TABLE 38 miR expression (in florescence units) distinguishing between chromophobe renal cell carcinoma tumors and clear cell or papillary renal cell carcinoma tumors

| median values | | auROC | fold-change | p-value | SEQ ID NO. | miR name |
|---|---|---|---|---|---|---|
| 8.8e+001 | 2.1e+003 | 0.99 | 23.68 (+) | 4.7e−017 | 13 | hsa-miR-141 |
| 3.0e+002 | 5.7e+003 | 0.99 | 18.81 (+) | 8.4e−012 | 30 | hsa-miR-200c |
| 6.6e+001 | 9.8e+002 | 0.99 | 14.85 (+) | 7.5e−019 | 361 | hsa-miR-874 |
| 5.0e+001 | 7.4e+002 | 0.97 | 14.80 (+) | 1.0e−014 | 280 | hsa-miR-187 |
| 5.0e+001 | 7.2e+002 | 0.98 | 14.47 (+) | 4.7e−018 | 362 | hsa-miR-891a |
| 5.3e+003 | 7.4e+004 | 0.98 | 13.97 (+) | 5.3e−017 | 147 | hsa-miR-221 |
| 7.6e+003 | 9.0e+004 | 0.97 | 11.89 (+) | 1.4e−015 | 40 | hsa-miR-222 |
| 5.3e+001 | 5.1e+002 | 0.98 | 9.66 (+) | 1.2e−017 | 291 | hsa-miR-222* |
| 1.4e+002 | 1.1e+003 | 0.94 | 8.01 (+) | 2.7e−010 | 387 | MID-23751 |
| 7.4e+001 | 5.4e+002 | 0.97 | 7.32 (+) | 4.4e−015 | 290 | hsa-miR-221* |
| 1.1e+002 | 5.6e+002 | 0.93 | 4.97 (+) | 3.2e−010 | 299 | hsa-miR-296-5p |
| 3.2e+002 | 1.5e+003 | 0.90 | 4.90 (+) | 3.1e−007 | 152 | hsa-miR-182 |
| 8.4e+002 | 3.3e+003 | 0.73 | 3.89 (+) | 6.3e−003 | 178 | hsa-miR-193b |
| 5.4e+003 | 1.7e+004 | 0.92 | 3.26 (+) | 2.2e−007 | 303 | hsa-miR-30b |
| 1.1e+003 | 3.5e+003 | 0.74 | 3.20 (+) | 8.1e−003 | 242 | MID-16489 |
| 6.2e+003 | 3.3e+002 | 0.85 | 18.53 (−) | 4.3e−006 | 49 | hsa-miR-31 |

TABLE 38-continued miR expression (in florescence units) distinguishing between chromophobe renal cell carcinoma tumors and clear cell or papillary renal cell carcinoma tumors

| median values | | auROC | fold-change | p-value | SEQ ID NO. | miR name |
|---|---|---|---|---|---|---|
| 6.1e+002 | 5.0e+001 | 0.90 | 12.13 (−) | 2.1e−007 | 11 | hsa-miR-138 |
| 1.8e+003 | 2.2e+002 | 0.98 | 8.38 (−) | 6.7e−014 | 35 | hsa-miR-21* |
| 7.9e+004 | 1.0e+004 | 0.95 | 7.54 (−) | 3.1e−013 | 34 | hsa-miR-21 |
| 3.7e+003 | 5.4e+002 | 0.92 | 6.79 (−) | 3.1e−009 | 36 | hsa-miR-210 |
| 9.8e+002 | 1.7e+002 | 0.97 | 5.71 (−) | 3.1e−013 | 206 | hsa-miR-455-3p |
| 1.0e+003 | 2.5e+002 | 0.91 | 4.07 (−) | 4.7e−008 | 16 | hsa-miR-146a |
| 6.0e+002 | 1.7e+002 | 0.89 | 3.64 (−) | 7.1e−007 | 170 | hsa-miR-155 |
| 7.5e+002 | 2.1e+002 | 0.78 | 3.48 (−) | 1.6e−003 | 177 | hsa-miR-192 |
| 8.6e+002 | 2.5e+002 | 0.86 | 3.39 (−) | 6.6e−006 | 17 | hsa-miR-146b-5p |

+ the higher expression of this miR is in chromophobe renal cell carcinoma tumors
− the higher expression of this miR is in clear cell or papillary renal cell carcinoma tumors hsa-miR-210 (SEQ ID NO: 36) and hsa-miR-221 (SEQ ID NO: 147) are used at node #37 of the binary-tree-classifier detailed in the invention to distinguish between chromophobe renal cell carcinoma tumors and clear cell or papillary renal cell carcinoma tumors.

TABLE 39 miR expression (in florescence units) distinguishing between clear cell and papillary renal cell carcinoma tumors

| median values | | auROC | fold-change | p-value | SEQ ID NO. | miR name |
|---|---|---|---|---|---|---|
| 1.2e+002 | 5.7e+002 | 0.89 | 4.81 (+) | 2.3e−005 | 344 | hsa-miR-503 |
| 1.6e+003 | 5.9e+003 | 0.81 | 3.65 (+) | 5.8e−003 | 382 | MID-22331 |
| 1.8e+003 | 6.4e+003 | 0.94 | 3.54 (+) | 1.1e−005 | 9 | hsa-miR-126 |
| 1.7e+003 | 5.7e+003 | 0.82 | 3.45 (+) | 3.0e−003 | 338 | hsa-miR-494 |
| 1.1e+004 | 1.3e+003 | 0.87 | 8.35 (−) | 3.1e−004 | 29 | hsa-miR-200b |
| 8.7e+003 | 1.3e+003 | 0.81 | 6.61 (−) | 3.0e−002 | 49 | hsa-miR-31 |
| 5.1e+003 | 9.5e+002 | 0.92 | 5.30 (−) | 5.0e−005 | 28 | hsa-miR-200a |
| 2.1e+003 | 5.1e+002 | 1.00 | 4.10 (−) | 1.1e−009 | 195 | hsa-miR-30a* |
| 1.9e+004 | 5.0e+003 | 1.00 | 3.70 (−) | 4.5e−010 | 46 | hsa-miR-30a |
| 5.3e+003 | 1.6e+003 | 0.86 | 3.39 (−) | 6.9e−004 | 4 | hsa-miR-10a |
| 7.6e+002 | 2.3e+002 | 0.76 | 3.23 (−) | 2.0e−002 | 11 | hsa-miR-138 |
| 6.4e+002 | 2.0e+002 | 0.79 | 3.17 (−) | 7.4e−003 | 254 | MID-23291 |

+ the higher expression of this miR is in renal clear cell carcinoma tumors
− the higher expression of this miR is in papillary renal cell carcinoma tumors hsa-miR-31 (SEQ ID NO: 49) and hsa-miR-126 (SEQ ID NO: 9) are used at node 38 of the binary-tree-classifier detailed in the invention to distinguish between renal clear cell and papillary cell carcinoma tumors.

TABLE 40 miR expression (in florescence units) distinguishing between pleural mesothelioma and sarcoma tumors

| median values | | auROC | fold-change | p-value | SEQ ID NO. | miR name |
|---|---|---|---|---|---|---|
| 1.2e+002 | 1.7e+003 | 0.78 | 13.97 (+) | 1.7e−006 | 49 | hsa-miR-31 |
| 4.3e+002 | 2.1e+003 | 0.89 | 5.01 (+) | 2.0e−011 | 35 | hsa-miR-21* |
| 5.9e+002 | 1.6e+003 | 0.84 | 2.75 (+) | 2.1e−008 | 17 | hsa-miR-146b-5p |
| 2.5e+004 | 6.9e+004 | 0.89 | 2.71 (+) | 4.8e−010 | 34 | h'sa-miR-21 |
| 2.4e+003 | 6.1e+003 | 0.77 | 2.57 (+) | 2.3e−005 | 25 | hsa-miR-193a-3p |
| 1.2e+003 | 3.1e+003 | 0.75 | 2.49 (+) | 5.9e−005 | 36 | hsa-miR-210 |
| 4.6e+002 | 1.1e+003 | 0.70 | 2.33 (+) | 9.7e−004 | 168 | hsa-miR-150 |
| 2.9e+002 | 6.8e+002 | 0.75 | 2.33 (+) | 1.4e−004 | 170 | hsa-miR-155 |
| 3.2e+002 | 7.3e+002 | 0.76 | 2.25 (+) | 1.4e−005 | 26 | hsa-miR-193a-5p |
| 1.1e+003 | 2.4e+003 | 0.76 | 2.13 (+) | 1.7e−004 | 4 | hsa-miR-10a |
| 5.1e+002 | 1.0e+003 | 0.70 | 2.03 (+) | 1.1e−003 | 190 | hsa-miR-29b |
| 9.0e+002 | 1.8e+003 | 0.77 | 1.99 (+) | 1.5e−005 | 46 | hsa-miR-30a |
| 2.6e+003 | 4.9e+003 | 0.71 | 1.90 (+) | 8.9e−003 | 10 | hsa-miR-130a |
| 2.8e+003 | 5.2e+003 | 0.69 | 1.88 (+) | 1.6e−003 | 240 | MID-15965 |
| 4.3e+003 | 7.3e+003 | 0.67 | 1.71 (+) | 1.5e−002 | 43 | hsa-miR-29a |
| 5.0e+003 | 8.2e+003 | 0.72 | 1.65 (+) | 1.1e−004 | 39 | hsa-miR-22 |
| 3.8e+003 | 5.9e+003 | 0.64 | 1.57 (+) | 2.9e−002 | 385 | MID-23168 |
| 9.9e+002 | 1.5e+003 | 0.66 | 1.55 (+) | 1.4e−002 | 63 | hsa-miR-574-5p |
| 7.5e+002 | 1.2e+003 | 0.66 | 1.53 (+) | 2.8e−002 | 202 | hsa-miR-378 |

TABLE 40-continued miR expression (in florescence units) distinguishing between pleural mesothelioma and sarcoma tumors

| median values | | auROC | fold-change | p-value | SEQ ID NO. | miR name |
|---|---|---|---|---|---|---|
| 2.7e+004 | 7.4e+003 | 0.84 | 3.62 (−) | 3.3e−007 | 181 | hsa-miR-199a-3p |
| 1.1e+004 | 3.1e+003 | 0.81 | 3.45 (−) | 3.2e−006 | 37 | hsa-miR-214 |
| 2.8e+003 | 8.3e+002 | 0.85 | 3.36 (−) | 6.7e−008 | 5 | hsa-miR-10b |
| 2.9e+003 | 9.1e+002 | 0.74 | 3.19 (−) | 2.0e−004 | 183 | hsa-miR-199b-5p |
| 3.0e+004 | 1.1e+004 | 0.80 | 2.84 (−) | 6.0e−005 | 182 | hsa-miR-199a-5p |
| 8.4e+002 | 3.8e+002 | 0.78 | 2.22 (−) | 5.7e−005 | 38 | hsa-miR-214* |
| 1.2e+003 | 7.0e+002 | 0.75 | 1.69 (−) | 2.8e−004 | 206 | hsa-miR-455-3p |
| 7.0e+002 | 4.4e+002 | 0.75 | 1.61 (−) | 2.9e−003 | 296 | hsa-miR-26b |
| 5.0e+004 | 3.2e+004 | 0.71 | 1.58 (−) | 4.3e−003 | 1 | hsa-let-7c |

+ the higher expression of this miR is in pleural mesothelioma tumors
− the higher expression of this miR is in sarcoma tumors hsa-miR-21* (SEQ ID NO: 35) hsa-miR-130a (SEQ ID NO: 10) and hsa-miR-10b (SEQ ID NO: 5) are used at node 39 of the binary-tree-classifier detailed in the invention to distinguish between pleural mesothelioma tumors and sarcoma tumors.

TABLE 41 miR expression(in florescence units) distinguishing between synovial sarcoma and other sarcoma tumors

| median values | | auROC | fold-change | p-value | SEQ ID NO. | miR name |
|---|---|---|---|---|---|---|
| 5.1e+001 | 1.3e+003 | 0.89 | 25.03 (+) | 2.9e−009 | 152 | hsa-miR-182 |
| 5.0e+001 | 1.1e+003 | 0.92 | 21.59 (+) | 9.2e−009 | 29 | hsa-miR-200b |
| 5.0e+001 | 9.7e+002 | 0.88 | 19.35 (+) | 5.9e−007 | 159 | hsa-miR-124 |
| 5.0e+001 | 6.4e+002 | 0.92 | 12.81 (+) | 1.5e−008 | 28 | hsa-miR-200a |
| 1.3e+002 | 8.9e+002 | 0.88 | 7.00 (+) | 8.2e−005 | 339 | hsa-miR-495 |
| 1.6e+002 | 1.1e+003 | 0.89 | 6.94 (+) | 1.6e−005 | 275 | hsa-miR-154 |
| 1.1e+002 | 7.3e+002 | 0.87 | 6.53 (+) | 2.8e−004 | 352 | hsa-miR-543 |
| 1.4e+002 | 8.8e+002 | 0.91 | 6.51 (+) | 6.1e−006 | 19 | hsa-miR-149 |
| 3.3e+002 | 2.0e+003 | 0.86 | 6.22 (+) | 9.6e−005 | 320 | hsa-miR-376c |
| 1.0e+003 | 6.2e+003 | 0.84 | 6.05 (+) | 1.5e−003 | 155 | hsa-miR-127-3p |
| 9.7e+001 | 5.2e+002 | 0.84 | 5.40 (+) | 1.7e−004 | 262 | hsa-miR-127-5p |
| 7.8e+002 | 4.2e+003 | 0.86 | 5.33 (+) | 2.5e−004 | 38 | hsa-miR-214* |
| 9.5e+003 | 5.0e+004 | 0.84 | 5.29 (+) | 7.3e−003 | 37 | hsa-miR-214 |
| 2.9e+004 | 1.4e+005 | 0.87 | 4.90 (+) | 4.7e−003 | 182 | hsa-miR-199a-5p |
| 1.4e+002 | 6.4e+002 | 0.81 | 4.56 (+) | 1.9e−003 | 331 | hsa-miR-432 |
| 1.1e+002 | 5.0e+002 | 0.84 | 4.43 (+) | 2.7e−004 | 317 | hsa-miR-369-5p |
| 2.1e+002 | 8.9e+002 | 0.78 | 4.19 (+) | 9.6e−003 | 323 | hsa-miR-381 |
| 1.9e+002 | 7.7e+002 | 0.81 | 3.96 (+) | 2.7e−003 | 355 | hsa-miR-654-3p |
| 5.6e+003 | 2.1e+004 | 0.91 | 3.79 (+) | 9.6e−006 | 3 | hsa-miR-100 |
| 1.7e+002 | 6.5e+002 | 0.86 | 3.76 (+) | 2.8e−004 | 282 | hsa-miR-196a |
| 4.1e+002 | 1.5e+003 | 0.80 | 3.55 (+) | 6.0e−003 | 312 | hsa-miR-337-5p |
| 2.6e+004 | 9.1e+004 | 0.86 | 3.52 (+) | 7.4e−003 | 181 | hsa-miR-199a-3p |
| 1.6e+002 | 5.5e+002 | 0.80 | 3.41 (+) | 6.5e−003 | 269 | hsa-miR-134 |
| 1.9e+002 | 6.4e+002 | 0.79 | 3.32 (+) | 8.3e−003 | 318 | hsa-miR-370 |
| 3.2e+002 | 1.0e+003 | 0.78 | 3.08 (+) | 7.6e−003 | 59 | hsa-miR-487b |
| 2.1e+002 | 6.4e+002 | 0.87 | 3.02 (+) | 7.1e−007 | 266 | hsa-miR-132 |
| 2.2e+002 | 6.3e+002 | 0.78 | 2.92 (+) | 1.1e−002 | 322 | hsa-miR-379 |
| 4.4e+004 | 1.2e+005 | 0.92 | 2.83 (+) | 1.6e−004 | 8 | hsa-miR-125b |
| 2.4e+002 | 6.1e+002 | 0.78 | 2.58 (+) | 8.4e−003 | 324 | hsa-miR-382 |
| 2.4e+003 | 6.0e+003 | 0.80 | 2.45 (+) | 1.8e−003 | 10 | hsa-miR-130a |
| 9.2e+003 | 8.4e+002 | 0.96 | 10.95 (−) | 2.1e−010 | 40 | hsa-miR-222 |
| 6.8e+003 | 6.7e+002 | 0.96 | 10.19 (−) | 7.9e−010 | 147 | hsa-miR-221 |
| 1.8e+003 | 3.6e+002 | 0.88 | 4.92 (−) | 2.1e−005 | 169 | hsa-miR-152 |
| 7.9e+003 | 1.7e+003 | 0.72 | 4.72 (−) | 2.8e−002 | 205 | hsa-miR-451 |
| 2.7e+004 | 5.9e+003 | 0.84 | 4.59 (−) | 4.4e−005 | 34 | hsa-miR-21 |
| 5.9e+002 | 1.4e+002 | 0.83 | 4.32 (−) | 9.2e−004 | 168 | hsa-miR-150 |
| 5.5e+003 | 1.3e+003 | 0.92 | 4.15 (−) | 2.2e−007 | 14 | hsa-miR-143 |
| 9.5e+003 | 2.9e+003 | 0.93 | 3.30 (−) | 2.7e−007 | 15 | hsa-miR-145 |
| 3.5e+003 | 1.0e+003 | 0.91 | 3.30 (−) | 1.6e−003 | 12 | hsa-miR-140-3p |
| 1.0e+003 | 3.5e+002 | 0.78 | 2.92 (−) | 6.1e−003 | 46 | hsa-miR-30a |
| 1.0e+003 | 3.6e+002 | 0.82 | 2.86 (−) | 4.1e−004 | 255 | MID-23794 |
| 5.8e+003 | 2.0e+003 | 0.88 | 2.82 (−) | 1.9e−005 | 39 | hsa-miR-22 |
| 1.1e+003 | 4.0e+002 | 0.77 | 2.74 (−) | 3.9e−003 | 23 | hsa-miR-185 |
| 5.8e+002 | 2.4e+002 | 0.80 | 2.45 (−) | 6.8e−003 | 190 | hsa-miR-29b |
| 7.1e+002 | 3.1e+002 | 0.79 | 2.27 (−) | 4.9e−003 | 236 | MID-00689 |
| 6.7e+004 | 3.2e+004 | 0.85 | 2.10 (−) | 2.2e−004 | 386 | MID-23178 |

TABLE 41-continued miR expression(in florescence units) distinguishing between synovial sarcoma and other sarcoma tumors

| median values | | auROC | fold-change | p-value | SEQ ID NO. | miR name |
|---|---|---|---|---|---|---|
| 7.7e+004 | 3.7e+004 | 0.80 | 2.08 (−) | 2.9e−003 | 379 | MID-18395 |
| 7.8e+002 | 3.8e+002 | 0.78 | 2.07 (−) | 7.4e−003 | 202 | hsa-miR-378 |

+ the higher expression of this miR is in synovial sarcoma tumors
− the higher expression of this miR is in other sarcoma tumors hsa-miR-100 (SEQ ID NO: 3) hsa-miR-145 (SEQ ID NO: 15) and hsa-miR-222 (SEQ ID NO: 40) are used at node 40 of the binary-tree-classifier detailed in the invention to distinguish between synovial sarcoma tumors and other sarcoma tumors.

TABLE 42 miR expression (in florescence units) distinguishing between chondrosarcoma and other non synovial sarcoma tumors

| median values | | auROC | fold-change | p-value | SEQ ID NO. | miR name |
|---|---|---|---|---|---|---|
| 2.9e+003 | 2.2e+005 | 1.00 | 75.69 (+) | 2.1e−022 | 12 | hsa-miR-140-3p |
| 1.5e+002 | 5.1e+003 | 0.91 | 35.23 (+) | 8.5e−015 | 271 | hsa-miR-140-5p |
| 1.1e+003 | 1.6e+004 | 0.98 | 14.49 (+) | 6.1e−015 | 206 | hsa-miR-455-3p |
| 5.0e+001 | 5.5e+002 | 0.71 | 11.03 (+) | 3.1e−003 | 333 | hsa-miR-483-3p |
| 9.5e+001 | 1.1e+003 | 0.88 | 11.01 (+) | 1.2e−006 | 11 | hsa-miR-138 |
| 9.2e+001 | 8.2e+002 | 0.87 | 8.87 (+) | 6.3e−012 | 58 | hsa-miR-455-5p |
| 1.1e+003 | 4.7e+003 | 0.91 | 4.37 (+) | 1.5e−006 | 36 | hsa-miR-210 |
| 3.6e+002 | 1.4e+003 | 0.83 | 3.98 (+) | 3.1e−004 | 18 | hsa-miR-148a |
| 1.5e+003 | 3.6e+003 | 0.72 | 2.36 (+) | 2.3e−002 | 178 | hsa-miR-193b |
| 1.3e+004 | 2.8e+004 | 0.84 | 2.13 (+) | 1.5e−004 | 293 | hsa-miR-23b |
| 2.7e+003 | 5.5e+003 | 0.80 | 2.05 (+) | 5.8e−004 | 189 | hsa-miR-27b |
| 3.4e+003 | 6.7e+002 | 0.70 | 5.01 (−) | 1.1e−004 | 382 | MID-22331 |
| 6.6e+002 | 1.7e+002 | 0.81 | 3.91 (−) | 1.2e−004 | 381 | MID-19962 |
| 3.2e+003 | 8.5e+002 | 0.83 | 3.76 (−) | 1.9e−004 | 240 | MID-15965 |
| 1.5e+003 | 4.2e+002 | 0.79 | 3.47 (−) | 8.0e−004 | 249 | MID-20524 |
| 2.9e+003 | 9.0e+002 | 0.85 | 3.27 (−) | 1.3e−005 | 5 | hsa-miR-10b |
| 2.9e+003 | 1.0e+003 | 0.78 | 2.92 (−) | 6.9e−005 | 377 | MID-17866 |
| 7.1e+002 | 2.7e+002 | 0.75 | 2.62 (−) | 1.3e−003 | 235 | hsa-miR-1978 |
| 7.0e+002 | 2.8e+002 | 0.81 | 2.48 (−) | 4.4e−005 | 17 | hsa-miR-146b-5p |
| 1.3e+003 | 5.7e+002 | 0.71 | 2.36 (−) | 2.7e−002 | 20 | hsa-miR-17 |
| 4.5e+003 | 1.9e+003 | 0.73 | 2.36 (−) | 8.2e−003 | 385 | MID-23168 |
| 1.1e+004 | 5.0e+003 | 0.74 | 2.16 (−) | 4.8e−003 | 384 | MID-23017 |
| 1.1e+003 | 5.4e+002 | 0.79 | 2.04 (−) | 3.2e−004 | 46 | hsa-miR-30a |
| 1.6e+004 | 8.1e+003 | 0.83 | 2.02 (−) | 3.0e−004 | 283 | hsa-miR-1979 |

+ the higher expression of this miR is in chondrosarcoma tumors
− the higher expression of this miR is in other non-synovial sarcoma tumors hsa-miR-140-3p (SEQ ID NO: 12) and hsa-miR-455-5p (SEQ ID NO: 58) are used at node 41 of the binary-tree-classifier detailed in the invention to distinguish between chondrosarcoma tumors and other non-synovial sarcoma tumors.

TABLE 43 miR expression (in florescence units) distinguishing between liposarcoma and other non chondrosarcoma and non synovial sarcoma tumors

| median values | | auROC | fold-change | p-value | SEQ ID NO. | miR name |
|---|---|---|---|---|---|---|
| 1.9e+004 | 1.2e+005 | 0.93 | 6.18 (+) | 1.6e−011 | 295 | hsa-miR-26a |
| 4.2e+003 | 1.8e+004 | 0.73 | 4.20 (+) | 8.1e−003 | 205 | hsa-miR-451 |
| 1.5e+003 | 5.9e+003 | 0.84 | 3.94 (+) | 6.5e−006 | 25 | hsa-miR-193a-3p |
| 2.4e+002 | 8.8e+002 | 0.88 | 3.70 (+) | 7.5e−007 | 26 | hsa-miR-193a-5p |
| 6.1e+003 | 2.0e+004 | 0.88 | 3.24 (+) | 2.2e−005 | 231 | hsa-miR-99a |
| 2.3e+003 | 5.9e+003 | 0.75 | 2.60 (+) | 1.9e−003 | 183 | hsa-miR-199b-5p |
| 3.1e+002 | 7.9e+002 | 0.79 | 2.54 (+) | 1.7e−004 | 42 | hsa-miR-224 |
| 2.9e+002 | 7.4e+002 | 0.71 | 2.54 (+) | 9.9e−003 | 254 | MID-23291 |
| 4.2e+002 | 1.0e+003 | 0.71 | 2.38 (+) | 1.5e−002 | 168 | hsa-miR-150 |
| 3.2e+002 | 7.7e+002 | 0.77 | 2.36 (+) | 1.1e−004 | 64 | hsa-miR-652 |
| 4.8e+003 | 1.1e+004 | 0.84 | 2.27 (+) | 5.4e−006 | 14 | hsa-miR-143 |

TABLE 43-continued miR expression (in florescence units) distinguishing between liposarcoma
and other non chondrosarcoma and non synovial sarcoma tumors

| median values | | auROC | fold-change | p-value | SEQ ID NO. | miR name |
|---|---|---|---|---|---|---|
| 1.4e+003 | 3.0e+003 | 0.76 | 2.20 (+) | 2.7e−004 | 178 | hsa-miR-193b |
| 7.9e+003 | 1.7e+004 | 0.78 | 2.13 (+) | 1.1e−004 | 15 | hsa-miR-145 |
| 4.6e+003 | 9.7e+003 | 0.79 | 2.12 (+) | 9.8e−004 | 39 | hsa-miR-22 |
| 1.4e+003 | 3.1e+002 | 0.79 | 4.49 (−) | 1.8e−004 | 36 | hsa-miR-210 |
| 2.4e+003 | 9.0e+002 | 0.71 | 2.60 (−) | 1.2e−002 | 154 | hsa-miR-181b |
| 5.9e+002 | 2.6e+002 | 0.75 | 2.29 (−) | 4.0e−003 | 265 | hsa-miR-130b |
| 6.5e+002 | 3.0e+002 | 0.75 | 2.16 (−) | 3.2e−003 | 174 | hsa-miR-181d |
| 1.2e+004 | 5.6e+003 | 0.79 | 2.14 (−) | 2.0e−003 | 384 | MID-23017 |
| 3.3e+003 | 1.6e+003 | 0.80 | 2.04 (−) | 6.6e−004 | 67 | hsa-miR-92a |

+ the higher expression of this miR is in liposarcoma tumors
− the higher expression of this miR is in other non-chondrosarcoma and non-synovial sarcoma tumors hsa-miR-210 (SEQ ID NO: 36) and hsa-miR-193a-5p (SEQ ID NO: 26) are used at node 42 of the binary-tree-classifier detailed in the invention to distinguish between liposarcoma tumors and other non-chondrosarcoma and non-synovial sarcoma tumors.

TABLE 44 miR expression (in florescence units) distinguishing between Ewing sarcoma or
osteosarcoma; and rhabdomyosarcoma, malignant fibrous histiocytoma (MFH) or
fibrosarcoma

| median values | | auROC | fold-change | p-value | SEQ ID NO. | miR name |
|---|---|---|---|---|---|---|
| 1.9e+002 | 1.2e+003 | 0.87 | 6.62 (+) | 1.1e−006 | 22 | hsa-miR-181a* |
| 1.1e+003 | 6.4e+003 | 0.91 | 5.68 (+) | 8.7e−009 | 154 | hsa-miR-181b |
| 3.7e+003 | 2.1e+004 | 0.93 | 5.67 (+) | 2.9e−010 | 21 | hsa-miR-181a |
| 4.2e+002 | 1.8e+003 | 0.85 | 4.19 (+) | 3.5e−006 | 174 | hsa-miR-181d |
| 2.9e+003 | 9.4e+003 | 0.72 | 3.27 (+) | 1.2e−002 | 205 | hsa-miR-451 |
| 1.8e+003 | 4.7e+003 | 0.78 | 2.63 (+) | 2.9e−003 | 158 | hsa-miR-106a |
| 1.1e+003 | 2.8e+003 | 0.78 | 2.52 (+) | 2.9e−003 | 186 | hsa-miR-20a |
| 2.0e+003 | 4.9e+003 | 0.81 | 2.45 (+) | 9.2e−005 | 148 | hsa-miR-93 |
| 1.1e+003 | 2.6e+003 | 0.77 | 2.32 (+) | 5.1e−003 | 20 | hsa-miR-17 |
| 6.0e+002 | 1.3e+002 | 0.71 | 4.54 (−) | 1.1e−002 | 59 | hsa-miR-487b |
| 4.9e+004 | 1.7e+004 | 0.84 | 2.86 (−) | 2.9e−005 | 8 | hsa-miR-125b |
| 3.4e+003 | 1.3e+003 | 0.72 | 2.70 (−) | 9.4e−003 | 183 | hsa-miR-199b-5p |
| 8.1e+003 | 3.5e+003 | 0.76 | 2.34 (−) | 1.1e−003 | 231 | hsa-miR-99a |

+ the higher expression of this miR is in Ewing sarcoma or osteosarcoma tumors
− the higher expression of this miR is in rhabdomyosarcoma, malignant fibrous histiocytoma (MFH) or fibrosarcoma tumors hsa-miR-181a (SEQ ID NO: 21) is used at node 43 of the binary-tree-classifier detailed in the invention to distinguish between Ewing sarcoma or osteosarcoma tumors and rhabdomyosarcoma, malignant fibrous histiocytoma (MFH) or fibrosarcoma tumors.

TABLE 45 miR expression(in florescence units) distinguishing between Ewing sarcoma and
osteosarcoma

| median values | | auROC | fold-change | p-value | SEQ ID NO. | miR name |
|---|---|---|---|---|---|---|
| 1.6e+002 | 1.1e+003 | 1.00 | 6.60 (+) | 3.7e−006 | 155 | hsa-miR-127-3p |
| 1.4e+003 | 8.5e+003 | 0.97 | 5.85 (+) | 8.9e−004 | 179 | hsa-miR-195 |
| 2.8e+003 | 1.4e+004 | 0.86 | 4.90 (+) | 1.4e−002 | 43 | hsa-miR-29a |
| 1.4e+003 | 6.5e+003 | 1.00 | 4.58 (+) | 1.1e−004 | 208 | hsa-miR-497 |
| 1.7e+002 | 7.6e+002 | 0.88 | 4.42 (+) | 1.0e−003 | 278 | hsa-miR-181a-2* |
| 4.0e+002 | 1.6e+003 | 0.86 | 4.05 (+) | 6.0e−003 | 17 | hsa-miR-146b-5p |
| 3.4e+003 | 8.9e+003 | 0.81 | 2.64 (+) | 1.4e−002 | 385 | MID-23168 |
| 8.0e+002 | 2.1e+003 | 0.77 | 2.60 (+) | 1.5e−002 | 174 | hsa-miR-181d |
| 1.6e+003 | 4.1e+003 | 0.82 | 2.55 (+) | 1.3e−002 | 5 | hsa-miR-10b |
| 2.2e+003 | 4.9e+003 | 0.84 | 2.19 (+) | 7.1e−003 | 52 | hsa-miR-34a |
| 2.5e+004 | 5.4e+004 | 0.97 | 2.16 (+) | 2.7e−004 | 257 | hsa-let-7b |
| 2.5e+002 | 5.2e+002 | 0.88 | 2.12 (+) | 2.1e−003 | 366 | MID-00144 |
| 4.5e+002 | 9.4e+002 | 0.84 | 2.06 (+) | 6.2e−003 | 48 | hsa-miR-30e |

TABLE 45-continued miR expression(in florescence units) distinguishing between Ewing sarcoma and osteosarcoma

| median values | | auROC | fold-change | p-value | SEQ ID NO. | miR name |
|---|---|---|---|---|---|---|
| 1.3e+003 | 5.0e+001 | 0.96 | 25.44 (−) | 7.9e−005 | 49 | hsa-miR-31 |
| 1.2e+004 | 2.0e+003 | 0.89 | 5.72 (−) | 1.4e−003 | 12 | hsa-miR-140-3p |
| 3.8e+003 | 7.6e+002 | 0.94 | 4.92 (−) | 5.2e−005 | 25 | hsa-miR-193a-3p |
| 1.8e+003 | 4.4e+002 | 0.89 | 4.09 (−) | 3.3e−003 | 169 | hsa-miR-152 |
| 3.7e+004 | 1.2e+004 | 0.89 | 3.00 (−) | 3.2e−003 | 34 | hsa-miR-21 |
| 8.1e+002 | 2.7e+002 | 0.83 | 2.96 (−) | 1.7e−003 | 35 | hsa-miR-21* |
| 1.7e+003 | 6.7e+002 | 0.88 | 2.55 (−) | 4.2e−003 | 23 | hsa-miR-185 |
| 2.1e+004 | 8.2e+003 | 0.82 | 2.53 (−) | 1.7e−002 | 384 | MID-23017 |
| 4.3e+003 | 1.7e+003 | 0.84 | 2.52 (−) | 3.8e−003 | 189 | hsa-miR-27b |
| 5.1e+003 | 2.3e+003 | 0.80 | 2.18 (−) | 3.0e−002 | 377 | MID-17866 |
| 9.6e+002 | 4.4e+002 | 0.78 | 2.17 (−) | 3.0e−002 | 265 | hsa-miR-130b |
| 3.7e+004 | 1.8e+004 | 0.82 | 2.07 (−) | 3.3e−003 | 294 | hsa-miR-24 |
| 1.8e+004 | 8.8e+003 | 0.86 | 2.03 (−) | 9.0e−003 | 293 | hsa-miR-23b |
| 3.0e+004 | 1.5e+004 | 0.80 | 2.02 (−) | 1.6e−002 | 292 | hsa-miR-23a |

+ the higher expression of this miR is in Ewing sarcoma tumors
− the higher expression of this miR is in osteosarcoma tumors FIG. 24 demonstrates binary decisions at node #44 of the decision-tree. Tumors originating in Ewing sarcoma (diamonds) are easily distinguished from tumors of osteosarcoma origin (squares) using the expression levels of hsa-miR-31 (SEQ ID NO: 49, y-axis) and hsa-miR-193a-3p (SEQ ID NO: 25, x-axis).

TABLE 46 miR expression (in florescence units) distinguishing between rhabdomyosarcoma and malignant fibrous histiocytoma (MFH) or fibrosarcoma

| median values | | auROC | fold-change | p-value | SEQ ID NO. | miR name |
|---|---|---|---|---|---|---|
| 5.0e+001 | 4.1e+003 | 0.96 | 81.34 (+) | 1.9e−007 | 33 | hsa-miR-206 |
| 5.7e+001 | 4.3e+003 | 0.89 | 74.89 (+) | 1.8e−004 | 268 | hsa-miR-133b |
| 5.9e+001 | 3.9e+003 | 0.88 | 66.65 (+) | 3.2e−004 | 267 | hsa-miR-133a |
| 5.0e+001 | 1.3e+003 | 0.89 | 25.89 (+) | 3.9e−006 | 333 | hsa-miR-483-3p |
| 5.3e+001 | 5.2e+002 | 0.85 | 9.90 (+) | 1.3e−004 | 276 | hsa-miR-154* |
| 5.8e+001 | 5.6e+002 | 0.85 | 9.63 (+) | 1.2e−004 | 319 | hsa-miR-376a |
| 5.7e+001 | 5.1e+002 | 0.86 | 9.00 (+) | 4.8e−005 | 306 | hsa-miR-323-3p |
| 2.5e+002 | 1.8e+003 | 0.84 | 7.01 (+) | 2.8e−003 | 320 | hsa-miR-376c |
| 2.6e+002 | 1.7e+003 | 0.82 | 6.52 (+) | 3.9e−003 | 334 | hsa-miR-483-5p |
| 3.1e+002 | 1.9e+003 | 0.87 | 6.22 (+) | 5.1e−004 | 323 | hsa-miR-381 |
| 1.0e+002 | 6.3e+002 | 0.85 | 6.19 (+) | 5.4e−004 | 300 | hsa-miR-299-3p |
| 1.3e+002 | 7.9e+002 | 0.82 | 6.18 (+) | 1.4e−003 | 281 | hsa-miR-188-5p |
| 4.1e+002 | 2.3e+003 | 0.86 | 5.73 (+) | 1.4e−003 | 59 | hsa-miR-487b |
| 1.5e+002 | 8.4e+002 | 0.85 | 5.68 (+) | 8.1e−004 | 339 | hsa-miR-495 |
| 3.7e+002 | 1.7e+003 | 0.79 | 4.57 (+) | 3.1e−002 | 316 | hsa-miR-362-5p |
| 2.0e+002 | 9.2e+002 | 0.80 | 4.49 (+) | 2.4e−003 | 176 | hsa-miR-18a |
| 2.9e+002 | 1.3e+003 | 0.82 | 4.39 (+) | 1.4e−003 | 348 | hsa-miR-532-3p |
| 1.8e+002 | 7.8e+002 | 0.85 | 4.27 (+) | 4.0e−004 | 352 | hsa-miR-543 |
| 4.0e+002 | 1.7e+003 | 0.81 | 4.18 (+) | 2.3e−002 | 349 | hsa-miR-532-5p |
| 1.9e+003 | 7.8e+003 | 0.87 | 4.14 (+) | 4.9e−004 | 67 | hsa-miR-92a |
| 5.7e+002 | 2.4e+003 | 0.86 | 4.13 (+) | 9.2e−004 | 357 | hsa-miR-660 |
| 1.3e+002 | 5.6e+002 | 0.78 | 4.13 (+) | 4.2e−003 | 315 | hsa-miR-362-3p |
| 2.3e+002 | 8.6e+002 | 0.81 | 3.73 (+) | 2.8e−003 | 343 | hsa-miR-502-3p |
| 2.0e+002 | 7.2e+002 | 0.84 | 3.64 (+) | 1.5e−003 | 342 | hsa-miR-501-3p |
| 2.3e+002 | 8.5e+002 | 0.82 | 3.62 (+) | 6.7e−003 | 355 | hsa-miR-654-3p |
| 1.9e+002 | 6.7e+002 | 0.79 | 3.56 (+) | 1.3e−002 | 340 | hsa-miR-500 |
| 2.4e+002 | 8.4e+002 | 0.80 | 3.56 (+) | 7.9e−003 | 344 | hsa-miR-503 |
| 2.2e+003 | 7.6e+003 | 0.78 | 3.53 (+) | 7.2e−003 | 10 | hsa-miR-130a |
| 2.6e+002 | 8.8e+002 | 0.80 | 3.35 (+) | 3.7e−003 | 341 | hsa-miR-500* |
| 2.6e+002 | 7.9e+002 | 0.79 | 3.06 (+) | 7.3e−003 | 331 | hsa-miR-432 |
| 9.3e+002 | 2.7e+003 | 0.77 | 2.90 (+) | 1.4e−002 | 20 | hsa-miR-17 |
| 4.3e+002 | 1.2e+003 | 0.86 | 2.90 (+) | 1.0e−003 | 277 | hsa-miR-17* |
| 2.4e+002 | 6.7e+002 | 0.83 | 2.77 (+) | 7.0e−003 | 318 | hsa-miR-370 |
| 1.6e+003 | 4.5e+003 | 0.78 | 2.75 (+) | 1.4e−002 | 158 | hsa-miR-106a |
| 4.3e+002 | 1.1e+003 | 0.83 | 2.67 (+) | 3.0e−003 | 265 | hsa-miR-130b |
| 1.0e+003 | 2.7e+003 | 0.86 | 2.63 (+) | 7.1e−004 | 284 | hsa-miR-19b |
| 8.6e+002 | 2.1e+003 | 0.82 | 2.43 (+) | 8.6e−003 | 36 | hsa-miR-210 |
| 6.1e+003 | 6.8e+002 | 0.90 | 8.92 (−) | 1.8e−004 | 183 | hsa-miR-199b-5p |
| 1.9e+004 | 4.5e+003 | 0.83 | 4.15 (−) | 8.0e−004 | 40 | hsa-miR-222 |
| 1.1e+003 | 3.1e+002 | 0.90 | 3.55 (−) | 5.6e−005 | 63 | hsa-miR-574-5p |
| 1.1e+004 | 3.2e+003 | 0.82 | 3.52 (−) | 2.2e−003 | 147 | hsa-miR-221 |
| 5.9e+003 | 1.8e+003 | 0.80 | 3.25 (−) | 2.0e−003 | 43 | hsa-miR-29a |
| 5.2e+002 | 1.6e+002 | 0.82 | 3.19 (−) | 5.4e−003 | 289 | hsa-miR-22* |
| 5.1e+003 | 1.7e+003 | 0.82 | 3.04 (−) | 7.0e−003 | 52 | hsa-miR-34a |

TABLE 46-continued miR expression (in florescence units) distinguishing between rhabdomyosarcoma and malignant fibrous histiocytoma (MFH) or fibrosarcoma

| median values | | auROC | fold-change | p-value | SEQ ID NO. | miR name |
|---|---|---|---|---|---|---|
| 8.1e+002 | 2.9e+002 | 0.76 | 2.81 (−) | 1.4e−002 | 190 | hsa-miR-29b |
| 1.2e+003 | 4.5e+002 | 0.86 | 2.67 (−) | 4.7e−003 | 4 | hsa-miR-10a |
| 3.7e+003 | 1.5e+003 | 0.86 | 2.43 (−) | 1.3e−003 | 5 | hsa-miR-10b |
| 7.0e+003 | 2.9e+003 | 0.85 | 2.39 (−) | 1.5e−003 | 39 | hsa-miR-22 |
| 1.6e+003 | 6.9e+002 | 0.78 | 2.25 (−) | 1.5e−002 | 169 | hsa-miR-152 |
| 2.9e+003 | 1.3e+003 | 0.76 | 2.19 (−) | 2.8e−002 | 208 | hsa-miR-497 |

+ the higher expression of this miR is in rhabdomyosarcoma tumors
− the higher expression of this miR is in MFH or fibrosarcoma tumors FIG. 25 demonstrates binary decisions at node #45 of the decision-tree. Tumors originating in Rhabdomyosarcoma (diamonds) are easily distinguished from tumors of malignant fibrous histiocytoma (MFH) or fibrosarcoma origin (squares) using the expression levels of hsa-miR-206 (SEQ ID NO: 33, y-axis), hsa-miR-22 (SEQ ID NO: 39, x-axis) and hsa-miR-487b (SEQ ID NO: 59, z-axis).

TABLE 47

β values of the decision tree classifier
The classification at node 11 is based on the gender of subject rather than on beta values; accordingly, no data is provided for this node. $P_{TH}$ = 0.5 for all nodes

| | miR 3 | | | miR 2 | | | miR 1 | | β0 intercept | Node |
|---|---|---|---|---|---|---|---|---|---|---|
| β3 | SEQ ID NO | miR hsa- | β2 | SEQ ID NO | miR hsa- | β1 | SEQ ID NO | miR hsa- | | |
| | | | | | | 2.3127 | 55 | miR-372 | −23.3111 | 1 |
| | | | | | | 2.3127 | 6 | miR-122 | −26.9408 | 2 |
| | | | −1.379 | 9 | miR-126 | 1.8567 | 29 | miR-200b | −3.8519 | 3 |
| | | | −1.2306 | 46 | miR-30a | 1.9582 | 30 | miR-200c | −8.2646 | 4 |
| −0.88435 | 46 | miR-30a | −1.7697 | 2 | let-7e | 1.1979 | 16 | miR-146a | 17.4706 | 5 |
| | | | 1.7188 | 68 | miR-92b | 1.5475 | 66 | miR-9* | −32.5621 | 6 |
| | | | 2.0005 | 208 | miR-497 | −1.1606 | 40 | miR-222 | −9.5521 | 7 |
| 1.6602 | 56 | miR-375 | 1.2404 | 65 | miR-7 | −1.0267 | 25 | miR-193a-3p | −23.053 | 8 |
| | | | 1.1414 | 35 | miR-21* | 2.0115 | 27 | miR-194 | −29.3207 | 9 |
| | | | 0.9879 | 14 | miR-143 | −1.5458 | 21 | miR-181a | 1.244 | 10 |
| | | | −1.256 | 211 | miR-516a-5p | −1.942 | 29 | miR-200b | 21.3416 | 12 |
| −1.0128 | 51 | miR-345 | 1.1064 | 32 | miR-205 | −1.1455 | 7 | miR-125a-5p | 10.3775 | 13 |
| 0.82076 | 56 | miR-375 | 0.93196 | 50 | miR-342-3p | 1.9505 | 25 | miR-193a-3p | −40.666 | 14 |
| −0.91632 | 32 | miR-205 | 0.61098 | 4 | miR-10a | −1.8153 | 39 | miR-22 | 26.2937 | 15 |
| −1.119 | 4 | miR-10a | 1.5494 | 11 | miR-138 | −1.3023 | 148 | miR-93 | 9.4008 | 16 |
| | | | −1.4509 | 17 | miR-146b-5p | −1.801 | 34 | miR-21 | 42.5529 | 17 |
| −1.3119 | 67 | miR-92a | −0.63021 | 49 | miR-31 | 1.7974 | 25 | miR-193a-3p | 0.52521 | 18 |
| 1.6447 | 34 | miR-21 | −1.3077 | 202 | miR-378 | 0.9662 | 11 | miR-138 | −20.7179 | 19 |
| | | | −2.0444 | 34 | miR-21 | 1.0814 | 3 | miR-100 | 15.0039 | 20 |
| 1.734 | 69 | miR-934 | 0.22547 | 191 | miR-29c | 1.5137 | 24 | miR-191 | −31.6015 | 21 |
| 1.6178 | 54 | miR-361-5p | 0.86212 | 1 | let-7c | 1.41 | 5 | miR-10b | −44.3141 | 22 |
| −1.8652 | 23 | miR-185 | 1.3275 | 5 | miR-10b | −0.32773 | 11 | miR-138 | 7.6168 | 23 |
| | | | 1.5521 | 47 | miR-30d | −1.7146 | 50 | miR-342-3p | 2.4904 | 24 |
| | | | −1.3096 | 45 | miR-29c* | 1.9063 | 20 | miR-17 | −10.0563 | 26 |
| −0.63749 | 67 | miR-92a | −1.5907 | 68 | miR-92b | 1.5531 | 40 | miR-222 | −2.3904 | 27 |
| 1.0197 | 53 | miR-34c-5p | −0.65807 | 37 | miR-214 | 1.9688 | 64 | miR-652 | −22.027 | 28 |
| | | | −1.3936 | 18 | miR-148a | 1.8457 | 34 | miR-21 | −11.4697 | 29 |
| −0.50909 | 146 | 1201 | −0.79749 | 36 | miR-210 | −1.3059 | 42 | miR-224 | 21.7628 | 30 |

TABLE 47-continued

β values of the decision tree classifier
The classification at node 11 is based on the gender of subject rather than on beta values;
accordingly, no data is provided for this node. $P_{TH} = 0.5$ for all nodes

| | miR 3 | | | miR 2 | | | miR 1 | | | |
|---|---|---|---|---|---|---|---|---|---|---|
| β3 | SEQ ID NO | miR hsa- | β2 | SEQ ID NO | miR hsa- | β1 | SEQ ID NO | miR hsa- | β0 intercept | Node |
| −1.3361 | 46 | miR-30a | 1.6268 | 43 | miR-29a | 0.95763 | 20 | miR-17 | −17.747 | 31 |
| −1.8214 | 51 | miR-345 | 0.62041 | 16 | miR-146a | 1.0661 | 49 | miR-31 | −2.3716 | 32 |
| 1.0224 | 46 | miR-30a | −2.0172 | 19 | miR-149 | 0.48415 | 29 | miR-200b | −4.226 | 33 |
| | | | 0.87847 | 56 | miR-375 | 2.1394 | 65 | miR-7 | −29.6828 | 34 |
| −0.057027 | 38 | miR-214* | 0.76095 | 61 | miR-509-3p | 2.1832 | 31 | miR-202 | −23.6445 | 35 |
| | | | 1.9413 | 14 | miR-143 | 1.2571 | 45 | miR-29c* | −41.4047 | 36 |
| | | | −0.63202 | 36 | miR-210 | 2.2247 | 147 | miR-221 | −25.1227 | 37 |
| | | | 2.3043 | 9 | miR-126 | −0.19797 | 49 | miR-31 | −24.5409 | 38 |
| 1.7948 | 35 | miR-21* | −1.0484 | 5 | miR-10b | 1.014 | 10 | miR-130a | −20.7495 | 39 |
| −0.77759 | 15 | miR-145 | −1.0289 | 40 | miR-222 | 1.9198 | 3 | miR-100 | −6.0971 | 40 |
| | | | 1.6244 | 58 | miR-455-5p | 1.6462 | 12 | miR-140-3p | −38.5059 | 41 |
| | | | 1.9298 | 26 | miR-193a-5p | −0.84091 | 36 | miR-210 | −10.7873 | 42 |
| | | | | | | 2.3127 | 21 | miR-181a | −30.4778 | 43 |
| | | | −1.0974 | 49 | miR-31 | −2.0358 | 25 | miR-193a-3p | 31.0975 | 44 |
| 1.8651 | 487 | miR-206 | 1.0201 | 59 | miR-487b | −0.91078 | 39 | miR-22 | −17.5516 | 45 |

TABLE 48

Using fine-needle aspiration (FNA), pleural effusion or bronchial brushing for the identification of cancer tissue of origin

| Class identified | Biopsy Site | Histological Type | Sampling Method |
|---|---|---|---|
| lung-small | Lymph Node | Neuroendocrine; Small | percutaneous FNA |
| UpperSCC | Lung | Non-small; squamous | percutaneous FNA |
| UpperSCC | Lung | Non-small; adenocarcinoma | percutaneous FNA |
| lung-small | Lung | Neuroendocrine; Small | percutaneous FNA |
| lung-adeno | Lung | Non-small; adenocarcinoma | percutaneous FNA |
| UpperSCC | Lung | Non-small; squamous | percutaneous FNA |
| lung-small | Lymph Node | Neuroendocrine; Small | transbronchial FNA |
| lung-small | Lung | Neuroendocrine; Small | transbronchial FNA |
| lung-adeno | Lung pleura | Non-small; adenocarcinoma | Pleural effusion |
| lung-adeno | Lung pleura | Non-small; adenocarcinoma | Pleural effusion |
| Lung, small | Lung | Neuroendocrine; Small | bronchial brushing |
| Lung, small | Lung | Neuroendocrine; Small | bronchial brushing |
| Lung, small | Lung | Neuroendocrine; Small | bronchial brushing |
| Lung, small | Lung | Neuroendocrine; Small | bronchial brushing |
| Lung, small | Lung | Neuroendocrine; Small | bronchial brushing |

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

REFERENCES

1. Bentwich, I. et al. Identification of hundreds of conserved and nonconserved human microRNAs. *Nat Genet* (2005).
2. Farh, K. K. et al. The Widespread Impact of Mammalian MicroRNAs on mRNA Repression and Evolution. *Science* (2005).
3. Griffiths-Jones, S., Grocock, R. J., van Dongen, S., Bateman, A. & Enright, A. J. miRBase: microRNA sequences, targets and gene nomenclature. *Nucleic Acids Res* 34, D140-4 (2006).
4. He, L. et al. A microRNA polycistron as a potential human oncogene. *Nature* 435, 828-33 (2005).
5. Baskerville, S. & Bartel, D. P. Microarray profiling of microRNAs reveals frequent coexpression with neighboring miRNAs and host genes. *Rna* 11, 241-7 (2005).
6. Landgraf, P. et al. A Mammalian microRNA Expression Atlas Based on Small RNA Library Sequencing. *Cell* 129, 1401-14 (2007).
7. Volinia, S. et al. A microRNA expression signature of human solid tumors defines cancer gene targets. *Proc Natl Acad Sci USA* (2006).

8. Lu, J. et al. MicroRNA expression profiles classify human cancers. *Nature* 435, 834-8 (2005).
9. Varadhachary, G. R., Abbruzzese, J. L. & Lenzi, R. Diagnostic strategies for unknown primary cancer. *Cancer* 100, 1776-85 (2004).
10. Pimiento, J. M., Teso, D., Malkan, A., Dudrick, S. J. & Palesty, J. A. Cancer of unknown primary origin: a decade of experience in a community-based hospital. *Am J Surg* 194, 833-7; discussion 837-8 (2007).
11. Shaw, P. H., Adams, R., Jordan, C. & Crosby, T. D. A clinical review of the investigation and management of carcinoma of unknown primary in a single cancer network. *Clin Oncol (R Coll Radiol)* 19, 87-95 (2007).
12. Hainsworth, J. D. & Greco, F. A. Treatment of patients with cancer of an unknown primary site. *N Engl J Med* 329, 257-63 (1993).
13. Blaszyk, H., Hartmann, A. & Bjornsson, J. Cancer of unknown primary: clinicopathologic correlations. *Apmis* 111, 1089-94 (2003).
14. Bloom, G. et al. Multi-platform, multi-site, microarray-based human tumor classification. *Am J Pathol* 164, 9-16 (2004).
15. Ma, X. J. et al. Molecular classification of human cancers using a 92-gene real-time quantitative polymerase chain reaction assay. *Arch Pathol Lab Med* 130, 465-73 (2006).
16. Talantov, D. et al. A quantitative reverse transcriptase-polymerase chain reaction assay to identify metastatic carcinoma tissue of origin. *J Mol Diagn* 8, 320-9 (2006).
17. Tothill, R. W. et al. An expression-based site of origin diagnostic method designed for clinical application to cancer of unknown origin. *Cancer Res* 65, 4031-40 (2005).
18. Shedden, K. A. et al. Accurate molecular classification of human cancers based on gene expression using a simple classifier with a pathological tree-based framework. *Am J Pathol* 163, 1985-95 (2003).
19. Raver-Shapira, N. et al. Transcriptional Activation of miR-34a Contributes to p53-Mediated Apoptosis. *Mol Cell* (2007).
20. Xiao, C. et al. MiR-150 Controls B Cell Differentiation by Targeting the Transcription Factor c-Myb. *Cell* 131, 146-59 (2007).

---

The invention claimed is:

1. A method of identifying a tissue of origin of a cancer sample, said method comprising:
   (a) obtaining a biological sample from a subject in need thereof, wherein the sample is of a cancer selected from the group consisting of cancer of unknown primary (CUP), primary cancer, and metastatic cancer;
   (b) measuring the level of nucleic acids consisting of SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148, and optionally at least one control nucleic acid, in the biological sample and comparing said level to a reference level using a classifier algorithm, wherein the tissue of origin of the cancer is identified in the subject if the level of the nucleic acids in the biological sample is above a reference threshold, wherein the measuring comprises contacting the sample with probes to the nucleic acids, wherein each probe consists of the complement of one of SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148, or of the optional at least one control nucleic acid, and wherein the probes are attached to a solid substrate; and
   (c) identifying the tissue of origin of the sample based on the level of the nucleic acids measured in step (b).

2. The method of claim 1, wherein the classifier algorithm is selected from the group consisting of: decision tree classifier, K-nearest neighbor classifier (KNN), logistic regression classifier, nearest neighbor classifier, neural network classifier, Gaussian mixture model (GMM), Support Vector Machine (SVM) classifier, nearest centroid classifier, linear regression classifier and random forest classifier.

3. The method of claim 1, wherein the cancer is selected from the group consisting of adrenocortical carcinoma; anus or skin squamous cell carcinoma; biliary tract adenocarcinoma; Ewing sarcoma; gastrointestinal stomal tumor (GIST); gastrointestinal tract carcinoid; renal cell carcinoma: chromophobe, clear cell and papillary; pancreatic islet cell tumor; pheochromocytoma; urothelial cell carcinoma (TCC); lung, head & neck, or esophagus squamous cell carcinoma (SCC); brain: astrocytic tumor, oligodendroglioma; breast adenocarcinoma; uterine cervix squamous cell carcinoma; chondrosarcoma; germ cell cancer; sarcoma; colorectal adenocarcinoma; liposarcoma; hepatocellular carcinoma (HCC); lung large cell or adenocarcinoma; lung carcinoid; pleural mesothelioma; lung small cell carcinoma; B-cell lymphoma; T-cell lymphoma; melanoma; malignant fibrous histiocytoma (MFH) or fibrosarcoma; osteosarcoma; ovarian primitive germ cell tumor; ovarian carcinoma; pancreatic adenocarcinoma; prostate adenocarcinoma; rhabdomyosarcoma; gastric or esophageal adenocarcinoma; synovial sarcoma; non-seminomatous testicular germ cell tumor; seminomatous testicular germ cell tumor; thymoma thymic carcinoma; follicular thyroid carcinoma; medullary thyroid carcinoma; and papillary thyroid carcinoma.

4. The method of claim 3, wherein a level of SEQ ID NOS: 55 above the reference threshold indicates a cancer of germ cell origin selected from the group consisting of an ovarian primitive cell and a testis cell, and further wherein a level of SEQ ID NOS: 29 and 62 above the reference threshold indicates a testis cell cancer origin selected from the group consisting of seminomatous testicular germ cell and non-seminomatous testicular germ cell.

5. The method of claim 3, wherein a level of a nucleic acid sequence selected from the group consisting of SEQ ID NOS: 55, 6, 9 and 29 above the reference threshold indicates a cancer origin selected from the group consisting of biliary tract adenocarcinoma and hepatocellular carcinoma.

6. The method of claim 3, wherein a level of a nucleic acid sequence selected from the group consisting of SEQ ID NOS: 55, 6, 30, 46, 16, 156, 66 and 68 above the reference threshold indicates a cancer of brain origin, and further wherein a level of SEQ ID NOS: 40 and 60 above the reference threshold indicates a brain cancer origin selected from the group consisting of oligodendroglioma and astrocytoma.

7. The method of claim 3, wherein a level of a nucleic acid sequence selected from the group consisting of SEQ ID NOS: 55, 6, 30, 46, 56, 65, 25, 27, 35, 14 and 21 above the reference threshold indicates a cancer of prostate adenocarcinoma origin; wherein a level of a nucleic acid sequence selected from the group consisting of SEQ ID NOS: 55, 6, 30, 46, 56, 65, 27, 35, 14, 21, 32, 51, 7, 25, 50, 11, 148, 4, 49 and 67 above the reference threshold indicates a cancer of breast adenocarcinoma origin; wherein a level of a nucleic acid sequence selected from the group consisting of SEQ ID NOS: 55, 6, 30, 46, 56, 65, 27, 35, 14, 21, 32, 51, 7, 25, 4, 39, 50, 11, 148, 49, 67, 57 and 34 above the reference threshold indicates a cancer of an ovarian carcinoma origin; wherein a level of a nucleic acid sequence selected from the group consisting of SEQ ID NOS: 55, 6, 30, 46, 56, 65, 25, 27, 35, 14, 21, 32, 51, 7, 11, 148, 4, 49, 67, 57 and 34 above the reference threshold indicates a cancer of lung large cell or lung adenocarcinoma origin; and wherein a level of a nucleic acid sequence selected from the group consisting of SEQ ID NOS: 55, 6, 30, 46, 56, 65, 25, 20 and 45 above the reference threshold indicates a cancer of lung small cell carcinoma origin.

8. The method of claim 3, wherein a level of a nucleic acid sequence selected from the group consisting of SEQ ID NOS: 55, 6, 30, 46, 56, 65, 25, 27, 35, 14, 21, 32, 51, 7, 11, 148 and 4 above the reference threshold indicates a cancer of thyroid carcinoma origin, and further wherein a level of SEQ ID NOS: 17 and 34 above the threshold indicates that the thyroid carcinoma origin is follicular or papillary.

9. The method of claim 3, wherein a level of a nucleic acid sequence selected from the group consisting of SEQ ID NOS: 55, 6, 30, 46, 56, 65, 25, 27, 35, 14, 21, 32, 51, 7, 50, 4, 39, 3 and 34 above the reference threshold indicates a cancer of a thymic carcinoma origin; or wherein a level of a nucleic acid sequence selected from the group consisting of SEQ ID NOS: 55, 6, 30, 46, 56, 65, 25, 27, 35, 14, 21, 32, 51, 7, 50, 4, 39, 3, 34, 69, 24 and 44 above the reference threshold indicates a cancer of urothelial cell carcinoma or squamous cell carcinoma origin, and further wherein a level of SEQ ID NOS: 1, 5 and 54 above the reference threshold indicates that the squamous-cell-carcinoma origin is uterine cervix squamous-cell-carcinoma or non-uterine cervix squamous cell carcinoma; or further wherein a level of SEQ ID NOS: 11 and 23 above the reference threshold indicates that the non-uterine cervix squamous cell carcinoma origin is selected from the group consisting of: a) anus or skin squamous cell carcinoma, and b) lung, head & neck, and esophagus squamous cell carcinoma.

10. The method of claim 3, wherein a level of a nucleic acid sequence selected from the group consisting of SEQ ID NOS: 55, 6, 30, 46, 56, 65, 25, 20, 45, 40, 67 and 68 above the reference threshold indicates a cancer of medullary thyroid carcinoma origin; wherein a level of a nucleic acid sequence selected from the group consisting of SEQ ID NOS: 55, 6, 30, 46, 56, 65, 25, 20, 45, 40, 67, 68, 64, 53 and 37 above the reference threshold indicates a cancer of lung carcinoid origin; and wherein a level of a nucleic acid sequence selected from the group consisting of SEQ ID NOS: 55, 6, 30, 46, 56, 65, 25, 20, 45, 40, 67, 68, 64, 53, 37, 34 and 18 above the reference threshold indicates a cancer of gastrointestinal tract carcinoid or pancreatic islet cell tumor origin.

11. The method of claim 3, wherein a level of a nucleic acid sequence selected from the group consisting of SEQ ID NOS: 55, 6, 30, 46, 56, 65, 25, 27, 35, 42, 36 and 146 above the reference threshold indicates a cancer of gastric or esophageal adenocarcinoma origin; wherein a level of a nucleic acid sequence selected from the group consisting of SEQ ID NOS: 55, 6, 30, 46, 56, 65, 25, 27, 35, 42, 36, 146, 20 and 43 above the reference threshold indicates a cancer of colorectal adenocarcinoma origin; wherein a level of a nucleic acid sequence selected from the group consisting of SEQ ID NOS: 55, 6, 30, 46, 56, 65, 25, 27, 35, 42, 36, 146, 20, 43, 51, 49 and 16 above the reference threshold indicates a cancer of pancreatic adenocarcinoma or biliary tract adenocarcinoma origin; wherein a level of a nucleic acid sequence selected from the group consisting of SEQ ID NOS: 55, 6, 30, 46, 16, 2, 66, 68, 19 and 29 above the reference threshold indicates a cancer of renal cell carcinoma origin, and further wherein a level of SEQ ID NOS: 36 and 147 above the reference threshold indicates a chromophobe renal cell carcinoma origin, or further wherein a level of SEQ ID NOS: 49 and 9 above the reference threshold indicates that the renal cell carcinoma origin is clear cell or papillary.

12. The method of claim 3, wherein a level of a nucleic acid sequence selected from the group consisting of SEQ ID NOS: 55, 6, 30, 46, 16, 2, 66, 68, 19, 29, 65 and 56 above the reference threshold indicates a cancer of pheochromacytoma origin; wherein a level of a nucleic acid sequence selected from the group consisting of SEQ ID NOS: 55, 6, 30, 46, 16, 2, 66, 68, 19, 29, 65, 56, 31, 38 and 61 above the reference threshold indicates a cancer of adrenocortical origin; wherein a level of a nucleic acid sequence selected from the group consisting of SEQ ID NOS: 55, 6, 30, 46, 16, 2, 66, 68, 19, 29, 65, 56, 31, 38, 61, 14 and 45 above the reference threshold indicates a cancer of gastrointestinal stomal tumor origin; wherein a level of a nucleic acid sequence selected from the group consisting of SEQ ID NOS: 55, 6, 30, 46, 16, 2, 66, 68, 19, 29, 65, 56, 31, 38, 61, 14, 45, 35, 10 and 5 above the reference threshold indicates a cancer of pleural mesothelioma or sarcoma origin, and further wherein a level of SEQ ID NOS: 3, 40 and 15 above the reference threshold indicates that the sarcoma is synovial sarcoma, or further wherein a level of SEQ ID NOS: 3, 40, 15, 12 and 58 above the reference threshold indicates that the sarcoma is chondrosarcoma, or further wherein a level of SEQ ID NOS: 3, 40, 15, 12, 58, 36 and 26 above the reference threshold indicates that the sarcoma is liposarcoma, or further wherein a level of SEQ ID NOS: 3, 40, 15, 12, 58, 36, 26, 21, 25 and 49 above the reference threshold indicates that the sarcoma is Ewing sarcoma or osteosarcoma; or further wherein a level of SEQ ID NOS: 3, 40, 15, 12, 58, 36, 26, 21, 59, 39 and 33 above the reference threshold indicates that the sarcoma is selected from the group consisting of: a) rhabdomyosarcoma, and b) malignant fibrous histiocytoma and fibrosarcoma.

13. The method of claim 1, wherein the biological sample is selected from the group consisting of a bodily fluid, a cell line, a tissue sample, a biopsy sample, a needle biopsy sample, a fine needle biopsy (FNA) sample, a surgically removed sample, and a sample obtained by tissue-sampling procedures such as endoscopy, bronchoscopy, or laparoscopic methods.

14. The method of claim 13, wherein the tissue is a fresh, frozen, fixed, wax-embedded or formalin-fixed paraffin-embedded (FFPE) tissue.

15. The method of claim 1, wherein the level of the nucleic acids is determined by nucleic acid hybridization.

16. The method of claim 15, wherein nucleic acid hybridization is performed using a solid-phase nucleic acid biochip array.

17. A kit for performing the method of claim 1 comprising probes to nucleic acids consisting of SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148, and optionally at least one control nucleic acid, wherein each probe consists of the complement of one of SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148, or of the optional at least one control nucleic acid, wherein the probes are attached to a solid substrate.

18. A method of treating a cancer selected from the group consisting of cancer of unknown primary (CUP), primary cancer, and metastatic cancer, comprising:
    (a) identifying a tissue of origin of a cancer sample, said method comprising:
        (i) obtaining a biological sample from a subject in need thereof, wherein the sample is of a cancer selected from the group consisting of cancer of unknown primary (CUP), primary cancer, and metastatic cancer;
        (ii) measuring the level of nucleic acids comprising SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148, in the biological sample and comparing said level to a reference level using a classifier algorithm, wherein the tissue of origin of the cancer is identified in the subject if the level of the nucleic acids in the biological sample is above a reference threshold, wherein the measuring comprises contacting the sample with probes comprising the complements of SEQ ID NOS: 1; 2 or 156; 3-7; 9-12; 14-21; 23-27; 29-40; 42; 43; 44 or 191; 45-47; 49-51; 53-56; 57 or 202; 58; 59; 60 or 208; 61; 62 or 211; 64-69; and 146-148; and
        (iii) identifying the tissue of origin of the sample based on the level of the nucleic acids measured in step (ii); and
    (b) administering a cancer treatment to the subject according to the tissue of origin of the cancer identified in step (a).

19. The kit of claim 17, wherein the probes are attached to a solid substrate through a linker.

* * * * *

SEQUENCE LISTING

```
<160> NUMBER OF SEQ ID NOS: 390

<210> SEQ ID NO 1
<211> LENGTH: 22
<212> TYPE: RNA
<213> ORGANISM: Homo sapiens

<400> SEQUENCE: 1
ugagguagua gguuguaugg uu                                                  22

<210> SEQ ID NO 2
<211> LENGTH: 22
<212> TYPE: RNA
<213> ORGANISM: Homo sapiens

<400> SEQUENCE: 2
ugagguagga gguuguauag uu                                                  22

<210> SEQ ID NO 3
<211> LENGTH: 22
<212> TYPE: RNA
<213> ORGANISM: Homo sapiens

<400> SEQUENCE: 3
aacccguaga uccgaacuug ug                                                  22

<210> SEQ ID NO 4
<211> LENGTH: 23
<212> TYPE: RNA
<213> ORGANISM: Homo sapiens

<400> SEQUENCE: 4
uacccuguag auccgaauuu gug                                                 23

<210> SEQ ID NO 5
<211> LENGTH: 23
<212> TYPE: RNA
<213> ORGANISM: Homo sapiens

<400> SEQUENCE: 5
uacccuguag aaccgaauuu gug                                                 23
```

```
<210> SEQ ID NO 6
<211> LENGTH: 22
<212> TYPE: RNA
<213> ORGANISM: Homo sapiens

<400> SEQUENCE: 6
uggaguguga caauguguu ug                                          22

<210> SEQ ID NO 7
<211> LENGTH: 24
<212> TYPE: RNA
<213> ORGANISM: Homo sapiens

<400> SEQUENCE: 7
ucccugagac ccuuuaaccu guga                                       24

<210> SEQ ID NO 8
<211> LENGTH: 22
<212> TYPE: RNA
<213> ORGANISM: Homo sapiens

<400> SEQUENCE: 8
ucccugagac ccuaacuugu ga                                         22

<210> SEQ ID NO 9
<211> LENGTH: 22
<212> TYPE: RNA
<213> ORGANISM: Homo sapiens

<400> SEQUENCE: 9
ucguaccgug aguaauaaug cg                                         22

<210> SEQ ID NO 10
<211> LENGTH: 22
<212> TYPE: RNA
<213> ORGANISM: Homo sapiens

<400> SEQUENCE: 10
cagugcaaug uuaaaagggc au                                         22

<210> SEQ ID NO 11
<211> LENGTH: 23
<212> TYPE: RNA
<213> ORGANISM: Homo sapiens

<400> SEQUENCE: 11
agcugguguu gugaaucagg ccg                                        23

<210> SEQ ID NO 12
<211> LENGTH: 21
<212> TYPE: RNA
<213> ORGANISM: Homo sapiens

<400> SEQUENCE: 12
uaccacaggg uagaaccacg g                                          21

<210> SEQ ID NO 13
<211> LENGTH: 22
<212> TYPE: RNA
<213> ORGANISM: Homo sapiens

<400> SEQUENCE: 13
uaacacuguc ugguaaagau gg                                         22
```

```
<210> SEQ ID NO 14
<211> LENGTH: 21
<212> TYPE: RNA
<213> ORGANISM: Homo sapiens

<400> SEQUENCE: 14
ugagaugaag cacuguagcu c                                                    21

<210> SEQ ID NO 15
<211> LENGTH: 23
<212> TYPE: RNA
<213> ORGANISM: Homo sapiens

<400> SEQUENCE: 15
guccaguuuu cccaggaauc ccu                                                  23

<210> SEQ ID NO 16
<211> LENGTH: 22
<212> TYPE: RNA
<213> ORGANISM: Homo sapiens

<400> SEQUENCE: 16
ugagaacuga auuccauggg uu                                                   22

<210> SEQ ID NO 17
<211> LENGTH: 22
<212> TYPE: RNA
<213> ORGANISM: Homo sapiens

<400> SEQUENCE: 17
ugagaacuga auuccauagg cu                                                   22

<210> SEQ ID NO 18
<211> LENGTH: 22
<212> TYPE: RNA
<213> ORGANISM: Homo sapiens

<400> SEQUENCE: 18
ucagugcacu acagaacuuu gu                                                   22

<210> SEQ ID NO 19
<211> LENGTH: 23
<212> TYPE: RNA
<213> ORGANISM: Homo sapiens

<400> SEQUENCE: 19
ucuggcuccg ugucuucacu ccc                                                  23

<210> SEQ ID NO 20
<211> LENGTH: 23
<212> TYPE: RNA
<213> ORGANISM: Homo sapiens

<400> SEQUENCE: 20
caaagugcuu acagugcagg uag                                                  23

<210> SEQ ID NO 21
<211> LENGTH: 23
<212> TYPE: RNA
<213> ORGANISM: Homo sapiens

<400> SEQUENCE: 21
aacauucaac gcugucggug agu                                                  23
```

```
<210> SEQ ID NO 22
<211> LENGTH: 22
<212> TYPE: RNA
<213> ORGANISM: Homo sapiens

<400> SEQUENCE: 22
accaucgacc guugauugua cc                                            22

<210> SEQ ID NO 23
<211> LENGTH: 22
<212> TYPE: RNA
<213> ORGANISM: Homo sapiens

<400> SEQUENCE: 23
uggagagaaa ggcaguuccu ga                                            22

<210> SEQ ID NO 24
<211> LENGTH: 23
<212> TYPE: RNA
<213> ORGANISM: Homo sapiens

<400> SEQUENCE: 24
caacggaauc ccaaaagcag cug                                           23

<210> SEQ ID NO 25
<211> LENGTH: 22
<212> TYPE: RNA
<213> ORGANISM: Homo sapiens

<400> SEQUENCE: 25
aacuggccua caaaguccca gu                                            22

<210> SEQ ID NO 26
<211> LENGTH: 22
<212> TYPE: RNA
<213> ORGANISM: Homo sapiens

<400> SEQUENCE: 26
ugggucuuug cgggcgagau ga                                            22

<210> SEQ ID NO 27
<211> LENGTH: 22
<212> TYPE: RNA
<213> ORGANISM: Homo sapiens

<400> SEQUENCE: 27
uguaacagca acuccaugug ga                                            22

<210> SEQ ID NO 28
<211> LENGTH: 22
<212> TYPE: RNA
<213> ORGANISM: Homo sapiens

<400> SEQUENCE: 28
uaacacuguc ugguaacgau gu                                            22

<210> SEQ ID NO 29
<211> LENGTH: 22
<212> TYPE: RNA
<213> ORGANISM: Homo sapiens

<400> SEQUENCE: 29
```

-continued uaauacugcc ugguaaugau ga                                    22

<210> SEQ ID NO 30
<211> LENGTH: 23
<212> TYPE: RNA
<213> ORGANISM: Homo sapiens

<400> SEQUENCE: 30
uaauacugcc ggguaaugau gga                                   23

<210> SEQ ID NO 31
<211> LENGTH: 20
<212> TYPE: RNA
<213> ORGANISM: Homo sapiens

<400> SEQUENCE: 31
agagguauag ggcaugggaa                                       20

<210> SEQ ID NO 32
<211> LENGTH: 22
<212> TYPE: RNA
<213> ORGANISM: Homo sapiens

<400> SEQUENCE: 32
uccuucauuc caccggaguc ug                                    22

<210> SEQ ID NO 33
<211> LENGTH: 22
<212> TYPE: RNA
<213> ORGANISM: Homo sapiens

<400> SEQUENCE: 33
uggaauguaa ggaagugugu gg                                    22

<210> SEQ ID NO 34
<211> LENGTH: 22
<212> TYPE: RNA
<213> ORGANISM: Homo sapiens

<400> SEQUENCE: 34
uagcuuauca gacugauguu ga                                    22

<210> SEQ ID NO 35
<211> LENGTH: 21
<212> TYPE: RNA
<213> ORGANISM: Homo sapiens

<400> SEQUENCE: 35
caacaccagu cgaugggcug u                                     21

<210> SEQ ID NO 36
<211> LENGTH: 22
<212> TYPE: RNA
<213> ORGANISM: Homo sapiens

<400> SEQUENCE: 36
cugugcgugu gacagcggcu ga                                    22

<210> SEQ ID NO 37
<211> LENGTH: 22
<212> TYPE: RNA
<213> ORGANISM: Homo sapiens

<400> SEQUENCE: 37
acagcaggca cagacaggca gu                                          22

<210> SEQ ID NO 38
<211> LENGTH: 22
<212> TYPE: RNA
<213> ORGANISM: Homo sapiens

<400> SEQUENCE: 38
ugccugucua cacuugcugu gc                                          22

<210> SEQ ID NO 39
<211> LENGTH: 22
<212> TYPE: RNA
<213> ORGANISM: Homo sapiens

<400> SEQUENCE: 39
aagcugccag uugaagaacu gu                                          22

<210> SEQ ID NO 40
<211> LENGTH: 21
<212> TYPE: RNA
<213> ORGANISM: Homo sapiens

<400> SEQUENCE: 40
agcuacaucu ggcuacuggg u                                           21

<210> SEQ ID NO 41
<211> LENGTH: 22
<212> TYPE: RNA
<213> ORGANISM: Homo sapiens

<400> SEQUENCE: 41
ugucaguuug ucaaauaccc ca                                          22

<210> SEQ ID NO 42
<211> LENGTH: 21
<212> TYPE: RNA
<213> ORGANISM: Homo sapiens

<400> SEQUENCE: 42
caagucacua gugguuccgu u                                           21

<210> SEQ ID NO 43
<211> LENGTH: 22
<212> TYPE: RNA
<213> ORGANISM: Homo sapiens

<400> SEQUENCE: 43
uagcaccauc ugaaaucggu ua                                          22

<210> SEQ ID NO 44
<211> LENGTH: 22
<212> TYPE: RNA
<213> ORGANISM: Homo sapiens

<400> SEQUENCE: 44
uagcaccauu ugaaaucggu ua                                          22

<210> SEQ ID NO 45
<211> LENGTH: 22
<212> TYPE: RNA
<213> ORGANISM: Homo sapiens

<400> SEQUENCE: 45
ugaccgauuu cuccuggugu uc                                        22

<210> SEQ ID NO 46
<211> LENGTH: 22
<212> TYPE: RNA
<213> ORGANISM: Homo sapiens

<400> SEQUENCE: 46
uguaaacauc cucgacugga ag                                        22

<210> SEQ ID NO 47
<211> LENGTH: 22
<212> TYPE: RNA
<213> ORGANISM: Homo sapiens

<400> SEQUENCE: 47
uguaaacauc cccgacugga ag                                        22

<210> SEQ ID NO 48
<211> LENGTH: 22
<212> TYPE: RNA
<213> ORGANISM: Homo sapiens

<400> SEQUENCE: 48
uguaaacauc cuugacugga ag                                        22

<210> SEQ ID NO 49
<211> LENGTH: 21
<212> TYPE: RNA
<213> ORGANISM: Homo sapiens

<400> SEQUENCE: 49
aggcaagaug cuggcauagc u                                         21

<210> SEQ ID NO 50
<211> LENGTH: 23
<212> TYPE: RNA
<213> ORGANISM: Homo sapiens

<400> SEQUENCE: 50
ucucacacag aaaucgcacc cgu                                       23

<210> SEQ ID NO 51
<211> LENGTH: 22
<212> TYPE: RNA
<213> ORGANISM: Homo sapiens

<400> SEQUENCE: 51
gcugacuccu aguccagggc uc                                        22

<210> SEQ ID NO 52
<211> LENGTH: 22
<212> TYPE: RNA
<213> ORGANISM: Homo sapiens

<400> SEQUENCE: 52
uggcaguguc uuagcugguu gu                                        22

<210> SEQ ID NO 53
<211> LENGTH: 23
<212> TYPE: RNA
<213> ORGANISM: Homo sapiens -continued

```
<400> SEQUENCE: 53
aggcagugua guuagcugau ugc                                              23

<210> SEQ ID NO 54
<211> LENGTH: 22
<212> TYPE: RNA
<213> ORGANISM: Homo sapiens

<400> SEQUENCE: 54
uuaucagaau cuccagggu ac                                                22

<210> SEQ ID NO 55
<211> LENGTH: 23
<212> TYPE: RNA
<213> ORGANISM: Homo sapiens

<400> SEQUENCE: 55
aaagugcugc gacauuugag cgu                                              23

<210> SEQ ID NO 56
<211> LENGTH: 22
<212> TYPE: RNA
<213> ORGANISM: Homo sapiens

<400> SEQUENCE: 56
uuuguucguu cggcucgcgu ga                                               22

<210> SEQ ID NO 57
<211> LENGTH: 21
<212> TYPE: RNA
<213> ORGANISM: Homo sapiens

<400> SEQUENCE: 57
acuggacuug gagucagaag g                                                21

<210> SEQ ID NO 58
<211> LENGTH: 22
<212> TYPE: RNA
<213> ORGANISM: Homo sapiens

<400> SEQUENCE: 58
uaugugccuu uggacuacau cg                                               22

<210> SEQ ID NO 59
<211> LENGTH: 22
<212> TYPE: RNA
<213> ORGANISM: Homo sapiens

<400> SEQUENCE: 59
aaucguacag ggucauccac uu                                               22

<210> SEQ ID NO 60
<211> LENGTH: 21
<212> TYPE: RNA
<213> ORGANISM: Homo sapiens

<400> SEQUENCE: 60
cagcagcaca cuguggguug u                                                21

<210> SEQ ID NO 61
<211> LENGTH: 22
<212> TYPE: RNA
```

```
<213> ORGANISM: Homo sapiens

<400> SEQUENCE: 61
ugauugguac gucugugggu ag                                            22

<210> SEQ ID NO 62
<211> LENGTH: 23
<212> TYPE: RNA
<213> ORGANISM: Homo sapiens

<400> SEQUENCE: 62
uucucgagga aagaagcacu uuc                                           23

<210> SEQ ID NO 63
<211> LENGTH: 23
<212> TYPE: RNA
<213> ORGANISM: Homo sapiens

<400> SEQUENCE: 63
ugagugugug ugugagugug ugu                                           23

<210> SEQ ID NO 64
<211> LENGTH: 21
<212> TYPE: RNA
<213> ORGANISM: Homo sapiens

<400> SEQUENCE: 64
aauggcgcca cuagggguugu g                                            21

<210> SEQ ID NO 65
<211> LENGTH: 23
<212> TYPE: RNA
<213> ORGANISM: Homo sapiens

<400> SEQUENCE: 65
uggaagacua gugauuuugu ugu                                           23

<210> SEQ ID NO 66
<211> LENGTH: 22
<212> TYPE: RNA
<213> ORGANISM: Homo sapiens

<400> SEQUENCE: 66
auaaagcuag auaaccgaaa gu                                            22

<210> SEQ ID NO 67
<211> LENGTH: 22
<212> TYPE: RNA
<213> ORGANISM: Homo sapiens

<400> SEQUENCE: 67
uauugcacuu gucccggccu gu                                            22

<210> SEQ ID NO 68
<211> LENGTH: 22
<212> TYPE: RNA
<213> ORGANISM: Homo sapiens

<400> SEQUENCE: 68
uauugcacuc gucccggccu cc                                            22

<210> SEQ ID NO 69
<211> LENGTH: 22
```

```
<212> TYPE: RNA
<213> ORGANISM: Homo sapiens

<400> SEQUENCE: 69
ugucuacuac uggagacacu gg                                              22

<210> SEQ ID NO 70
<211> LENGTH: 84
<212> TYPE: RNA
<213> ORGANISM: Homo sapiens

<400> SEQUENCE: 70
gcauccgggu ugagguagua gguuguaugg uuuagaguua cacccuggga guuaacugua     60
caaccuucua gcuuuccuug gagc                                            84

<210> SEQ ID NO 71
<211> LENGTH: 79
<212> TYPE: RNA
<213> ORGANISM: Homo sapiens

<400> SEQUENCE: 71
cccgggcuga gguaggaggu uguauaguug aggaggacac ccaaggagau cacuauacgg     60
ccuccuagcu uuccccagg                                                  79

<210> SEQ ID NO 72
<211> LENGTH: 80
<212> TYPE: RNA
<213> ORGANISM: Homo sapiens

<400> SEQUENCE: 72
ccuguugcca caaacccgua gauccgaacu ugugguauua guccgcacaa gcuuguaucu     60
auagguaugu gucuguuagg                                                 80

<210> SEQ ID NO 73
<211> LENGTH: 110
<212> TYPE: RNA
<213> ORGANISM: Homo sapiens

<400> SEQUENCE: 73
gaucugucug ucuucuguau auacccugua gauccgaauu uguguaagga auuuguggu      60 cacaaauucg uaucuagggg aauauguagu ugacauaaac acuccgcucu               110

<210> SEQ ID NO 74
<211> LENGTH: 110
<212> TYPE: RNA
<213> ORGANISM: Homo sapiens

<400> SEQUENCE: 74
ccagagguug uaacguuguc uauauauacc cuguagaacc gaauugugu gguauccgua      60 uagucacaga uucgauucua ggggaauaua uggucgaugc aaaaacuuca               110

<210> SEQ ID NO 75
<211> LENGTH: 85
<212> TYPE: RNA
<213> ORGANISM: Homo sapiens

<400> SEQUENCE: 75
ccuuagcaga gcuguggagu gugacaaugg uguuugaguc uaaacuauca aacgccauua     60
ucacacuaaa uagcuacugc uaggc                                           85
```

<210> SEQ ID NO 76
<211> LENGTH: 86
<212> TYPE: RNA
<213> ORGANISM: Homo sapiens

<400> SEQUENCE: 76
ugccagucuc uaggucccug agacccuuua accugugagg acauccaggg ucacagguga      60
gguucuuggg agccuggcgu cuggcc                                          86

<210> SEQ ID NO 77
<211> LENGTH: 88
<212> TYPE: RNA
<213> ORGANISM: Homo sapiens

<400> SEQUENCE: 77
ugcgcuccuc ucaguvccug agacccuaac uugugauguu uaccguuuaa auccacgggu      60
uaggcucuug ggagcugcga gucgugcu                                        88

<210> SEQ ID NO 78
<211> LENGTH: 89
<212> TYPE: RNA
<213> ORGANISM: Homo sapiens

<400> SEQUENCE: 78
accagacuuu uccuagvccc ugagacccua acuugugagg uauuuuagua acaucacaag      60
ucaggcucuu gggaccuagg cggagggga                                       89

<210> SEQ ID NO 79
<211> LENGTH: 85
<212> TYPE: RNA
<213> ORGANISM: Homo sapiens

<400> SEQUENCE: 79
cgcuggcgac gggacauuau uacuuuuggu acgcgcugug acacuucaaa cucguaccgu      60
gaguaauaau gcgccgucca cggca                                           85

<210> SEQ ID NO 80
<211> LENGTH: 89
<212> TYPE: RNA
<213> ORGANISM: Homo sapiens

<400> SEQUENCE: 80
ugcugcuggc cagagcucuu uucacauugu gcuacugucu gcaccuguca cuagcagugc      60
aauguuaaaa gggcauuggc cguguagug                                       89

<210> SEQ ID NO 81
<211> LENGTH: 99
<212> TYPE: RNA
<213> ORGANISM: Homo sapiens

<400> SEQUENCE: 81
cccuggcaug gugugguggg gcagcugguhg uugugaauca ggccguugcc aaucagagaa      60
cggcuacuuc acaacaccag ggccacacca cacuacagg                            99

<210> SEQ ID NO 82
<211> LENGTH: 84
<212> TYPE: RNA
<213> ORGANISM: Homo sapiens

<400> SEQUENCE: 82

```
cguugcugca gcugguguug ugaaucaggc cgacgagcag cgcauccucu uacccggcua      60
uuucacgaca ccaggguugc auca                                            84

<210> SEQ ID NO 83
<211> LENGTH: 100
<212> TYPE: RNA
<213> ORGANISM: Homo sapiens

<400> SEQUENCE: 83 ugugcucuc ucuguguccu gccagugguu uuacccuaug guagguuacg ucaugcuguu       60
cuaccacagg guagaaccac ggacaggaua ccggggcacc                          100

<210> SEQ ID NO 84
<211> LENGTH: 95
<212> TYPE: RNA
<213> ORGANISM: Homo sapiens

<400> SEQUENCE: 84
cggccggccc uggguccauc uuccaguaca guguuggaug gucuaauugu gaagcuccua      60
acacugucug guaaagaugg cucccggguc gguuc                                95

<210> SEQ ID NO 85
<211> LENGTH: 106
<212> TYPE: RNA
<213> ORGANISM: Homo sapiens

<400> SEQUENCE: 85
gcgcagcgcc cugucuccca gccugaggug cagugcugca ucucggucu guugggaguc       60 ugagaugaag cacuguagcu caggaagaga gaaguuguuc ugcagc                   106

<210> SEQ ID NO 86
<211> LENGTH: 88
<212> TYPE: RNA
<213> ORGANISM: Homo sapiens

<400> SEQUENCE: 86
caccuugucc ucacggucca guuuucccag gaaucccuua gaugcuaaga uggggauucc      60
uggaaauacu guucuugagg ucauggguu                                       88

<210> SEQ ID NO 87
<211> LENGTH: 99
<212> TYPE: RNA
<213> ORGANISM: Homo sapiens

<400> SEQUENCE: 87
ccgaugugua uccucagcuu ugagaacuga auccauggg uugugucagu gucagaccuc       60
ugaaauucag uucuucagcu gggauaucuc ugucaucgu                            99

<210> SEQ ID NO 88
<211> LENGTH: 73
<212> TYPE: RNA
<213> ORGANISM: Homo sapiens

<400> SEQUENCE: 88
ccuggcacug agaacugaau uccauaggcu gugagcucua gcaaugcccu guggacucag      60
uucuggugcc cgg                                                        73

<210> SEQ ID NO 89
```

```
<211> LENGTH: 68
<212> TYPE: RNA
<213> ORGANISM: Homo sapiens

<400> SEQUENCE: 89
gaggcaaagu ucugagacac uccgacucug aguaugauag aagucagugc acuacagaac    60
uuugucuc                                                             68

<210> SEQ ID NO 90
<211> LENGTH: 89
<212> TYPE: RNA
<213> ORGANISM: Homo sapiens

<400> SEQUENCE: 90
gccggcgccc gagcucuggc uccgugucuu cacucccgug cuuguccgag gagggaggga    60
gggacggggg cugugcuggg gcagcugga                                      89

<210> SEQ ID NO 91
<211> LENGTH: 84
<212> TYPE: RNA
<213> ORGANISM: Homo sapiens

<400> SEQUENCE: 91
gucagaauaa ugucaaagug cuuacagugc agguagugau augugcaucu acugcaguga    60
aggcacuugu agcauuaugg ugac                                           84

<210> SEQ ID NO 92
<211> LENGTH: 110
<212> TYPE: RNA
<213> ORGANISM: Homo sapiens

<400> SEQUENCE: 92
ugaguuuuga gguugcuuca gugaacauuc aacgcugucg gugaguuugg aauuaaaauc    60
aaaaccaucg accguugauu guacccuaug gcuaaccauc aucuacucca               110

<210> SEQ ID NO 93
<211> LENGTH: 110
<212> TYPE: RNA
<213> ORGANISM: Homo sapiens

<400> SEQUENCE: 93
agaagggcua ucaggccagc cuucagagga cuccaaggaa cauucaacgc ugucggugag    60
uuugggauuu gaaaaaacca cugaccguug acuguaccuu ggggguccuua              110

<210> SEQ ID NO 94
<211> LENGTH: 82
<212> TYPE: RNA
<213> ORGANISM: Homo sapiens

<400> SEQUENCE: 94
agggggcgag ggauuggaga gaaaggcagu uccugauggu ccccuccccca ggggcuggcu   60 uuccucuggu ccuucccucc ca                                             82

<210> SEQ ID NO 95
<211> LENGTH: 92
<212> TYPE: RNA
<213> ORGANISM: Homo sapiens

<400> SEQUENCE: 95
cggcuggaca gcgggcaacg gaaucccaaa agcagcuguu gucuccagag cauuccagcu    60
```

```
gcgcuuggau uucgucccu gcucuccugc cu                                   92
```

<210> SEQ ID NO 96
<211> LENGTH: 88
<212> TYPE: RNA
<213> ORGANISM: Homo sapiens

<400> SEQUENCE: 96

```
cgaggaugggg agcugagggc uggggucuuug cgggcgagau gagggugucg gaucaacugg   60
ccuacaaagu cccaguucuc ggcccccg                                        88
```

<210> SEQ ID NO 97
<211> LENGTH: 85
<212> TYPE: RNA
<213> ORGANISM: Homo sapiens

<400> SEQUENCE: 97

```
augguguuau caaguguaac agcaacucca uguggacugu guaccaauuu ccaguggaga     60
ugcuguuacu uuugauugguu accaa                                          85
```

<210> SEQ ID NO 98
<211> LENGTH: 85
<212> TYPE: RNA
<213> ORGANISM: Homo sapiens

<400> SEQUENCE: 98

```
ugguucccgc cccuguaac agcaacucca uggaagug cccacugguu ccaggggggc       60
ugcuguuauc uggggcgagg gccag                                           85
```

<210> SEQ ID NO 99
<211> LENGTH: 90
<212> TYPE: RNA
<213> ORGANISM: Homo sapiens

<400> SEQUENCE: 99

```
ccgggccccu gugagcaucu uaccggacag ugcuggauuu cccagcuuga cucuaacacu     60
gucugguaac gauguucaaa ggugacccgc                                      90
```

<210> SEQ ID NO 100
<211> LENGTH: 95
<212> TYPE: RNA
<213> ORGANISM: Homo sapiens

<400> SEQUENCE: 100

```
ccagcucggg cagccguggc caucuuacug ggcagcauug gauggaguca ggucucuaau     60
acugccuggu aaugaugacg gcggagcccu gcacg                                95
```

<210> SEQ ID NO 101
<211> LENGTH: 68
<212> TYPE: RNA
<213> ORGANISM: Homo sapiens

<400> SEQUENCE: 101

```
cccucgucuu acccagcagu guuuggugc gguugggagu cucuaauacu gccggguaau      60
gauggagg                                                              68
```

<210> SEQ ID NO 102
<211> LENGTH: 110
<212> TYPE: RNA

<213> ORGANISM: Homo sapiens

<400> SEQUENCE: 102

| cgccucagag ccgcccgccg uuccuuuuuc cuaugcauau acuucuuuga ggaucuggcc | 60 |
| uaaagaggua uagggcaugg gaaaacgggg cggucggguc cucccagcg | 110 |

<210> SEQ ID NO 103
<211> LENGTH: 110
<212> TYPE: RNA
<213> ORGANISM: Homo sapiens

<400> SEQUENCE: 103

| aaagauccuc agacaaucca ugugcuucuc uguccuuca uuccaccgga gucugucuca | 60 |
| uacccaacca gauuucagug gagugaaguu caggaggcau ggagcugaca | 110 |

<210> SEQ ID NO 104
<211> LENGTH: 86
<212> TYPE: RNA
<213> ORGANISM: Homo sapiens

<400> SEQUENCE: 104

| ugcuucccga ggccacaugc uucuuuauau ccccauaugg auuacuuugc uauggaaugu | 60 |
| aaggaagugu gugguuucgg caagug | 86 |

<210> SEQ ID NO 105
<211> LENGTH: 72
<212> TYPE: RNA
<213> ORGANISM: Homo sapiens

<400> SEQUENCE: 105

| ugucggguag cuuaucagac ugauguugac uguugaaucu cauggcaaca ccagucgaug | 60 |
| ggcugucuga ca | 72 |

<210> SEQ ID NO 106
<211> LENGTH: 110
<212> TYPE: RNA
<213> ORGANISM: Homo sapiens

<400> SEQUENCE: 106

| acccggcagu gccuccaggc gcagggcagc cccugcccac cgcacacugc gcugcccag | 60 |
| acccacugug cgugugacag cggcugaucu ugccugggc agcgcgaccc | 110 |

<210> SEQ ID NO 107
<211> LENGTH: 110
<212> TYPE: RNA
<213> ORGANISM: Homo sapiens

<400> SEQUENCE: 107

| ggccuggcug gacagaguug ucaugugucu gccugcuac acuugcugug cagaacaucc | 60 |
| gcucaccugu acagcaggca cagacaggca gucacaugac aacccagccu | 110 |

<210> SEQ ID NO 108
<211> LENGTH: 85
<212> TYPE: RNA
<213> ORGANISM: Homo sapiens

<400> SEQUENCE: 108

| ggcugagccg caguaguucu ucagggcaa gcuuuauguc cugacccagc uaaagcugcc | 60 |
| aguugaagaa cuguugcccu cugcc | 85 |

```
<210> SEQ ID NO 109
<211> LENGTH: 110
<212> TYPE: RNA
<213> ORGANISM: Homo sapiens

<400> SEQUENCE: 109
gcugcuggaa gguguaggua cccucaaugg cucaguagcc aguguagauc cugucuuucg    60
uaaucagcag cuacaucugg cuacuggguc ucgauggca ucuucuagcu               110

<210> SEQ ID NO 110
<211> LENGTH: 110
<212> TYPE: RNA
<213> ORGANISM: Homo sapiens

<400> SEQUENCE: 110
ccuggccucc ugcagugcca cgcuccgugu auuugacaag cugaguugga cacuccaugu    60
gguagagugu caguuuguca aauacCCCaa gugcggcaca ugcuuaccag               110

<210> SEQ ID NO 111
<211> LENGTH: 81
<212> TYPE: RNA
<213> ORGANISM: Homo sapiens

<400> SEQUENCE: 111
gggcuuucaa gucacuagug guccguuua guagaugauu gugcauuguu ucaaaauggu    60
gcccuaguga cuacaaagcc c                                              81

<210> SEQ ID NO 112
<211> LENGTH: 64
<212> TYPE: RNA
<213> ORGANISM: Homo sapiens

<400> SEQUENCE: 112
augacugauu ucuuuuggug uucagaguca auauaauuuu cuagcaccau cugaaaucgg    60
uuau                                                                 64

<210> SEQ ID NO 113
<211> LENGTH: 88
<212> TYPE: RNA
<213> ORGANISM: Homo sapiens

<400> SEQUENCE: 113
aucucuuaca caggcugacc gauuucuccu gguguucaga gucuguuuuu gucuagcacc    60
auuugaaauc gguuaugaug uaggggga                                       88

<210> SEQ ID NO 114
<211> LENGTH: 71
<212> TYPE: RNA
<213> ORGANISM: Homo sapiens

<400> SEQUENCE: 114
gcgacuguaa acauccucga cuggaagcug ugaagccaca gaugggcuuu cagucggaug    60
uuugcagcug c                                                         71

<210> SEQ ID NO 115
<211> LENGTH: 70
<212> TYPE: RNA
<213> ORGANISM: Homo sapiens
```

<400> SEQUENCE: 115
guuguuguaa acaucccga cuggaagcug uaagacacag cuaagcuuuc agucagaugu    60
uugcugcuac                                                          70

<210> SEQ ID NO 116
<211> LENGTH: 92
<212> TYPE: RNA
<213> ORGANISM: Homo sapiens

<400> SEQUENCE: 116
gggcagucuu ugcuacugua aacauccuug acuggaagcu guaagguguu cagaggagcu    60
uucagucgga guuuacagc ggcaggcugc ca                                  92

<210> SEQ ID NO 117
<211> LENGTH: 71
<212> TYPE: RNA
<213> ORGANISM: Homo sapiens

<400> SEQUENCE: 117
ggagaggagg caagaugcug gcauagcugu gaacugggga accugcuaug ccaacauauu    60
gccaucuuuc c                                                        71

<210> SEQ ID NO 118
<211> LENGTH: 99
<212> TYPE: RNA
<213> ORGANISM: Homo sapiens

<400> SEQUENCE: 118
gaaacugggc ucaaggugag gggugcuauc ugugauugag ggacaugguu aauggaauug    60
ucucacacag aaaucgcacc cgucaccuug gccuacuua                          99

<210> SEQ ID NO 119
<211> LENGTH: 98
<212> TYPE: RNA
<213> ORGANISM: Homo sapiens

<400> SEQUENCE: 119
acccaaaccc uaggucugcu gacuccuagu ccagggcucg ugauggcugg ugggcccuga    60 acgaggguc uggaggccug gguugaaua ucgacagc                             98

<210> SEQ ID NO 120
<211> LENGTH: 110
<212> TYPE: RNA
<213> ORGANISM: Homo sapiens

<400> SEQUENCE: 120
ggccagcugu gaguguuucu uuggcagugu cuuagcuggu uguugagc aauaguaagg     60 aagcaaucag caaguauacu gcccuagaag ugcugcacgu ugugggccc              110

<210> SEQ ID NO 121
<211> LENGTH: 77
<212> TYPE: RNA
<213> ORGANISM: Homo sapiens

<400> SEQUENCE: 121
agucuaguua cuaggcagug uaguuagcug auugcuaaua guaccaauca cuaaccacac    60
ggccagguaa aaagauu                                                  77

```
<210> SEQ ID NO 122
<211> LENGTH: 72
<212> TYPE: RNA
<213> ORGANISM: Homo sapiens

<400> SEQUENCE: 122
ggagcuuauc agaaucucca gggguacuuu auaauuucaa aaaguccccc aggugugauu    60
cugauuugcu uc                                                      72

<210> SEQ ID NO 123
<211> LENGTH: 67
<212> TYPE: RNA
<213> ORGANISM: Homo sapiens

<400> SEQUENCE: 123
gugggccuca aaugguggagc acuauucuga uguccaagug aaagugcug cgacauuuga    60 gcgucac                                                            67

<210> SEQ ID NO 124
<211> LENGTH: 64
<212> TYPE: RNA
<213> ORGANISM: Homo sapiens

<400> SEQUENCE: 124
ccccgcgacg agcccccucgc acaaaccgga ccugagcguu uuguucguuc ggcucgcgug    60
aggc                                                               64

<210> SEQ ID NO 125
<211> LENGTH: 66
<212> TYPE: RNA
<213> ORGANISM: Homo sapiens

<400> SEQUENCE: 125
agggcuccug acuccagguc cuguguguua ccuagaaaua gcacuggacu uggagucaga    60
aggccu                                                             66

<210> SEQ ID NO 126
<211> LENGTH: 96
<212> TYPE: RNA
<213> ORGANISM: Homo sapiens

<400> SEQUENCE: 126
ucccuggcgu gaggguaugu gccuuuggac uacaucgugg aagccagcac caugcagucc    60
augggcauau acacuugccu caaggccuau gucauc                            96

<210> SEQ ID NO 127
<211> LENGTH: 84
<212> TYPE: RNA
<213> ORGANISM: Homo sapiens

<400> SEQUENCE: 127
uugguacuug gagaguggu aucccugucc uguucguuuu gcucaugucg aaucguacag     60
ggucauccac uuuuucagua ucaa                                         84

<210> SEQ ID NO 128
<211> LENGTH: 112
<212> TYPE: RNA
<213> ORGANISM: Homo sapiens

<400> SEQUENCE: 128
```

```
ccaccccggu ccugcucccg ccccagcagc acacugugu uuguacggca cuguggccac    60
guccaaacca cacugguug uuagagcgag ggugggggag gcaccgccga gg            112
```

<210> SEQ ID NO 129
<211> LENGTH: 94
<212> TYPE: RNA
<213> ORGANISM: Homo sapiens

<400> SEQUENCE: 129

```
caugcugugu gugguacccu acugcagaca guggcaauca uguauaauua aaaugauug     60 guacgucugu ggguagagua cugcaugaca caug                                94
```

<210> SEQ ID NO 130
<211> LENGTH: 91
<212> TYPE: RNA
<213> ORGANISM: Homo sapiens

<400> SEQUENCE: 130

```
caugcugugu gugguacccu acugcagaca guggcaauca uguauaauua aaaugauug     60 guacgucugu ggguagagua cugcaugaca c                                   91
```

<210> SEQ ID NO 131
<211> LENGTH: 75
<212> TYPE: RNA
<213> ORGANISM: Homo sapiens

<400> SEQUENCE: 131

```
gugguacccu acugcagacg uggcaaucau guauaauuaa aaaugauugg uacgucugug    60
gguagaguac ugcau                                                     75
```

<210> SEQ ID NO 132
<211> LENGTH: 90
<212> TYPE: RNA
<213> ORGANISM: Homo sapiens

<400> SEQUENCE: 132

```
ucucaggcug ugaccuucuc gaggaaagaa gcacuuucug uugucugaaa gaaaagaaag    60
ugcuuccuuu cagagggua cgguuugaga                                      90
```

<210> SEQ ID NO 133
<211> LENGTH: 90
<212> TYPE: RNA
<213> ORGANISM: Homo sapiens

<400> SEQUENCE: 133

```
ucucagguug ugaccuucuc gaggaaagaa gcacuuucug uugucugaaa gaaaagaaag    60
ugcuuccuuu cagagggua cgguuugaga                                      90
```

<210> SEQ ID NO 134
<211> LENGTH: 96
<212> TYPE: RNA
<213> ORGANISM: Homo sapiens

<400> SEQUENCE: 134

```
gggaccugcg uggugcggg cgugugagug ugugugugug agugugguc gcuccggguc      60 cacgcucaug cacacaccca cacgcccaca cucagg                              96
```

<210> SEQ ID NO 135
<211> LENGTH: 98

```
<212> TYPE: RNA
<213> ORGANISM: Homo sapiens

<400> SEQUENCE: 135
acgaauggcu augcacugca caacccuagg agagggugcc auucacauag acuauaauug      60
aauggcgcca cuagguugu gcagugcaca accuacac                              98

<210> SEQ ID NO 136
<211> LENGTH: 110
<212> TYPE: RNA
<213> ORGANISM: Homo sapiens

<400> SEQUENCE: 136
uuggauguug gccuaguucu guguggaaga cuagugauuu uguuguuuuu agauaacuaa      60
aucgacaaca aaucacaguc ugccauaugg cacaggccau gccucuacag                110

<210> SEQ ID NO 137
<211> LENGTH: 110
<212> TYPE: RNA
<213> ORGANISM: Homo sapiens

<400> SEQUENCE: 137
cuggauacag aguggaccgg cuggccccau cuggaagacu agugauuuug uuguugucuu      60
acugcgcuca caacaaauc ccagucuacc uaauggugcc agccaucgca                 110

<210> SEQ ID NO 138
<211> LENGTH: 110
<212> TYPE: RNA
<213> ORGANISM: Homo sapiens

<400> SEQUENCE: 138
agauuagagu ggcugugguc uagugcugug uggaagacua gugauuuugu uguucugaug      60
uacuacgaca acaagucaca gccggccuca uagcgcagac ucccuucgac                110

<210> SEQ ID NO 139
<211> LENGTH: 89
<212> TYPE: RNA
<213> ORGANISM: Homo sapiens

<400> SEQUENCE: 139
cgggguuggu uguuaucuuu gguuaucuag cuguaugagu ggugguggagu cuucauaaag      60 cuagauaacc gaaaguaaaa auaacccca                                        89

<210> SEQ ID NO 140
<211> LENGTH: 87
<212> TYPE: RNA
<213> ORGANISM: Homo sapiens

<400> SEQUENCE: 140
ggaagcgagu uguuaucuuu gguuaucuag cuguaugagu guauuggucu ucauaaagcu      60
agauaaccga aaguaaaaac uccuuca                                         87

<210> SEQ ID NO 141
<211> LENGTH: 90
<212> TYPE: RNA
<213> ORGANISM: Homo sapiens

<400> SEQUENCE: 141
ggaggcccgu uucucucuuu gguuaucuag cuguaugagu gccacagagc cgucauaaag      60
```

```
cuagauaacc gaaaguagaa augauucuca                                        90

<210> SEQ ID NO 142
<211> LENGTH: 78
<212> TYPE: RNA
<213> ORGANISM: Homo sapiens

<400> SEQUENCE: 142
cuuucuacac agguugggau cgguugcaau gcuguguuuc uguauggau ugcacuuguc        60 ccggccuguu gaguuugg                                                     78

<210> SEQ ID NO 143
<211> LENGTH: 75
<212> TYPE: RNA
<213> ORGANISM: Homo sapiens

<400> SEQUENCE: 143
ucaucccugg guggggauuu guugcauuac uuguguucua auaaaguau ugcacuuguc        60 ccggccugug aaga                                                         75

<210> SEQ ID NO 144
<211> LENGTH: 96
<212> TYPE: RNA
<213> ORGANISM: Homo sapiens

<400> SEQUENCE: 144
cgggccccgg gcgggcggga gggacgggac gcggugcagu guuguuuuu cccccgccaa        60 uauugcacuc gucccggccu ccggcccccc cggccc                                 96

<210> SEQ ID NO 145
<211> LENGTH: 83
<212> TYPE: RNA
<213> ORGANISM: Homo sapiens

<400> SEQUENCE: 145
agaaauaagg cuucugucua cuacuggaga cacugguagu auaaaaccca gagucccag        60 uaauggacgg gagccuuauu ucu                                               83

<210> SEQ ID NO 146
<211> LENGTH: 24
<212> TYPE: RNA
<213> ORGANISM: Homo sapiens

<400> SEQUENCE: 146
agccugauua aacacaugcu cuga                                              24

<210> SEQ ID NO 147
<211> LENGTH: 23
<212> TYPE: RNA
<213> ORGANISM: Homo sapiens

<400> SEQUENCE: 147
agcuacauug ucugcugggu uuc                                               23

<210> SEQ ID NO 148
<211> LENGTH: 23
<212> TYPE: RNA
<213> ORGANISM: Homo sapiens

<400> SEQUENCE: 148
caaagugcug uucgugcagg uag                                               23
```

<210> SEQ ID NO 149
<211> LENGTH: 85
<212> TYPE: RNA
<213> ORGANISM: Homo sapiens

<400> SEQUENCE: 149
uuuacaguuu gccaugauga aaugcauguu aaguccgugu uucagcugau cagccugauu    60
aaacacaugc ucugagcaga cuaaa                                         85

<210> SEQ ID NO 150
<211> LENGTH: 110
<212> TYPE: RNA
<213> ORGANISM: Homo sapiens

<400> SEQUENCE: 150
ugaacaucca ggucggggc augaaccugg cauacaaugu agauuucugu guucguuagg    60
caacagcuac auugucugcu ggguuucagg cuaccuggaa acauguucuc              110

<210> SEQ ID NO 151
<211> LENGTH: 80
<212> TYPE: RNA
<213> ORGANISM: Homo sapiens

<400> SEQUENCE: 151 cuggggcuc caaagugcug uucgugcagg uagugugauu acccaaccua cugcugagcu    60
agcacuuccc gagccccgg                                                80

<210> SEQ ID NO 152
<211> LENGTH: 24
<212> TYPE: RNA
<213> ORGANISM: Homo sapiens

<400> SEQUENCE: 152
uuuggcaaug guagaacuca cacu                                          24

<210> SEQ ID NO 153
<211> LENGTH: 22
<212> TYPE: RNA
<213> ORGANISM: Homo sapiens

<400> SEQUENCE: 153
agagguagua gguugcauag uu                                            22

<210> SEQ ID NO 154
<211> LENGTH: 23
<212> TYPE: RNA
<213> ORGANISM: Homo sapiens

<400> SEQUENCE: 154
aacauucauu gcugucggug ggu                                           23

<210> SEQ ID NO 155
<211> LENGTH: 22
<212> TYPE: RNA
<213> ORGANISM: Homo sapiens

<400> SEQUENCE: 155
ucggauccgu cugagcuugg cu                                            22

<210> SEQ ID NO 156

```
<211> LENGTH: 22
<212> TYPE: RNA
<213> ORGANISM: Homo sapiens

<400> SEQUENCE: 156
ugagguagga gguuguauag uu                                              22

<210> SEQ ID NO 157
<211> LENGTH: 22
<212> TYPE: RNA
<213> ORGANISM: Homo sapiens

<400> SEQUENCE: 157
ugagguagua guuugugcug uu                                              22

<210> SEQ ID NO 158
<211> LENGTH: 23
<212> TYPE: RNA
<213> ORGANISM: Homo sapiens

<400> SEQUENCE: 158
aaaagugcuu acagugcagg uag                                             23

<210> SEQ ID NO 159
<211> LENGTH: 20
<212> TYPE: RNA
<213> ORGANISM: Homo sapiens

<400> SEQUENCE: 159
uaaggcacgc ggugaaugcc                                                 20

<210> SEQ ID NO 160
<211> LENGTH: 27
<212> TYPE: RNA
<213> ORGANISM: Homo sapiens

<400> SEQUENCE: 160
accuucuugu auaagcacug ugcuaaa                                         27

<210> SEQ ID NO 161
<211> LENGTH: 21
<212> TYPE: RNA
<213> ORGANISM: Homo sapiens

<400> SEQUENCE: 161
ucacagugaa ccggucucuu u                                               21

<210> SEQ ID NO 162
<211> LENGTH: 22
<212> TYPE: RNA
<213> ORGANISM: Homo sapiens

<400> SEQUENCE: 162
aagcccuuac cccaaaaagc au                                              22

<210> SEQ ID NO 163
<211> LENGTH: 22
<212> TYPE: RNA
<213> ORGANISM: Homo sapiens

<400> SEQUENCE: 163
ucaaaacuga ggggcauuuu cu                                              22
```

```
<210> SEQ ID NO 164
<211> LENGTH: 21
<212> TYPE: RNA
<213> ORGANISM: Homo sapiens

<400> SEQUENCE: 164
cauaaaguag aaagcacuac u                                              21

<210> SEQ ID NO 165
<211> LENGTH: 22
<212> TYPE: RNA
<213> ORGANISM: Homo sapiens

<400> SEQUENCE: 165
ggugcagugc ugcaucucug gu                                             22

<210> SEQ ID NO 166
<211> LENGTH: 22
<212> TYPE: RNA
<213> ORGANISM: Homo sapiens

<400> SEQUENCE: 166
ugcccugugg acucaguucu gg                                             22

<210> SEQ ID NO 167
<211> LENGTH: 21
<212> TYPE: RNA
<213> ORGANISM: Homo sapiens

<400> SEQUENCE: 167
agggagggac gggggcugug c                                              21

<210> SEQ ID NO 168
<211> LENGTH: 22
<212> TYPE: RNA
<213> ORGANISM: Homo sapiens

<400> SEQUENCE: 168
ucucccaacc cuuguaccag ug                                             22

<210> SEQ ID NO 169
<211> LENGTH: 21
<212> TYPE: RNA
<213> ORGANISM: Homo sapiens

<400> SEQUENCE: 169
ucagugcaug acagaacuug g                                              21

<210> SEQ ID NO 170
<211> LENGTH: 23
<212> TYPE: RNA
<213> ORGANISM: Homo sapiens

<400> SEQUENCE: 170
uuaaugcuaa ucgugauagg ggu                                            23

<210> SEQ ID NO 171
<211> LENGTH: 22
<212> TYPE: RNA
<213> ORGANISM: Homo sapiens

<400> SEQUENCE: 171
uagcagcaca uaaugguuug ug                                             22
```

```
<210> SEQ ID NO 172
<211> LENGTH: 22
<212> TYPE: RNA
<213> ORGANISM: Homo sapiens

<400> SEQUENCE: 172
uagcagcaca ucaugguuua ca                                              22

<210> SEQ ID NO 173
<211> LENGTH: 22
<212> TYPE: RNA
<213> ORGANISM: Homo sapiens

<400> SEQUENCE: 173
aacauucaac cugucgguga gu                                              22

<210> SEQ ID NO 174
<211> LENGTH: 23
<212> TYPE: RNA
<213> ORGANISM: Homo sapiens

<400> SEQUENCE: 174
aacauucauu guugucggug ggu                                             23

<210> SEQ ID NO 175
<211> LENGTH: 22
<212> TYPE: RNA
<213> ORGANISM: Homo sapiens

<400> SEQUENCE: 175
uauggcacug guagaauuca cu                                              22

<210> SEQ ID NO 176
<211> LENGTH: 23
<212> TYPE: RNA
<213> ORGANISM: Homo sapiens

<400> SEQUENCE: 176
uaaggugcau cuagugcaga uag                                             23

<210> SEQ ID NO 177
<211> LENGTH: 21
<212> TYPE: RNA
<213> ORGANISM: Homo sapiens

<400> SEQUENCE: 177
cugaccuaug aauugacagc c                                               21

<210> SEQ ID NO 178
<211> LENGTH: 22
<212> TYPE: RNA
<213> ORGANISM: Homo sapiens

<400> SEQUENCE: 178
aacuggcccu caaagucccg cu                                              22

<210> SEQ ID NO 179
<211> LENGTH: 21
<212> TYPE: RNA
<213> ORGANISM: Homo sapiens

<400> SEQUENCE: 179
uagcagcaca gaaauauugg c                                               21
```

```
<210> SEQ ID NO 180
<211> LENGTH: 19
<212> TYPE: RNA
<213> ORGANISM: Homo sapiens

<400> SEQUENCE: 180
accgugcaaa gguagcaua                                                    19

<210> SEQ ID NO 181
<211> LENGTH: 22
<212> TYPE: RNA
<213> ORGANISM: Homo sapiens

<400> SEQUENCE: 181
acaguagucu gcacauuggu ua                                                22

<210> SEQ ID NO 182
<211> LENGTH: 23
<212> TYPE: RNA
<213> ORGANISM: Homo sapiens

<400> SEQUENCE: 182
cccaguguuc agacuaccug uuc                                               23

<210> SEQ ID NO 183
<211> LENGTH: 23
<212> TYPE: RNA
<213> ORGANISM: Homo sapiens

<400> SEQUENCE: 183
cccaguguuu agacuaucug uuc                                               23

<210> SEQ ID NO 184
<211> LENGTH: 22
<212> TYPE: RNA
<213> ORGANISM: Homo sapiens

<400> SEQUENCE: 184
gugaaauguu uaggaccacu ag                                                22

<210> SEQ ID NO 185
<211> LENGTH: 21
<212> TYPE: RNA
<213> ORGANISM: Homo sapiens

<400> SEQUENCE: 185
gauuucagug gagugaaguu c                                                 21

<210> SEQ ID NO 186
<211> LENGTH: 23
<212> TYPE: RNA
<213> ORGANISM: Homo sapiens

<400> SEQUENCE: 186
uaaagugcuu auagugcagg uag                                               23

<210> SEQ ID NO 187
<211> LENGTH: 22
<212> TYPE: RNA
<213> ORGANISM: Homo sapiens

<400> SEQUENCE: 187
```
agaauugugg cuggacaucu gu                                              22

<210> SEQ ID NO 188
<211> LENGTH: 22
<212> TYPE: RNA
<213> ORGANISM: Homo sapiens

<400> SEQUENCE: 188
cauugcacuu gucucggucu ga                                              22

<210> SEQ ID NO 189
<211> LENGTH: 21
<212> TYPE: RNA
<213> ORGANISM: Homo sapiens

<400> SEQUENCE: 189
uucacagugg cuaaguucug c                                               21

<210> SEQ ID NO 190
<211> LENGTH: 23
<212> TYPE: RNA
<213> ORGANISM: Homo sapiens

<400> SEQUENCE: 190
uagcaccauu ugaaaucagu guu                                             23

<210> SEQ ID NO 191
<211> LENGTH: 22
<212> TYPE: RNA
<213> ORGANISM: Homo sapiens

<400> SEQUENCE: 191
uagcaccauu ugaaaucggu ua                                              22

<210> SEQ ID NO 192
<211> LENGTH: 23
<212> TYPE: RNA
<213> ORGANISM: Homo sapiens

<400> SEQUENCE: 192
uaagugcuuc cauguuuugg uga                                             23

<210> SEQ ID NO 193
<211> LENGTH: 23
<212> TYPE: RNA
<213> ORGANISM: Homo sapiens

<400> SEQUENCE: 193
acuuaaacgu ggauguacuu gcu                                             23

<210> SEQ ID NO 194
<211> LENGTH: 23
<212> TYPE: RNA
<213> ORGANISM: Homo sapiens

<400> SEQUENCE: 194
uaagugcuuc cauguuugag ugu                                             23

<210> SEQ ID NO 195
<211> LENGTH: 22
<212> TYPE: RNA
<213> ORGANISM: Homo sapiens

<400> SEQUENCE: 195
cuuucagucg gauguuugca gc                                         22

<210> SEQ ID NO 196
<211> LENGTH: 23
<212> TYPE: RNA
<213> ORGANISM: Homo sapiens

<400> SEQUENCE: 196
uguaaacauc cuacacucuc agc                                        23

<210> SEQ ID NO 197
<211> LENGTH: 21
<212> TYPE: RNA
<213> ORGANISM: Homo sapiens

<400> SEQUENCE: 197
gccccugggc cuauccuaga a                                          21

<210> SEQ ID NO 198
<211> LENGTH: 21
<212> TYPE: RNA
<213> ORGANISM: Homo sapiens

<400> SEQUENCE: 198
aggggugcua ucugugauug a                                          21

<210> SEQ ID NO 199
<211> LENGTH: 22
<212> TYPE: RNA
<213> ORGANISM: Homo sapiens

<400> SEQUENCE: 199
aauugcacgg uauccaucug ua                                         22

<210> SEQ ID NO 200
<211> LENGTH: 23
<212> TYPE: RNA
<213> ORGANISM: Homo sapiens

<400> SEQUENCE: 200
aagugccgcc aucuuuugag ugu                                        23

<210> SEQ ID NO 201
<211> LENGTH: 20
<212> TYPE: RNA
<213> ORGANISM: Homo sapiens

<400> SEQUENCE: 201
acucaaacug uggggggcacu                                           20

<210> SEQ ID NO 202
<211> LENGTH: 21
<212> TYPE: RNA
<213> ORGANISM: Homo sapiens

<400> SEQUENCE: 202
acuggacuug gagucagaag g                                          21

<210> SEQ ID NO 203
<211> LENGTH: 22
<212> TYPE: RNA
<213> ORGANISM: Homo sapiens

```
<400> SEQUENCE: 203
acuggacuua gggucagaag gc                                           22

<210> SEQ ID NO 204
<211> LENGTH: 23
<212> TYPE: RNA
<213> ORGANISM: Homo sapiens

<400> SEQUENCE: 204
aaugacacga ucaccccgu uga                                           23

<210> SEQ ID NO 205
<211> LENGTH: 22
<212> TYPE: RNA
<213> ORGANISM: Homo sapiens

<400> SEQUENCE: 205
aaaccguuac cauuacugag uu                                           22

<210> SEQ ID NO 206
<211> LENGTH: 21
<212> TYPE: RNA
<213> ORGANISM: Homo sapiens

<400> SEQUENCE: 206
gcaguccaug ggcauauaca c                                            21

<210> SEQ ID NO 207
<211> LENGTH: 22
<212> TYPE: RNA
<213> ORGANISM: Homo sapiens

<400> SEQUENCE: 207
uccuguacug agcugccccg ag                                           22

<210> SEQ ID NO 208
<211> LENGTH: 21
<212> TYPE: RNA
<213> ORGANISM: Homo sapiens

<400> SEQUENCE: 208
cagcagcaca cugugguuug u                                            21

<210> SEQ ID NO 209
<211> LENGTH: 23
<212> TYPE: RNA
<213> ORGANISM: Homo sapiens

<400> SEQUENCE: 209
uuucaagcca gggggcguuu uuc                                          23

<210> SEQ ID NO 210
<211> LENGTH: 23
<212> TYPE: RNA
<213> ORGANISM: Homo sapiens

<400> SEQUENCE: 210
cacucagccu ugagggcacu uuc                                          23

<210> SEQ ID NO 211
<211> LENGTH: 23
<212> TYPE: RNA
<213> ORGANISM: Homo sapiens
```

```
<400> SEQUENCE: 211
uucucgagga aagaagcacu uuc                                        23

<210> SEQ ID NO 212
<211> LENGTH: 22
<212> TYPE: RNA
<213> ORGANISM: Homo sapiens

<400> SEQUENCE: 212
aucuggaggu aagaagcacu uu                                         22

<210> SEQ ID NO 213
<211> LENGTH: 22
<212> TYPE: RNA
<213> ORGANISM: Homo sapiens

<400> SEQUENCE: 213
aucgugcauc ccuuuagagu gu                                         22

<210> SEQ ID NO 214
<211> LENGTH: 22
<212> TYPE: RNA
<213> ORGANISM: Homo sapiens

<400> SEQUENCE: 214
aucgugcauc cuuuuagagu gu                                         22

<210> SEQ ID NO 215
<211> LENGTH: 22
<212> TYPE: RNA
<213> ORGANISM: Homo sapiens

<400> SEQUENCE: 215
gaaagcgcuu cccuuugcug ga                                         22

<210> SEQ ID NO 216
<211> LENGTH: 21
<212> TYPE: RNA
<213> ORGANISM: Homo sapiens

<400> SEQUENCE: 216
aaagcgcuuc ccuucagagu g                                          21

<210> SEQ ID NO 217
<211> LENGTH: 22
<212> TYPE: RNA
<213> ORGANISM: Homo sapiens

<400> SEQUENCE: 217
cucuagaggg aagcacuuuc uc                                         22

<210> SEQ ID NO 218
<211> LENGTH: 22
<212> TYPE: RNA
<213> ORGANISM: Homo sapiens

<400> SEQUENCE: 218
aaagugcauc cuuuuagagu gu                                         22

<210> SEQ ID NO 219
<211> LENGTH: 22
<212> TYPE: RNA
```

<213> ORGANISM: Homo sapiens

<400> SEQUENCE: 219
caaagugccu cccuuuagag ug                       22

<210> SEQ ID NO 220
<211> LENGTH: 21
<212> TYPE: RNA
<213> ORGANISM: Homo sapiens

<400> SEQUENCE: 220
cuccagaggg aaguacuuuc u                        21

<210> SEQ ID NO 221
<211> LENGTH: 22
<212> TYPE: RNA
<213> ORGANISM: Homo sapiens

<400> SEQUENCE: 221
aaagugcuuc cuuuuagagg gu                       22

<210> SEQ ID NO 222
<211> LENGTH: 20
<212> TYPE: RNA
<213> ORGANISM: Homo sapiens

<400> SEQUENCE: 222
cuacaaaggg aagcccuuuc                          20

<210> SEQ ID NO 223
<211> LENGTH: 22
<212> TYPE: RNA
<213> ORGANISM: Homo sapiens

<400> SEQUENCE: 223
cuacaaaggg aagcacuuuc uc                       22

<210> SEQ ID NO 224
<211> LENGTH: 20
<212> TYPE: RNA
<213> ORGANISM: Homo sapiens

<400> SEQUENCE: 224
cugcaaaggg aagcccuuuc                          20

<210> SEQ ID NO 225
<211> LENGTH: 21
<212> TYPE: RNA
<213> ORGANISM: Homo sapiens

<400> SEQUENCE: 225
gcgacccaua cuugguuuca g                        21

<210> SEQ ID NO 226
<211> LENGTH: 21
<212> TYPE: RNA
<213> ORGANISM: Homo sapiens

<400> SEQUENCE: 226 aggggggaaag uucuauaguc c                       21

<210> SEQ ID NO 227
<211> LENGTH: 23

<212> TYPE: RNA
<213> ORGANISM: Homo sapiens

<400> SEQUENCE: 227
ugcaccaugg uugucugagc aug                                    23

<210> SEQ ID NO 228
<211> LENGTH: 21
<212> TYPE: RNA
<213> ORGANISM: Homo sapiens

<400> SEQUENCE: 228
cgcgggugcu uacugacccu u                                      21

<210> SEQ ID NO 229
<211> LENGTH: 23
<212> TYPE: RNA
<213> ORGANISM: Homo sapiens

<400> SEQUENCE: 229
ucuuugguua ucuagcugua uga                                    23

<210> SEQ ID NO 230
<211> LENGTH: 23
<212> TYPE: RNA
<213> ORGANISM: Homo sapiens

<400> SEQUENCE: 230
cgggucggag uuagcucaag cgg                                    23

<210> SEQ ID NO 231
<211> LENGTH: 22
<212> TYPE: RNA
<213> ORGANISM: Homo sapiens

<400> SEQUENCE: 231
aacccguaga uccgaucuug ug                                     22

<210> SEQ ID NO 232
<211> LENGTH: 22
<212> TYPE: RNA
<213> ORGANISM: Homo sapiens

<400> SEQUENCE: 232
caagcucgcu ucuauggguc ug                                     22

<210> SEQ ID NO 233
<211> LENGTH: 23
<212> TYPE: RNA
<213> ORGANISM: Homo sapiens

<400> SEQUENCE: 233
gaagugcuuc gauuuugggg ugu                                    23

<210> SEQ ID NO 234
<211> LENGTH: 22
<212> TYPE: RNA
<213> ORGANISM: Homo sapiens

<400> SEQUENCE: 234
gauuagggug cuuagcuguu aa                                     22

<210> SEQ ID NO 235

```
<211> LENGTH: 21
<212> TYPE: RNA
<213> ORGANISM: Homo sapiens

<400> SEQUENCE: 235
gguuuggucc uagccuuucu a                                              21

<210> SEQ ID NO 236
<211> LENGTH: 22
<212> TYPE: RNA
<213> ORGANISM: Homo sapiens

<400> SEQUENCE: 236
uggacuugga gucaggaggc cu                                             22

<210> SEQ ID NO 237
<211> LENGTH: 22
<212> TYPE: RNA
<213> ORGANISM: Homo sapiens

<400> SEQUENCE: 237
aaucugcagg gggagccugg gu                                             22

<210> SEQ ID NO 238
<211> LENGTH: 21
<212> TYPE: RNA
<213> ORGANISM: Homo sapiens

<400> SEQUENCE: 238
acaugaaaag gggagagggc a                                              21

<210> SEQ ID NO 239
<211> LENGTH: 22
<212> TYPE: RNA
<213> ORGANISM: Homo sapiens

<400> SEQUENCE: 239
acccccccca gccauacaua ga                                             22

<210> SEQ ID NO 240
<211> LENGTH: 25
<212> TYPE: RNA
<213> ORGANISM: Homo sapiens

<400> SEQUENCE: 240
acuaccccag gaugccagca uaguu                                          25

<210> SEQ ID NO 241
<211> LENGTH: 22
<212> TYPE: RNA
<213> ORGANISM: Homo sapiens

<400> SEQUENCE: 241
agcugguuug augggagcc au                                              22

<210> SEQ ID NO 242
<211> LENGTH: 22
<212> TYPE: RNA
<213> ORGANISM: Homo sapiens

<400> SEQUENCE: 242
agggugacag ggaacaguag au                                             22
```

```
<210> SEQ ID NO 243
<211> LENGTH: 22
<212> TYPE: RNA
<213> ORGANISM: Homo sapiens

<400> SEQUENCE: 243
augugggugg uggucaccgu uu                                              22

<210> SEQ ID NO 244
<211> LENGTH: 22
<212> TYPE: RNA
<213> ORGANISM: Homo sapiens

<400> SEQUENCE: 244
cacugauuau cgaggcgauu cu                                              22

<210> SEQ ID NO 245
<211> LENGTH: 20
<212> TYPE: RNA
<213> ORGANISM: Homo sapiens

<400> SEQUENCE: 245
gaacccuacu ccugguacca                                                 20

<210> SEQ ID NO 246
<211> LENGTH: 22
<212> TYPE: RNA
<213> ORGANISM: Homo sapiens

<400> SEQUENCE: 246
gaauuuccug aggggagggg gc                                              22

<210> SEQ ID NO 247
<211> LENGTH: 22
<212> TYPE: RNA
<213> ORGANISM: Homo sapiens

<400> SEQUENCE: 247
ggcaggacgg cguaggucuu ga                                              22

<210> SEQ ID NO 248
<211> LENGTH: 22
<212> TYPE: RNA
<213> ORGANISM: Homo sapiens

<400> SEQUENCE: 248
gggcugggca gguuucagga au                                              22

<210> SEQ ID NO 249
<211> LENGTH: 21
<212> TYPE: RNA
<213> ORGANISM: Homo sapiens

<400> SEQUENCE: 249
uaggucaagg uguagcccau a                                               21

<210> SEQ ID NO 250
<211> LENGTH: 22
<212> TYPE: RNA
<213> ORGANISM: Homo sapiens

<400> SEQUENCE: 250
uauguacaag guggaggggg cg                                              22
```

-continued

<210> SEQ ID NO 251
<211> LENGTH: 22
<212> TYPE: RNA
<213> ORGANISM: Homo sapiens

<400> SEQUENCE: 251 uccccaccc uuagcuuaga ua					22

<210> SEQ ID NO 252
<211> LENGTH: 22
<212> TYPE: RNA
<213> ORGANISM: Homo sapiens

<400> SEQUENCE: 252
uggagcaggc uggggcuuug ag					22

<210> SEQ ID NO 253
<211> LENGTH: 23
<212> TYPE: RNA
<213> ORGANISM: Homo sapiens

<400> SEQUENCE: 253
ugugcuccgg aguuaccucg uuu					23

<210> SEQ ID NO 254
<211> LENGTH: 18
<212> TYPE: RNA
<213> ORGANISM: Homo sapiens

<400> SEQUENCE: 254
uguggguucg aguuccau					18

<210> SEQ ID NO 255
<211> LENGTH: 18
<212> TYPE: RNA
<213> ORGANISM: Homo sapiens

<400> SEQUENCE: 255
uucccggcca augcauua					18

<210> SEQ ID NO 256
<211> LENGTH: 22
<212> TYPE: RNA
<213> ORGANISM: Homo sapiens

<400> SEQUENCE: 256
ugagguagua gguuguauag uu					22

<210> SEQ ID NO 257
<211> LENGTH: 22
<212> TYPE: RNA
<213> ORGANISM: Homo sapiens

<400> SEQUENCE: 257
ugagguagua gguugugugg uu					22

<210> SEQ ID NO 258
<211> LENGTH: 22
<212> TYPE: RNA
<213> ORGANISM: Homo sapiens

<400> SEQUENCE: 258
ugagguagua gauuguauag uu					22

```
<210> SEQ ID NO 259
<211> LENGTH: 22
<212> TYPE: RNA
<213> ORGANISM: Homo sapiens

<400> SEQUENCE: 259
ugagguagua guuuguacag uu                                              22

<210> SEQ ID NO 260
<211> LENGTH: 21
<212> TYPE: RNA
<213> ORGANISM: Homo sapiens

<400> SEQUENCE: 260
uaaagugcug acagugcaga u                                               21

<210> SEQ ID NO 261
<211> LENGTH: 22
<212> TYPE: RNA
<213> ORGANISM: Homo sapiens

<400> SEQUENCE: 261
uuuccggcuc gcgugggugu gu                                              22

<210> SEQ ID NO 262
<211> LENGTH: 22
<212> TYPE: RNA
<213> ORGANISM: Homo sapiens

<400> SEQUENCE: 262
cugaagcuca gagggcucug au                                              22

<210> SEQ ID NO 263
<211> LENGTH: 22
<212> TYPE: RNA
<213> ORGANISM: Homo sapiens

<400> SEQUENCE: 263
aagcccuuac cccaaaaagu au                                              22

<210> SEQ ID NO 264
<211> LENGTH: 21
<212> TYPE: RNA
<213> ORGANISM: Homo sapiens

<400> SEQUENCE: 264
cuuuuugcgg ucugggcuug c                                               21

<210> SEQ ID NO 265
<211> LENGTH: 22
<212> TYPE: RNA
<213> ORGANISM: Homo sapiens

<400> SEQUENCE: 265
cagugcaaug augaaagggc au                                              22

<210> SEQ ID NO 266
<211> LENGTH: 22
<212> TYPE: RNA
<213> ORGANISM: Homo sapiens

<400> SEQUENCE: 266
```
uaacagucua cagccauggu cg    22

<210> SEQ ID NO 267
<211> LENGTH: 22
<212> TYPE: RNA
<213> ORGANISM: Homo sapiens

<400> SEQUENCE: 267
uuuggucccc uucaaccagc ug    22

<210> SEQ ID NO 268
<211> LENGTH: 22
<212> TYPE: RNA
<213> ORGANISM: Homo sapiens

<400> SEQUENCE: 268
uuuggucccc uucaaccagc ua    22

<210> SEQ ID NO 269
<211> LENGTH: 22
<212> TYPE: RNA
<213> ORGANISM: Homo sapiens

<400> SEQUENCE: 269
ugugacuggu ugaccagagg gg    22

<210> SEQ ID NO 270
<211> LENGTH: 22
<212> TYPE: RNA
<213> ORGANISM: Homo sapiens

<400> SEQUENCE: 270
ucuacagugc acgugucucc ag    22

<210> SEQ ID NO 271
<211> LENGTH: 22
<212> TYPE: RNA
<213> ORGANISM: Homo sapiens

<400> SEQUENCE: 271
cagugguuuu acccuauggu ag    22

<210> SEQ ID NO 272
<211> LENGTH: 22
<212> TYPE: RNA
<213> ORGANISM: Homo sapiens

<400> SEQUENCE: 272
ggauuccugg aaauacuguu cu    22

<210> SEQ ID NO 273
<211> LENGTH: 22
<212> TYPE: RNA
<213> ORGANISM: Homo sapiens

<400> SEQUENCE: 273
ucagugcauc acagaacuuu gu    22

<210> SEQ ID NO 274
<211> LENGTH: 21
<212> TYPE: RNA
<213> ORGANISM: Homo sapiens

<400> SEQUENCE: 274

```
cuagacugaa gcuccuugag g                                              21

<210> SEQ ID NO 275
<211> LENGTH: 22
<212> TYPE: RNA
<213> ORGANISM: Homo sapiens

<400> SEQUENCE: 275
uagguuaucc guguugccuu cg                                             22

<210> SEQ ID NO 276
<211> LENGTH: 22
<212> TYPE: RNA
<213> ORGANISM: Homo sapiens

<400> SEQUENCE: 276
aaucauacac gguugaccua uu                                             22

<210> SEQ ID NO 277
<211> LENGTH: 22
<212> TYPE: RNA
<213> ORGANISM: Homo sapiens

<400> SEQUENCE: 277
acugcaguga aggcacuugu ag                                             22

<210> SEQ ID NO 278
<211> LENGTH: 22
<212> TYPE: RNA
<213> ORGANISM: Homo sapiens

<400> SEQUENCE: 278
accacugacc guugacugua cc                                             22

<210> SEQ ID NO 279
<211> LENGTH: 27
<212> TYPE: RNA
<213> ORGANISM: Homo sapiens

<400> SEQUENCE: 279
auugaucauc gacacuucga acgcaau                                        27

<210> SEQ ID NO 280
<211> LENGTH: 22
<212> TYPE: RNA
<213> ORGANISM: Homo sapiens

<400> SEQUENCE: 280
ucgugucuug uguugcagcc gg                                             22

<210> SEQ ID NO 281
<211> LENGTH: 21
<212> TYPE: RNA
<213> ORGANISM: Homo sapiens

<400> SEQUENCE: 281
caucccuugc augguggagg g                                              21

<210> SEQ ID NO 282
<211> LENGTH: 22
<212> TYPE: RNA
<213> ORGANISM: Homo sapiens
```

```
<400> SEQUENCE: 282
uagguaguuu cauguuguug gg                                              22

<210> SEQ ID NO 283
<211> LENGTH: 22
<212> TYPE: RNA
<213> ORGANISM: Homo sapiens

<400> SEQUENCE: 283
cucccacugc uucacuugac ua                                              22

<210> SEQ ID NO 284
<211> LENGTH: 23
<212> TYPE: RNA
<213> ORGANISM: Homo sapiens

<400> SEQUENCE: 284
ugugcaaauc caugcaaaac uga                                             23

<210> SEQ ID NO 285
<211> LENGTH: 23
<212> TYPE: RNA
<213> ORGANISM: Homo sapiens

<400> SEQUENCE: 285
caaagugcuc auagugcagg uag                                             23

<210> SEQ ID NO 286
<211> LENGTH: 22
<212> TYPE: RNA
<213> ORGANISM: Homo sapiens

<400> SEQUENCE: 286
uaaucucagc uggcaacugu ga                                              22

<210> SEQ ID NO 287
<211> LENGTH: 22
<212> TYPE: RNA
<213> ORGANISM: Homo sapiens

<400> SEQUENCE: 287
aaaucucugc aggcaaaugu ga                                              22

<210> SEQ ID NO 288
<211> LENGTH: 23
<212> TYPE: RNA
<213> ORGANISM: Homo sapiens

<400> SEQUENCE: 288
uacugcauca ggaacugauu gga                                             23

<210> SEQ ID NO 289
<211> LENGTH: 22
<212> TYPE: RNA
<213> ORGANISM: Homo sapiens

<400> SEQUENCE: 289
aguucuucag uggcaagcuu ua                                              22

<210> SEQ ID NO 290
<211> LENGTH: 22
<212> TYPE: RNA
<213> ORGANISM: Homo sapiens
```

```
<400> SEQUENCE: 290
accuggcaua caauguagau uu                                              22

<210> SEQ ID NO 291
<211> LENGTH: 22
<212> TYPE: RNA
<213> ORGANISM: Homo sapiens

<400> SEQUENCE: 291
cucaguagcc aguguagauc cu                                              22

<210> SEQ ID NO 292
<211> LENGTH: 21
<212> TYPE: RNA
<213> ORGANISM: Homo sapiens

<400> SEQUENCE: 292
aucacauugc cagggauuuc c                                               21

<210> SEQ ID NO 293
<211> LENGTH: 21
<212> TYPE: RNA
<213> ORGANISM: Homo sapiens

<400> SEQUENCE: 293
aucacauugc cagggauuac c                                               21

<210> SEQ ID NO 294
<211> LENGTH: 22
<212> TYPE: RNA
<213> ORGANISM: Homo sapiens

<400> SEQUENCE: 294
uggcucaguu cagcaggaac ag                                              22

<210> SEQ ID NO 295
<211> LENGTH: 22
<212> TYPE: RNA
<213> ORGANISM: Homo sapiens

<400> SEQUENCE: 295
uucaaguaau ccaggauagg cu                                              22

<210> SEQ ID NO 296
<211> LENGTH: 21
<212> TYPE: RNA
<213> ORGANISM: Homo sapiens

<400> SEQUENCE: 296
uucaaguaau ucaggauagg u                                               21

<210> SEQ ID NO 297
<211> LENGTH: 21
<212> TYPE: RNA
<213> ORGANISM: Homo sapiens

<400> SEQUENCE: 297
uucacagugg cuaaguuccg c                                               21

<210> SEQ ID NO 298
<211> LENGTH: 22
<212> TYPE: RNA
```

<213> ORGANISM: Homo sapiens

<400> SEQUENCE: 298
cacuagauug ugagcccug ga                    22

<210> SEQ ID NO 299
<211> LENGTH: 21
<212> TYPE: RNA
<213> ORGANISM: Homo sapiens

<400> SEQUENCE: 299
agggcccccc cucaauccug u                    21

<210> SEQ ID NO 300
<211> LENGTH: 22
<212> TYPE: RNA
<213> ORGANISM: Homo sapiens

<400> SEQUENCE: 300
uaugugggau gguaaaccgc uu                   22

<210> SEQ ID NO 301
<211> LENGTH: 22
<212> TYPE: RNA
<213> ORGANISM: Homo sapiens

<400> SEQUENCE: 301
cugguuucac augguggcuu ag                   22

<210> SEQ ID NO 302
<211> LENGTH: 23
<212> TYPE: RNA
<213> ORGANISM: Homo sapiens

<400> SEQUENCE: 302
cagugcaaua guauugucaa agc                  23

<210> SEQ ID NO 303
<211> LENGTH: 22
<212> TYPE: RNA
<213> ORGANISM: Homo sapiens

<400> SEQUENCE: 303
uguaaacauc cuacacucag cu                   22

<210> SEQ ID NO 304
<211> LENGTH: 22
<212> TYPE: RNA
<213> ORGANISM: Homo sapiens

<400> SEQUENCE: 304
cuuucagucg gauguuuaca gc                   22

<210> SEQ ID NO 305
<211> LENGTH: 22
<212> TYPE: RNA
<213> ORGANISM: Homo sapiens

<400> SEQUENCE: 305
ugcuaugcca acauauugcc au                   22

<210> SEQ ID NO 306
<211> LENGTH: 21

<212> TYPE: RNA
<213> ORGANISM: Homo sapiens

<400> SEQUENCE: 306
cacauuacac ggucgaccuc u                                    21

<210> SEQ ID NO 307
<211> LENGTH: 23
<212> TYPE: RNA
<213> ORGANISM: Homo sapiens

<400> SEQUENCE: 307
cgcauccccu agggcauugg ugu                                  23

<210> SEQ ID NO 308
<211> LENGTH: 22
<212> TYPE: RNA
<213> ORGANISM: Homo sapiens

<400> SEQUENCE: 308
cuggcccucu cugcccuucc gu                                   22

<210> SEQ ID NO 309
<211> LENGTH: 22
<212> TYPE: RNA
<213> ORGANISM: Homo sapiens

<400> SEQUENCE: 309
aacacaccug guuaaccucu uu                                   22

<210> SEQ ID NO 310
<211> LENGTH: 23
<212> TYPE: RNA
<213> ORGANISM: Homo sapiens

<400> SEQUENCE: 310
gcaaagcaca cggccugcag aga                                  23

<210> SEQ ID NO 311
<211> LENGTH: 23
<212> TYPE: RNA
<213> ORGANISM: Homo sapiens

<400> SEQUENCE: 311
ucaagagcaa uaacgaaaaa ugu                                  23

<210> SEQ ID NO 312
<211> LENGTH: 21
<212> TYPE: RNA
<213> ORGANISM: Homo sapiens

<400> SEQUENCE: 312
gaacggcuuc auacaggagu u                                    21

<210> SEQ ID NO 313
<211> LENGTH: 22
<212> TYPE: RNA
<213> ORGANISM: Homo sapiens

<400> SEQUENCE: 313
uccagcauca gugauuuugu ug                                   22

<210> SEQ ID NO 314

```
<211> LENGTH: 23
<212> TYPE: RNA
<213> ORGANISM: Homo sapiens

<400> SEQUENCE: 314 uccccaggu gugauucuga uuu                                            23

<210> SEQ ID NO 315
<211> LENGTH: 22
<212> TYPE: RNA
<213> ORGANISM: Homo sapiens

<400> SEQUENCE: 315
aacacaccua uucaaggauu ca                                            22

<210> SEQ ID NO 316
<211> LENGTH: 24
<212> TYPE: RNA
<213> ORGANISM: Homo sapiens

<400> SEQUENCE: 316
aauccuugga accuaggugu gagu                                          24

<210> SEQ ID NO 317
<211> LENGTH: 22
<212> TYPE: RNA
<213> ORGANISM: Homo sapiens

<400> SEQUENCE: 317
agaucgaccg uguuauauuc gc                                            22

<210> SEQ ID NO 318
<211> LENGTH: 22
<212> TYPE: RNA
<213> ORGANISM: Homo sapiens

<400> SEQUENCE: 318
gccugcuggg guggaaccug gu                                            22

<210> SEQ ID NO 319
<211> LENGTH: 21
<212> TYPE: RNA
<213> ORGANISM: Homo sapiens

<400> SEQUENCE: 319
aucauagagg aaaauccacg u                                             21

<210> SEQ ID NO 320
<211> LENGTH: 21
<212> TYPE: RNA
<213> ORGANISM: Homo sapiens

<400> SEQUENCE: 320
aacauagagg aaauuccacg u                                             21

<210> SEQ ID NO 321
<211> LENGTH: 22
<212> TYPE: RNA
<213> ORGANISM: Homo sapiens

<400> SEQUENCE: 321
agagguugcc cuuggugaau uc                                            22
```

```
<210> SEQ ID NO 322
<211> LENGTH: 21
<212> TYPE: RNA
<213> ORGANISM: Homo sapiens

<400> SEQUENCE: 322
ugguagacua uggaacguag g                                              21

<210> SEQ ID NO 323
<211> LENGTH: 22
<212> TYPE: RNA
<213> ORGANISM: Homo sapiens

<400> SEQUENCE: 323
uauacaaggg caagcucucu gu                                             22

<210> SEQ ID NO 324
<211> LENGTH: 22
<212> TYPE: RNA
<213> ORGANISM: Homo sapiens

<400> SEQUENCE: 324
gaaguuguuc gugguggauu cg                                             22

<210> SEQ ID NO 325
<211> LENGTH: 22
<212> TYPE: RNA
<213> ORGANISM: Homo sapiens

<400> SEQUENCE: 325
gaauguugcu cggugaaccc cu                                             22

<210> SEQ ID NO 326
<211> LENGTH: 23
<212> TYPE: RNA
<213> ORGANISM: Homo sapiens

<400> SEQUENCE: 326
agguuacccg agcaacuuug cau                                            23

<210> SEQ ID NO 327
<211> LENGTH: 21
<212> TYPE: RNA
<213> ORGANISM: Homo sapiens

<400> SEQUENCE: 327
aauauaacac agauggccug u                                              21

<210> SEQ ID NO 328
<211> LENGTH: 21
<212> TYPE: RNA
<213> ORGANISM: Homo sapiens

<400> SEQUENCE: 328
uaguagaccg uauagcguac g                                              21

<210> SEQ ID NO 329
<211> LENGTH: 22
<212> TYPE: RNA
<213> ORGANISM: Homo sapiens

<400> SEQUENCE: 329
aucgggaaug ucguguccgc cc                                             22
```

<210> SEQ ID NO 330
<211> LENGTH: 22
<212> TYPE: RNA
<213> ORGANISM: Homo sapiens

<400> SEQUENCE: 330
caggucgucu ugcagggcuu cu                                              22

<210> SEQ ID NO 331
<211> LENGTH: 23
<212> TYPE: RNA
<213> ORGANISM: Homo sapiens

<400> SEQUENCE: 331
ucuuggagua ggucauuggg ugg                                             23

<210> SEQ ID NO 332
<211> LENGTH: 22
<212> TYPE: RNA
<213> ORGANISM: Homo sapiens

<400> SEQUENCE: 332
aucaugaugg gcuccucggu gu                                              22

<210> SEQ ID NO 333
<211> LENGTH: 21
<212> TYPE: RNA
<213> ORGANISM: Homo sapiens

<400> SEQUENCE: 333
ucacuccucu ccucccgucu u                                               21

<210> SEQ ID NO 334
<211> LENGTH: 22
<212> TYPE: RNA
<213> ORGANISM: Homo sapiens

<400> SEQUENCE: 334
aagacgggag gaaagaaggg ag                                              22

<210> SEQ ID NO 335
<211> LENGTH: 22
<212> TYPE: RNA
<213> ORGANISM: Homo sapiens

<400> SEQUENCE: 335
gucauacacg gcucuccucu cu                                              22

<210> SEQ ID NO 336
<211> LENGTH: 22
<212> TYPE: RNA
<213> ORGANISM: Homo sapiens

<400> SEQUENCE: 336
agaggcuggc cgugaugaau uc                                              22

<210> SEQ ID NO 337
<211> LENGTH: 22
<212> TYPE: RNA
<213> ORGANISM: Homo sapiens

<400> SEQUENCE: 337
aaucauacag ggacauccag uu                                              22

```
<210> SEQ ID NO 338
<211> LENGTH: 22
<212> TYPE: RNA
<213> ORGANISM: Homo sapiens

<400> SEQUENCE: 338
ugaaacauac acgggaaacc uc                                              22

<210> SEQ ID NO 339
<211> LENGTH: 22
<212> TYPE: RNA
<213> ORGANISM: Homo sapiens

<400> SEQUENCE: 339
aaacaaacau ggugcacuuc uu                                              22

<210> SEQ ID NO 340
<211> LENGTH: 23
<212> TYPE: RNA
<213> ORGANISM: Homo sapiens

<400> SEQUENCE: 340
uaauccuugc uaccugggug aga                                             23

<210> SEQ ID NO 341
<211> LENGTH: 22
<212> TYPE: RNA
<213> ORGANISM: Homo sapiens

<400> SEQUENCE: 341
augcaccugg gcaaggauuc ug                                              22

<210> SEQ ID NO 342
<211> LENGTH: 22
<212> TYPE: RNA
<213> ORGANISM: Homo sapiens

<400> SEQUENCE: 342
aaugcacccg ggcaaggauu cu                                              22

<210> SEQ ID NO 343
<211> LENGTH: 22
<212> TYPE: RNA
<213> ORGANISM: Homo sapiens

<400> SEQUENCE: 343
aaugcaccug ggcaaggauu ca                                              22

<210> SEQ ID NO 344
<211> LENGTH: 23
<212> TYPE: RNA
<213> ORGANISM: Homo sapiens

<400> SEQUENCE: 344
uagcagcggg aacaguucug cag                                             23

<210> SEQ ID NO 345
<211> LENGTH: 21
<212> TYPE: RNA
<213> ORGANISM: Homo sapiens

<400> SEQUENCE: 345
```
uaaggcaccc uucugaguag a                              21

<210> SEQ ID NO 346
<211> LENGTH: 22
<212> TYPE: RNA
<213> ORGANISM: Homo sapiens

<400> SEQUENCE: 346
uacugcagac guggcaauca ug                             22

<210> SEQ ID NO 347
<211> LENGTH: 18
<212> TYPE: RNA
<213> ORGANISM: Homo sapiens

<400> SEQUENCE: 347
uucacaggga ggugucau                                  18

<210> SEQ ID NO 348
<211> LENGTH: 22
<212> TYPE: RNA
<213> ORGANISM: Homo sapiens

<400> SEQUENCE: 348
ccucccacac ccaaggcuug ca                             22

<210> SEQ ID NO 349
<211> LENGTH: 22
<212> TYPE: RNA
<213> ORGANISM: Homo sapiens

<400> SEQUENCE: 349
caugccuuga guguaggacc gu                             22

<210> SEQ ID NO 350
<211> LENGTH: 22
<212> TYPE: RNA
<213> ORGANISM: Homo sapiens

<400> SEQUENCE: 350
ggagaaauua uccuuggugu gu                             22

<210> SEQ ID NO 351
<211> LENGTH: 23
<212> TYPE: RNA
<213> ORGANISM: Homo sapiens

<400> SEQUENCE: 351
ucggggauca ucaugucacg aga                            23

<210> SEQ ID NO 352
<211> LENGTH: 22
<212> TYPE: RNA
<213> ORGANISM: Homo sapiens

<400> SEQUENCE: 352
aaacauucgc ggugcacuuc uu                             22

<210> SEQ ID NO 353
<211> LENGTH: 22
<212> TYPE: RNA
<213> ORGANISM: Homo sapiens

<400> SEQUENCE: 353
uacgucaucg uugucaucgu ca                                          22

<210> SEQ ID NO 354
<211> LENGTH: 25
<212> TYPE: RNA
<213> ORGANISM: Homo sapiens

<400> SEQUENCE: 354
gcugggcagg gcuucugagc uccuu                                       25

<210> SEQ ID NO 355
<211> LENGTH: 22
<212> TYPE: RNA
<213> ORGANISM: Homo sapiens

<400> SEQUENCE: 355
uaugucugcu gaccaucacc uu                                          22

<210> SEQ ID NO 356
<211> LENGTH: 25
<212> TYPE: RNA
<213> ORGANISM: Homo sapiens

<400> SEQUENCE: 356
ggcggaggga aguagguccg uuggu                                       25

<210> SEQ ID NO 357
<211> LENGTH: 22
<212> TYPE: RNA
<213> ORGANISM: Homo sapiens

<400> SEQUENCE: 357
uacccauugc auaucggagu ug                                          22

<210> SEQ ID NO 358
<211> LENGTH: 20
<212> TYPE: RNA
<213> ORGANISM: Homo sapiens

<400> SEQUENCE: 358
accaggaggc ugaggccccu                                             20

<210> SEQ ID NO 359
<211> LENGTH: 23
<212> TYPE: RNA
<213> ORGANISM: Homo sapiens

<400> SEQUENCE: 359
aaggagcuua caaucuagcu ggg                                         23

<210> SEQ ID NO 360
<211> LENGTH: 21
<212> TYPE: RNA
<213> ORGANISM: Homo sapiens

<400> SEQUENCE: 360
gcaggaacuu gugagucucc u                                           21

<210> SEQ ID NO 361
<211> LENGTH: 22
<212> TYPE: RNA
<213> ORGANISM: Homo sapiens

```
<400> SEQUENCE: 361
cugcccuggc ccgagggacc ga                                              22

<210> SEQ ID NO 362
<211> LENGTH: 22
<212> TYPE: RNA
<213> ORGANISM: Homo sapiens

<400> SEQUENCE: 362
ugcaacgaac cugagccacu ga                                              22

<210> SEQ ID NO 363
<211> LENGTH: 22
<212> TYPE: RNA
<213> ORGANISM: Homo sapiens

<400> SEQUENCE: 363
cacccguaga accgaccuug cg                                              22

<210> SEQ ID NO 364
<211> LENGTH: 22
<212> TYPE: RNA
<213> ORGANISM: Homo sapiens

<400> SEQUENCE: 364
aacuggggcg ggaaggggga ag                                              22

<210> SEQ ID NO 365
<211> LENGTH: 22
<212> TYPE: RNA
<213> ORGANISM: Homo sapiens

<400> SEQUENCE: 365
aagugauugg aggugggugg gg                                              22

<210> SEQ ID NO 366
<211> LENGTH: 22
<212> TYPE: RNA
<213> ORGANISM: Homo sapiens

<400> SEQUENCE: 366
agaagcugaa gggagagaga ca                                              22

<210> SEQ ID NO 367
<211> LENGTH: 22
<212> TYPE: RNA
<213> ORGANISM: Homo sapiens

<400> SEQUENCE: 367
gugguuaucc cugcuguguu cg                                              22

<210> SEQ ID NO 368
<211> LENGTH: 22
<212> TYPE: RNA
<213> ORGANISM: Homo sapiens

<400> SEQUENCE: 368
ugcagcuggu ggagucuggg gg                                              22

<210> SEQ ID NO 369
<211> LENGTH: 22
<212> TYPE: RNA
<213> ORGANISM: Homo sapiens
```

<400> SEQUENCE: 369
aaucugcagg gggagccugg gu                                    22

<210> SEQ ID NO 370
<211> LENGTH: 24
<212> TYPE: RNA
<213> ORGANISM: Homo sapiens

<400> SEQUENCE: 370
acucccaugu cccuugggaa gguc                                  24

<210> SEQ ID NO 371
<211> LENGTH: 23
<212> TYPE: RNA
<213> ORGANISM: Homo sapiens

<400> SEQUENCE: 371
agcgagguug cccuuuguau auu                                   23

<210> SEQ ID NO 372
<211> LENGTH: 19
<212> TYPE: RNA
<213> ORGANISM: Homo sapiens

<400> SEQUENCE: 372
agggcugggg acagagaug                                        19

<210> SEQ ID NO 373
<211> LENGTH: 19
<212> TYPE: RNA
<213> ORGANISM: Homo sapiens

<400> SEQUENCE: 373
agugaagcau uggacugua                                        19

<210> SEQ ID NO 374
<211> LENGTH: 18
<212> TYPE: RNA
<213> ORGANISM: Homo sapiens

<400> SEQUENCE: 374
aucccacucc ugacacca                                         18

<210> SEQ ID NO 375
<211> LENGTH: 21
<212> TYPE: RNA
<213> ORGANISM: Homo sapiens

<400> SEQUENCE: 375
cauccuagcc cuaagucugg c                                     21

<210> SEQ ID NO 376
<211> LENGTH: 28
<212> TYPE: RNA
<213> ORGANISM: Homo sapiens

<400> SEQUENCE: 376
cccaggcugg aguguagugg cgugaucu                              28

<210> SEQ ID NO 377
<211> LENGTH: 22
<212> TYPE: RNA
<213> ORGANISM: Homo sapiens

```
<400> SEQUENCE: 377
cgccugugaa uagucacugc ac                                          22

<210> SEQ ID NO 378
<211> LENGTH: 20
<212> TYPE: RNA
<213> ORGANISM: Homo sapiens

<400> SEQUENCE: 378
gaaagcugag cgugaacgug                                             20

<210> SEQ ID NO 379
<211> LENGTH: 20
<212> TYPE: RNA
<213> ORGANISM: Homo sapiens

<400> SEQUENCE: 379
gaaucccacu ucugacacca                                             20

<210> SEQ ID NO 380
<211> LENGTH: 23
<212> TYPE: RNA
<213> ORGANISM: Homo sapiens

<400> SEQUENCE: 380
guuccuguug gccgagugga gac                                         23

<210> SEQ ID NO 381
<211> LENGTH: 19
<212> TYPE: RNA
<213> ORGANISM: Homo sapiens

<400> SEQUENCE: 381
uaaaaggaac ucggcaaau                                              19

<210> SEQ ID NO 382
<211> LENGTH: 17
<212> TYPE: RNA
<213> ORGANISM: Homo sapiens

<400> SEQUENCE: 382
ugcagaucuu gguggua                                                17

<210> SEQ ID NO 383
<211> LENGTH: 22
<212> TYPE: RNA
<213> ORGANISM: Homo sapiens

<400> SEQUENCE: 383
uggggccucc cacagcuguu uc                                          22

<210> SEQ ID NO 384
<211> LENGTH: 17
<212> TYPE: RNA
<213> ORGANISM: Homo sapiens

<400> SEQUENCE: 384
ugguggucua gugguua                                                17

<210> SEQ ID NO 385
<211> LENGTH: 25
<212> TYPE: RNA
<213> ORGANISM: Homo sapiens
```

```
<400> SEQUENCE: 385
uguccaaagu aaacgcccug acgca                    25

<210> SEQ ID NO 386
<211> LENGTH: 19
<212> TYPE: RNA
<213> ORGANISM: Homo sapiens

<400> SEQUENCE: 386
ugucccuucg uggucgcca                           19

<210> SEQ ID NO 387
<211> LENGTH: 20
<212> TYPE: RNA
<213> ORGANISM: Homo sapiens

<400> SEQUENCE: 387
uucaugggga agcagauuug                          20

<210> SEQ ID NO 388
<211> LENGTH: 23
<212> TYPE: RNA
<213> ORGANISM: Homo sapiens

<400> SEQUENCE: 388
ugaggggcag agagcgagac uuu                      23

<210> SEQ ID NO 389
<211> LENGTH: 24
<212> TYPE: RNA
<213> ORGANISM: Homo sapiens

<400> SEQUENCE: 389
cauagcccgg ucgcugguac auga                     24

<210> SEQ ID NO 390
<211> LENGTH: 23
<212> TYPE: RNA
<213> ORGANISM: Homo sapiens

<400> SEQUENCE: 390
gccgagacua gagucacauc cug                      23
```